United States Patent
Aukerman et al.

(10) Patent No.: US 9,040,773 B2
(45) Date of Patent: May 26, 2015

(54) PLANTS HAVING ALTERED AGRONOMIC CHARACTERISTICS UNDER NITROGEN LIMITING CONDITIONS AND RELATED CONSTRUCTS AND METHODS INVOLVING GENES ENCODING LNT1 POLYPEPTIDES AND HOMOLOGS THEREOF

(71) Applicants: EI DU PONT DE NEMOURS AND COMPANY, Wilmington, DE (US); PIONEER HI BRED INTERNATIONAL INC, Johnston, IA (US)

(72) Inventors: Milo Aukerman, Newark, DE (US); Stephen M Allen, Wilmington, DE (US); Dale F. Loussaert, Clive, IA (US); Stanley Luck, Wilmington, DE (US); Hajime Sakai, Newark, DE (US); Scott V. Tingey, Wilmington, DE (US)

(73) Assignees: EI DU PONT DE NEMOURS AND COMPANY, Wilmington, DE (US); PIONEER HI BRED INTERNATIONAL INC, Johnston, IA (US)

( * ) Notice: Subject to any disclaimer, the term of this patent is extended or adjusted under 35 U.S.C. 154(b) by 0 days.

(21) Appl. No.: 14/016,295

(22) Filed: Sep. 3, 2013

(65) Prior Publication Data
US 2014/0007290 A1 Jan. 2, 2014

Related U.S. Application Data

(62) Division of application No. 12/999,074, filed as application No. PCT/US2009/049878 on Jul. 8, 2009, now Pat. No. 8,541,650.

(60) Provisional application No. 61/078,949, filed on Jul. 8, 2009.

(51) Int. Cl.
| | |
|---|---|
| *A01H 1/00* | (2006.01) |
| *C12N 5/04* | (2006.01) |
| *C12N 15/00* | (2006.01) |
| *C12N 15/82* | (2006.01) |
| *C07H 21/04* | (2006.01) |

(52) U.S. Cl.
CPC ........ *C12N 15/8271* (2013.01); *C12N 15/8241* (2013.01); *C12N 15/8261* (2013.01)

(58) Field of Classification Search
None
See application file for complete search history.

(56) References Cited

U.S. PATENT DOCUMENTS

| | | |
|---|---|---|
| 2004/0031072 A1 | 2/2004 | La Rosa et al. |
| 2004/0214272 A1 | 10/2004 | LaRosa et al. |
| 2004/0216190 A1 | 10/2004 | Kovalic |
| 2007/0011783 A1 | 1/2007 | Liu et al. |
| 2007/0039067 A1* | 2/2007 | Feldmann et al. ............ 800/278 |
| 2009/0087878 A9 | 4/2009 | LaRosa et al. |

OTHER PUBLICATIONS

Detlef Weigel et al., Activation Tagging in *Arabidopsis*, Plant Physiology, Apr. 2000, pp. 1003-1013, vol. 122.

National Center for Biotechnology Information General Identifier No. 145337238, May 28, 2011, Accession No. NM105376, A. Theologis et al, Sequence and analysis of chromosome 1 of the plant *Arabidopsis thaliana*.

National Center for Biotechnology Information General Identifier No. 157341431, Oct. 8, 2007, Accession No. CA049338, O. Jaillon et al., The grapevine genome sequencce suggests ancestral hexaploidization in major angiosperm phyla.

National Center for Biotechnology Information General Identifier No. 157343572, Oct. 8, 2007, Accession No. CA068078, O. Jaillon et al., The grapevine genome sequence suggests ancestral hexaploidization in major angiosperm phyla.

National Center for Biotechnology Information General Identifier No. 212275704, Jun. 16, 2012, Accession No. NP_001130069, C. Soderlund et al., Sequencing, mapping, and analysis of 27,455 maize full-length cDNAs.

National Center for Biotechnology Information General Identifier No. 42563004, May 28, 2011, Accession No. NP_176877, A. Theologis et al., Sequence and analysis of chromosome 1 of the plant *Arabidopsis thaliana*.

\* cited by examiner

*Primary Examiner* — Eileen B O Hara
*Assistant Examiner* — Matthew Keogh

(57) ABSTRACT

Isolated polynucleotides and polypeptides and recombinant DNA constructs particularly useful for altering agronomic characteristics of plants under nitrogen limiting conditions, compositions (such as plants or seeds) comprising these recombinant DNA constructs, and methods utilizing these recombinant DNA constructs. The recombinant DNA construct comprises a polynucleotide operably linked to a promoter functional in a plant, wherein said polynucleotide encodes an LNT1 polypeptide.

6 Claims, 24 Drawing Sheets

FIG. 11

| | | | | | | | |
|---|---|---|---|---|---|---|---|
| O 3 | O 4 | O 2 | O 1 | O 5 | O 3 | O C1 | O 4 |
| O 4 | O 2 | O 1 | O 5 | O 3 | O C1 | O 4 | O 2 |
| O 2 | O 1 | O 5 | O 3 | O C1 | O 4 | O 2 | O 5 |
| O 1 | O 5 | O 3 | O C1 | O 4 | O 2 | O 5 | O 4 |
| O 5 | O 3 | O C1 | O 1 | O 2 | O 5 | O 4 | O 3 |
| O 3 | O C1 | O 1 | O 2 | O 5 | O 4 | O 3 | O 1 |
| O C1 | O 1 | O 2 | O 5 | O 4 | O 3 | O 1 | O C1 |
| O 1 | O 2 | O 5 | O 4 | O 3 | O 1 | O C1 | O 2 |

Typical grid pattern for 5 lines (labeled 1 through 5), plus wild-type control C1, used in screens.

FIG. 13

Modified Hoagland's solutions -
16X concentrations for semi-hydroponics maize growth.

| Nutrient | 1 mM KNO$_3$ | 2 mM KNO$_3$ | 3 mM KNO$_3$ | 4 mM KNO$_3$ |
|---|---|---|---|---|
| KNO$_3$ | 16 mM | 32 mM | 48 mM | 64 mM |
| KCl | 48 mM | 32 mM | 16 mM | ---- |
| KH$_2$PO$_4$ | 11 mM | 11 mM | 11 mM | 11 mM |
| MgSO$_4$ | 16 mM | 16 mM | 16 mM | 16 mM |
| CaCl$_2$·2H$_2$O | 16 mM | 16 mM | 16 mM | 16 mM |
| Sprint 330 | 1.6 g/L | 1.6 g/L | 1.6 g/L | 1.6 g/L |
| H$_3$BO$_3$ | 24 µM | 24 µM | 24 µM | 24 µM |
| 5 mM MnCl$_2$·4H$_2$O | 8 µM | 8 µM | 8 µM | 8 µM |
| 5 mM ZnSO$_4$·7H$_2$O | 8 M | 8 µM | 8 µM | 8 µM |
| 0.5 mM CuSO$_4$·5H$_2$O | 800 nM | 800 nM | 800 nM | 800 nM |
| 0.5 mM H$_2$MoO$_4$·H$_2$O | 800 nM | 800 nM | 800 nM | 800 nM |

Dilute 16X with tap water and determine the pH of the final mixture.
Add 3-12 mL H$_2$SO$_4$ if the pH is above 6.5.
Optimum pH is 5.0 - 5.5

FIG. 14

The effect of different nitrate concentrations on the growth and development of Gaspe Bay Flint derived maize lines (see Example 18).

| [nitrate] | root (g dwt) | shoot (g dwt) | total vegetative (g dwt) | ear & husk (g dwt) | tassel (g dwt) | tiller # | tiller (g dwt) |
|---|---|---|---|---|---|---|---|
| 1 week after emergence | | | | | | | |
| 1 mM | 0.070a | 0.105b | 0.175b | | | | |
| 2 mM | 0.073a | 0.137ab | 0.209ab | | | | |
| 3 mM | 0.056a | 0.120ab | 0.176ab | | | | |
| 4 mM | 0.074a | 0.157a | 0.231a | | | | |
| 2 weeks after emergence | | | | | | | |
| 1 mM | 0.331ab | 0.544c | 0.875c | | | | |
| 2 mM | 0.266b | 0.951b | 1.217b | | | | |
| 3 mM | 0.352a | 1.171a | 1.523a | | | | |
| 4 mM | 0.303ab | 1.209a | 1.512a | | | | |
| 3 weeks after emergence | | | | | | | |
| 1 mM | 0.757a | 1.283b | 2.040b | 0.379c | 0.239c | 0.8c | 0.080b |
| 2 mM | 0.785a | 2.033a | 2.819a | 0.718a | 0.363bc | 2.3 | 0.506a |
| 3 mM | 0.664a | 1.911a | 2.574a | 0.451bc | 0.403ab | 2.8ab | 0.441a |
| 4 mM | 0.845a | 2.129a | 2.974a | 0.650ab | 0.506a | 3.3a | 0.688a |
| 4 weeks after emergence | | | | | | | |
| 1 mM | 0.842b | 2.010b | 2.852b | 1.318b | 0.677b | * | * |
| 2 mM | 1.493a | 3.772a | 5.265a | 3.130a | 1.018a | * | * |
| 3 mM | 1.232ab | 3.563a | 4.795a | 3.060a | 0.875ab | * | * |
| 4 mM | 1.010b | 2.943a | 3.952a | 2.787a | 0.891ab | * | * |

* Tillers removed 3 weeks after emergence
Means with similar letters are not different by protected Least Significant Difference (LSD) (0.05)

FIG. 15A

```
        M--PNWELRXCCDHDQXIFXATVGVFTVILLLMRTFLLTPFKLITVFLH Majority
                 10        20        30        40        50

1   MA--VNWELQGCCHRDQRIFIAAVGVSTVILLLMRTFLLTPFKLITVFLH  SEQ ID NO:18  (maize)
  1   MA--VNWELRGCCDHDQRIFIAAVGVSTVILLLMRTFLLTPFKLITVFLH  SEQ ID NO:20  (maize)
  1   M--PNWELRNCCDHDQKVFIACVAAFTVVLVLMRTFLLTPFKLITVFLH   SEQ ID NO:22  (soybean)
  1   M--PNWELRNCCDHDQKIFIACVAAFTVVLVLMRTFLLTPFKLITVFLH   SEQ ID NO:24  (soybean)
  1   MTSPNWELKNCCDRDQKFFLATVGIYSLVILALMRTFLLTPFKLITVFLH  SEQ ID NO:26  (sunflower)
  1   MA--NWELRDCCNHDQLLFLITLAFCVIVILALMRTIVLLPFKLVTIFLH  SEQ ID NO:28  (sunflower)
  1   M------------------------------------------------  SEQ ID NO:30  (rice)
  1   MDSPNWELRGCCNRNQNTFLITIGVFTVVILLLMRTFLLTPFKLITVFLH  SEQ ID NO:32  (Arabidopsis)
  1   M--ANWELKNCCKHDQVVFLATIGVFTVVILLLMRTFLLTPFKLITVFLH  SEQ ID NO:33  (grape)
  1   M----ANWELKKCCNHEQVVFLTTISICTVILAIMRTILLTPFKLVTVFLH SEQ ID NO:34  (grape)
  1   MA--VNWELQGCCHRDQRIFIAAVGVSTVILLLMRTFLLTPFKLITVFLH  SEQ ID NO:37  (maize)

EASHAIACKLTCGDVEGMQVHANEGGVTQTRGGIYWIILPAGYLGSSFWG Majority
                 60        70        80        90        100

50   ETSHALACKLTCGDVEGMQVHANEGGVTQTRGGIYWIILPAGYLGSSFWG  SEQ ID NO:18  (maize)
 50   ETSHALACKLTCGDVEGMQVHANEGGVTQTRGGIYWIILPAGYLGSSFWG  SEQ ID NO:20  (maize)
 49   EASHAIACWLTCGKVEGIQVHANEGGVTQTRGGVYWVILPAGYLGSSFWG  SEQ ID NO:22  (soybean)
 49   EASHAIACWLTCGKVEGIQVHANEGGVTQTRGGIYWVILPAGYLGSSFWG  SEQ ID NO:24  (soybean)
 51   EASHAIACKLTCGEVMGMEVHANEGGVTQTRGGVYWLILPAGYLGSSFWG  SEQ ID NO:26  (sunflower)
 49   EASHAVACKLTCGHVEGMQIFADEGGMTQTRGGVYWFILPAGYLGSSFWG  SEQ ID NO:28  (sunflower)
  2   ------------QVHPNEGGVTQTRGGIYWIILPAGYLGSSFWG        SEQ ID NO:30  (rice)
 51   EASHAIACKLTCGDVEGMEVNANEGGSTTTRGGIYWLILPAGYLGSSFWG  SEQ ID NO:32  (Arabidopsis)
 49   EASHAIACKLTCGQVEGIQVNADEGGVTQTRGGVYWLILPAGYLGSSFWG  SEQ ID NO:33  (grape)
 49   EASHAIACKLTCGHVEGIQVHADEGGTTQTRGGIYWLILPAGYLGSSFWG  SEQ ID NO:34  (grape)
 50   ETSHALACKLTCGDVEGMQVHANEGGVTQTRGGIYWIILPAGYLGSSFWG  SEQ ID NO:37  (maize)
```

FIG. 15B

```
              MVLIIASTNLLTARIAAGCFIIALIIVLFIAVV Majority
              110       120       130       140       150
100 MVFIIASTNLLTTRIAAGCFIIALFIVLFVADNWFLRWLCLGFIVFIAVV  SEQ ID NO:18  (maize)
100 MVFIIASTNLLTTRIAAGCFIIALFIVLFVAENWFLRWLCLGFIVFIAVV  SEQ ID NO:20  (maize)
 99 MALIIASTNLLTAKIAAGCFIAALIVVLFLAALIVLFLAKNWTLRGLCIGFIVFIAVI  SEQ ID NO:22  (soybean)
 99 MVLIIASTNLLTAKIAAGCFIAALIVVLFLAKNWTLRGLCIGFIVFIAVI  SEQ ID NO:24  (soybean)
101 MLLIIASTDLITARIAAGCLAAALLIVLFIAKNWTLRGLCIGFIVFLAIV  SEQ ID NO:26  (sunflower)
 99 MVLIIASTNLIAARVAAGCLAAALIIVLFVAKNWTLRGLCIGFIVLAVV  SEQ ID NO:28  (sunflower)
 34 MVFIIASTNLLTTRIAAGCFIIALIIVLFVAKNWFLRWLCIGFIVFLAVV  SEQ ID NO:30  (rice)
101 MALIIASTNLLTTRIAAGLIAAAGLGLALFIVLFLTAKNWTLRGLCIGFIVFIAVI  SEQ ID NO:32  (Arabidopsis)
 99 MVFIIASTNLLTSRIAAGCFAVALIVVLFIAKNWTLRGLCIGFIIFLAII  SEQ ID NO:33  (grape)
 99 MVLIIASTNVLTAKIAAGCFAFALLIVVLFVAKNWTLRGLCIGFIILIAVV  SEQ ID NO:34  (grape)
100 MVFIIASTNLLTTRIAAGCFIIALFIVLFVADNWFLRWLCLGFIVFIAVV  SEQ ID NO:37  (maize)

WVLQEFTTVHILRYVILFIGVMNSLFSVYDIYDDLISRRVHSSDAEKFAE Majority
              160       170       180       190       200
150 WVIQEFTSFHILKYVILFIGVMNSLFSVYDIYDDLISRRVNTSDAEKFAE  SEQ ID NO:18  (maize)
150 WVIQEFTSFHVLKYVILFIGVMNSLFSVYDIYDDLISRRVNTSDAEKFAE  SEQ ID NO:20  (maize)
149 WLLQEKTTVHVLRYVILFIGVMNSLFSVYDIYDDLISRRVHSSDAEKFAE  SEQ ID NO:22  (soybean)
149 WLLQEKTTVKLLRYVILFIGVMNSLFSVYDIYDDLISRRVHSSDAEKFAE  SEQ ID NO:24  (soybean)
151 WLLQEKTTVRILRYVILFIGVMNSLFSVYDIYDDLISRRVNSSDAEKFAE  SEQ ID NO:26  (sunflower)
149 WILQETTKVRILRYIIMFIGVMNSVFSIYDIYGDLISRQVHTSDAEKFAE  SEQ ID NO:28  (sunflower)
 84 WVIQEFTKFHSLKYVILFIGVMNSLFSVYDIYDDLISRRVNTSDAEKFAE  SEQ ID NO:30  (rice)
151 WVLQELTTVKILRYVILRFETLFMGVMNSLFSVYDIYDDLISRRVHSSDAEKFAE  SEQ ID NO:32  (Arabidopsis)
149 WVLQETTKVRILRFETLFMGVMNSLFSVYDIYDDLISRRVHSSDAEKFAE  SEQ ID NO:33  (grape)
149 WLLQETTEIRILRYIILFIGVMNSLFSVYDIYDDLISRRVNSSDAEKFAE  SEQ ID NO:34  (grape)
150 WVIQEFTSFHILKYVILFIGVMNSLFSVYDIYDDLISRRVNTSDAEKFAE  SEQ ID NO:37  (maize)
```

FIG. 15C

```
         ICPCPCNGFGWGVIWGMISFIFLCASIYLGLVILS---         Majority

200      ICPCPCNGFAWGVIWGFISFIFLCASIYLGLVILS.            SEQ ID NO:18 (maize)
200      ICPCPCNGFAWGVIWGFISFIFLCASIYLGLVILS.            SEQ ID NO:20 (maize)
199      VCPCPCNGFGWGVIWGMISFAFLCASLYLGLVILSG.           SEQ ID NO:22 (soybean)
199      VCPCPCNGFGWGVIWGMISFAFLCASLYLGLVILSG.           SEQ ID NO:24 (soybean)
201      ICPCPCNGVAWGVIWGMISFTFLSASVYLGLVILS.            SEQ ID NO:26 (sunflower)
199      VCPCPCNGVGWGVIWGLISLIFLGIATYFGLVILSQV.          SEQ ID NO:28 (sunflower)
134      ICPCPCNGCAWGVIWGFISFIFLCASIYLGLVILS.            SEQ ID NO:30 (rice)
201      ICPC-CTGCGWGVIWGMISFAFLCASLYLGLVILS.            SEQ ID NO:32 (Arabidopsis)
199      ICPCPCNGVGWGVIWGFISFLFLAAAMYLGLVIL---S          SEQ ID NO:33 (grape)
199      VCPCPCNGVGWGVIWGLISFLFLCGAMYLGLVIL---S          SEQ ID NO:34 (grape)
200      ICPCPCNGFAWGVIWGFISFIFLCASIYLGLVIL---S          SEQ ID NO:37 (maize)
```

FIG. 16

Percent Identity

|    | 1    | 2    | 3    | 4    | 5    | 6    | 7    | 8    | 9    | 10   | 11    |    |                              |
|----|------|------|------|------|------|------|------|------|------|------|-------|----|------------------------------|
| 1  |      | 97.4 | 79.6 | 80.4 | 78.3 | 68.9 | 92.9 | 77.4 | 78.1 | 75.1 | 100.0 | 1  | SEQ ID NO:18 (maize)         |
| 2  | 2.2  |      | 81.3 | 82.1 | 77.9 | 69.4 | 92.9 | 77.0 | 78.1 | 75.1 | 97.9  | 2  | SEQ ID NO:20 (maize)         |
| 3  | 22.4 | 20.1 |      | 98.7 | 82.6 | 72.8 | 84.0 | 80.4 | 82.8 | 81.1 | 79.9  | 3  | SEQ ID NO:22 (soybean)       |
| 4  | 21.2 | 19.0 | 0.9  |      | 82.6 | 73.2 | 84.6 | 80.0 | 82.8 | 81.1 | 80.8  | 4  | SEQ ID NO:24 (soybean)       |
| 5  | 24.6 | 25.2 | 18.4 | 18.4 |      | 73.7 | 81.1 | 81.3 | 82.8 | 79.4 | 78.6  | 5  | SEQ ID NO:26 (sunflower)     |
| 6  | 37.6 | 36.9 | 32.9 | 32.2 | 30.3 |      | 74.0 | 71.1 | 76.4 | 78.5 | 69.2  | 6  | SEQ ID NO:28 (sunflower)     |
| 7  | 6.9  | 6.9  | 16.6 | 15.9 | 21.2 | 31.3 |      | 78.7 | 81.7 | 78.1 | 92.9  | 7  | SEQ ID NO:30 (rice)          |
| 8  | 23.6 | 24.1 | 19.1 | 19.6 | 19.5 | 32.4 | 21.4 |      | 80.3 | 75.1 | 77.8  | 8  | SEQ ID NO:32 (Arabidopsis)   |
| 9  | 25.5 | 25.5 | 19.6 | 19.6 | 19.1 | 28.7 | 19.8 | 20.3 |      | 83.7 | 78.1  | 9  | SEQ ID NO:33 (grape)         |
| 10 | 29.8 | 29.8 | 21.9 | 21.9 | 23.7 | 25.6 | 24.6 | 27.4 | 18.4 |      | 75.1  | 10 | SEQ ID NO:34 (grape)         |
| 11 | 0.0  | 2.2  | 22.5 | 21.3 | 24.7 | 37.8 | 6.9  | 23.7 | 25.3 | 29.7 |       | 11 | SEQ ID NO:37 (maize)         |
|    | 1    | 2    | 3    | 4    | 5    | 6    | 7    | 8    | 9    | 10   | 11    |    |                              |

FIG. 17A Evaluation of Individual Gaspe Flint Derived Maize Lines Transformed with PHP30116

| Treatment | Event name | % green_end exponential | % green_harvest | % lightgreen_end exponential | % lightgreen_harvest |
|---|---|---|---|---|---|
| 1.0 mMol KNO3 | EA2393.375.1.1 | [0.021] | [0.035] | 0.012 | 0.059 |
| 1.0 mMol KNO3 | EA2393.375.1.11 | [0.074] | NS | 0.074 | 0.023 |
| 1.0 mMol KNO3 | EA2393.375.1.3 | 0.079 | NS | [0.046] | NS |
| 1.0 mMol KNO3 | EA2393.375.1.6 | 0.059 | NS | NS | NS |
| 1.0 mMol KNO3 | EA2393.375.1.7 | [0.009] | NS | 0.023 | NS |
| 1.0 mMol KNO3 | EA2393.375.1.9 | NS | NS | NS | NS |
| 6.5 mMol KNO3 | EA2393.375.1.1 | NS | NS | NS | NS |
| 6.5 mMol KNO3 | EA2393.375.1.11 | 0.000 | 0.000 | 0.016 | 0.000 |
| 6.5 mMol KNO3 | EA2393.375.1.3 | [0.011] | NS | NS | NS |
| 6.5 mMol KNO3 | EA2393.375.1.6 | NS | NS | [0.083] | NS |
| 6.5 mMol KNO3 | EA2393.375.1.7 | NS | [0.091] | NS | NS |
| 6.5 mMol KNO3 | EA2393.375.1.9 | NS | [0.034] | NS | 0.021 |

Significant positive results have p-values less than or equal to 0.1.
Significant negative results are in brackets.
"NS" when difference not significant.

FIG. 17B Evaluation of Individual Gaspe Flint Derived Maize Lines Transformed with PHP30116

| Treatment | Event name | area_end exponential | area_harvest | days to emergence | ear diameter |
|---|---|---|---|---|---|
| 1.0 mMol KNO3 | EA2393.375.1.1 | NS | NS | NS | NS |
| 1.0 mMol KNO3 | EA2393.375.1.11 | NS | NS | NS | NS |
| 1.0 mMol KNO3 | EA2393.375.1.3 | NS | NS | NS | NS |
| 1.0 mMol KNO3 | EA2393.375.1.6 | NS | NS | NS | [0.020] |
| 1.0 mMol KNO3 | EA2393.375.1.7 | 0.028 | 0.009 | NS | NS |
| 1.0 mMol KNO3 | EA2393.375.1.9 | NS | [0.059] | NS | NS |
| 6.5 mMol KNO3 | EA2393.375.1.1 | 0.091 | NS | NS | 0.074 |
| 6.5 mMol KNO3 | EA2393.375.1.11 | [0.085] | [0.046] | NS | NS |
| 6.5 mMol KNO3 | EA2393.375.1.3 | [0.001] | [0.001] | NS | NS |
| 6.5 mMol KNO3 | EA2393.375.1.6 | [0.087] | NS | NS | 0.037 |
| 6.5 mMol KNO3 | EA2393.375.1.7 | NS | NS | NS | [0.058] |
| 6.5 mMol KNO3 | EA2393.375.1.9 | NS | NS | NS | [0.080] |

Significant positive results have p-values less than or equal to 0.1.
Significant negative results are in brackets.
"NS" when difference not significant.

FIG. 17C Evaluation of Individual Gaspe Flint Derived Maize Lines Transformed with PHP30116

| Treatment | Event name | ear dry weight | ear fresh weight | maximum area | sgr - r2 > 0.9 |
|---|---|---|---|---|---|
| 1.0 mMol KNO3 | EA2393.375.1.1 | NS | NS | NS | 0.035 |
| 1.0 mMol KNO3 | EA2393.375.1.11 | NS | NS | NS | NS |
| 1.0 mMol KNO3 | EA2393.375.1.3 | NS | NS | NS | NS |
| 1.0 mMol KNO3 | EA2393.375.1.6 | NS | NS | NS | NS |
| 1.0 mMol KNO3 | EA2393.375.1.7 | NS | NS | 0.055 | NS |
| 1.0 mMol KNO3 | EA2393.375.1.9 | NS | NS | [0.071] | [0.048] |
| 6.5 mMol KNO3 | EA2393.375.1.1 | 0.019 | 0.016 | NS | NS |
| 6.5 mMol KNO3 | EA2393.375.1.11 | NS | NS | [0.048] | NS |
| 6.5 mMol KNO3 | EA2393.375.1.3 | NS | NS | [0.001] | [0.008] |
| 6.5 mMol KNO3 | EA2393.375.1.6 | 0.022 | 0.025 | NS | NS |
| 6.5 mMol KNO3 | EA2393.375.1.7 | NS | NS | NS | NS |
| 6.5 mMol KNO3 | EA2393.375.1.9 | NS | NS | NS | [0.016] |

Significant positive results have p-values less than or equal to 0.1. Significant negative results are in brackets. "NS" when difference not significant.

FIG. 17D Evaluation of Individual Gaspe Flint Derived Maize Lines Transformed with PHP30116

| Treatment | Event name | shoot dry weight | shoot fresh weight | shoot+ear dry weight | shoot+ear fresh weight |
|---|---|---|---|---|---|
| 1.0 mMol KNO3 | EA2393.375.1.1 | NS | NS | NS | NS |
| 1.0 mMol KNO3 | EA2393.375.1.11 | NS | NS | NS | NS |
| 1.0 mMol KNO3 | EA2393.375.1.3 | NS | 0.022 | NS | 0.036 |
| 1.0 mMol KNO3 | EA2393.375.1.6 | NS | NS | NS | NS |
| 1.0 mMol KNO3 | EA2393.375.1.7 | 0.016 | 0.028 | 0.056 | NS |
| 1.0 mMol KNO3 | EA2393.375.1.9 | NS | [0.006] | NS | NS |
| 6.5 mMol KNO3 | EA2393.375.1.1 | NS | NS | NS | NS |
| 6.5 mMol KNO3 | EA2393.375.1.11 | [0.039] | [0.053] | NS | NS |
| 6.5 mMol KNO3 | EA2393.375.1.3 | [0.001] | [0.002] | [0.029] | [0.045] |
| 6.5 mMol KNO3 | EA2393.375.1.6 | [0.054] | [0.098] | NS | NS |
| 6.5 mMol KNO3 | EA2393.375.1.7 | NS | NS | NS | NS |
| 6.5 mMol KNO3 | EA2393.375.1.9 | 0.036 | NS | NS | NS |

Significant positive results have p-values less than or equal to 0.1. Significant negative results are in brackets. "NS" when difference not significant.

FIG. 17E Evaluation of Individual Gaspe Flint Derived Maize Lines Transformed with PHP30116

| Treatment | Event name | stalk+ear diameter |
|---|---|---|
| 1.0 mMol KNO3 | EA2393.375.1.1 | NS |
| 1.0 mMol KNO3 | EA2393.375.1.11 | NS |
| 1.0 mMol KNO3 | EA2393.375.1.3 | [0.099] |
| 1.0 mMol KNO3 | EA2393.375.1.6 | [0.012] |
| 1.0 mMol KNO3 | EA2393.375.1.7 | NS |
| 1.0 mMol KNO3 | EA2393.375.1.9 | 0.014 |
| 6.5 mMol KNO3 | EA2393.375.1.1 | 0.044 |
| 6.5 mMol KNO3 | EA2393.375.1.11 | NS |
| 6.5 mMol KNO3 | EA2393.375.1.3 | NS |
| 6.5 mMol KNO3 | EA2393.375.1.6 | NS |
| 6.5 mMol KNO3 | EA2393.375.1.7 | NS |
| 6.5 mMol KNO3 | EA2393.375.1.9 | NS |

Significant positive results have p-values less than or equal to 0.1. Significant negative results are in brackets. "NS" when difference not significant.

FIG. 18 Summary Evaluation of Gaspe Flint Derived Maize Lines Transformed with PHP30116

| Treatment | Event name | % green_end exponential | % green_harvest | % lightgreen_end exponential | % lightgreen_harvest | area_end exponential |
|---|---|---|---|---|---|---|
| 1.0 mMol KNO3 | All Events | NS | NS | 0.081 | NS | NS |
| 6.5 mMol KNO3 | All Events | [0.020] | [0.001] | NS | 0.004 | [0.088] |

| Treatment | Event name | area_harvest | days to emergence | ear diameter | ear dry weight | ear fresh weight |
|---|---|---|---|---|---|---|
| 1.0 mMol KNO3 | All Events | 0.036 | NS | NS | NS | NS |
| 6.5 mMol KNO3 | All Events | [0.006] | NS | NS | NS | NS |

| Treatment | Event name | maximum area | sgr - r2 > 0.9 | shoot dry weight | shoot fresh weight | shoot+ear dry weight |
|---|---|---|---|---|---|---|
| 1.0 mMol KNO3 | All Events | NS | NS | NS | 0.047 | NS |
| 6.5 mMol KNO3 | All Events | [0.013] | [0.003] | [0.015] | [0.030] | NS |

| Treatment | Event name | shoot+ear fresh weight | stalk+ear diameter |
|---|---|---|---|
| 1.0 mMol KNO3 | All Events | NS | [0.015] |
| 6.5 mMol KNO3 | All Events | NS | NS |

Significant positive results have p-values less than or equal to 0.1.
Significant negative results are in brackets.
"NS" when difference not significant.

SEQUENCE LISTING

<160> NUMBER OF SEQ ID NOS: 37

<210> SEQ ID NO 1
<211> LENGTH: 18491
<212> TYPE: DNA
<213> ORGANISM: Artificial Sequence
<220> FEATURE:
<223> OTHER INFORMATION: pHSbarENDs2 activation tagging vector

<400> SEQUENCE: 1
catgaatcaa acaaacatac acagcgactt attcacacga gctcaaatta caacggtata      60

-continued

```
tatcctgccg tcgacaacca tggtctagac aggatcccg ggtaccgagc tcgaatttgc    120
aggtcgactg cgtcatccct tacgtcagtg gagatatcac atcaatccac ttgctttgaa   180
gacgtggttg gaacgtcttc ttttccacg atgctcctcg tgggtggggg tccatctttg    240
ggaccactgt cggcagaggc atcttgaacg atagcctttc ctttatcgca atgatggcat   300
ttgtaggtgc caccttcctt ttctactgtc cttttgatga agtgacagat agctgggcaa   360
tggaatccga ggaggtttcc cgatattacc ctttgttgaa aagtctcaat tgcccttttgg  420 tcttctgaga ctgttgcgtc atcccttacg tcagtggaga tatcacatca atccacttgc   480
tttgaagacg tggttggaac gtcttctttt tccacgatgc tcctcgtggg tggggtcca    540 tctttgggac cactgtcggc agaggcatct tgaacgatag cctttccttt atcgcaatga   600
tggcatttgt aggtgccacc ttccttttct actgtccttt tgatgaagtg acagatagct   660
gggcaatgga atccgaggag gtttcccgat attaccttttgttgaaaagt ctcagttaac    720 ccgcgatcct gcgtcatccc ttacgtcagt ggagatatca catcaatcca cttgctttga   780
agacgtggtt ggaacgtctt cttttccac gatgctcctc gtgggtgggg gtccatcttt    840
gggaccactg tcggcagagg catcttgaac gatagccttt cctttatcgc aatgatggca   900
tttgtaggtg ccaccttcct tttctactgt ccttttgatg aagtgacaga tagctgggca   960
atggaatccg aggaggtttc cgatattac ccttttgttga aaagtctcaa ttgcccttttg  1020 gtcttctgag actgttgcgt catcccttac gtcagtggag atatcacatc aatccacttg   1080
ctttgaagac gtggttggaa cgtcttcttt tccacgatg ctcctcgtgg gtgggggtcc    1140
atctttggga ccactgtcgg cagaggcatc ttgaacgata gcctttcctt tatcgcaatg   1200
atggcatttg taggtgccac cttcctttc tactgtcctt ttgatgaagt gacagatagc    1260
tgggcaatgg aatccgagga ggtttcccga tattacccct tgttgaaaag tctcagttaa   1320
cccgcaattc actggccgtc gttttacaac gtcgtgactg ggaaaaccct ggcgttaccc   1380
aacttaatcg ccttgcagca catccccctt cgccagctg gcgtaatagc gaagaggccc    1440
gcaccgatcg cccttcccaa cagttgcgca gcctgaatgg cgaatggatc gatccgtcga   1500
tcgaccaaag cggccatcgt gcctccccac tcctgcagtt cgggggcatg gatgcgcgga   1560
tagccgctgc tggtttcctg gatgccgacg gatttgcact gccggtagaa ctccgcgagg   1620
tcgtccagcc tcaggcagca gctgaaccaa ctcgcgaggg gatcgagccc ctgctgagcc   1680
tcgacatgtt gtcgcaaaat cgccctgga cccgcccaac gatttgtcgt cactgtcaag    1740
gtttgacctg cacttcattt ggggcccaca tacaccaaaa aaatgctgca taattctcgg   1800
ggcagcaagt cggttacccg gccgccgtgc tggaccgggt tgaatggtgc ccgtaacttt   1860
cggtagagcg gacggccaat actcaacttc aaggaatctc acccatgcgc gccggcgggg   1920
aaccggagtt cccttcagtg aacgttatta gttcgccgct cggtgtgtcg tagatactag   1980
cccctggggc cttttgaaat ttgaataaga tttatgtaat cagtctttta ggtttgaccg   2040
gttctgccgc tttttttaaa attggatttg taataataaa acgcaattgt tgttattgt    2100 ggcgctctat catagatgtc gctataaacc tattcagcac aatatattgt tttcatttta   2160
atattgtaca tataagtagt agggtacaat cagtaaattg aacggagaat attattcata   2220
aaaatacgat agtaacgggt gatatattca ttagaatgaa ccgaaaccgg cggtaaggat   2280
ctgagctaca catgctcagg ttttttacaa cgtgcacaac agaattgaaa gcaaatatca   2340
tgcgatcata ggcgtctcgc atatctcatt aaagcagggg gtgggcgaag aactccagca   2400
```

```
tgagatcccc gcgctggagg atcatccagc cggcgtcccg gaaaacgatt ccgaagccca    2460
acctttcata gaaggcggcg gtggaatcga aatctcgtga tggcaggttg ggcgtcgctt    2520
ggtcggtcat ttcgaacccc agagtcccgc tcagaagaac tcgtcaagaa ggcgatagaa    2580
ggcgatgcgc tgcgaatcgg gagcggcgat accgtaaagc acgaggaagc ggtcagccca    2640
ttcgccgcca agctcttcag caatatcacg ggtagccaac gctatgtcct gatagcggtc    2700
cgccacaccc agccgccac agtcgatgaa tccagaaaag cggccatttt ccaccatgat    2760
attcggcaag caggcatcgc catgggtcac gacgagatcc tcgccgtcgg gcatgccccc    2820
caattcactg gccgtcgttt tacaacgtcg tgactgggaa acccctggcg ttacccaact    2880
taatcgcctt gcagcacatc cccctttcgc cagctggcgt aatagcgaag aggcccgcac    2940
cgatcgccct tcccaacagt tgcgcagcct gaatggcgaa tggcgcctga tgcggtattt    3000
tctccttacg catctgtgcg gtatttcaca ccgcatatgg tgcactctca gtacaatctg    3060
ctctgatgcc gcatagttaa gccagccccg acacccgcca cacccgctg acgcgccctg    3120 acgggcttgt ctgctcccgg catccgctta cagacaagct gtgaccgtct ccgggagctg    3180
catgtgtcag aggttttcac cgtcatcacc gaaacgcgcg agacgaaagg gcctcgtgat    3240
acgcctattt ttataggtta atgtcatgat aataatggtt tcttagacgt caggtggcac    3300
ttttcgggga aatgtgcgcg gaaccccctat ttgtttattt ttctaaatac attcaaatat    3360
gtatccgctc atgagacaat aaccctgata aatgcttcaa taatattgaa aaaggaagag    3420
tatgagtatt caacatttcc gtgtcgccct tattccctt tttgcggcat tttgccttcc    3480
tgtttttgct cacccagaaa cgctggtgaa agtaaaagat gctgaagatc agttgggtgc    3540
acgagtgggt tacatcgaac tggatctcaa cagcggtaag atccttgaga gttttcgccc    3600
cgaagaacgt tttccaatga tgagcacttt taaagttctg ctatgtggcg cggtattatc    3660
ccgtattgac gccgggcaag agcaactcgg tcgccgcata cactattctc agaatgactt    3720
ggttgagtac tcaccagtca cagaaaagca tcttacggat ggcatgacag taagagaatt    3780
atgcagtgct gccataacca tgagtgataa cactgcggcc aacttacttc tgacaacgat    3840
cggaggaccg aaggagctaa ccgcttttt gcacaacatg ggggatcatg taactcgcct    3900
tgatcgttgg gaaccggagc tgaatgaagc cataccaaac gacgagcgtg acaccacgat    3960
gcctgtagca atggcaacaa cgttgcgcaa actattaact ggcgaactac ttactctagc    4020
ttcccggcaa caattaatag actggatgga ggcggataaa gttgcaggac cacttctgcg    4080
ctcggccctt ccggctggct ggtttattgc tgataaatct ggagccggtg agcgtgggtc    4140
tcgcggtatc attgcagcac tggggccaga tggtaagccc tcccgtatcg tagttatcta    4200
cacgacgggg agtcaggcaa ctatggatga acgaaataga cagatcgctg agataggtgc    4260
ctcactgatt aagcattggt aactgtcaga ccaagtttac tcatatatac tttagattga    4320
tttaaaactt catttttaat ttaaaaggat ctaggtgaag atccttttg ataatctcat    4380 gaccaaaatc ccttaacgtg agttttcgtt ccactgagcg tcagaccccg tagaaaagat    4440
caaaggatct tcttgagatc cttttttct gcgcgtaatc tgctgcttgc aaacaaaaaa    4500
accaccgcta ccagcggtgg tttgtttgcc ggatcaagag ctaccaactc tttttccgaa    4560
ggtaactggc ttcagcagag cgcagatacc aaatactgtc cttctagtgt agccgtagtt    4620
aggccaccac ttcaagaact ctgtagcacc gcctacatac ctcgctctgc taatcctgtt    4680
accagtggct gctgccagtg gcgataagtc gtgtcttacc gggttggact caagacgata    4740
gttaccggat aaggcgcagc ggtcgggctg aacggggggt tcgtgcacac agcccagctt    4800
```

```
ggagcgaacg acctacaccg aactgagata cctacagcgt gagcattgag aaagcgccac    4860
gcttcccgaa gggagaaagg cggacaggta tccggtaagc ggcagggtcg aacaggaga    4920 gcgcacgagg gagcttccag ggggaaacgc ctggtatctt tatagtcctg tcgggtttcg    4980
ccacctctga cttgagcgtc gattttttgtg atgctcgtca gggggcgga gcctatggaa    5040 aaacgccagc aacgcggcct ttttacggtt cctggccttt tgctggcctt ttgctcacat    5100
gttctttcct gcgttatccc ctgattctgt ggataaccgt attaccgcct ttgagtgagc    5160
tgataccgct cgccgcagcc gaacgaccga gcgcagcgag tcagtgagcg aggaagcgga    5220
agagcgccca atacgcaaac cgcctctccc cgcgcgttgg ccgattcatt aatgcagctg    5280
gcacgacagg tttcccgact ggaaagcggg cagtgagcgc aacgcaatta atgtgagtta    5340
gctcactcat taggcacccc aggctttaca ctttatgctt ccggctcgta tgttgtgtgg    5400
aattgtgagc ggataacaat ttcacacagg aaacagctat gaccatgatt acgccaagct    5460 ttctagggggg ggggtaccga tctgagatcg gtaacgaaaa cgaacgggta gggatgaaaa    5520
cggtcggtaa cggtcggtaa aatacctcta ccgtttttcat tttcatatttt aacttgcggg    5580 acggaaacga aaacgggata taccggtaac gaaaacgaac gggataaata cggtaatcga    5640
aaaccgatac gatccggtcg ggttaaagtc gaaatcggac gggaaccggt atttttgttc    5700
ggtaaaatca cacatgaaaa catatattca aaacttaaaa acaaatataa aaaattgtaa    5760
acacaagtct taatgatcac tagtggcgcg cctaggagat ctcgagtagg gataacaggg    5820
taatacatag ataaaatcca tataaatctg gagcacacat agtttaatgt agcacataag    5880
tgataagtct tgggctcttg gctaacataa gaagccatat aagtctacta gcacacatga    5940
cacaatataa agtttaaaac acatattcat aatcacttgc tcacatctgg atcacttagc    6000
atgctacagc tagtgcaata ttagacactt tccaatattt ctcaaacttt tcactcattg    6060
caacggccat tctcctaatg acaattttt catgaacaca ccattggtca atcaaatcct    6120
ttatctcaca gaaacctttg taaaataaat ttgcagtgga atattgagta ccagatagga    6180
gttcagtgag atcaaaaaac ttcttcaaac acttaaaaag agttaatgcc atcttccact    6240
cctcggcttt aggacaaatt gcatcgtacc tacaataatt gacatttgat taattgagaa    6300
tttataatga tgcatgtac aacaattgag acaaacatac ctgcgaggat cacttgtttt    6360
aagccgtgtt agtgcaggct tataatataa ggcatccctc aacatcaaat aggttgaatt    6420
ccatctagtt gagacatcat atgagatccc tttagattta tccaagtcac attcactagc    6480
acacttcatt agttcttccc actgcaaagg agaagatttt acagcaagaa caatcgcttt    6540
gattttctca attgttcctg caattacagc caagccatcc tttgcaacca agttcagtat    6600
gtgacaagca cacctcacat gaaagaaagc accatcacaa actagatttg aatcagtgtc    6660
ctgcaaatcc tcaattatat cgtgcacagc tacttcattt gcactagcat tatccaaaga    6720
caaggcaaac aatttttttct caatgttcca cttaaccatg attgcagtga aggtttgtga    6780
taacctttgg ccagtgtggc gcccttcaac atgaaaaaag ccaacaattc ttttttggag    6840
acaccaatca tcatcaatcc aatggatggt gacacacatg tatgactat tttgacaaga    6900 tgtccacata tccatagttg tactgaagcg agactgaaca tctttttagtt ttccatacaa    6960 cttttctttt tcttccaaat acaaatccat gatatatttt ctagcagtga cacgggactt    7020
tattggaaag tgagggcgca gagacttaac aaactcaaca aagtactcat gttctacaat    7080
attgaaagga tattcatgca tgattattgc caaatgaagc ttctttaggc taaccacttc    7140
```

```
atcgtactta taaggctcaa tgagatttat gtctttgcca tgatccttt cacttttag    7200
acacaactga cctttaacta aactatgtga tgttctcaag tgatttcgaa atccgcttgt    7260
tccatgatga ccctcagccc tatacttagc cttgcaatta ggaaagttgc aatgtccca    7320
tacctgaacg tatttctttc catcgacctc cacttcaatt tccttcttgg tgaaatgctg    7380
ccatacatcc gatgtgcact tctttgccct cttctgtggt gcttcttctt cgggttcagg    7440
ttgtggctgt ggttgtggtt ctggttgtgg ttgtggttgt ggttgtggtt catgaacaat    7500
agccatatca tcttgactcg gatctgtagc tgtaccattt gcattactac tgcttacact    7560
ctgaataaaa tgcctctcgg cctcagctgt tgatgatgat ggtgatgtgc ggccacatcc    7620
atgcccacgc gcacgtgcac gtacattctg aatccgacta aagaggctt cagcttttct    7680
tttcaaccct gttataaaca gattttcgt attattctac agtcaatatg atgcttccca    7740
atctacaacc aattagtaat gctaatgcta ttgctactgt ttttctaata tatccttga    7800
gcatatgcag agaatacgga atttgttttg cgagtagaag gcgctcttgt ggtagacatc    7860
aacttggcca atcttatggc tgagcctgag ggaggattat ttccaaccgg aggcgtcatc    7920
tgaggaatgg agtcgtagcc ggctagccga agtggagagc agagccctgg acagcaggtg    7980
ttcagcaatc agcttggtgc tgtactgctg tgacttgtga gcacctggac ggctggacag    8040
caatcagcag gtgttgcaga gccctggac agcacacaaa tgacacaaca gcttggtgca    8100
atggtgctga cgtgctgtac tgctaagtgc tgtgagcctg tgagcagccg tggagacagg    8160
gagaccgcgg atggccggat gggcgagcgc cgagcagtgg aggtctggag accgctgac    8220
cgcagatggc ggatgcgga tgggcggacc gcggatgggc gagcagtgga gtggaggtct    8280
gggcggatgg gcggaccgcg gcgcggatgg gcgagtcgcg agcagtggag tggagggcgg    8340
accgtggatg gcggcgtctg cgtccggcgt gccgcgtcac ggccgtcacc gcgtgtggtg    8400
cctggtgcag cccagcggcc ggccggctgg agacaggga gagtcggaga gagcaggcga    8460
gagcgagacg cgtcgccggc gtcggcgtgc ggctggcggc gtccggactc cggcgtgggc    8520
gcgtggcggc gtgtgaatgt gtgatgctgt tactcgtgtg gtgcctggcc gcctgggaga    8580
gaggcagagc agcgttcgct aggtatttct tacatgggct gggcctcagt ggttatggat    8640
gggagttgga gctggccata ttgcagtcat cccgaattag aaaatacggt aacgaaacgg    8700
gatcatcccg attaaaaacg ggatcccggt gaaacggtcg ggaaactagc tctaccgttt    8760
ccgtttccgt ttaccgtttt gtatatcccg tttccgttcc gttttcgttt tttacctcgg    8820
gttcgaaatc gatcgggata aaactaacaa aatcggttat acgataacgg tcggtacggg    8880
attttcccat cctactttca tccctgagat tattgtcgtt tctttcgcag atcggtaccc    8940
cccccctaga gtcgacatcg atctagtaac atagatgaca ccgcgcgcga taatttatcc    9000
tagtttgcgc gctatatttt gttttctatc gcgtattaaa tgtataattg cgggactcta    9060
atcataaaaa cccatctcat aaataacgtc atgcattaca tgttaattat tacatgctta    9120
acgtaattca acagaaatta tatgataatc atcgcaagac cggcaacagg attcaatctt    9180
aagaaacttt attgccaaat gtttgaacga tctgcttcga cgcactcctt ctttaggtac    9240
ggactagatc tcggtgacgg gcaggaccgg acggggcggt accggcaggc tgaagtccag    9300
ctgccagaaa cccacgtcat gccagttccc gtgcttgaag ccggccgccc gcagcatgcc    9360
gcgggggggca tatccgagcg cctcgtgcat gcgcacgctc gggtcgttgg gcagcccgat    9420
gacagcgacc acgtcttga agccctgtgc ctccaggac ttcagcaggt gggtgtagag    9480
cgtggagccc agtccgtcc gctggtggcg gggggagacg tacacggtcg actcggccgt    9540
```

```
ccagtcgtag gcgttgcgtg ccttccaggg gcccgcgtag gcgatgccgg cgacctcgcc    9600
gtccacctcg gcgacgagcc agggatagcg ctcccgcaga cggacgaggt cgtccgtcca    9660
ctcctgcggt tcctgcggct cggtacggaa gttgaccgtg cttgtctcga tgtagtggtt    9720
gacgatggtg cagaccgccg gcatgtccgc ctcggtggca cggcggatgt cggccgggcg    9780
tcgttctggg ctcatggatc tggattgaga gtgaatatga gactctaatt ggataccgag    9840
gggaatttat ggaacgtcag tggagcattt ttgacaagaa atatttgcta gctgatagtg    9900
accttaggcg acttttgaac gcgcaataat ggtttctgac gtatgtgctt agctcattaa    9960
actccagaaa cccgcggctg agtggctcct tcaatcgttg cggttctgtc agttccaaac   10020
gtaaaacggc ttgtcccgcg tcatcggcgg gggtcataac gtgactccct taattctccg   10080
ctcatgatcc ccgggtaccg agctcgaatt gcggctgagt ggctccttca atcgttgcgg   10140
ttctgtcagt tccaaacgta aaacggcttg tcccgcgtca tcggcggggg tcataacgtg   10200
actcccttaa ttctccgctc atgatcttga tcccctgcgc catcagatcc ttggcggcaa   10260
gaaagccatc cagtttactt tgcagggctt cccaaccttg ccagagggcg ccccagctgg   10320
caattccggt tcgcttgctg tatcgatatg gtggatttat cacaaatggg acccgccgcc   10380
gacagaggtg tgatgttagg ccaggacttt gaaaatttgc gcaactatcg tatagtggcc   10440
gacaaattga cgccgagttg acagactgcc tagcatttga gtgaattatg tgaggtaatg   10500
ggctacactg aattggtagc tcaaactgtc agtatttatg tatatgagtg tatatttcg   10560
cataatctca gaccaatctg aagatgaaat gggtatctgg gaatggcgaa atcaaggcat   10620
cgatcgtgaa gtttctcatc taagccccca tttggacgtg aatgtagaca cgtcgaaata   10680
aagatttccg aattagaata atttgtttat tgctttcgcc tataaatacg acggatcgta   10740
atttgtcgtt ttatcaaaat gtactttcat tttataataa cgctgcggac atctacattt   10800
ttgaattgaa aaaaaattgg taattactct ttctttttct ccatattgac catcatactc   10860
attgctgatc catgtagatt tcccggacat gaagccattt acaattgaat atatcctgcc   10920
gccgctgccg ctttgcaccc ggtggagctt gcatgttggt ttctacgcag aactgagccg   10980
gttaggcaga taatttccat tgagaactga gccatgtgca ccttccccccc aacacggtga   11040
gcgacgggc aacggagtga tccacatggg acttttaaac atcatccgtc ggatggcgtt   11100
gcgagagaag cagtcgatcc gtgagatcag ccgacgcacc gggcaggcgc gcaacacgat   11160
cgcaaagtat ttgaacgcag gtacaatcga gccgacgttc accgtcaccc tggatgctgt   11220
aggcataggc ttggttatgc cggtactgcc gggcctcttg cgggatatcg tccattccga   11280
cagcatcgcc agtcactatg gcgtgctgct agcgctatat gcgttgatgc aatttctatg   11340
cgcaccgtt tcggagcac tgtccgaccg ctttggccgc cgcccagtcc tgctcgcttc   11400
gctacttgga gccactatcg actacgcgat catggcgacc acaccgtcc tgtggtccaa   11460
cccctccgct gctatagtgc agtcggcttc tgacgttcag tgcagccgtc ttctgaaaac   11520
gacatgtcgc acaagtccta agttacgcga caggctgccg ccctgccctt ttcctggcgt   11580
tttcttgtcg cgtgttttag tcgcataaag tagaatactt gcgactagaa ccggagacat   11640
tacgccatga acaagagcgc cgccgctggc ctgctgggct atgcccgcgt cagcaccgac   11700
gaccaggact tgaccaacca acgggccgaa ctgcacgcgg ccggctgcac caagctgttt   11760
tccgagaaga tcaccggcac caggcgcgac cgcccgagc tggccaggat gcttgaccac   11820
ctacgccctg gcgacgttgt gacagtgacc aggctagacc gcctggcccg cagcacccgc   11880
```

```
gacctactgg acattgccga gcgcatccag gaggccggcg cgggcctgcg tagcctggca   11940
gagccgtggg ccgacaccac cacgccggcc ggccgcatgg tgttgaccgt gttcgccggc   12000
attgccgagt tcgagcgttc cctaatcatc gaccgcaccc ggagcgggcg cgaggccgcc   12060
aaggcccgag gcgtgaagtt tggccccgc cctaccctca ccccggcaca gatcgcgcac    12120
gcccgcgagc tgatcgacca ggaaggccgc accgtgaaag aggcggctgc actgcttggc   12180
gtgcatcgct cgaccctgta ccgcgcactt gagcgcagcg aggaagtgac gcccaccgag   12240
gccaggcggc gcggtgcctt ccgtgaggac gcattgaccg aggccgacgc cctggcggcc   12300
gccgagaatg aacgccaaga ggaacaagca tgaaaccgca ccaggacggc caggacgaac   12360
cgttttttcat taccgaagag atcgaggcgg agatgatcgc ggccgggtac gtgttcgagc   12420
cgcccgcgca cgtctcaacc gtgcggctgc atgaaatcct ggccggtttg tctgatgcca   12480
agctggcggc ctggccggcc agcttggccg ctgaagaaac cgagcgccgc cgtctaaaaa   12540
ggtgatgtgt atttgagtaa aacagcttgc gtcatgcggt cgctgcgtat atgatgcgat   12600
gagtaaataa acaaatacgc aagggaacgc atgaagttat cgctgtactt aaccagaaag   12660
gcgggtcagg caagacgacc atcgcaaccc atctagcccg cgccctgcaa ctcgccgggg   12720
ccgatgttct gttagtcgat tccgatcccc agggcagtgc ccgcgattgg gcggccgtgc   12780
gggaagatca accgctaacc gttgtcggca tcgaccgccc gacgattgac cgcgacgtga   12840
aggccatcgg ccggcgcgac ttcgtagtga tcgacggagc gccccaggcg gcggacttgg   12900
ctgtgtccgc gatcaaggca gccgacttcg tgctgattcc ggtgcagcca agcccttacg   12960
acatatgggc caccgccgac ctggtggagc tggttaagca gcgcattgag gtcacggatg   13020
gaaggctaca agcggccttt gtcgtgtcgc gggcgatcaa aggcacgcgc atcggcggtg   13080
aggttgccga ggcgctggcc gggtacgagc tgcccattct tgagtcccgt atcacgcagc   13140
gcgtgagcta cccaggcact gccgccgccg gcacaaccgt tcttgaatca aacccgagg    13200
gcgacgctgc ccgcgaggtc caggcgctgg ccgctgaaat taaatcaaaa ctcatttgag   13260
ttaatgaggt aaagagaaaa tgagcaaaag cacaaacacg ctaagtgccg gccgtccgag   13320
cgcacgcagc agcaaggctg caacgttggc cagcctggca gacacgccag ccatgaagcg   13380
ggtcaacttt cagttgccgg cggaggatca caccaagctg aagatgtacg cggtacgcca   13440
aggcaagacc attaccgagc tgctatctga atacatcgcg cagctaccag agtaaatgag   13500
caaatgaata aatgagtaga tgaattttag cggctaaagg aggcggcatg gaaaatcaag   13560
aacaaccagg caccgacgcc gtggaatgcc ccatgtgtgg aggaacgggc ggttggccag   13620
gcgtaagcgg ctgggttgtc tgccggccct gcaatggcac tggaaccccc aagcccgagg   13680
aatcggcgtg agcggtcgca aaccatccgg cccggtacaa atcggcgcgg cgctgggtga   13740
tgacctggtg gagaagttga aggccgcgca ggccgcccag cggcaacgca tcgaggcaga   13800
agcacgcccc ggtgaatcgt ggcaagcggc cgctgatcga atccgcaaag aatcccggca   13860
accgccggca gccggtgcgc cgtcgattag gaagccgccc aagggcgacg agcaaccaga   13920
ttttttcgtt ccgatgctct atgacgtggg cacccgcgat agtcgcagca tcatggacgt   13980
ggccgttttc cgtctgtcga agcgtgaccg acgagctggc gaggtgatcc gctacgagct   14040
tccagacggg cacgtagagg tttccgcagg ccggccggc atggccagtg tgtgggatta    14100
cgacctggta ctgatggcgg tttcccatct aaccgaatcc atgaaccgat accgggaagg   14160
gaagggagac aagcccggcc gcgtgttccg tccacacgtt gcggacgtac tcaagttctg   14220
ccggcgagcc gatggcggaa agcagaaaga cgacctggta gaaacctgca ttcggttaaa   14280
```

-continued

```
caccacgcac gttgccatgc agcgtacgaa gaaggccaag aacggccgcc tggtgacggt    14340
atccgagggt gaagccttga ttagccgcta caagatcgta aagagcgaaa ccgggcggcc    14400
ggagtacatc gagatcgagc tagctgattg gatgtaccgc gagatcacag aaggcaagaa    14460 cccgacgtg ctgacggttc accccgatta cttttttgatc gatcccggca tcggccgttt     14520
tctctaccgc ctggcacgcc gcgccgcagg caaggcagaa gccagatggt tgttcaagac    14580
gatctacgaa cgcagtggca gcgccggaga gttcaagaag ttctgtttca ccgtgcgcaa    14640
gctgatcggg tcaaatgacc tgccggagta cgatttgaag gaggaggcgg ggcaggctgg    14700
cccgatccta gtcatgcgct accgcaacct gatcgagggc gaagcatccg ccggttccta    14760
atgtacggag cagatgctag gcaaattgc cctagcaggg gaaaaaggtc gaaaaggtct     14820 cttcctgtg gatagcacgt acattgggaa cccaaagccg tacattggga accggaaccc     14880
gtacattggg aacccaaagc cgtacattgg gaaccggtca cacatgtaag tgactgatat    14940
aaaagagaaa aaaggcgatt tttccgccta aaactcttta aaacttatta aaactcttaa    15000
aacccgcctg gcctgtgcat aactgtctgg ccagcgcaca gccgaagagc tgcaaaaagc    15060
gcctacccct cggtcgctgc gctccctacg ccccgccgct tcgcgtcggc ctatcgcggc    15120
cgctggccgc tcaaaaatgg ctggcctacg gccaggcaat ctaccagggc gcggacaagc    15180
cgcgccgtcg ccactcgacc gccggcgccc acatcaaggc accctgcctc gcgcgtttcg    15240
gtgatgacgg tgaaaacctc tgacacatgc agctcccgga gacggtcaca gcttgtctgt    15300
aagcggatgc cggagcaga caagcccgtc agggcgcgtc agcgggtgtt ggcgggtgtc      15360
ggggcgcagc catgacccag tcacgtagcg atagcggagt gtatactggc ttaactatgc    15420
ggcatcagag cagattgtac tgagagtgca ccatatgcgg tgtgaaatac cgcacagatg    15480
cgtaaggaga aaataccgca tcaggcgctc ttccgcttcc tcgctcactg actcgctgcg    15540
ctcggtcgtt cggctgcggc gagcggtatc agctcactca aaggcggtaa tacggttatc    15600
cacagaatca ggggataacg caggaaagaa catgtgagca aaaggccagc aaaaggccag    15660
gaaccgtaaa aaggccgcgt tgctggcgtt tttccatagg ctccgccccc ctgacgagca    15720
tcacaaaaat cgacgctcaa gtcagaggtg gcgaaacccg acaggactat aaagatacca    15780
ggcgtttccc cctggaagct ccctcgtgcg ctctcctgtt ccgaccctgc cgcttaccgg    15840
atacctgtcc gcctttctcc cttcgggaag cgtggcgctt tctcatagct cacgctgtag    15900
gtatctcagt tcggtgtagg tcgttcgctc caagctgggc tgtgtgcacg aaccccccgt    15960
tcagcccgac cgctgcgcct tatccggtaa ctatcgtctt gagtccaacc cggtaagaca    16020
cgacttatcg ccactggcag cagccactgg taacaggatt agcagagcga ggtatgtagg    16080
cggtgctaca gagttcttga agtggtggcc taactacggc tacactagaa ggacagtatt    16140
tggtatctgc gctctgctga agccagttac cttcggaaaa agagttggta gctcttgatc    16200
cggcaaacaa accaccgctg gtagcggtgg ttttttgtt tgcaagcagc agattacgcg      16260
cagaaaaaaa ggatctcaag aagatccttt gatcttttct acggggtctg acgctcagtg    16320
gaacgaaaac tcacgttaag ggattttggt catgagatta tcaaaaagga tcttcaccta    16380 gatccttta aattaaaaat gaagttttaa atcaatctaa agtatatatg agtaaacttg      16440
gtctgacagt taccaatgct taatcagtga ggcacctatc tcagcgatct gtctatttcg    16500
ttcatccata gttgcctgac tccccgtcgt gtagataact acgatacggg agggcttacc    16560
atctggcccc agtgctgcaa tgataccgcg agacccacgc tcaccggctc cagatttatc    16620
```

| | |
|---|---:|
| agcaataaac cagccagccg aagggccga gcgcagaagt ggtcctgcaa ctttatccgc | 16680 |
| ctccatccag tctattaatt gttgccggga agctagagta agtagttcgc cagttaatag | 16740 |
| tttgcgcaac gttgttgcca ttgctacagg catcgtggtg tcacgctcgt cgtttggtat | 16800 |
| ggcttcattc agctccggtt cccaacgatc aaggcgagtt acatgatccc ccatgttgtg | 16860 |
| caaaaaagcg gttagctcct tcggtcctcc gatcgttgtc agaagtaagt tggccgcagt | 16920 |
| gttatcactc atggttatgg cagcactgca taattctctt actgtcatgc catccgtaag | 16980 |
| atgcttttct gtgactggtg agtactcaac caagtcattc tgagaatagt gtatgcggcg | 17040 |
| accgagttgc tcttgcccgg cgtcaacacg ggataatacc gcgccacata gcagaacttt | 17100 |
| aaaagtgctc atcattggaa aagacctgca gggggggggg ggaaagccac gttgtgtctc | 17160 |
| aaaatctctg atgttacatt gcacaagata aaaatatatc atcatgaaca ataaaactgt | 17220 |
| ctgcttacat aaacagtaat acaaggggtg ttatgagcca tattcaacgg gaaacgtctt | 17280 |
| gctcgaggcc gcgattaaat tccaacatgg atgctgattt atatgggtat aaatgggctc | 17340 |
| gcgataatgt cgggcaatca ggtgcgacaa tctatcgatt gtatgggaag cccgatgcgc | 17400 |
| cagagttgtt tctgaaacat ggcaaaggta gcgttgccaa tgatgttaca gatgagatgg | 17460 |
| tcagactaaa ctggctgacg gaatttatgc ctcttccgac catcaagcat tttatccgta | 17520 |
| ctcctgatga tgcatggtta ctcaccactg cgatccccgg aaaacagca ttccaggtat | 17580 |
| tagaagaata tcctgattca ggtgaaaata ttgttgatgc gctggcagtg ttcctgcgcc | 17640 |
| ggttgcattc gattcctgtt tgtaattgtc cttttaacag cgatcgcgta tttcgtctcg | 17700 |
| ctcaggcgca atcacgaatg aataacggtt tggttgatgc gagtgatttt gatgacgagc | 17760 |
| gtaatggctg gcctgttgaa caagtctgga agaaatgca taagcttttg ccattctcac | 17820 |
| cggattcagt cgtcactcat ggtgatttct cacttgataa ccttattttt gacgagggga | 17880 |
| aattaatagg ttgtattgat gttggacgag tcggaatcgc agaccgatac caggatcttg | 17940 |
| ccatcctatg gaactgcctc ggtgagtttt ctccttcatt acagaaacgg ctttttcaaa | 18000 |
| aatatggtat tgataatcct gatatgaata aattgcagtt tcatttgatg ctcgatgagt | 18060 |
| ttttctaatc agaattggtt aattggttgt aacactggca gagcattacg ctgacttgac | 18120 |
| gggacggcgg ctttgttgaa taaatcgaac ttttgctgag ttgaaggatc agatcacgca | 18180 |
| tcttcccgac aacgcagacc gttccgtggc aaagcaaaag ttcaaaatca ccaactggtc | 18240 |
| cacctacaac aaagctctca tcaaccgtgg ctccctcact ttctggctgg atgatggggc | 18300 |
| gattcaggcc tggtatgagt cagcaacacc ttcttcacga ggcagacctc agcgcccccc | 18360 |
| cccccctgca ggtcaattcg gtcgatatgg ctattacgaa gaaggctcgt gcgcggagtc | 18420 |
| ccgtgaactt tcccacgcaa caagtgaacc gcaccgggtt tgccggaggc catttcgtta | 18480 |
| aaatgcgcag c | 18491 |

```
<210> SEQ ID NO 2
<211> LENGTH: 4291
<212> TYPE: DNA
<213> ORGANISM: Artificial Sequence
<220> FEATURE:
<223> OTHER INFORMATION: pDONRZeo construct

<400> SEQUENCE: 2
```

| | |
|---|---:|
| ctttcctgcg ttatcccctg attctgtgga taaccgtatt accgcctttg agtgagctga | 60 |
| taccgctcgc cgcagccgaa cgaccgagcg cagcgagtca gtgagcgagg aagcggaaga | 120 |
| gcgcccaata cgcaaaccgc ctctccccgc gcgttggccg attcattaat gcagctggca | 180 |

```
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt cccagtcac gacgttgtaa     540 aacgacggcc agtcttaagc tcgggcccca ataatgatt ttattttgac tgatagtgac     600
ctgttcgttg caacacattg atgagcaatg cttttttata atgccaactt tgtacaaaaa    660
agctgaacga gaaacgtaaa atgatataaa tatcaatata ttaaattaga ttttgcataa    720
aaaacagact acataatact gtaaaacaca acatatccag tcactatgaa tcaactactt    780
agatggtatt agtgacctgt agtcgaccga cagccttcca aatgttcttc gggtgatgct    840
gccaacttag tcgaccgaca gccttccaaa tgttcttctc aaacggaatc gtcgtatcca    900
gcctactcgc tattgtcctc aatgccgtat taaatcataa aaagaaataa gaaaagagg    960 tgcgagcctc ttttttgtgt gacaaaataa aaacatctac ctattcatat acgctagtgt   1020
catagtcctg aaaatcatct gcatcaagaa caatttcaca actcttatac ttttctctta   1080
caagtcgttc ggcttcatct ggattttcag cctctatact tactaaacgt gataaagttt   1140
ctgtaatttc tactgtatcg acctgcagac tggctgtgta aagggagcc tgacatttat    1200 attccccaga acatcaggtt aatggcgttt ttgatgtcat tttcgcggtg gctgagatca   1260
gccacttctt ccccgataac ggagaccggc acactggcca tatcggtggt catcatgcgc   1320
cagctttcat ccccgatatg caccaccggg taaagttcac gggagacttt atctgacagc   1380
agacgtgcac tggccagggg gatcaccatc cgtcgcccgg gcgtgtcaat aatatcactc   1440
tgtacatcca caaacagacg ataacggctc tctcttttat aggtgtaaac cttaaactgc   1500
atttcaccag cccctgttct cgtcagcaaa agagccgttc atttcaataa accgggcgac   1560
ctcagccatc ccttcctgat tttccgcttt ccagcgttcg gcacgcagac gacgggcttc   1620
attctgcatg gttgtgctta ccagaccgga gatattgaca tcatatatgc cttgagcaac   1680
tgatagctgt cgctgtcaac tgtcactgta atacgctgct tcatagcata cctctttttg   1740
acatacttcg ggtatacata tcagtatata ttcttatacc gcaaaaatca gcgcgcaaat   1800
acgcatactg ttatctggct tttagtaagc cggatccacg cggcgtttac gccccgccct   1860
gccactcatc gcagtactgt tgtaattcat taagcattct gccgacatgg aagccatcac   1920
agacggcatg atgaacctga atcgccagcg gcatcagcac cttgtcgcct gcgtataat    1980 atttgcccat ggtgaaaacg ggggcgaaga agttgtccat attggccacg tttaaatcaa   2040
aactggtgaa actcacccag ggattggctg agacgaaaaa catattctca ataaacccctt  2100 tagggaaata ggccaggttt tcaccgtaac acgccacatc ttgcgaatat atgtgtagaa   2160
actgccggaa atcgtcgtgg tattcactcc agagcgatga aaacgtttca gtttgctcat   2220
ggaaaacggt gtaacaaggg tgaacactat cccatatcac cagctcaccg tctttcattg   2280 ccatacgaa ttccgatga gcattcatca ggcgggcaag aatgtgaata aaggccggat     2340
aaaacttgtg cttattttc tttacggtct ttaaaaaggc cgtaatatcc agctgaacgg    2400
tctggttata ggtacattga gcaactgact gaaatgcctc aaaatgttct ttacgatgcc   2460
attgggatat atcaacggtg gtatatccag tgattttttt ctccatttta gcttccttag   2520
```

| | |
|---|---|
| ctcctgaaaa tctcgataac tcaaaaaata cgcccggtag tgatcttatt tcattatggt | 2580 |
| gaaagttgga acctcttacg tgccgatcaa cgtctcattt tcgccaaaag ttggcccagg | 2640 |
| gcttcccggt atcaacaggg acaccaggat ttatttattc tgcgaagtga tcttccgtca | 2700 |
| caggtattta ttcggcgcaa agtgcgtcgg gtgatgctgc caacttagtc gactacaggt | 2760 |
| cactaatacc atctaagtag ttgattcata gtgactggat atgttgtgtt ttacagtatt | 2820 |
| atgtagtctg tttttatgc aaaatctaat ttaatatatt gatatttata tcattttacg | 2880 |
| tttctcgttc agctttcttg tacaaagttg gcattataag aaagcattgc ttatcaattt | 2940 |
| gttgcaacga acaggtcact atcagtcaaa ataaaatcat tatttgccat ccagctgata | 3000 |
| tcccctatag tgagtcgtat tacatggtca tagctgtttc ctggcagctc tggcccgtgt | 3060 |
| ctcaaaatct ctgatgttac attgcacaag ataaataat atcatcatga tcagtcctgc | 3120 |
| tcctcggcca cgaagtgcac gcagttgccg gccgggtcgc gcagggcgaa ctcccgcccc | 3180 |
| cacggctgct cgccgatctc ggtcatggcc ggcccggagg cgtcccggaa gttcgtggac | 3240 |
| acgacctccg accactcggc gtacagctcg tccaggccgc gcacccacac ccaggccagg | 3300 |
| gtgttgtccg gcaccacctg gtcctggacc gcgctgatga acagggtcac gtcgtcccgg | 3360 |
| accacaccgg cgaagtcgtc ctccacgaag tcccgggaga cccgagccg tcggtccag | 3420 |
| aactcgaccg ctccggcgac gtcgcgcgcg gtgagcaccg gaacggcact ggtcaacttg | 3480 |
| gccatggttt agttcctcac cttgtcgtat tatactatgc cgatatacta tgccgatgat | 3540 |
| taattgtcaa cacgtgctga tcatgaccaa aatcccttaa cgtgagttac gcgtcgttcc | 3600 |
| actgagcgtc agacccgta gaaaagatca aaggatcttc ttgagatcct ttttttctgc | 3660 |
| gcgtaatctg ctgcttgcaa acaaaaaaac caccgctacc agcggtggtt tgtttgccgg | 3720 |
| atcaagagct accaactctt tttccgaagg taactggctt cagcagagcg cagataccaa | 3780 |
| atactgttct tctagtgtag ccgtagttag gccaccactt caagaactct gtagcaccgc | 3840 |
| ctacatacct cgctctgcta atcctgttac cagtggctgc tgccagtggc gataagtcgt | 3900 |
| gtcttaccgg gttggactca agacgatagt taccggataa ggcgcagcgg tcgggctgaa | 3960 |
| cggggggttc gtgcacacag cccagcttgg agcgaacgac ctacaccgaa ctgagatacc | 4020 |
| tacagcgtga gctatgagaa agcgccacgc ttcccgaagg agaaaggcg acaggtatc | 4080 |
| cggtaagcgg cagggtcgga acaggagagc gcacgaggga gcttccaggg ggaaacgcct | 4140 |
| ggtatcttta tagtcctgtc gggtttcgcc acctctgact tgagcgtcga ttttttgtgat | 4200 |
| gctcgtcagg gggcggagc ctatggaaaa acgccagcaa cgcggccttt ttacggttcc | 4260 |
| tggccttttg ctggcctttt gctcacatgt t | 4291 |

<210> SEQ ID NO 3
<211> LENGTH: 4762
<212> TYPE: DNA
<213> ORGANISM: Artificial Sequence
<220> FEATURE:
<223> OTHER INFORMATION: pDONR221

<400> SEQUENCE: 3

| | |
|---|---|
| ctttcctgcg ttatccctg attctgtgga taaccgtatt accgcctttg agtgagctga | 60 |
| taccgctcgc cgcagccgaa cgaccgagcg cagcgagtca gtgagcgagg aagcggaaga | 120 |
| gcgcccaata cgcaaaccgc ctctccccgc gcgttggccg attcattaat gcagctggca | 180 |
| cgacaggttt cccgactgga aagcgggcag tgagcgcaac gcaattaata cgcgtaccgc | 240 |
| tagccaggaa gagtttgtag aaacgcaaaa aggccatccg tcaggatggc cttctgctta | 300 |

```
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt cccagtcac gacgttgtaa     540 aacgacggcc agtcttaagc tcgggcccca aataatgatt ttattttgac tgatagtgac    600
ctgttcgttg caacacattg atgagcaatg cttttttata atgccaactt tgtacaaaaa    660
agctgaacga gaaacgtaaa atgatataaa tatcaatata ttaaattaga ttttgcataa    720
aaaacagact acataatact gtaaaacaca acatatccag tcactatgaa tcaactactt    780
agatggtatt agtgacctgt agtcgaccga cagccttcca aatgttcttc gggtgatgct    840
gccaacttag tcgaccgaca gccttccaaa tgttcttctc aaacggaatc gtcgtatcca    900
gcctactcgc tattgtcctc aatgccgtat taaatcataa aaagaaataa gaaaaagagg    960
tgcgagcctc tttttgtgt gacaaaataa aaacatctac ctattcatat acgctagtgt    1020
catagtcctg aaaatcatct gcatcaagaa caatttcaca actcttatac ttttctctta    1080
caagtcgttc ggcttcatct ggattttcag cctctatact tactaaacgt gataaagttt    1140
ctgtaatttc tactgtatcg acctgcagac tggctgtgta aagggagcc tgacatttat     1200 attccccaga acatcaggtt aatggcgttt ttgatgtcat tttcgcggtg gctgagatca    1260
gccacttctt ccccgataac ggagaccggc acactggcca tatcggtggt catcatgcgc    1320
cagctttcat ccccgatatg caccaccggg taaagttcac gggagacttt atctgacagc    1380
agacgtgcac tggccagggg gatcaccatc cgtcgcccgg gcgtgtcaat aatatcactc    1440
tgtacatcca caaacagacg ataacggctc tctcttttat aggtgtaaac cttaaactgc    1500
atttcaccag cccctgttct cgtcagcaaa agagccgttc atttcaataa accgggcgac    1560
ctcagccatc ccttcctgat tttccgcttt ccagcgttcg gcacgcagac gacgggcttc    1620
attctgcatg gttgtgctta ccagaccgga gatattgaca tcatatatgc cttgagcaac    1680
tgatagctgt cgctgtcaac tgtcactgta atacgctgct tcatagcata cctcttttg    1740 acatacttcg ggtatacata tcagtatata ttcttatacc gcaaaaatca gcgcgcaaat    1800
acgcatactg ttatctggct tttagtaagc cggatccacg cggcgtttac gccccgccct    1860
gccactcatc gcagtactgt tgtaattcat taagcattct gccgacatgg aagccatcac    1920
agacggcatg atgaacctga atcgccagcg gcatcagcac cttgtcgcct tgcgtataat    1980
atttgcccat ggtgaaaacg ggggcgaaga agttgtccat attggccacg tttaaatcaa    2040
aactggtgaa actcacccag ggattggctg agacgaaaaa catattctca ataaaccctt    2100
tagggaaata ggccaggttt tcaccgtaac acgccacatc ttgcgaatat atgtgtagaa    2160
actgccggaa atcgtcgtgg tattcactcc agagcgatga aaacgtttca gtttgctcat    2220
ggaaaacggt gtaacaaggg tgaacactat cccatatcac cagctcaccg tctttcattg    2280
ccatacggaa ttccggatga gcattcatca ggcgggcaag aatgtgaata aaggccggat    2340
aaaacttgtg cttatttttc tttacggtct ttaaaaaggc cgtaatatcc agctgaacgg    2400
tctggttata ggtacattga gcaactgact gaaatgcctc aaaatgttct ttacgatgcc    2460
attgggatat atcaacggtg gtatatccag tgatttttt ctccatttta gcttccttag    2520
ctcctgaaaa tctcgataac tcaaaaaata cgcccggtag tgatcttatt tcattatggt    2580
gaaagttgga acctcttacg tgccgatcaa cgtctcattt tcgccaaaag ttggcccagg    2640
```

```
gcttcccggt atcaacaggg acaccaggat ttatttattc tgcgaagtga tcttccgtca    2700
caggtattta ttcggcgcaa agtgcgtcgg gtgatgctgc caacttagtc gactacaggt    2760
cactaatacc atctaagtag ttgattcata gtgactggat atgttgtgtt ttacagtatt    2820
atgtagtctg ttttttatgc aaaatctaat ttaatatatt gatatttata tcattttacg    2880
tttctcgttc agctttcttg tacaaagttg gcattataag aaagcattgc ttatcaattt    2940
gttgcaacga acaggtcact atcagtcaaa ataaaatcat tatttgccat ccagctgata    3000
tcccctatag tgagtcgtat tacatggtca tagctgtttc ctggcagctc tggcccgtgt    3060
ctcaaaatct ctgatgttac attgcacaag ataaataat atcatcatga acaataaaac     3120
tgtctgctta cataaacagt aatacaaggg gtgttatgag ccatattcaa cgggaaacgt    3180
cgaggccgcg attaaattcc aacatggatg ctgatttata tgggtataaa tgggctcgcg    3240
ataatgtcgg gcaatcaggt gcgacaatct atcgcttgta tgggaagccc gatgcgccag    3300
agttgtttct gaaacatggc aaaggtagcg ttgccaatga tgttacagat gagatggtca    3360
gactaaactg gctgacggaa tttatgcctc ttccgaccat caagcatttt atccgtactc    3420
ctgatgatgc atggttactc accactgcga tccccggaaa aacagcattc caggtattag    3480
aagaatatcc tgattcaggt gaaaatattg ttgatgcgct ggcagtgttc ctgcgccggt    3540
tgcattcgat tcctgtttgt aattgtcctt ttaacagcga tcgcgtattt cgtctcgctc    3600
aggcgcaatc acgaatgaat aacggtttgg ttgatgcgag tgattttgat gacgagcgta    3660
atggctggcc tgttgaacaa gtctggaaag aaatgcataa acttttgcca ttctcaccgg    3720
attcagtcgt cactcatggt gatttctcac ttgataacct tattttgac gaggggaaat     3780 taataggttg tattgatgtt ggacgagtcg gaatcgcaga ccgataccag gatcttgcca    3840
tcctatggaa ctgcctcggt gagttttctc cttcattaca gaaacggctt tttcaaaaat    3900
atggtattga taatcctgat atgaataaat tgcagtttca tttgatgctc gatgagtttt    3960
tctaatcaga attggttaat tggttgtaac actggcagag cattacgctg acttgacggg    4020
acggcgcaag ctcatgacca aaatccctta acgtgagtta cgcgtcgttc cactgagcgt    4080
cagaccccgt agaaaagatc aaaggatctt cttgagatcc ttttttttctg cgcgtaatct    4140 gctgcttgca acaaaaaaaa ccaccgctac cagcggtggt ttgtttgccg gatcaagagc    4200
taccaactct ttttccgaag gtaactggct tcagcagagc gcagatacca atactgttc     4260 ttctagtgta gccgtagtta ggccaccact tcaagaactc tgtagcaccg cctacatacc    4320
tcgctctgct aatcctgtta ccagtggctg ctgccagtgg cgataagtcg tgtcttaccg    4380
ggttggactc aagacgatag ttaccggata aggcgcagcg gtcgggctga acgggggtt     4440 cgtgcacaca gcccagcttg gagcgaacga cctacaccga actgagatac ctacagcgtg    4500
agctatgaga aagcgccacg cttcccgaag ggagaaaggc ggacaggtat ccggtaagcg    4560
gcagggtcgg aacaggagag cgcacgaggg agcttccagg gggaaacgcc tggtatcttt    4620
atagtcctgt cgggtttcgc cacctctgac ttgagcgtcg atttttgtga tgctcgtcag    4680
gggggcggag cctatggaaa aacgccagca acgcggcctt tttacggttc ctggccttt     4740 gctggccttt tgctcacatg tt                                             4762
```

<210> SEQ ID NO 4
<211> LENGTH: 16843
<212> TYPE: DNA
<213> ORGANISM: Artificial Sequence
<220> FEATURE:
<223> OTHER INFORMATION: pBC-yellow construct

<400> SEQUENCE: 4

```
ccgggctggt tgccctcgcc gctgggctgg cggccgtcta tggccctgca aacgcgccag      60
aaacgccgtc gaagccgtgt gcgagacacc gcggccgccg gcgttgtgga tacctcgcgg     120
aaaacttggc cctcactgac agatgagggg cggacgttga cacttgaggg gccgactcac     180
ccggcgcggc gttgacagat gaggggcagg ctcgatttcg gccggcgacg tggagctggc     240
cagcctcgca aatcggcgaa aacgcctgat tttacgcgag tttcccacag atgatgtgga     300
caagcctggg gataagtgcc ctgcggtatt gacacttgag gggcgcgact actgacagat     360
gaggggcgcg atccttgaca cttgaggggc agagtgctga cagatgaggg gcgcacctat     420
tgacatttga gggctgtcc acaggcagaa atccagcat ttgcaagggt tccgcccgt      480
ttttcggcca ccgctaacct gtcttttaac ctgcttttaa accaatattt ataaaccttg     540
tttttaacca gggctgcgcc ctgtgcgcgt gaccgcgcac gccgaagggg ggtgcccccc     600
cttctcgaac cctcccggcc cgctaacgcg ggcctcccat cccccagggg gctgcgcccc     660
tcggccgcga acggcctcac cccaaaaatg gcagcgctgg cagtccttgc cattgccggg     720
atcggggcag taacgggatg ggcgatcagc ccgagcgcga cgcccggaag cattgacgtg     780
ccgcaggtgc tggcatcgac attcagcgac caggtgccgg gcagtgaggg cggcggcctg     840
ggtggcggcc tgcccttcac ttcggccgtc ggggcattca cggacttcat ggcggggccg     900
gcaattttta ccttgggcat tcttggcata gtggtcgcgg gtgccgtgct cgtgttcggg     960
ggtgcgataa acccagcgaa ccatttgagg tgataggtaa gattataccg aggtatgaaa    1020
acgagaattg gacctttaca gaattactct atgaagcgcc atatttaaaa agctaccaag    1080
acgaagagga tgaagaggat gaggaggcag attgccttga atatattgac aatactgata    1140
agataatata tcttttatat agaagatatc gccgtatgta aggatttcag ggggcaaggc    1200
ataggcagcg cgcttatcaa tatatctata gaatgggcaa agcataaaaa cttgcatgga    1260
ctaatgcttg aaacccagga caataacctt atagcttgta aattctatca taattgggta    1320
atgactccaa cttattgata gtgttttatg ttcagataat gcccgatgac tttgtcatgc    1380
agctccaccg attttgagaa cgacagcgac ttccgtccca gccgtgccag gtgctgcctc    1440
agattcaggt tatgccgctc aattcgctgc gtatatcgct tgctgattac gtgcagcttt    1500
cccttcaggc gggattcata cagcggccag ccatccgtca tccatatcac cacgtcaaag    1560
ggtgacagca ggctcataag acgccccagc gtcgccatag tgcgttcacc gaatacgtgc    1620
gcaacaaccg tcttccggag actgtcatac gcgtaaaaca gccagcgctg gcgcgattta    1680
gccccgacat agccccactg ttcgtccatt tccgcgcaga cgatgacgtc actgcccggc    1740
tgtatgcgcg aggttaccga ctgcggcctg agttttttaa gtgacgtaaa atcgtgttga    1800
ggccaacgcc cataatgcgg gctgttgccc ggcatccaac gccattcatg gccatatcaa    1860
tgatttctg gtgcgtaccg ggttgagaag cggtgtaagt gaactgcagt tgccatgttt    1920
tacggcagtg agagcagaga tagcgctgat gtccggcggt gcttttgccg ttacgcacca    1980
ccccgtcagt agctgaacag gagggacagc tgatagacac agaagccact ggagcacctc    2040
aaaaacacca tcatacacta aatcagtaag ttggcagcat cacccataat tgtggtttca    2100
aaatcggctc cgtcgatact atgttatacg ccaactttga aaacaacttt gaaaaagctg    2160
ttttctggta tttaaggttt tagaatgcaa ggaacagtga attggagttc gtcttgttat    2220
aattagcttc ttggggtatc tttaaatact gtagaaaaga ggaaggaaat aataaatggc    2280
```

```
taaaatgaga atatcaccgg aattgaaaaa actgatcgaa aaataccgct gcgtaaaaga    2340
tacggaagga atgtctcctg ctaaggtata aagctggtg ggagaaaatg aaaacctata    2400
tttaaaaatg acggacagcc ggtataaagg gaccaccta t gatgtggaac gggaaaagga   2460
catgatgcta tggctggaag gaaagctgcc tgttccaaag gtcctgcact ttgaacggca    2520
tgatggctgg agcaatctgc tcatgagtga ggccgatggc gtcctttgct cggaagagta    2580
tgaagatgaa caaagccctg aaaagattat cgagctgtat gcggagtgca tcaggctctt    2640
tcactccatc gacatatcgg attgtcccta tacgaatagc ttagacagcc gcttagccga    2700
attggattac ttactgaata cgatctggcc gatgtggat tgcgaaaact gggaagaaga    2760
cactccattt aaagatccgc gcgagctgta tgattttttta aagacggaaa agcccgaaga    2820
ggaacttgtc ttttcccacg gcgacctggg agacagcaac atctttgtga agatggcaa    2880
agtaagtggc tttattgatc ttgggagaag cggcagggcg acaagtggt atgacattgc    2940
cttctgcgtc cggtcgatca gggaggatat cggggaagaa cagtatgtcg agctatttttt    3000
tgacttactg gggatcaagc ctgattggga gaaaataaaa tattatatttt tactggatga    3060
attgttttag tacctagatg tggcgcaacg atgccggcga caagcaggag cgcaccgact    3120
tcttccgcat caagtgtttt ggctctcagg ccgaggccca cggcaagtat ttgggcaagg    3180
ggtcgctggt attcgtgcag gcaagattc ggaataccaa gtacgagaag gacggccaga    3240
cggtctacgg gaccgacttc attgccgata aggtggatta tctggacacc aaggcaccag    3300
gcgggtcaaa tcaggaataa gggcacattg ccccggcgtg agtcggggca atcccgcaag    3360
gagggtgaat gaatcggacg tttgaccgga aggcatacag gcaagaactg atcgacgcgg    3420
ggttttccgc cgaggatgcc gaaaccatcg caagccgcac cgtcatgcgt gcgccccgcg    3480
aaaccttcca gtccgtcggc tcgatggtcc agcaagctac ggccaagatc gagcgcgaca    3540
gcgtgcaact ggctcccct gccctgcccg cgccatcggc cgccgtggag cgttcgcgtc    3600
gtctcgaaca ggaggcggca ggtttggcga agtcgatgac catcgacacg cgaggaacta    3660
tgacgaccaa gaagcgaaaa accgccggcg aggacctggc aaaacaggtc agcgaggcca    3720
agcaggccgc gttgctgaaa cacacgaagc agcagatcaa ggaaatgcag ctttccttgt    3780
tcgatattgc gccgtggccg gacacgatgc gagcgatgcc aaacgacacg gcccgctctg    3840
ccctgttcac cacgcgcaac aagaaaatcc gcgcgaggc gctgcaaaac aaggtcattt    3900
tccacgtcaa caaggacgtg aagatcacct acaccggcgt cgagctgcgg gccgacgatg    3960
acgaactggt gtggcagcag gtgttggagt acgcgaagcg caccctatc ggcgagccga    4020
tcaccttcac gttctacgag ctttgccagg acctggctg gtcgatcaat ggccggtatt    4080
acacgaaggc cgaggaatgc ctgtcgcgcc tacaggcgac ggcgatgggc ttcacgtccg    4140
accgcgttgg gcacctggaa tcggtgtcgc tgctgcaccg cttccgcgtc ctggaccgtg    4200
gcaagaaaac gtcccgttgc caggtcctga tcgacgagga atcgtcgtg ctgtttgctg    4260
gcgaccacta cacgaaattc atatgggaga agtaccgcaa gctgtcgccg acggcccgac    4320
ggatgttcga ctatttcagc tcgcaccggg agccgtaccc gctcaagctg gaaaccttcc    4380
gcctcatgtg cggatcggat tccacccgcg tgaagaagtg gcgcgagcag gtcggcgaag    4440
cctgcgaaga gttgcgaggc agcggcctgg tgaacacgc ctgggtcaat gatgacctgg    4500
tgcattgcaa acgctagggc cttgtggggt cagttccggc tgggggttca gcagccagcg    4560
ctttactggc atttcaggaa caagcgggca ctgctcgacg cacttgcttc gctcagtatc    4620
gctcgggacg cacggcgcgc tctacgaact gccgataaac agaggattaa aattgacaat    4680
```

```
tgtgattaag gctcagattc gacggcttgg agcggccgac gtgcaggatt ccgcgagat    4740
ccgattgtcg gccctgaaga aagctccaga gatgttcggg tccgtttacg agcacgagga    4800
gaaaaagccc atggaggcgt tcgctgaacg gttgcgagat gccgtggcat tcggcgccta    4860
catcgacggc gagatcattg gctgtcggt cttcaaacag gaggacggcc caaggacgc     4920
tcacaaggcg catctgtccg gcgttttcgt ggagcccgaa cagcgaggcc gagggtcgc    4980
cggtatgctg ctgcgggcgt tgccggcggg tttattgctc gtgatgatcg tccgacagat    5040
tccaacggga atctggtgga tgcgcatctt catcctcggc gcacttaata tttcgctatt    5100
ctggagcttg ttgtttattt cggtctaccg cctgccgggc ggggtcgcgg cgacggtagg    5160
cgctgtgcag ccgctgatgg tcgtgttcat ctctgccgct ctgctaggta gcccgatacg    5220
attgatggcg gtcctggggg ctatttgcgg aactgcgggc gtggcgctgt tggtgttgac    5280
accaaacgca gcgctagatc ctgtcggcgt cgcagcgggc ctggcggggg cggtttccat    5340
ggcgttcgga accgtgctga cccgcaagtg gcaacctccc gtgcctctgc tcacctttac    5400
cgcctggcaa ctggcggccg gaggacttct gctcgttcca gtagctttag tgtttgatcc    5460
gccaatcccg atgcctacag gaaccaatgt tctcggcctg gcgtggctcg gcctgatcgg    5520
agcgggttta acctacttcc tttggttccg ggggatctcg cgactcgaac ctacagttgt    5580
ttccttactg ggctttctca gccccagatc tggggtcgat cagccgggga tgcatcaggc    5640
cgacagtcgg aacttcgggt ccccgacctg taccattcgg tgagcaatgg ataggggagt    5700
tgatatcgtc aacgttcact tctaaagaaa tagcgccact cagcttcctc agcggcttta    5760
tccagcgatt tcctattatg tcggcatagt tctcaagatc gacagcctgt cacggttaag    5820
cgagaaatga ataagaaggc tgataattcg gatctctgcg agggagatga tatttgatca    5880
caggcagcaa cgctctgtca tcgttacaat caacatgcta ccctccgcga gatcatccgt    5940
gtttcaaacc cggcagctta gttgccgttc ttccgaatag catcggtaac atgagcaaag    6000
tctgccgcct tacaacggct ctcccgctga cgccgtcccg gactgatggg ctgcctgtat    6060
cgagtggtga ttttgtgccg agctgccggt cggggagctg ttggctggct ggtggcagga    6120
tatattgtgg tgtaaacaaa ttgacgctta gacaacttaa taacacattg cggacgtttt    6180
taatgtactg gggtggtttt tcttttcacc agtgagacgg gcaacagctg attgcccttc    6240
accgcctggc cctgagagag ttgcagcaag cggtccacgc tggtttgccc cagcaggcga    6300
aaatcctgtt tgatggtggt tccgaaatcg gcaaaatccc ttataaatca aaagaatagc    6360
ccgagatagg gttgagtgtt gttccagttt ggaacaagag tccactatta agaacgtgg     6420
actccaacgt caaagggcga aaaccgtct atcagggcga tggcccacta cctgtatggc     6480
cgcattcgca aaacacacct agactagatt tgttttgcta acccaattga tattaattat    6540
atatgattaa tatttatatg tatatggatt tggttaatga atgcatctg  gttcatcaaa    6600
gaattataaa gacacgtgac attcatttag gataagaaat atggatgatc tctttctctt    6660
ttattcagat aactagtaat tacacataac acacaacttt gatgcccaca ttatagtgat    6720
tagcatgtca ctatgtgtgc atccttttat ttcatacatt aattaagttg gccaatccag    6780
aagatggaca agtctaggtt aaccatgtgg tacctacgcg ttcgaatatc catgggccgc    6840
ttcaggccag ggcgctgggg aaggcgatgg cgtgctcggt cagctgccac ttctggttct    6900
tggcgtcgct ccggtcctcc cgcagcagct tgtgctggat gaagtgccac tcgggcatct    6960
tgctgggcac gctcttggcc ttgtacacgg tgtcgaactg gcaccggtac cggccgccgt    7020
```

```
ccttcagcag caggtacatg ctcacgtcgc ccttcaggat gccctgctta ggcacgggca    7080
tgatcttctc gcagctggcc tcccagttgg tggtcatctt cttcatcacg ggccgtcgg    7140
cggggaagtt cacgccgttg aagatgctct tgtggtagat gcagttctcc ttcacgctca    7200
cggtgatgtc cacgttacag atgcacacgg cgccgtcctc gaacaggaag ctccggcccc    7260
aggtgtagcc ggcggggcag ctgttcttga agtagtccac gatgtcctgg gggtactcgg    7320
tgaagatccg gtcgccgtac ttgaagccgg cgctcaggat gtcctcgctg aagggcaggg    7380
ggccgccctc gatcacgcac aggttgatgg tctgcttgcc cttgaagggg tagccgatgc    7440
cctcgccggt gatcacgaac ttgtggccgt cacgcagcc ctccatgtgg tacttcatgg     7500
tcatctcctc cttcaggccg tgcttgctgt gggccatggt ggcgaccggt gaattcgagc    7560
tcggtacccg gggatcctga gtaaaacaga ggagggtctc actaagttta tagagagact    7620
gagagagata aagggacacg tatgaagcgt ctgttttcgt ggtgtgacgt caaagtcatt    7680
ttgctctcta cgcgtgtctg tgtcggcttg atcttttttt ttgcttttg gaactcatgt     7740
cggtagtata tcttttatt attttttctt ttttccctt tcttcaaa ctgatgtcgg         7800
tatgatattt attccatcct aaaatgtaac ttactattat tagtagtcgg tccatgtcta    7860
ttggcccatc atgtggtcat tttacgttta cgtcgtgtgg ctgtttatta taacaaacgg    7920
cacatccttc tcattcgaat tgtatttctc cttaatcgtt ctaataggta tgatcttta     7980
ttttatacgt aaaattaaaa ttgaatgatg tcaagaacga aaattaattt gtatttacaa    8040
aggagctaaa tattgtttat tcctctactg gtagaagata aagaagtag atgaaataat     8100
gatcttacta gagaatattc ctcatttaca ctagtcaaat ggaaatcttg taaactttta    8160
caataattta tcctgaaaat atgaaaaaat agaagaaaat gtttacctcc tctctcctct    8220
taattcacct acgatcggtg cgggcctctt cgctattacg ccagctggcg aaaggggat     8280
gtgctgcaag gcgattaagt tgggtaacgc cagggttttc ccagtcacga cgttgtaaaa    8340
cgacggccag tgaattcgag ctcggtaccc ggggatcctc tagagtcgac ctgcaggcat    8400
gcaagcttgt tgaaacatcc ctgaagtgtc tcattttatt ttatttattc tttgctgata    8460
aaaaaataaa ataaagaag ctaagcacac ggtcaaccat tgctctactg ctaaaagggt     8520
tatgtgtagt gttttactgc ataaattatg cagcaaacaa gacaactcaa attaaaaaat    8580
ttcctttgct tgtttttttg ttgtctctga cttgactttc ttgtggaagt tggttgtata    8640
aggattggga cacaccattg tccttcttaa tttaattta tttctttgct gataaaaaaa     8700
aaaaatttca tatagtgtta ataataatt tgttaaataa ccaaaaagtc aaatatgttt     8760
actctcgttt aaataattga gagtcgtcca gcaaggctaa acgattgtat agatttatga    8820
caatatttac ttttttatag ataaatgtta tattataata aatttatata catatattat    8880
atgttattta ttatttatta ttattttaaa tccttcaata ttttatcaaa ccaactcata    8940
attttttttt tatctgtaag aagcaataaa attaaataga cccacttta ggatgatcca     9000
accttatac agagtaagag agttcaaata gtacccttc atatacatat caactaaaat      9060
attagaaata tcatggatca aaccttataa agacattaaa taagtggata agtataatat    9120
ataaatggg agtatataat atataaatgg atacaaactt ctctctttat aattgttatg    9180
tctccttaac atcctaatat aatacataag tgggtaatat ataatatata aatggagaca    9240
aacttcttcc attataattg ttatgtcttc ttaacactta tgtctcgttc acaatgctaa    9300
agttagaatt gtttagaaag tcttatagta cacatttgtt tttgtactat ttgaagcatt    9360
ccataagccg tcacgattca gatgattat aataataaga ggaaatttat catgagacaa    9420
```

```
taaggtgcat agatagagtg ttaatatatc ataacatcct ttgtttattc atagaagaag   9480
tgagatggag ctcagttatt atactgttac atggtcggat acaatattcc atgctctcca   9540
tgagctctta cacctacatg cattttagtt catacttcat gcacgtggcc atcacagcta   9600
gctgcagcta catatttaca ttttacaaca ccaggagaac tgccctgtta gtgcataaca   9660
atcagaagat ggccgtggct actcgagtta tcgaaccact ttgtacaaga aagctgaacg   9720
agaaacgtaa aatgatataa atatcaatat attaaattag attttgcata aaaaacagac   9780
tacataatac tgtaaaacac aacatatcca gtcactatgg tcgacctgca gactggctgt   9840
gtataaggga gcctgacatt tatattcccc agaacatcgg ttaatggcg ttttgatgt      9900 cattttcgcg gtggctgaga tcagccactt cttccccgat aacggagacc ggcacactgg   9960
ccatatcggt ggtcatcatg cgccagcttt catccccgat atgcaccacc gggtaaagtt  10020
cacgggagac tttatctgac agcagacgtg cactggccag ggggatcacc atccgtcgcc  10080
cgggcgtgtc aataatatca ctctgtacat ccacaaacag acgataacgg ctctctcttt  10140
tataggtgta aaccttaaac tgcatttcac cagtccctgt tctcgtcagc aaaagagccg  10200
ttcatttcaa taaccgggc gacctcagcc atcccttcct gattttccgc tttccagcgt    10260
tcggcacgca gacgacgggc ttcattctgc atggttgtgc ttaccagacc ggagatattg  10320
acatcatata tgccttgagc aactgatagc tgtcgctgtc aactgtcact gtaatacgct  10380
gcttcatagc acacctcttt ttgacatact tcgggtatac atatcagtat atattcttat  10440
accgcaaaaa tcagcgcgca aatacgcata ctgttatctg gcttttagta agccggatcc  10500
tctagattac gccccgccct gccactcatc gcagtactgt tgtaattcat taagcattct  10560
gccgacatgg aagccatcac agacggcatg atgaacctga atcgccagcg gcatcagcac  10620
cttgtcgcct tgcgtataat atttgcccat ggtgaaaacg ggggcgaaga agttgtccat  10680
attggccacg tttaaatcaa aactggtgaa actcacccag ggattggctg agacgaaaaa  10740
catattctca ataaacccctt tagggaaata ggccaggttt tcaccgtaac acgccacatc  10800
ttgcgaatat atgtgtagaa actgccggaa atcgtcgtgg tattcactcc agagcgatga  10860
aaacgtttca gtttgctcat ggaaaacggt gtaacaaggg tgaacactat cccatatcac  10920
cagctcaccg tctttcattg ccatacggaa ttccggatga gcattcatca ggcgggcaag  10980
aatgtgaata aaggccggat aaaacttgtg cttattttc tttacggtct ttaaaaaggc    11040
cgtaatatcc agctgaacgg tctggttata ggtacattga gcaactgact gaaatgcctc  11100
aaaatgttct ttacgatgcc attgggatat atcaacggtg gtatatccag tgatttttt     11160 ctccatttta gcttccttag ctcctgaaaa tctcgccgga tcctaactca aaatccacac  11220
attatacgag ccggaagcat aaagtgtaaa gcctggggtg cctaatgcgg ccgccatagt  11280
gactggatat gttgtgtttt acagtattat gtagtctgtt ttttatgcaa aatctaattt   11340
aatatattga tatttatatc attttacgtt tctcgttcag ctttttttgta caaacttgtt  11400 tgataaccgg tactagtgtg cacgtcgagc gtgtcctctc caaatgaaat gaacttcctt  11460
atatagagga agggtcttgc gaaggatagt gggattgtgc gtcatccctt acgtcagtgg  11520
agatgtcaca tcaatccact tgctttgaag acgtggttgg aacgtcttct ttttccacga   11580
tgctcctcgt gggtgggggt ccatctttgg gaccactgtc ggcagaggca tcttgaatga  11640 tagccttttcc tttatcgcaa tgatggcatt tgtaggagcc accttccttt tctactgtcc  11700
tttcgatgaa gtgacagata gctgggcaat ggaatccgag gaggtttccc gaaattatcc  11760
```

```
tttgttgaaa agtctcaata gcccttggt cttctgagac tgtatctttg acattttgg      11820
agtagaccag agtgtcgtgc tccaccatgt tgacgaagat tttcttcttg tcattgagtc      11880
gtaaaagact ctgtatgaac tgttcgccag tcttcacggc gagttctgtt agatcctcga      11940
tttgaatctt agactccatg catggcctta gattcagtag gaactacctt tttagagact      12000
ccaatctcta ttacttgcct tggtttatga agcaagcctt gaatcgtcca tactggaata      12060
gtacttctga tcttgagaaa tatgtctttc tctgtgttct tgatgcaatt agtcctgaat      12120
cttttgactg catctttaac cttcttggga aggtatttga tctcctggag attgttactc      12180
gggtagatcg tcttgatgag acctgctgcg taggcctctc taaccatctg tgggtcagca      12240
ttctttctga aattgaagag gctaaccttc tcattatcag tggtgaacat agtgtcgtca      12300
ccttcacctt cgaacttcct tcctagatcg taaagataga ggaaatcgtc cattgtaatc      12360
tccggggcaa aggagatctc ttttggggct ggatcactgc tgggcctttt ggttcctagc      12420
gtgagccagt gggcttttg ctttggtggg cttgttaggg ccttagcaaa gctcttgggc      12480
ttgagttgag cttctccttt ggggatgaag ttcaacctgt ctgtttgctg acttgttgtg      12540
tacgcgtcag ctgctgctct tgcctctgta atagtggcaa atttcttgtg tgcaactccg      12600
ggaacgccgt ttgttgccgc cttttgtacaa ccccagtcat cgtatatacc ggcatgtgga      12660
ccgttataca caacgtagta gttgatatga gggtgttgaa tacccgattc tgctctgaga      12720
ggagcaactg tgctgttaag ctcagatttt tgtgggattg gaattggatc ctctagagca      12780
aagcttggcg taatcatggt catagctgtt tcctgtgtga aattgttatc cgctcacaat      12840
tccacacaac atacgagccg gaagcataaa gtgtaaagcc tggggtgcct aatgagtgag      12900
ctaactcaca ttaattgcgt tgcgctcact gcccgctttc cagtcgggaa acctgtcgtg      12960
ccagctgcat taatgaatcg gccaacgcgc ggggagaggc ggtttgcgta ttgggccaaa      13020
gacaaaaggg cgacattcaa ccgattgagg gagggaaggt aaatattgac ggaaattatt      13080
cattaaaggt gaattatcac cgtcaccgac ttgagccatt tgggaattag agccagcaaa      13140
atcaccagta gcaccattac cattagcaag gccggaaacg tcaccaatga aaccatcatc      13200
tagtaacata gatgacaccg cgcgcgataa tttatcctag tttgcgcgct atattttgtt      13260
ttctatcgcg tattaaatgt ataattgcgg gactctaatc ataaaaaccc atctcataaa      13320
taacgtcatg cattacatgt taattattac atgcttaacg taattcaaca gaaattatat      13380
gataatcatc gcaagaccgg caacaggatt caatcttaag aaactttatt gccaaatgtt      13440
tgaacgatct gcttcgacgc actccttctt taggtacgga ctagatctcg gtgacgggca      13500
ggaccggacg gggcggtacc ggcaggctga agtccagctg ccagaaaccc acgtcatgcc      13560
agttcccgtg cttgaagccg gccgcccgca gcatgccgcg gggggcatat ccgagcgcct      13620
cgtgcatgcg cacgctcggg tcgttgggca gcccgatgac agcgaccacg ctcttgaagc      13680
cctgtgcctc cagggacttc agcaggtggg tgtagagcgt ggagcccagt cccgtccgct      13740
ggtggcgggg ggagacgtac acggtcgact cggccgtcca gtcgtaggcg ttgcgtgcct      13800
tccaggggcc cgcgtaggcg atgccggcga cctcgccgtc cacctcggcg acgagccagg      13860
gatagcgctc ccgcagacgg acgaggtcgt ccgtccactc ctgcggttcc tgcggctcgg      13920
tacggaagtt gaccgtgctt gtctcgatgt agtggttgac gatggtgcag accgccggca      13980
tgtccgcctc ggtggcacgg cggatgtcgg ccgggcgtcg ttctgggctc atggatctgg      14040
attgagagtg aatatgagac tctaattgga taccgagggg aatttatgga acgtcagtgg      14100
agcattttg acaagaaata tttgctagct gatagtgacc ttaggcgact tttgaacgcg      14160
```

```
caataatggt ttctgacgta tgtgcttagc tcattaaact ccagaaaccc gcggctgagt   14220
ggctccttca acgttgcggt tctgtcagtt ccaaacgtaa aacggcttgt cccgcgtcat   14280 cggcggggt cataacgtga ctcccttaat tctccgctca tgatcagatt gtcgtttccc    14340
gccttcagtt taaactatca gtgtttgaca ggatatattg gcgggtaaac ctaagagaaa   14400
agagcgttta ttagaataat cggatattta aagggcgtg aaaaggttta tccgttcgtc    14460
catttgtatg tgcatgccaa ccacagggtt ccccagatct ggcgccggcc agcgagacga   14520
gcaagattgg ccgccgcccg aaacgatccg acagcgcgcc cagcacaggt gcgcaggcaa   14580
attgcaccaa cgcatacagc gccagcagaa tgccatagtg ggcggtgacg tcgttcgagt   14640
gaaccagatc gcgcaggagg cccggcagca ccggcataat caggccgatg ccgacagcgt   14700
cgagcgcgac agtgctcaga attacgatca ggggtatgtt gggtttcacg tctgcctcc    14760 ggaccagcct ccgctggtcc gattgaacgc gcggattctt tatcactgat aagttggtgg   14820
acatattatg tttatcagtg ataaagtgtc aagcatgaca aagttgcagc cgaatacagt   14880
gatccgtgcc gccctggacc tgttgaacga ggtcggcgta gacggtctga cgacacgcaa   14940
actggcggaa cggttggggg ttcagcagcc ggcgctttac tggcacttca ggaacaagcg   15000
ggcgctgctc gacgcactgg ccgaagccat gctggcggag aatcatacgc attcggtgcc   15060
gagagccgac gacgactggc gctcatttct gatcggaat gcccgcagct tcaggcaggc    15120
gctgctcgcc taccgcgatg gcgcgcgcat ccatgccggc acgcgaccgg gcgcaccgca   15180
gatggaaacg gccgacgcgc agcttcgctt cctctgcgag gcgggttttt cggccgggga   15240
cgccgtcaat gcgctgatga caatcagcta cttcactgtt ggggccgtgc ttgaggagca   15300
ggccggcgac agcgatgccg gcgagcgcgg cggcaccgtt gaacaggctc cgctctcgcc   15360
gctgttgcgg gccgcgatag acgccttcga cgaagccggt ccggacgcag cgttcgagca   15420
gggactcgcg gtgattgtcg atggattggc gaaaaggagg ctcgttgtca ggaacgttga   15480
aggaccgaga aagggtgacg attgatcagg accgctgccg gagcgcaacc cactcactac   15540
agcagagcca tgtagacaac atcccctccc cctttccacc gcgtcagacg cccgtagcag   15600
cccgctacgg gcttttttcat gccctgccct agcgtccaag cctcacggcc gcgctcggcc   15660
tctctggcgg cctttctggcg ctcttccgct tcctcgctca ctgactcgct gcgctcggtc   15720
gttcggctgc ggcgagcggt atcagctcac tcaaaggcgg taatacgttt atccacagaa   15780
tcaggggata acgcaggaaa gaacatgtga gcaaaaggcc agcaaaaggc caggaaccgt   15840
aaaaaggccg cgttgctggc gttttccat aggctccgcc cccctgacga gcatcacaaa     15900
aatcgacgct caagtcagag gtggcgaaac ccgacaggac tataaagata ccaggcgttt   15960 cccctggaa gctccctcgt gcgctctcct gttccgaccc tgccgcttac cggatacctg    16020
tccgcctttc tcccttcggg aagcgtggcg ctttccgct gcataaccct gcttcggggt     16080
cattatagcg attttttcgg tatatccatc cttttcgca cgatatacag gattttgcca    16140
aagggttcgt gtagactttc cttggtgtat ccaacggcgt cagccgggca ggataggtga   16200
agtaggccca cccgcgagcg ggtgttcctt cttcactgtc ccttattcgc acctggcggt   16260
gctcaacggg aatcctgctc tgcgaggctg ccggctacc gccggcgtaa cagatgaggg    16320
caagcggatg gctgatgaaa ccaagccaac caggaagggc agcccaccta tcaaggtgta   16380
ctgccttcca gacgaacgaa gagcgattga ggaaaggcg gcgcggccg gcatgagcct    16440 gtcggcctac ctgctggccg tcggccaggg ctacaaaatc acgggcgtcg tggactatga   16500
```

```
gcacgtccgc gagctggccc gcatcaatgg cgacctgggc cgcctgggcg gcctgctgaa    16560
actctggctc accgacgacc cgcgcacggc gcggttcggt gatgccacga tcctcgccct    16620
gctggcgaag atcgaagaga agcaggacga gcttggcaag gtcatgatgg gcgtggtccg    16680
cccgagggca gagccatgac ttttttagcc gctaaaacgg ccgggggggtg cgcgtgattg    16740 ccaagcacgt ccccatgcgc tccatcaaga agagcgactt cgcggagctg gtgaagtaca    16800
tcaccgacga gcaaggcaag accgagcgcc tttgcgacgc tca                      16843
```

<210> SEQ ID NO 5
<211> LENGTH: 9142
<212> TYPE: DNA
<213> ORGANISM: Artificial Sequence
<220> FEATURE:
<223> OTHER INFORMATION: PHP27840 construct

<400> SEQUENCE: 5

```
ctagttatct gaataaaaga gaaagagatc atccatatttt cttatcctaa atgaatgtca      60
cgtgtcttta taattctttg atgaaccaga tgcatttcat taaccaaatc catatacata     120
taaatattaa tcatatataa ttaatatcaa ttgggttagc aaaacaaatc tagtctaggt     180
gtgttttgcg aattcgatat caagcttgat gggtaccggc gcgccgatc atccggatat      240 agttcctcct ttcagcaaaa aaccccctcaa gacccgttta gaggccccaa ggggttatgc    300
tagttattgc tcagcggtgg cagcagccaa ctcagcttcc tttcgggctt tgttagcagc    360
cggatcgatc caagctgtac ctcactattc ctttgccctc ggacgagtgc tggggcgtcg    420
gtttccacta tcggcgagta cttctacaca gccatcggtc cagacggccg cgcttctgcg    480
ggcgatttgt gtacgcccga cagtcccggc tccggatcgg acgattgcgt cgcatcgacc    540
ctgcgcccaa gctgcatcat cgaaattgcc gtcaaccaag ctctgataga gttggtcaag    600
accaatgcgg agcatatacg cccggagccg cggcgatcct gcaagctccg gatgcctccg    660
ctcgaagtag cgcgtctgct gctccataca agccaaccac ggcctccaga agaagatgtt    720
ggcgacctcg tattgggaat ccccgaacat cgcctcgctc cagtcaatga ccgctgttat    780
gcggccattg tccgtcagga cattgttgga gccgaaatcc gcgtgcacga ggtgccggac    840
ttcggggcag tcctcggccc aaagcatcag ctcatcgaga gcctgcgcga cggacgcact    900
gacggtgtcg tccatcacag tttgccagtg atacacatgg ggatcagcaa tcgcgcatat    960
gaaatcacgc catgtagtgt attgaccgat tccttgcggt ccgaatgggc cgaacccgct   1020
cgtctggcta agatcggccg cagcgatcgc atccatagcc tccgcgaccg gctgcagaac   1080
agcgggcagt tcggtttcag gcaggtcttg caacgtgaca cccgtgcac ggcgggagat    1140 gcaataggtc aggctctcgc tgaattcccc aatgtcaagc acttccggaa tcgggagcgc    1200
ggccgatgca aagtgccgat aaacataacg atctttgtag aaaccatcgg cgcagctatt   1260
tacccgcagg acatatccac gccctcctac atcgaagctg aaagcacgag attcttcgcc   1320
ctccgagagc tgcatcaggt cggagacgct gtcgaacttt tcgatcagaa acttctcgac   1380
agacgtcgcg gtgagttcag gctttttccat gggtatatct ccttcttaaa gttaaacaaa   1440
attatttcta gagggaaacc gttgtggtct ccctatagtg agtcgtatta atttcgcggg   1500
atcgagatct gatcaacctg cattaatgaa tcggccaacg cgcggggaga ggcggtttgc    1560
gtattgggcg ctcttccgct tcctcgctca ctgactcgct gcgctcggtc gttcggctgc    1620
ggcgagcggt atcagctcac tcaaaggcgg taatacggtt atccacagaa tcaggggata   1680
acgcaggaaa gaacatgtga gcaaaaggcc agcaaaaggc caggaaccgt aaaaaggccg    1740
```

-continued

```
cgttgctggc gtttttccat aggctccgcc ccccTgacga gcatcacaaa aatcgacgct    1800
caagtcagag gtggcgaaac ccgacaggac tataaagata ccaggcgttt cccccTggaa    1860
gctccctcgt gcgctctcct gttccgaccc tgccgcttac cggatacctg tccgcctttc    1920
tcccttcggg aagcgtggcg ctttctcaat gctcacgctg taggtatctc agttcggtgt    1980
aggtcgttcg ctccaagctg gctgtgtgc acgaaccccc cgttcagccc gaccgctgcg    2040
ccttatccgg taactatcgt cttgagtcca acccggtaag acacgactta tcgccactgg    2100
cagcagccac tggtaacagg attagcagag cgaggtatgt aggcggtgct acagagttct    2160
tgaagtggtg cctaactac ggctacacta aaggacagt atttggtatc tgcgctctgc    2220
tgaagccagt taccttcgga aaaagagttg gtagctcttg atccggcaaa caaaccaccg    2280
ctggtagcgg tggttttttt gtttgcaagc agcagattac gcgcagaaaa aaggatctc    2340 aagaagatcc tttgatcttt tctacggggt ctgacgctca gtggaacgaa aactcacgtt    2400
aagggatttt ggtcatgaca ttaacctata aaaataggcg tatcacgagg ccctttcgtc    2460
tcgcgcgttt cggtgatgac ggtgaaaacc tctgacacat gcagctcccg gagacggtca    2520
cagcttgtct gtaagcggat gccgggagca gacaagcccg tcaggcgcg tcagcgggtg    2580 ttggcgggtg tcggggctgg cttaactatg cggcatcaga gcagattgta ctgagagtgc    2640
accatatgga catattgtcg ttagaacgcg gctacaatta atacataacc ttatgtatca    2700
tacacatacg atttaggtga cactatagaa cggcgcgcca agctgggtct agaactagaa    2760
acgtgatgcc acttgttatt gaagtcgatt acagcatcta ttctgtttta ctatttataa    2820
ctttgccatt tctgactttt gaaaactatc tctggatttc ggtatcgctt tgtgaagatc    2880
gagcaaaaga gacgttttgt ggacgcaatg gtccaaatcc gttctacatg aacaaattgg    2940
tcacaatttc cactaaaagt aaataaatgg caagttaaaa aaggaatatg catttactg    3000 attgcctagg tgagctccaa gagaagttga atctacacgt ctaccaaccg ctaaaaaaag    3060
aaaaacattg aatatgtaac ctgattccat tagcttttga cttcttcaac agattctcta    3120
cttagatttc taacagaaat attattacta gcacatcatt ttcagtctca ctacagcaaa    3180
aaatccaacg gcacaataca gacaacagga gatatcagac tacagagata gatagatgct    3240
actgcatgta gtaagttaaa taaaaggaaa ataaaatgtc ttgctaccaa aactactaca    3300
gactatgatg ctcaccacag gccaaatcct gcaactagga cagcattatc ttatatatat    3360
tgtacaaaac aagcatcaag gaacatttgg tctaggcaat cagtacctcg ttctaccatc    3420
accctcagtt atcacatcct tgaaggatcc attactggga atcatcggca acacatgctc    3480
ctgatggggc acaatgacat caagaaggta ggggccaggg gtgtccaaca ttctctgaat    3540
tgccgctcta agctcttcct tcttcgtcac tcgcgctgcc ggtatccac aagcatcagc    3600 aaacttgagc atgtttggga atatctcgct ctcgctagac ggatctccaa gataggtgtg    3660
agctctattg gacttgtaga acctatcctc caactgaacc accatacccaa atgctgatt    3720 gttcaacaac aatatcttaa ctgggagatt ctccactctt atagtggcca actcctgaac    3780
attcatgatg aaactaccat ccccatcaat gtcaaccaca acagcccag ggttagcaac    3840 agcagcacca atagccgcag gcaatccaaa acccatggcc caagacccc ctgaggtcaa    3900 ccactgcctc ggtctcttgt acttgtaaaa ctgcgcagcc cacatttgat gctgcccaac    3960
cccagtacta acaatagcat ctccattagt caactcatca agaacctcga tagcatgctg    4020
cggagaaatc gcgtcctgga atgtcttgta acccaatgga aacttgtgtt tctgcacatt    4080
```

```
aatctcttct ctccaacctc caagatcaaa cttaccctcc actcctttct cctccaaaat    4140
catattaatt cccttcaagg ccaacttcaa atccgcgcaa accgacacgt gcgcctgctt    4200
gttcttccca atctcggcag aatcaatatc aatgtgaaca atcttagccc tactagcaaa    4260
agcctcaagc ttcccagtaa cacggtcatc aaaccttacc ccaaaggcaa gcaacaaatc    4320
actattgtca acagcatagt tagcataaac agtaccatgc atacccagca tctgaaggga    4380
atattcatca ccaataggaa aagttccaag acccattaaa gtgctagcaa cgggaatacc    4440
agtgagttca acaaagcgcc tcaattcagc actggaattc aaactgccac cgccgacgta    4500
gagaacgggc ttttgggcct ccatgatgag tctgacaatg tgttccaatt gggcctcggc    4560
gggggggcctg ggcagcctgg cgaggtaacc ggggaggtta acgggctcgt cccaattagg    4620
cacggcgagt tgctgctgaa cgtctttggg aatgtcgatg aggaccggac cggggcggcc    4680
ggaggtggcg acgaagaaag cctcggcgac gacgcggggg atgtcgtcga cgtcgaggat    4740
gaggtagttg tgcttcgtga tggatctgct cacctccacg atcggggttt cttggaaggc    4800
gtcggtgccg atcatccggc gggcgacctg gccggtgatg cgacgactg ggacgctgtc    4860
cattaaagcg tcggcgaggc cgctcacgag gttggtggcg ccggggccgg aggtggcaat    4920
gcagacgccg gggaggccgg aggaacgcgc gtagccttcg gcggcgaaga cgccgccctg    4980
ctcgtggcgc gggagcacgt tgcggatggc ggcggagcgc gtgagcgcct ggtggatctc    5040
catcgacgca ccgccggggt acgcgaacac cgtcgtcacg ccctgcctct ccagcgcctc    5100
cacaaggatg tccgcgccct tgcgaggttc gccggaggcg aaccgtgaca cgaagggctc    5160
cgtggtcggc gcttccttgg tgaagggcgc cgccgtgggg ggtttggaga tggaacattt    5220
gattttgaga gcgtggttgg gtttggtgag ggtttgatga gagagaggga gggtggatct    5280
agtaatgcgt ttggggaagg tggggtgtga agaggaagaa gagaatcggg tggttctgga    5340
agcggtggcc gccattgtgt tgtgtggcat ggttatactt caaaaactgc acaacaagcc    5400
tagagttagt acctaaacag taaatttaca acagagagca aagacacatg caaaaatttc    5460
agccataaaa aaagttataa tagaatttaa agcaaaagtt tcatttttta aacatatata    5520
caaacaaact ggatttgaag gaagggatta attcccctgc tcaaagtttg aattcctatt    5580
gtgacctata ctcgaataaa attgaagcct aaggaatgta tgagaaacaa gaaaacaaaa    5640
caaaactaca gacaaacaag tacaattaca aaattcgcta aaattctgta atcaccaaac    5700
cccatctcag tcagcacaag gcccaaggtt tattttgaaa taaaaaaaaa gtgattttat    5760
ttctcataag ctaaaagaaa gaaaggcaat tatgaaatga tttcgactag atctgaaagt    5820
caaacgcgta ttccgcagat attaaagaaa gagtagagtt tcacatggat cctagatgga    5880
cccagttgag gaaaagcaa ggcaaagcaa accagaagtg caagatccga aattgaacca    5940
cggaatctag gatttggtag agggagaaga aaagtacctt gagaggtaga agagaagaga    6000
agagcagaga gatatatgaa cgagtgtgtc ttggtctcaa ctctgaagcg atacgagttt    6060
agaggggagc attgagttcc aatttatagg gaaaccgggt ggcaggggtg agttaatgac    6120
ggaaaagccc ctaagtaacg agattggatt gtgggttaga ttcaaccgtt tgcatccgcg    6180
gcttagattg gggaagtcag agtgaatctc aaccgttgac tgagttgaaa attgaatgta    6240
gcaaccaatt gagccaaccc cagcctttgc cctttgattt tgatttgttt gttgcatact    6300
ttttatttgt cttctggttc tgactctctt tctctcgttt caatgccagg ttgcctactc    6360
ccacaccact cacaagaaga ttctactgtt agtattaaat attttttaat gtattaaatg    6420
atgaatgctt ttgtaaacag aacaagacta tgtctaataa gtgtcttgca acattttta    6480
```

```
agaaattaaa aaaaatatat ttattatcaa aatcaaatgt atgaaaaatc atgaataata    6540
taattttata cattttttta aaaaatcttt taatttctta attaatatct taaaaataat    6600
gattaatatt taacccaaaa taattagtat gattggtaag gaagatatcc atgttatgtt    6660
tggatgtgag tttgatctag agcaaagctt actagagtcg acctgcagcc cctccaccgc    6720
ggtggcggcc gctctagaga tccgtcaaca tggtggagca cgacactctc gtctactcca    6780
agaatatcaa agatacagtc tcagaagacc aaagggctat tgagactttt caacaaaggg    6840
taatatcggg aaacctcctc ggattccatt gcccagctat ctgtcacttc atcaaaagga    6900
cagtagaaaa ggaaggtggc acctacaaat gccatcattg cgataaagga aaggctatcg    6960
ttcaagatgc ctctgccgac agtggtccca agatggaccc ccacccacg aggagcatcg    7020 tggaaaaaga agacgttcca accacgtctt caaagcaagt ggattgatgt gatgatccta    7080
tgcgtatggt atgacgtgtg ttcaagatga tgacttcaaa cctacctatg acgtatggta    7140
tgacgtgtgt cgactgatga cttagatcca ctcgagcggc tataaatacg tacctacgca    7200
ccctgcgcta ccatccctag agctgcagct tattttaca acaattacca acaacaacaa    7260
acaacaaaca acattacaat tactatttac aattacagtc gacccatcaa caagtttgta    7320
caaaaaagct gaacgagaaa cgtaaaatga tataaatatc aatatattaa attagatttt    7380
gcataaaaaa cagactacat aatactgtaa aacacaacat atccagtcat attggcggcc    7440
gcattaggca ccccaggctt tacactttat gcttccggct cgtataatgt gtggattttg    7500
agttaggatc cgtcgagatt ttcaggagct aaggaagcta aaatggagaa aaaaatcact    7560
ggatatacca ccgttgatat atcccaatgg catcgtaaag aacattttga ggcatttcag    7620
tcagttgctc aatgtaccta taaccagacc gttcagctgg atattacggc cttttttaaag    7680 accgtaaaga aaaataagca caagttttat ccggccttta ttcacattct tgcccgcctg    7740
atgaatgctc atccggaatt ccgtatggca atgaaagacg gtgagctggt gatatgggat    7800
agtgttcacc cttgttacac cgttttccat gagcaaactg aaacgttttc atcgctctgg    7860
agtgaatacc acgacgattt ccggcagttt ctacacatat attcgcaaga tgtggcgtgt    7920
tacggtgaaa acctggccta tttccctaaa gggtttattg agaatatgtt tttcgtctca    7980
gccaatccct gggtgagttt caccagtttt gatttaaacg tggccaatat ggacaacttc    8040 ttcgccccg ttttcaccat gggcaaatat tatacgcaag cgacaaggt gctgatgccg    8100 ctggcgattc aggttcatca tgccgtttgt gatggcttcc atgtcggcag aatgcttaat    8160
gaattacaac agtactgcga tgagtggcag ggcggggcgt aaagatctgg atccggctta    8220
ctaaaagcca gataacagta tgcgtatttg cgcgctgatt tttgcggtat aagaatatat    8280
actgatatgt atacccgaag tatgtcaaaa agaggtatgc tatgaagcag cgtattacag    8340
tgacagttga cagcgacagc tatcagttgc tcaaggcata tatgatgtca atatctccgg    8400
tctggtaagc acaaccatgc agaatgaagc ccgtcgtctg cgtgccgaac gctggaaagc    8460
ggaaaatcag gaagggatgg ctgaggtcgc ccggtttatt gaaatgaacg gctcttttgc    8520
tgacgagaac aggggctggt gaaatgcagt ttaaggttta cacctataaa agagagagcc    8580
gttatcgtct gtttgtggat gtacagagtg atattattga cacgcccggg cgacggatgg    8640
tgatccccct ggccagtgca cgtctgctgt cagataaagt ctcccgtgaa ctttacccgg    8700
tggtgcatat cggggatgaa agctggcgca tgatgaccac cgatatggcc agtgtgccgg    8760
tctccgttat cggggaagaa gtggctgatc tcagccaccg cgaaaatgac atcaaaaacg    8820
```

| | |
|---|---:|
| ccattaacct gatgttctgg ggaatataaa tgtcaggctc ccttatacac agccagtctg | 8880 |
| caggtcgacc atagtgactg gatatgttgt gttttacagt attatgtagt ctgtttttta | 8940 |
| tgcaaaatct aatttaatat attgatattt atatcatttt acgtttctcg ttcagctttc | 9000 |
| ttgtacaaag tggttgataa cctagacttg tccatcttct ggattggcca acttaattaa | 9060 |
| tgtatgaaat aaaaggatgc acacatagtg acatgctaat cactataatg tgggcatcaa | 9120 |
| agttgtgtgt tatgtgtaat ta | 9142 |

<210> SEQ ID NO 6
<211> LENGTH: 49911
<212> TYPE: DNA
<213> ORGANISM: Artificial Sequence
<220> FEATURE:
<223> OTHER INFORMATION: PHP23236 construct

<400> SEQUENCE: 6

| | |
|---|---:|
| gtgcagcgtg acccggtcgt gcccctctct agagataatg agcattgcat gtctaagtta | 60 |
| taaaaaatta ccacatattt tttttgtcac acttgtttga agtgcagttt atctatcttt | 120 |
| atacatatat ttaaacttta ctctacgaat aatataatct atagtactac aataatatca | 180 |
| gtgttttaga gaatcatata aatgaacagt tagacatggt ctaaaggaca attgagtatt | 240 |
| ttgacaacag gactctacag ttttatcttt ttagtgtgca tgtgttctcc ttttttttg | 300 |
| caaatagctt cacctatata atacttcatc cattttatta gtacatccat ttagggttta | 360 |
| gggttaatgg ttttatctatcaga ctaatttttt tagtacatct atttatttct atttagccct | 420 |
| ctaaattaag aaaactaaaa ctctattta gttttttat ttaataattt agatataaaa | 480 |
| tagaatataaa taaagtgact aaaaattaaa caaatacact ttaagaaatt aaaaaaacta | 540 |
| aggaaacatt tttcttgttt cgagtagata atgccagcct gttaaacgcc gtcgacgagt | 600 |
| ctaacggaca ccaaccagcg aaccagcagc gtcgcgtcgg gccaagcgaa gcagacggca | 660 |
| cggcatctct gtcgctgcct ctggaccccct ctcgagagtt ccgctccacc gttgacttg | 720 |
| ctccgctgtc ggcatccaga aattgcgtgg cggagcggca gacgtgagcc ggcacggcag | 780 |
| gcggcctcct cctcctctca cggcacggca gctacggggg attcctttcc caccgctcct | 840 |
| tcgctttccc ttcctcgccc gccgtaataa atagacaccc cctccacacc ctcttttccc | 900 |
| aacctcgtgt tgttcggagc gcacacacac acaaccagat ctcccccaaa tccacccgtc | 960 |
| ggcacctccg cttcaaggta cgccgctcgt cctccccccc cccccctctc taccttctct | 1020 |
| agatcggcgt tccggtccat ggttagggcc cggtagttct acttctgttc atgtttgtgt | 1080 |
| tagatccgtg tttgtgttag atccgtgctg ctagcgttcg tacacggatg cgacctgtac | 1140 |
| gtcagacacg ttctgattgc taacttgcca gtgtttctct ttggggaatc ctgggatggc | 1200 |
| tctagccgtt ccgcagacgg gatcgatttc atgatttttt ttgtttcgtt gcatagggtt | 1260 |
| tggtttgccc ttttccttta tttcaatata tgccgtgcac ttgtttgtcg ggtcatcttt | 1320 |
| tcatgctttt ttttgtcttg gttgtgatga tgtggtctgg ttgggcggtc gttctagatc | 1380 |
| ggagtagaat tctgtttcaa actacctggt ggatttatta attttggatc tgtatgtgtg | 1440 |
| tgccatacat attcatagtt acgaattgaa gatgatggat ggaaatatcg atctaggata | 1500 |
| ggtatacatg ttgatgcggg ttttactgat gcatatacag agatgctttt tgttcgcttg | 1560 |
| gttgtgatga tgtggtgtgg ttgggcggtc gttcattcgt tctagatcgg agtagaatac | 1620 |
| tgtttcaaac tacctggtgt atttattaat tttggaactg tatgtgtgtg tcatacatct | 1680 |
| tcatagttac gagtttaaga tggatggaaa tatcgatcta ggataggtat acatgttgat | 1740 |

-continued

```
gtgggtttta ctgatgcata tacatgatgg catatgcagc atctattcat atgctctaac    1800
cttgagtacc tatctattat aataaacaag tatgttttat aattattttg atcttgatat    1860
acttggatga tggcatatgc agcagctata tgtggatttt tttagccctg ccttcatacg    1920
ctatttattt gcttggtact gtttcttttg tcgatgctca ccctgttgtt tggtgttact    1980
tctgcaggtc gactctagag gatccacaag tttgtacaaa aaagctgaac gagaaacgta    2040
aaatgatata aatatcaata tattaaatta gattttgcat aaaaaacaga ctacataata    2100
ctgtaaaaca caacatatcc agtcactatg gcggccgcat taggcacccc aggctttaca    2160
ctttatgctt ccggctcgta taatgtgtgg attttgagtt aggatttaaa tacgcgttga    2220
tccggcttac taaaagccag ataacagtat gcgtatttgc gcgctgattt ttgcggtata    2280
agaatatata ctgatatgta tacccgaagt atgtcaaaaa gaggtatgct atgaagcagc    2340
gtattacagt gacagttgac agcgacagct atcagttgct caaggcatat atgatgtcaa    2400
tatctccggt ctggtaagca caaccatgca gaatgaagcc cgtcgtctgc gtgccgaacg    2460
ctggaaagcg gaaaatcagg aagggatggc tgaggtcgcc cggtttattg aaatgaacgg    2520
ctcttttgct gacgagaaca ggggctggtg aaatgcagtt taaggtttac acctataaaa    2580
gagagagccg ttatcgtctg tttgtggatg tacagagtga tatcattgac acgcccggtc    2640
gacggatggt gatcccectg gccagtgcac gtctgctgtc agataaagtc tcccgtgaac    2700
tttacccggt ggtgcatatc ggggatgaaa gctggcgcat gatgaccacc gatatggcca    2760
gtgtgccggt ctccgttatc ggggaagaag tggctgatct cagccaccgc gaaaatgaca    2820
tcaaaaacgc cattaacctg atgttctggg aatataaat gtcaggctcc cttatacaca    2880
gccagtctgc aggtcgacca tagtgactgg atatgttgtg ttttacagta ttatgtagtc    2940
tgttttttat gcaaaatcta atttaatata ttgatattta tatcatttta cgtttctcgt    3000
tcagctttct tgtacaaagt ggtgttaacc tagacttgtc catcttctgg attggccaac    3060
ttaattaatg tatgaaataa aaggatgcac acatagtgac atgctaatca ctataatgtg    3120
ggcatcaaag ttgtgtgtta tgtgtaatta ctagttatct gaataaaaga gaaagagatc    3180
atccatattt cttatcctaa atgaatgtca cgtgtcttta taattctttg atgaaccaga    3240
tgcatttcat taaccaaatc catatacata taaatattaa tcatatataa ttaatatcaa    3300
ttgggttagc aaaacaaatc tagtctaggt gtgttttgcg aattgcggcc gccaccgcgg    3360
tggagctcga attccggtcc gggtcaccTt tgtccaccaa gatggaactg cggccgctca    3420
ttaattaagt caggcgcgcc tctagttgaa gacacgttca tgtcttcatc gtaagaagac    3480
actcagtagt cttcggccag aatggccatc tggattcagc aggcctagaa ggccatttaa    3540
atcctgagga tctggtcttc ctaaggaccc gggatatcgg accgattaaa ctttaattcg    3600
gtccgaagct tgcatgcctg cagtgcagcg tgacccggtc gtgccctct ctagagataa    3660
tgagcattgc atgtctaagt tataaaaaat taccacatat ttttttgtc acacttgttt    3720
gaagtgcagt ttatctatct ttatacatat atttaaactt tactctacga ataatataat    3780
ctatagtact acaataatat cagtgtttta gagaatcata taaatgaaca gttagacatg    3840
gtctaaagga caattgagta ttttgacaac aggactctac agtttatctt ttttagtgtg    3900
catgtgttct ccttttttttt tgcaaatagc ttcacctata taatacttca tccattttat    3960
tagtacatcc atttagggtt tagggttaat ggttttata gactaatttt tttagtacat    4020
ctatttattt ctattttagc ctctaaatta agaaaactaa aactctatt tagttttttt    4080
```

```
atttaataat ttagatataa aatagaataa aataaagtga ctaaaaatta aacaaatacc    4140
ctttaagaaa ttaaaaaaac taaggaaaca tttttcttgt ttcgagtaga taatgccagc    4200
ctgttaaacg ccgtcgacga gtctaacgga caccaaccag cgaaccagca gcgtcgcgtc    4260
gggccaagcg aagcagacgg cacggcatct ctgtcgctgc ctctggaccc ctctcgagag    4320
ttccgctcca ccgttggact tgctccgctg tcggcatcca gaaattgcgt ggcggagcgg    4380
cagacgtgag ccggcacggc aggcggcctc ctcctcctct cacggcaccg gcagctacgg    4440
gggattcctt tcccaccgct ccttcgcttt cccttcctcg cccgccgtaa taaatagaca    4500
ccccctccac accctctttc cccaacctcg tgttgttcgg agcgcacaca cacacaacca    4560
gatctccccc aaatccaccc gtcggcacct ccgcttcaag gtacgccgct cgtcctcccc    4620
ccccccccct c tctaccttct ctagatcggc gttccggtcc atgcatggtt agggcccggt    4680
agttctactt ctgttcatgt ttgtgttaga tccgtgtttg tgttagatcc gtgctgctag    4740
cgttcgtaca cggatgcgac ctgtacgtca gacacgttct gattgctaac ttgccagtgt    4800
ttctcttt gg ggaatcctgg gatggctcta gccgttccgc agacgggatc gatttcatga    4860
tttttttt gt ttcgttgcat agggtttggt ttgccctttt cctttatttc aatatatgcc    4920
gtgcacttgt ttgtcgggtc atcttttcat gctttttttt gtcttggttg tgatgatgtg    4980
gtctggttgg gcggtcgttc tagatcggag tagaattctg tttcaaacta cctggtggat    5040
ttattaattt tggatctgta tgtgtgtgcc atacatattc atagttacga attgaagatg    5100
atggatggaa atatcgatct aggataggta tacatgttga tgcgggtttt actgatgcat    5160
atacagagat gcttttttgtt cgcttggttg tgatgatgtg gtgtggttgg gcggtcgttc    5220
attcgttcta gatcggagta gaatactgtt tcaaactacc tggtgtattt attaattttg    5280
gaactgtatg tgtgtgtcat acatcttcat agttacgagt ttaagatgga tggaaatatc    5340
gatctaggat aggtatacat gttgatgtgg gttttactga tgcatataca tgatggcata    5400
tgcagcatct attcatatgc tctaaccttg agtacctatc tattataata aacaagtatg    5460
ttttataatt attttgatct tgatatactt ggatgatggc atatgcagca gctatatgtg    5520
gattttttta gccctgcctt catacgctat ttatttgctt ggtactgttt cttttgtcga    5580
tgctcaccct gttgtttggt gttacttctg caggtcgact ttaacttagc ctaggatcca    5640
cacgacacca tgtcccccga gcgccgcccc gtcgagatcc gcccggccac cgccgccgac    5700
atggccgccg tgtgcgacat cgtgaaccac tacatcgaga cctccaccgt gaacttccgc    5760
accgagccgc agacccccgca ggagtggatc gacgacctgg agcgcctcca ggaccgctac    5820
ccgtggctcg tggccgaggt ggagggcgtg gtggccggca tcgcctacgc cggcccgtgg    5880
aaggcccgca acgcctacga ctggaccgtg gagtccaccg tgtacgtgtc ccaccgccac    5940
cagcgcctcg gcctcggctc cacccctctac acccaccctcc tcaagagcat ggaggcccag    6000
ggcttcaagt ccgtggtggc cgtgatcggc ctcccgaacg accgtccgt gcgcctccac    6060
gaggccctcg gctacaccgc ccgcggcacc ctccgcgccg ccggctacaa gcacggcggc    6120
tggcacgacg tcggcttctg gcagcgcgac ttcgagctgc cggccccgcc gcgcccggtg    6180
cgccggtga cgcagatctg agtcgaaacc tagacttgtc catcttctgg attggccaac    6240
ttaattaatg tatgaaataa aaggatgcac acatagtgac atgctaatca ctataatgtg    6300
ggcatcaaag ttgtgtgtta tgtgtaatta ctagttatct gaataaaaga gaaagagatc    6360
atccatattt cttatcctaa atgaatgtca cgtgtcttta taattctttg atgaaccaga    6420
tgcatttcat taaccaaatc catatacata taaatattaa tcatatataa ttaatatcaa    6480
```

```
ttgggttagc aaaacaaatc tagtctaggt gtgttttgcg aattgcggcc gccaccgcgg   6540
tggagctcga attcattccg attaatcgtg gcctcttgct cttcaggatg aagagctatg   6600
tttaaacgtg caagcgctac tagacaattc agtacattaa aaacgtccgc aatgtgttat   6660
taagttgtct aagcgtcaat ttggtttaca ccacaatata tcctgccacc agccagccaa   6720
cagctccccg accggcagct cggcacaaaa tcaccactcg atacaggcag cccatcagtc   6780
cgggacggcg tcagcgggag agccgttgta aggcggcaga ctttgctcat gttaccgatg   6840
ctattcggaa gaacggcaac taagctgccg ggtttgaaac acggatgatc tcgcggaggg   6900
tagcatgttg attgtaacga tgacagagcg ttgctgcctg tgatcaaata tcatctccct   6960
cgcagagatc cgaattatca gccttcttat tcatttctcg cttaaccgtg acaggctgtc   7020
gatcttgaga actatgccga cataatagga aatcgctgga taaagccgct gaggaagctg   7080
agtggcgcta tttctttaga agtgaacgtt gacgatcgtc gaccgtaccc cgatgaatta   7140
attcggacgt acgttctgaa cacagctgga tacttacttg ggcgattgtc atacatgaca   7200
tcaacaatgt acccgtttgt gtaaccgtct cttggaggtt cgtatgacac tagtggttcc   7260
cctcagcttg cgactagatg ttgaggccta acattttatt agagagcagg ctagttgctt   7320
agatacatga tcttcaggcc gttatctgtc agggcaagcg aaaattggcc atttatgacg   7380
accaatgccc cgcagaagct cccatctttg ccgccataga cgccgcgccc cccttttggg   7440
gtgtagaaca tccttttgcc agatgtggaa aagaagttcg ttgtcccatt gttggcaatg   7500
acgtagtagc cggcgaaagt gcgagaccca tttgcgctat atataagcct acgatttccg   7560
ttgcgactat tgtcgtaatt ggatgaacta ttatcgtagt tgctctcaga gttgtcgtaa   7620
tttgatggac tattgtcgta attgcttatg gagttgtcgt agttgcttgg agaaatgtcg   7680
tagttggatg gggagtagtc atagggaaga cgagcttcat ccactaaaac aattggcagg   7740
tcagcaagtg cctgccccga tgccatcgca agtacgaggc ttagaaccac cttcaacaga   7800
tcgcgcatag tcttccccag ctctctaacg cttgagttaa gccgcgccgc gaagcggcgt   7860
cggcttgaac gaattgttag acattatttg ccgactacct tggtgatctc gcctttcacg   7920
tagtgaacaa attcttccaa ctgatctgcg cgcgaggcca agcgatcttc ttgtccaaga   7980
taagcctgcc tagcttcaag tatgacgggc tgatactggg ccggcaggcg ctccattgcc   8040
cagtcggcag cgacatcctt cggcgcgatt ttgccggtta ctgcgctgta ccaaatgcgg   8100
gacaacgtaa gcactacatt tcgctcatcg ccagcccagt cgggcggcga gttccatagc   8160
gttaaggttt catttagcgc ctcaaataga tcctgttcag gaaccggatc aaagagttcc   8220
tccgccgctg gacctaccaa ggcaacgcta tgttctcttg cttttgtcag caagatagcc   8280
agatcaatgt cgatcgtggc tggctcgaag atacctgcaa gaatgtcatt gcgctgccat   8340
tctccaaatt gcagttcgcg cttagctgga taacgccacg gaatgatgtc gtcgtgcaca   8400
acaatggtga cttctacagc gcggagaatc tcgctctctc caggggaagc cgaagtttcc   8460
aaaaggtcgt tgatcaaagc tcgccgcgtt gtttcatcaa gccttacagt caccgtaacc   8520
agcaaatcaa tatcactgtg tggcttcagg ccgccatcca ctgcggagcc gtacaaatgt   8580
acggccagca acgtcggttc gagatggcgc tcgatgacgc caactacctc tgatagttga   8640
gtcgatactt cggcgatcac cgcttccctc atgatgttta actcctgaat taagccgcgc   8700
cgcgaagcgg tgtcggcttg aatgaattgt taggcgtcat cctgtgctcc cgagaaccag   8760
taccagtaca tcgctgtttc gttcgagact tgaggtctag tttatacgt gaacaggtca   8820
```

```
atgccgccga gagtaaagcc acattttgcg tacaaattgc aggcaggtac attgttcgtt    8880
tgtgtctcta atcgtatgcc aaggagctgt ctgcttagtg cccactttt cgcaaattcg     8940
atgagactgt gcgcgactcc tttgcctcgg tgcgtgtgcg acacaacaat gtgttcgata    9000
gaggctagat cgttccatgt tgagttgagt tcaatcttcc cgacaagctc ttggtcgatg    9060
aatgcgccat agcaagcaga gtcttcatca gagtcatcat ccgagatgta atccttccgg    9120
tagggctca cacttctggt agatagttca aagccttggt cggataggtg cacatcgaac     9180
acttcacgaa caatgaaatg gttctcagca tccaatgttt ccgccacctg ctcagggatc    9240
accgaaatct tcatatgacg cctaacgcct ggcacagcgg atcgcaaacc tggcgcggct    9300
tttggcacaa aaggcgtgac aggtttgcga atccgttgct gccacttgtt aacccttttg    9360
ccagatttgg taactataat ttatgttaga ggcgaagtct tgggtaaaaa ctggcctaaa    9420
attgctgggg atttcaggaa agtaaacatc accttccggc tcgatgtcta ttgtagatat    9480
atgtagtgta tctacttgat cgggggatct gctgcctcgc gcgtttcggt gatgacggtg    9540
aaaacctctg acacatgcag ctcccggaga cggtcacagc ttgtctgtaa gcggatgccg    9600
ggagcagaca agcccgtcag ggcgcgtcag cgggtgttgg cgggtgtcgg ggcgcagcca    9660
tgacccagtc acgtagcgat agcggagtgt atactggctt aactatgcgg catcagagca    9720
gattgtactg agagtgcacc atatgcggtg tgaaataccg cacagatgcg taaggagaaa    9780
ataccgcatc aggcgctctt ccgcttcctc gctcactgac tcgctgcgct cggtcgttcg    9840
gctgcggcga gcggtatcag ctcactcaaa ggcggtaata cggttatcca cagaatcagg    9900
ggataacgca ggaaagaaca tgtgagcaaa aggccagcaa aaggccagga accgtaaaaa    9960
ggccgcgttg ctggcgtttt tccataggct ccgccccct gacgagcatc acaaaaatcg   10020
acgctcaagt cagaggtggc gaaacccgac aggactataa agataccagg cgtttccccc   10080
tggaagctcc ctcgtgcgct ctcctgttcc gaccctgccg cttaccggat acctgtccgc   10140
ctttctccct tcgggaagcg tggcgctttc tcatagctca cgctgtaggt atctcagttc   10200
ggtgtaggtc gttcgctcca agctgggctg tgtgcacgaa ccccccgttc agcccgaccg   10260
ctgcgcctta tccggtaact atcgtcttga gtccaacccg gtaagacacg acttatcgcc   10320
actggcagca gccactggta acaggattag cagagcgagg tatgtaggcg gtgctacaga   10380
gttcttgaag tggtggccta actacggcta cactagaagg acagtatttg gtatctgcgc   10440
tctgctgaag ccagttacct tcggaaaaag agttggtagc tcttgatccg gcaaacaaac   10500
caccgctggt agcggtggtt tttttgtttg caagcagcag attacgcgca gaaaaaaagg   10560
atctcaagaa gatcctttga tcttttctac ggggtctgac gctcagtgga acgaaaactc   10620
acgttaaggg attttggtca tgagattatc aaaaaggatc ttcacctaga tccttttaaa   10680
ttaaaaatga agttttaaat caatctaaag tatatatgag taaacttggt ctgacagtta   10740
ccaatgctta atcagtgagg cacctatctc agcgatctgt ctatttcgtt catccatagt   10800
tgcctgactc cccgtcgtgt agataactac gatacgggag ggcttaccat ctggccccag   10860
tgctgcaatg ataccgcgag acccacgctc accggctcca gatttatcag caataaacca   10920
gccagccgga agggccgagc gcagaagtgg tcctgcaact ttatccgcct ccatccagtc   10980
tattaattgt tgccgggaag ctagagtaag tagttcgcca gttaatagtt tgcgcaacgt   11040
tgttgccatt gctgcagggg ggggggggg ggggacttc cattgttcat tccacggaca   11100
aaacagaga aggaaacga cagaggccaa aaagcctcgc tttcagcacc tgtcgtttcc   11160
tttctttca gagggtattt taaataaaaa cattaagtta tgacgaagaa gaacggaaac   11220
```

```
gccttaaacc ggaaaatttt cataaatagc gaaaacccgc gaggtcgccg ccccgtaacc    11280
tacctgtcgg atcaccggaa aggacccgta aagtgataat gattatcatc tacatatcac    11340
aacgtgcgtg gaggccatca aaccacgtca ataatcaat tatgacgcag gtatcgtatt    11400
aattgatctg catcaactta acgtaaaaac aacttcagac aatacaaatc agcgacactg    11460
aatacggggc aacctcatgt ccccccccc cccccccctg caggcatcgt ggtgtcacgc    11520
tcgtcgtttg gtatggcttc attcagctcc ggttcccaac gatcaaggcg agttacatga    11580
tcccccatgt tgtgcaaaaa agcggttagc tccttcggtc ctccgatcgt tgtcagaagt    11640
aagttggccg cagtgttatc actcatggtt atggcagcac tgcataattc tcttactgtc    11700
atgccatccg taagatgctt ttctgtgact ggtgagtact caaccaagtc attctgagaa    11760
tagtgtatgc ggcgaccgag ttgctcttgc ccggcgtcaa cacgggataa taccgcgcca    11820
catagcagaa ctttaaaagt gctcatcatt ggaaaacgtt cttcggggcg aaaactctca    11880
aggatcttac cgctgttgag atccagttcg atgtaaccca ctcgtgcacc caactgatct    11940
tcagcatctt ttactttcac cagcgtttct gggtgagcaa aaacaggaag gcaaaatgcc    12000
gcaaaaaagg gaataagggc gacacggaaa tgttgaatac tcatactctt cctttttcaa    12060
tattattgaa gcatttatca gggttattgt ctcatgagcg gatacatatt tgaatgtatt    12120
tagaaaaata aacaaatagg ggttccgcgc acatttcccc gaaaagtgcc acctgacgtc    12180
taagaaacca ttattatcat gacattaacc tataaaaata ggcgtatcac gaggcccttt    12240
cgtcttcaag aattcggagc ttttgccatt ctcaccggat tcagtcgtca ctcatggtga    12300
tttctcactt gataaacctta tttttgacga ggggaaatta ataggttgta ttgatgttgg    12360
acgagtcgga atcgcagacc gataccagga tcttgccatc ctatggaact gcctcggtga    12420
gttttctcct tcattacaga aacggctttt tcaaaaatat ggtattgata atcctgatat    12480
gaataaattg cagtttcatt tgatgctcga tgagttttc taatcagaat tggttaattg    12540
gttgtaacac tggcagagca ttacgctgac ttgacgggac ggcggctttg ttgaataaat    12600 cgaactttg ctgagttgaa ggatcagatc acgcatcttc ccgacaacgc agaccgttcc    12660
gtggcaaagc aaaagttcaa aatcaccaac tggtccacct acaacaaagc tctcatcaac    12720
cgtggctccc tcactttctg gctggatgat ggggcgattc aggcctggta tgagtcagca    12780
acaccttctt cacgaggcag acctcagcgc cagaaggccg ccagagaggc cgagcgcggc    12840
cgtgaggctt ggacgctagg gcagggcatg aaaaagcccg tagcgggctg ctacgggcgt    12900
ctgacgcggt ggaaggggg aggggatgtt gtctacatgg ctctgctgta gtgagtgggt    12960
tgcgctccgg cagcggtcct gatcaatcgt caccctttct cggtccttca acgttcctga    13020
caacgagcct cctttttcgcc aatccatcga caatcaccgc gagtccctgc tcgaacgctg    13080
cgtccggacc ggcttcgtcg aaggcgtcta tcgcggcccg caacagcggc gagagcggag    13140
cctgttcaac ggtgccgccg cgctcgccgg catcgctgtc gccggcctgc tcctcaagca    13200
cggccccaac agtgaagtag ctgattgtca tcagcgcatt gacggcgtcc ccggccgaaa    13260
aacccgcctc gcagaggaag cgaagctgcg cgtcggccgt ttccatctgc ggtgcgcccg    13320
gtcgcgtgcc ggcatggatg cgcgcgccat gcgcgtaggc gagcagcgcc tgcctgaagc    13380
tgcgggcatt cccgatcaga aatgagcgcc agtcgtcgtc ggctctcggc accgaatgcg    13440
tatgattctc cgccagcatg gcttcggcca gtgcgtcgag cagcgcccgc ttgttcctga    13500
agtgccagta aagcgccggc tgctgaaccc ccaaccgttc cgccagtttg cgtgtcgtca    13560
```

```
gaccgtctac gccgacctcg ttcaacaggt ccagggcggc acggatcact gtattcggct    13620
gcaactttgt catgcttgac actttatcac tgataaacat aatatgtcca ccaacttatc    13680
agtgataaag aatccgcgcg ttcaatcgga ccagcggagg ctggtccgga ggccagacgt    13740
gaaacccaac atacccctga tcgtaattct gagcactgtc gcgctcgacg ctgtcggcat    13800
cggcctgatt atgccggtgc tgccgggcct cctgcgcgat ctggttcact cgaacgacgt    13860
caccgcccac tatggcattc tgctggcgct gtatgcgttg gtgcaatttg cctgcgcacc    13920
tgtgctgggc gcgctgtcgg atcgtttcgg gcggcggcca atcttgctcg tctcgctggc    13980
cggcgccact gtcgactacg ccatcatggc gacagcgcct ttcctttggg ttctctatat    14040
cgggcggatc gtggccggca tcaccggggc gactggggcg gtagccggcg cttatattgc    14100
cgatatcact gatggcgatg agcgcgcgcg gcacttcggc ttcatgagcg cctgtttcgg    14160
gttcgggatg gtcgcgggac ctgtgctcgg tgggctgatg ggcggtttct ccccccacgc    14220
tccgttcttc gccgcggcag ccttgaacgg cctcaatttc ctgacgggct gtttccttt    14280 gccggagtcg cacaaaggcg aacgccggcc gttacgccgg gaggctctca cccgctcgc    14340 ttcgttccgg tgggcccggg gcatgaccgt cgtcgccgcc ctgatggcgg tcttcttcat    14400
catgcaactt gtcggacagg tgccggccgc gctttgggtc attttcggcg aggatcgctt    14460
tcactgggac gcgaccacga tcggcatttc gcttgccgca tttggcattc tgcattcact    14520
cgcccaggca atgatcaccg gccctgtagc cgcccggctc ggcgaaaggc gggcactcat    14580
gctcggaatg attgccgacg gcacaggcta catcctgctt gccttcgcga cacggggatg    14640 gatgcgttc ccgatcatgg tcctgcttgc ttcgggtggc atcggaatgc cggcgctgca    14700
agcaatgttg tccaggcagg tggatgagga acgtcagggg cagctgcaag gctcactggc    14760
ggcgctcacc agcctgacct cgatcgtcgg accctcctc ttcacggcga tctatgcggc    14820
ttctataaca acgtggaacg ggtgggcatg gattgcaggc gctgccctct acttgctctg    14880
cctgccggcg ctgcgtcgcg ggcttttggag cggcgcaggg caacgagccg atcgctgatc    14940
gtggaaacga taggcctatg ccatgcgggt caaggcgact tccggcaagc tatacgcgcc    15000
ctaggagtgc ggttggaacg ttggcccagc cagatactcc cgatcacgag caggacgccg    15060
atgatttgaa gcgcactcag cgtctgatcc aagaacaacc atcctagcaa cacggcggtc    15120
cccgggctga gaaagcccag taaggaaaca actgtaggtt cgagtcgcga atccccgg    15180 aaccaaagga agtaggttaa acccgctccg atcaggccga gccacgccag gccgagaaca    15240
ttggttcctg taggcatcgg gattggcgga tcaaacacta aagctactgg aacgagcaga    15300
agtcctccgg ccgccagttg ccaggcggta aaggtgagca gaggcacggg aggttgccac    15360
ttgcgggtca gcacggttcc gaacgccatg gaaaccgccc ccgccaggcc cgctgcgacg    15420
ccgacaggat ctagcgctgc gtttggtgtc aacaccaaca gcgccacgcc cgcagttccg    15480
caaatagccc ccaggaccgc catcaatcgt atcgggctac ctagcagagc ggcagagatg    15540
aacacgacca tcagcggctg cacagcgcct accgtcgccg cgaccccgcc cggcaggcgg    15600
tagaccgaaa taaacaacaa gctccagaat agcgaaatat aagtgcgcc gaggatgaag    15660 atgcgcatcc accagattcc cgttggaatc tgtcggacga tcatcacgag caataaaccc    15720
gccggcaacg cccgcagcag cataccggcg accectcggc ctcgctgttc gggctccacg    15780
aaaacgccgg acagatgcgc cttgtgagcg tccttgggc cgtcctcctg tttgaagacc    15840
gacagcccaa tgatctcgcc gtcgatgtag gcgccgaatg ccacggcatc tcgcaaccgt    15900
tcagcgaacg cctccatggg cttttttctcc tcgtgctcgt aaacggaccc gaacatctct    15960
```

```
ggagctttct tcagggccga caatcggatc tcgcggaaat cctgcacgtc ggccgctcca    16020
agccgtcgaa tctgagcctt aatcacaatt gtcaatttta atcctctgtt tatcggcagt    16080
tcgtagagcg cgccgtgcgt cccgagcgat actgagcgaa gcaagtgcgt cgagcagtgc    16140
ccgcttgttc ctgaaatgcc agtaaagcgc tggctgctga accccagcc ggaactgacc     16200 ccacaaggcc ctagcgtttg caatgcacca ggtcatcatt gacccaggcg tgttccacca    16260
ggccgctgcc tcgcaactct tcgcaggctt cgccgacctg ctcgcgccac ttcttcacgc    16320
gggtggaatc cgatccgcac atgaggcgga aggtttccag cttgagcggg tacggctccc    16380
ggtgcgagct gaaatagtcg aacatccgtc gggccgtcgg cgacagcttg cggtacttct    16440
cccatatgaa tttcgtgtag tggtcgccag caaacagcac gacgatttcc tcgtcgatca    16500
ggacctggca acgggacgtt ttcttgccac ggtccaggac gcggaagcgg tgcagcagcg    16560
acaccgattc caggtgccca acgcggtcgg acgtgaagcc catcgccgtc gcctgtaggc    16620
gcgacaggca ttcctcggcc ttcgtgtaat accggccatt gatcgaccag cccaggtcct    16680
ggcaaagctc gtagaacgtg aaggtgatcg gctcgccgat agggtgcgc ttcgcgtact      16740 ccaacacctg ctgccacacc agttcgtcat cgtcggcccg cagctcgacg ccggtgtagg    16800
tgatcttcac gtccttgttg acgtggaaaa tgaccttgtt ttgcagcgcc tcgcgcggga    16860
ttttcttgtt gcgcgtggtg aacagggcag agcgggccgt gtcgtttggc atcgctcgca    16920
tcgtgtccgg ccacggcgca atatcgaaca aggaaagctg catttccttg atctgctgct    16980
tcgtgtgttt cagcaacgcg gcctgcttgg cctcgctgac ctgttttgcc aggtcctcgc    17040
cggcggtttt tcgcttcttg gtcgtcatag ttcctcgcgt gtcgatggtc atcgacttcg    17100
ccaaacctgc cgcctcctgt tcgagacgac gcgaacgctc cacggcggcc gatggcgcgg    17160
gcagggcagg gggagccagt tgcacgctgt cgcgctcgat cttggccgta gcttgctgga    17220
ccatcgagcc gacggactgg aaggtttcgc ggggcgcacg catgacgtg cggcttgcga     17280 tggtttcggc atcctcggcg gaaaaccccg cgtcgatcag ttcttgcctg tatgccttcc    17340
ggtcaaacgt ccgattcatt caccctcctt gcgggattgc cccgactcac gccggggcaa    17400
tgtgccctta ttcctgattt gacccgcctg gtgccttggt gtccagataa tccacctat     17460 cggcaatgaa gtcggtcccg tagaccgtct ggccgtcctt ctcgtacttg gtattccgaa    17520
tcttgccctg cacgaatacc agcgacccct tgcccaaata cttgccgtgg gcctcggcct    17580
gagagccaaa acacttgatg cggaagaagt cggtgcgctc ctgcttgtcg ccggcatcgt    17640
tgcgccactc ttcattaacc gctatatcga aaattgcttg cggcttgtta gaattgccat    17700
gacgtacctc ggtgtcacgg gtaagattac cgataaactg gaactgatta tggctcatat    17760
cgaaagtctc cttgagaaag gagactctag tttagctaaa cattggttcc gctgtcaaga    17820
actttagcgg ctaaaatttt gcgggccgcg accaaaggtg cgaggggcgg cttccgctgt    17880
gtacaaccag atatttttca ccaacatcct tcgtctgctc gatgagcggg gcatgacgaa    17940
acatgagctg tcggagaggg caggggtttc aatttcgttt ttatcagact taaccaacgg    18000
taaggccaac ccctcgttga aggtgatgga ggccattgcc gacgccctgg aaactcccct    18060
acctcttctc ctggagtcca ccgacttga ccgcgaggca ctcgcggaga ttgcgggtca     18120
tcctttcaag agcagcgtgc cgcccggata cgaacgcatc agtgtggttt tgccgtcaca    18180
taaggcgttt atcgtaaaga aatggggcga cgacacccga aaaagctgc gtggaaggct     18240 ctgacgccaa gggttagggc ttgcacttcc ttctttagcc gctaaaacgg ccccttctct    18300
```

```
gcgggccgtc ggctcgcgca tcatatcgac atcctcaacg aagccgtgc cgcgaatggc    18360
atcgggcggg tgcgctttga cagttgtttt ctatcagaac ccctacgtcg tgcggttcga    18420
ttagctgttt gtcttgcagg ctaaacactt tcggtatatc gtttgcctgt gcgataatgt    18480
tgctaatgat ttgttgcgta ggggttactg aaaagtgagc gggaaagaag agtttcagac    18540
catcaaggag cgggccaagc gcaagctgga acgcgacatg ggtgcggacc tgttggccgc    18600
gctcaacgac ccgaaaaccg ttgaagtcat gctcaacgcg gacggcaagg tgtggcacga    18660
acgccttggc gagccgatgc ggtacatctg cgacatgcgg cccagccagt cgcaggcgat    18720
tatagaaacg gtggccggat ccacggcaa agaggtcacg cggcattcgc ccatcctgga    18780
aggcgagttc cccttggatg gcagccgctt tgccggccaa ttgccgccgg tcgtggccgc    18840
gccaaccttt gcgatccgca agcgcgcggt cgccatcttc acgctggaac agtacgtcga    18900
ggcgggcatc atgacccgcg agcaatacga ggtcattaaa agcgccgtcg cggcgcatcg    18960
aaacatcctc gtcattggcg gtactggctc gggcaagacc acgctcgtca acgcgatcat    19020
caatgaaatg gtcgccttca acccgtctga gcgcgtcgtc atcatcgagg acaccggcga    19080
aatccagtgc gccgcagaga acgccgtcca ataccacacc agcatcgacg tctcgatgac    19140
gctgctgctc aagacaacgc tgcgtatgcg ccccgaccgc atcctggtcg gtgaggtacg    19200
tggccccgaa gcccttgatc tgttgatggc ctggaacacc gggcatgaag gaggtgccgc    19260
caccctgcac gcaaacaacc ccaaagcggg cctgagccgg ctcgccatgc ttatcagcat    19320
gcacccggat tcaccgaaac ccattgagcc gctgattggc gaggcggttc atgtggtcgt    19380
ccatatcgcc aggaccccta gcggccgtcg agtgcaagaa attctcgaag ttcttggtta    19440
cgagaacggc cagtacatca ccaaaaccct gtaaggagta tttccaatga caacggctgt    19500
tccgttccgt ctgaccatga atcgcggcat tttgttctac cttgccgtgt tcttcgttct    19560
cgctctcgcg ttatccgcgc atccggcgat ggcctcggaa ggcaccggcg gcagcttgcc    19620
atatgagagc tggctgacga acctgcgcaa ctccgtaacc ggcccggtgg ccttcgcgct    19680
gtccatcatc ggcatcgtcg tcgccggcgg cgtgctgatc ttcggcggcg aactcaacgc    19740
cttcttccga accctgatct tcctggttct ggtgatggcg ctgctggtcg gcgcgcagaa    19800
cgtgatgagc accttcttcg gtcgtggtgc cgaaatcgcg gccctcggca acggggcgct    19860
gcaccaggtg caagtcgcgg cggcggatgc cgtgcgtgcg gtagcggctg gacggctcgc    19920
ctaatcatgg ctctgcgcac gatccccatc cgtcgcgcag gcaaccgaga aaacctgttc    19980
atgggtggtg atcgtgaact ggtgatgttc tcgggcctga tggcgtttgc gctgattttc    20040
agcgcccaag agctgcgggc caccgtggtc ggtctgatcc tgtggttcgg ggcgctctat    20100
gcgttccgaa tcatggcgaa ggccgatccg aagatgcggt tcgtgtacct gcgtcaccgc    20160
cggtacaagc cgtattaccc ggcccgctcg accccgttcc gcgagaacac caatagccaa    20220
gggaagcaat accgatgatc caagcaattg cgattgcaat cgcgggcctc ggcgcgcttc    20280
tgttgttcat cctctttgcc cgcatccgcg cggtcgatgc cgaactgaaa ctgaaaaagc    20340
atcgttccaa ggacgccggc ctggccgatc tgctcaacta cgccgctgtc gtcgatgacg    20400
gcgtaatcgt gggcaagaac ggcagcttta tggctgcctg gctgtacaag ggcgatgaca    20460
acgcaagcag caccgaccag cagcgcgaag tagtgtccgc ccgcatcaac caggccctcg    20520
cgggcctggg aagtgggtgg atgatccatg tggacgccgt gcggcgtcct gctccgaact    20580
acgcggagcg gggcctgtcg gcgttccctg accgtctgac ggcagcgatt gaagaagagc    20640
gctcggtctt gccttgctcg tcggtgatgt acttcaccag ctccgcgaag tcgctcttct    20700
```

```
tgatggagcg catggggacg tgcttggcaa tcacgcgcac cccccggccg ttttagcggc    20760
taaaaaagtc atggctctgc cctcgggcgg accacgccca tcatgacctt gccaagctcg    20820
tcctgcttct cttcgatctt cgccagcagg gcgaggatcg tggcatcacc gaaccgcgcc    20880
gtgcgcgggt cgtcggtgag ccagagtttc agcaggccgc ccaggcggcc caggtcgcca    20940
ttgatgcggg ccagctcgcg gacgtgctca tagtccacga cgcccgtgat tttgtagccc    21000
tggccgacgg ccagcaggta ggccgacagg ctcatgccgg ccgccgccgc cttttcctca    21060
atcgctcttc gttcgtctgg aaggcagtac accttgatag gtgggctgcc cttcctggtt    21120
ggcttggttt catcagccat ccgcttgccc tcatctgtta cgccggcggt agccggccag    21180
cctcgcagag caggattccc gttgagcacc gccaggtgcg aataagggac agtgaagaag    21240
gaacacccgc tcgcgggtgg gcctacttca cctatcctgc ccggctgacg ccgttggata    21300
caccaaggaa agtctacacg aacccttggg caaaatcctg tatatcgtgc gaaaaggat    21360
ggataccg aaaaaatcgc tataatgacc ccgaagcagg ttatgcagc ggaaagcgc    21420
tgcttccctg ctgttttgtg gaatatctac cgactggaaa caggcaaatg caggaaatta    21480
ctgaactgag gggacaggcg agagacgatg ccaaagagct acaccgacga gctggccgag    21540
tgggttgaat cccgcgcggc caagaagcgc cggcgtgatg aggctgcggt tgcgttcctg    21600
gcggtgaggg cggatgtcga ggcggcgtta gcgtccggct atgcgctcgt caccatttgg    21660
gagcacatgc gggaaacggg gaaggtcaag ttctcctacg agacgttccg ctcgcacgcc    21720
aggcggcaca tcaaggccaa gcccgccgat gtgcccgcac cgcaggccaa ggctgcggaa    21780
cccgcgccgg cacccaagac gccggagcca cggcggccga agcaggggg caaggctgaa    21840
aagccggccc ccgctgcggc cccgaccggc ttcaccttca acccaacacc ggacaaaaag    21900
gatctactgt aatggcgaaa attcacatgg ttttgcaggg caagggcggg gtcggcaagt    21960
cggccatcgc cgcgatcatt gcgcagtaca agatggacaa ggggcagaca cccttgtgca    22020
tcgacaccga cccggtgaac gcgacgttcg agggctacaa ggccctgaac gtccgccggc    22080
tgaacatcat ggccggcgac gaaattaact cgcgcaactt cgacaccctg gtcgagctga    22140
ttgcgccgac caaggatgac gtggtgatcg acaacggtgc cagctcgttc gtgcctctgt    22200
cgcattacct catcagcaac caggtgccgg ctctgctgca agaaatgggg catgagctgg    22260
tcatccatac cgtcgtcacc ggcggccagg ctctcctgga cacggtgagc ggcttcgccc    22320
agctcgccag ccagttcccg gccgaagcgc ttttcgtggt ctggctgaac ccgtattggg    22380
ggcctatcga gcatgagggc aagagctttg agcagatgaa ggcgtacacg gccaacaagg    22440
cccgcgtgtc gtccatcatc cagattccgg ccctcaagga agaaacctac ggccgcgatt    22500
tcagcgacat gctgcaagag cggctgacgt tcgaccaggc gctggccgat gaatcgctca    22560
cgatcatgac gcggcaacgc ctcaagatcg tgcggcgcgg cctgtttgaa cagctcgacg    22620
cggcggccgt gctatgagcg accagattga agagctgatc cggagattg cggccaagca    22680
cggcatcgcc gtcggccgcg acgacccggt gctgatcctg cataccatca acgcccggct    22740
catggccgac agtgcggcca agcaagagga aatccttgcc gcgttcaagg aagagctgga    22800
agggatcgcc catcgttggg gcgaggacgc caaggcaaaa gcggagcgga tgctgaacgc    22860
ggccctggcg gccagcaagg acgcaatggc gaaggtaatg aaggacagcg ccgcgcaggc    22920
ggccgaagcg atccgcaggg aaatcgacga cggccttggc cgccagctcg cggccaaggt    22980
cgcggacgcg cggcgcgtgg cgatgatgaa catgatcgcc ggcggcatgg tgttgttcgc    23040
```

```
ggccgccctg gtggtgtggg cctcgttatg aatcgcagag gcgcagatga aaaagcccgg    23100
cgttgccggg cttttgttttt gcgttagctg ggcttgtttg acaggcccaa gctctgactg   23160
cgcccgcgct cgcgctcctg ggcctgtttc ttctcctgct cctgcttgcg catcagggcc    23220
tggtgccgtc gggctgcttc acgcatcgaa tcccagtcgc cggccagctc gggatgctcc    23280
gcgcgcatct tgcgcgtcgc cagttcctcg atcttgggcg cgtgaatgcc catgccttcc    23340
ttgatttcgc gcaccatgtc cagccgcgtg tgcagggtct gcaagcgggc ttgctgttgg    23400
gcctgctgct gctgccaggc ggcctttgta cgcggcaggg acagcaagcc gggggcattg    23460
gactgtagct gctgcaaacg cgcctgctga cggtctacga gctgttctag gcggtcctcg    23520
atgcgctcca cctggtcatg ctttgcctgc acgtagagcg caagggtctg ctggtaggtc    23580
tgctcgatgg gcgcggattc taagagggcc tgctgttccg tctcggcctc ctgggccgcc    23640
tgtagcaaat cctcgccgct gttgccgctg gactgcttta ctgccgggga ctgctgttgc    23700
cctgctcgcg ccgtcgtcgc agttcggctt gcccccactc gattgactgc ttcatttcga    23760
gccgcagcga tgcgatctcg gattgcgtca acggacgggg cagcgcggag gtgtccggct    23820
tctccttggg tgagtcggtc gatgccatag ccaaaggttt ccttccaaaa tgcgtccatt    23880
gctggaccgt gtttctcatt gatgcccgca agcatcttcg gcttgaccgc caggtcaagc    23940
gcgccttcat gggcggtcat gacggacgcc gccatgacct tgccgccgtt gttctcgatg    24000
tagccgcgta atgaggcaat ggtgccgccc atcgtcagcg tgtcatcgac aacgatgtac    24060
ttctggccgg ggatcacctc cccctcgaaa gtcgggttga acgccaggcg atgatctgaa    24120
ccggctccgg ttcgggcgac cttctcccgc tgcacaatgt ccgtttcgac ctcaaggcca    24180
aggcggtcgg ccagaacgac cgccatcatg gccggaatct tgttgttccc cgccgcctcg    24240
acggcgagga ctgaacgat gcggggcttg tcgtcgccga tcagcgtctt gagctgggca    24300
acagtgtcgt ccgaaatcag gcgctcgacc aaattaagcg ccgcttccgc gtcgccctgc    24360
ttcgcagcct ggtattcagg ctcgttggtc aaagaaccaa ggtcgccgtt gcgaaccacc    24420
ttcgggaagt ctccccacgg tgcgcgctcg gctctgctgt agctgctcaa gacgcctccc    24480
tttttagccg ctaaaactct aacgagtgcg cccgcgactc aacttgacgc tttcggcact    24540
tacctgtgcc ttgccacttg cgtcataggt gatgcttttc gcactcccga tttcaggtac    24600
tttatcgaaa tctgaccggg cgtgcattac aaagttcttc cccacctgtt ggtaaatgct    24660
gccgctatct gcgtggacga tgctgccgtc gtggcgctgc gacttatcgg ccttttgggc    24720
catatagatg ttgtaaatgc caggtttcag ggccccggct ttatctacct tctggttcgt    24780
ccatgcgcct tggttctcgg tctggacaat tctttgccca ttcatgacca ggaggcggtg    24840
tttcattggg tgactcctga cggttgcctc tggtgttaaa cgtgtcctgg tcgcttgccg    24900
gctaaaaaaa agccgacctc ggcagttcga ggccggcttt ccctagagcc gggcgcgtca    24960
aggttgttcc atctatttta gtgaactgcg ttcgatttat cagttacttt cctcccgctt    25020
tgtgtttcct cccactcgtt tccgcgtcta gccgaccct caacatagcg gcctcttctt    25080
gggctgcctt tgcctcttgc gcgcgcttcgt cacgctcggc ttgcaccgtc gtaaagcgct    25140
cggcctgcct ggccgcctct tgcgccgcca acttcctttg ctcctggtgg gcctcggcgt    25200
cggcctgcgc cttcgctttc accgctgcca actccgtgcg caaactctcc gcttcgcgcc    25260
tggtggcgtc gcgctcgccg cgaagcgcct gcatttcctg gttggccgcg tccagggtct    25320
tgcggctctc ttctttgaat gcgcgggcgt cctggtgagc gtagtccagc tcggcgcgca    25380
gctcctgcgc tcgacgctcc acctcgtcgg cccgctgcgt cgccagcgcg gcccgctgct    25440
```

```
cggctcctgc cagggcggtg cgtgcttcgg ccagggcttg ccgctggcgt gcggccagct   25500
cggccgcctc ggcggcctgc tgctctagca atgtaacgcg cgcctgggct tcttccagct   25560
cgcgggcctg cgcctcgaag gcgtcggcca gctcccgcg cacggcttcc aactcgttgc    25620
gctcacgatc ccagccggct tgcgctgcct gcaacgattc attggcaagg gcctgggcgg   25680
cttgccagag ggcggccacg gcctggttgc cggcctgctg caccgcgtcc ggcacctgga   25740
ctgccagcgg ggcggcctgc gccgtgcgct ggcgtcgcca ttcgcgcatg ccggcgctgg   25800
cgtcgttcat gttgacgcgg gcggccttac gcactgcatc cacggtcggg aagttctccc   25860
ggtcgccttg ctcgaacagc tcgtccgcag ccgcaaaaat gcggtcgcgc gtctctttgt   25920
tcagttccat gttggctccg gtaattggta agaataataa tactcttacc taccttatca   25980
gcgcaagagt ttagctgaac agttctcgac ttaacggcag ttttttagc ggctgaaggg    26040 caggcaaaaa aagccccgca cggtcggcgg gggcaaaggg tcagcgggaa ggggattagc   26100
gggcgtcggg cttcttcatg cgtcgggcc gcgcttcttg ggatggagca cgacgaagcg    26160
cgcacgcgca tcgtcctcgg ccctatcggc ccgcgtcgcg gtcaggaact tgtcgcgcgc   26220
taggtcctcc ctggtgggca ccaggggcat gaactcggcc tgctcgatgt aggtccactc   26280
catgaccgca tcgcagtcga ggccgcgttc cttcaccgtc tcttgcaggt cgcggtacgc   26340
ccgctcgttg agcggctggt aacgggccaa ttggtcgtaa atggctgtcg gccatgagcg   26400
gcctttcctg ttgagccagc agccgacgac gaagccggca atgcaggccc ctggcacaac   26460
caggccgacg ccgggggcag gggatggcag cagctcgcca accaggaacc ccgccgcgat   26520
gatgccgatg ccggtcaacc agcccttgaa actatccggc cccgaaacac ccctgcgcat   26580
tgcctggatg ctgcgccgga tagcttgcaa catcaggagc cgtttctttt gttcgtcagt   26640
catggtccgc cctcaccagt tgttcgtatc ggtgtcggac gaactgaaat cgcaagagct   26700
gccggtatcg gtccagccgc tgtccgtgtc gctgctgccg aagcacgcg agggtccgc     26760 gaacgccgca gacggcgtat ccggccgcag cgcatcgccc agcatggccc cggtcagcga   26820
gccgccggcc aggtagccca gcatggtgct gttggtcgcc ccggccacca gggccgacgt   26880
gacgaaatcg ccgtcattcc ctctggattg ttcgctgctc ggcggggcag tgcgccgcgc   26940
cggcggcgtc gtggatggct cgggttggct ggcctgcgac ggccggcgaa aggtgcgcag   27000
cagctcgtta tcgaccggct gcggcgtcgg ggccgccgcc ttgcgctgcg gtcggtgttc   27060
cttcttcggc tcgcgcagct tgaacagcat gatcgcggaa accagcagca acgccgcgcc   27120
tacgcctccc gcgatgtaga acagcatcgg attcattctt cggtcctcct tgtagcggaa   27180
ccgttgtctg tgcggcgcgg gtggcccgcg ccgctgtctt tggggatcag ccctcgatga   27240
gcgcgaccag tttcacgtcg gcaaggttcg cctcgaactc ctggccgtcg tcctcgtact   27300
tcaaccaggc atagccttcc gccggcggcc gacggttgag gataaggcgg gcagggcgct   27360
cgtcgtgctc gacctggacg atggcctttt tcagcttgtc cgggtccggc tccttcgcgc   27420
ccttttcctt ggcgtcctta ccgtcctggt cgccgtcctc gccgtcctgg ccgtcgccgg   27480
cctccgcgtc acgctcggca tcagtctggc cgttgaaggc atcgacggtg ttgggatcgc   27540
ggcccttctc gtccaggaac tcgcgcagca gcttgaccgt gccgcgcgtg atttcctggg   27600
tgtcgtcgtc aagccacgcc tcgacttcct ccgggcgctt cttgaaggcc gtcaccagct   27660
cgttcaccac ggtcacgtcg cgcacgcggc cggtgttgaa cgcatcggcg atcttctccg   27720
gcaggtccag cagcgtgacg tgctgggtga tgaacgccgg cgacttgccg atttccttgg   27780
```

```
cgatatcgcc tttcttcttg cccttcgcca gctcgcggcc aatgaagtcg gcaatttcgc    27840
gcggggtcag ctcgttgcgt tgcaggttct cgataacctg gtcggcttcg ttgtagtcgt    27900
tgtcgatgaa cgccgggatg gacttcttgc cggcccactt cgagccacgg tagcggcggg    27960
cgccgtgatt gatgatatag cggcccggct gctcctggtt ctcgcgcacc gaaatgggtg    28020
acttcacccc gcgctctttg atcgtggcac cgatttccgc gatgctctcc ggggaaaagc    28080
cggggttgtc ggccgtccgc ggctgatgcg gatcttcgtc gatcaggtcc aggtccagct    28140
cgatagggcc ggaaccgccc tgagacgccg caggagcgtc caggaggctc gacaggtcgc    28200
cgatgctatc caaccccagg ccggacggct gcgccgcgcc tgcggcttcc tgagcggccg    28260
cagcggtgtt tttcttggtg gtcttggctt gagccgcagt cattgggaaa tctccatctt    28320
cgtgaacacg taatcagcca gggcgcgaac ctctttcgat gccttgcgcg cggccgtttt    28380
cttgatcttc cagaccggca caccggatgc gagggcatcg gcgatgctgc tgcgcaggcc    28440
aacggtggcc ggaatcatca tcttggggta cgcggccagc agctcggctt ggtggcgcgc    28500
gtggcgcgga ttccgcgcat cgaccttgct gggcaccatg ccaaggaatt gcagcttggc    28560
gttcttctgg cgcacgttcg caatggtcgt gaccatcttc ttgatgccct ggatgctgta    28620
cgcctcaagc tcgatggggg acagcacata gtcggccgcg aagagggcgg ccgccaggcc    28680
gacgccaagg gtcggggccg tgtcgatcag gcacacgtcg aagccttggt tcgccagggc    28740
cttgatgttc gccccgaaca gctcgcgggc gtcgtccagc gacagccgtt cggcgttcgc    28800
cagtaccggg ttggactcga tgagggcgag gcgcgcggcc tggccgtcgc cggctgcggg    28860
tgcggtttcg gtccagccgc cggcaggac agcgccgaac agcttgcttg catgcaggcc    28920
ggtagcaaag tccttgagcg tgtaggacgc attgccctgg gggtccaggt cgatcacggc    28980
aacccgcaag ccgcgctcga aaagtcgaa ggcaagatgc acaagggtcg aagtcttgcc    29040
gacgccgcct ttctggttgg ccgtgaccaa agttttcatc gtttggtttc ctgttttttc    29100
ttggcgtccg cttcccactt ccggacgatg tacgcctgat gttccggcag aaccgccgtt    29160
acccgcgcgt accctcggg caagttcttg tcctcgaacg cggcccacac gcgatgcacc    29220
gcttgcgaca ctgcgcccct ggtcagtccc agcgacgttg cgaacgtcgc ctgtggcttc    29280
ccatcgacta agacgccccg cgctatctcg atggtctgct gccccacttc cagcccctgg    29340
atcgcctcct ggaactggct ttcggtaagc cgtttcttca tggataacac ccataatttg    29400
ctccgcgcct tggttgaaca tagcggtgac agccgccagc acatgagaga agtttagcta    29460
aacatttctc gcacgtcaac accttttagcc gctaaaactc gtccttggcg taacaaaaca    29520
aaagcccgga aaccgggctt tcgtctcttg ccgcttatgg ctctgcaccc ggctccatca    29580
ccaacaggtc gcgcacgcgc ttcactcggt tgcggatcga cactgccagc caacaaagc    29640 cggttgccgc cgccgccagg atcgcgccga tgatgccggc cacaccggcc atcgcccacc    29700
aggtcgccgc cttccggttc cattcctgct ggtactgctt cgcaatgctg gacctcggct    29760
caccataggc tgaccgctcg atggcgtatg ccgcttctcc ccttggcgta aaacccagcg    29820
ccgcaggcgg cattgccatg ctgcccgccg cttccccgac cacgacgcgc gcaccaggct    29880
tgcggtccag accttcggcc acggcgagct gcgcaaggca ataatcagcc gccgacttgg    29940
ctccacgcgc ctcgatcagc tcttgcactc gcgcgaaatc cttggcctcc acggccgcca    30000
tgaatcgcgc acgcggcgaa ggctccgcag ggcggcgtc gtgatcgccg ccagaatgc    30060 ccttcaccaa gttcgacgac acgaaaatca tgctgacggc tatcaccatc atgcagacgg    30120
atcgcacgaa cccgctgaat tgaacacgag cacggcaccc gcgaccacta tgccaagaat    30180
```

```
gcccaaggta aaaattgccg gccccgccat gaagtccgtg aatgcccga cggccgaagt    30240
gaagggcagg ccgccaccca ggccgccgcc ctcactgccc ggcacctggt cgctgaatgt    30300
cgatgccagc acctgcggca cgtcaatgct tccgggcgtc gcgctcgggc tgatcgccca    30360
tcccgttact gccccgatcc cggcaatggc aaggactgcc agcgctgcca tttttggggt    30420
gaggccgttc gcggccgagg ggcgcagccc ctgggggat gggaggcccg cgttagcggg     30480
ccgggagggt tcgagaaggg ggggcacccc ccttcggcgt gcgcggtcac gcgcacaggg    30540
cgcagccctg gttaaaaaca aggtttataa atattggttt aaaagcaggt taaaagacag    30600
gttagcggtg gccgaaaaac gggcggaaac ccttgcaaat gctggatttt ctgcctgtgg    30660
acagcccctc aaatgtcaat aggtgcgccc ctcatctgtc agcactctgc ccctcaagtg    30720
tcaaggatcg cgcccctcat ctgtcagtag tcgcgcccct caagtgtcaa taccgcaggg    30780
cacttatccc caggcttgtc cacatcatct gtgggaaact cgcgtaaaat caggcgtttt    30840
cgccgatttg cgaggctggc cagctccacg tcgccggccg aaatcgagcc tgcccctcat    30900
ctgtcaacgc cgcgccgggt gagtcggccc ctcaagtgtc aacgtccgcc cctcatctgt    30960
cagtgagggc caagttttcc gcgaggtatc cacaacgccg gcggccgcgg tgtctcgcac    31020
acggcttcga cggcgtttct ggcgcgtttg cagggccata gacggccgcc agcccagcgg    31080
cgagggcaac cagcccggtg agcgtcggaa aggcgctgga agccccgtag cgacgcggag    31140
aggggcgaga caagccaagg gcgcaggctc gatgcgcagc acgacatagc cggttctcgc    31200
aaggacgaga atttccctgc ggtgcccctc aagtgtcaat gaaagtttcc aacgcgagcc    31260
attcgcgaga gccttgagtc cacgctagat gagagctttg ttgtaggtgg accagttggt    31320
gattttgaac ttttgctttg ccacggaacg gtctgcgttg tcgggaagat gcgtgatctg    31380
atccttcaac tcagcaaaag ttcgatttat tcaacaaagc cacgttgtgt ctcaaaatct    31440
ctgatgttac attgcacaag ataaaaatat atcatcatga acaataaaac tgtctgctta    31500
cataaacagt aatacaaggg gtgttatgag ccatattcaa cgggaaacgt cttgctcgac    31560
tctagagctc gttcctcgag gaacggtacc tgcggggaag cttacaataa tgtgtgttgt    31620
taagtcttgt tgcctgtcat cgtctgactg actttcgtca taaatcccgg cctccgtaac    31680
ccagctttgg gcaagctcac ggatttgatc cggcggaacg ggaatatcga gatgccgggc    31740
tgaacgctgc agttccagct ttcccttcg ggacaggtac tccagctgat tgattatctg     31800
ctgaagggtc ttggttccac ctcctggcac aatgcgaatg attacttgag cgcgatcggg    31860
catccaattt tctcccgtca ggtgcgtggt caagtgctac aaggcacctt tcagtaacga    31920
gcgaccgtcg atccgtcgcc gggatacgga caaaatggag cgcagtagtc catcgagggc    31980
ggcgaaagcc tcgccaaaag caatacgttc atctcgcaca gcctccagat ccgatcgagg    32040
gtcttcggcg taggcagata gaagcatgga tacattgctt gagagtattc cgatggactg    32100
aagtatggct tccatctttt ctcgtgtgtc tgcatctatt tcgagaaagc ccccgatgcg    32160
gcgcaccgca acgcgaattg ccatactatc cgaaagtccc agcaggcgcg cttgatagga    32220
aaaggtttca tactcggccg atcgcagacg ggcactcacg accttgaacc cttcaacttt    32280
cagggatcga tgctggttga tggtagtctc actcgacgtg gctctggtgt gttttgacat    32340
agcttcctcc aaagaaagcg gaaggtctgg atactccagc acgaaatgtg cccgggtaga    32400
cggatggaag tctagccctg ctcaatatga aatcaacagt acatttacag tcaatactga    32460
atatacttgc tacatttgca attgtcttat aacgaatgtg aaataaaaat agtgtaacaa    32520
```

```
cgcttttact catcgataat cacaaaaaca tttatacgaa caaaaatcaa aatgcactcc   32580
ggtttcacag dataggcggg atcagaatat gcaacttttg acgttttgtt ctttcaaagg   32640
gggtgctggc aaaaccaccg cactcatggg cctttgcgct gctttggcaa atgacggtaa   32700
acgagtggcc ctctttgatg ccgacgaaaa ccggcctctg acgcgatgga gagaaaacgc   32760
cttacaaagc agtactggga tcctcgctgt gaagtctatt ccgccgacga aatgcccctt   32820
cttgaagcag cctatgaaaa tgccgagctc gaaggatttg attatgcgtt ggccgatacg   32880
cgtggcggct cgagcgagct caacaacaca atcatcgcta gctcaaacct gcttctgatc   32940
cccaccatgc taacgccgct cgacatcgat gaggcactat ctacctaccg ctacgtcatc   33000
gagctgctgt tgagtgaaaa tttggcaatt cctacagctg ttttgcgcca acgcgtcccg   33060
gtcggccgat tgacaacatc gcaacgcagg atgtcagaga cgctagagag ccttccagtt   33120
gtaccgtctc ccatgcatga aagagatgca tttgccgcga tgaaagaacg cggcatgttg   33180
catcttacat tactaaacac gggaactgat ccgacgatgc gcctcataga gaggaatctt   33240
cggattgcga tggaggaagt cgtggtcatt tcgaaactga tcagcaaaat cttggaggct   33300
tgaagatggc aattcgcaag cccgcattgt cggtcggcga agcacggcgg cttgctggtg   33360
ctcgacccga gatccaccat cccaaccega cacttgttcc ccagaagctg gacctccagc   33420
acttgcctga aaaagccgac gagaaagacc agcaacgtga gcctctcgtc gccgatcaca   33480
tttacagtcc cgatcgacaa cttaagctaa ctgtggatgc ccttagtcca cctccgtccc   33540
cgaaaaagct ccaggttttt ctttcagcgc gaccgcccgc gcctcaagtg tcgaaaacat   33600
atgcaacctc cgttcggcaa tacagtccct cgaagtcgct acaaatgatt ttaaggcgcg   33660
cgttggacga tttcgaaagc atgctggcag atggatcatt tcgcgtggcc ccgaaaagtt   33720
atccgatccc ttcaactaca gaaaaatccg ttctcgttca gacctcacgc atgttcccgg   33780
ttgcgttgct cgaggtcgct cgaagtcatt ttgatccgtt ggggttggag accgctcgag   33840
cttccggcca caagctggct accgccgcgc tcgcgtcatt ctttgctgga gagaagccat   33900
cgagcaattg gtgaagaggg acctatcgga accectcacc aaatattgag tgtaggtttg   33960
aggccgctgg ccgcgtcctc agtcaccttt tgagccagat aattaagagc caaatgcaat   34020
tggctcaggc tgccatcgtc cccccgtgcg aaacctgcac gtccgcgtca agaaataac   34080 cggcacctct tgctgttttt atcagttgag ggcttgacgg atccgcctca gtttgcggc   34140 gcagccgcaa aatgagaaca tctatactcc tgtcgtaaac ctcctcgtcg cgtactcgac   34200
tggcaatgag aagttgctcg cgcgatgaa cgtcgcgggg tttctctaaa aacgcgagga   34260
gaagattgaa ctcacctgcc gtaagtttca cctcaccgcc agcttcggac atcaagcgac   34320
gttgcctgag attaagtgtc cagtcagtaa aacaaaaaga ccgtcggtct ttggagcgga   34380
caacgttggg gcgcacgcgc aaggcaaccc gaatgcgtgc aagaaactct ctcgtactaa   34440
acggcttagc gataaaatca cttgctccta gctcgagtgc aacaacttta tccgtctcct   34500
caaggcggtc gccactgata attatgattg gaatatcaga ctttgccgcc agatttcgaa   34560
cgatctcaag cccatcttca cgacctaaat ttagatcaac aaccacgaca tcgaccgtcg   34620
cggaagagag tactctagtg aactgggtgc tgtcggctac cgcggtcact ttgaaggcgt   34680
ggatcgtaag gtattcgata ataagatgcc gcatagcgac atcgtcatcg ataagaagaa   34740 cgtgttttcaa cggctcacct ttcaatctaa aatctgaacc cttgttcaca gcgcttgaga   34800 aatttttcacg tgaaggatgt acaatcatct ccagctaaat gggcagttcg tcagaattgc   34860
ggctgaccgc ggatgacgaa aatgcgaacc aagtatttca atttatgac aaaagttctc   34920
```

```
aatcgttgtt acaagtgaaa cgcttcgagg ttacagctac tattgattaa ggagatcgcc   34980
tatggtctcg ccccggcgtc gtgcgtccgc cgcgagccag atctcgccta cttcataaac   35040
gtcctcatag gcacggaatg gaatgatgac atcgatcgcc gtagagagca tgtcaatcag   35100
tgtgcgatct tccaagctag caccttgggc gctactttttg acaagggaaa acagtttctt   35160
gaatccttgg attggattcg cgccgtgtat tgttgaaatc gatcccggat gtcccgagac   35220
gacttcactc agataagccc atgctgcatc gtcgcgcatc tcgccaagca atatccggtc   35280
cggccgcata cgcagacttg cttggagcaa gtgctcggcg ctcacagcac ccagcccagc   35340
accgttcttg gagtagagta gtctaacatg attatcgtgt ggaatgacga gttcgagcgt   35400
atcttctatg gtgattagcc tttcctgggg ggggatggcg ctgatcaagg tcttgctcat   35460
tgttgtcttg ccgcttccgg tagggccaca tagcaacatc gtcagtcggc tgacgacgca   35520
tgcgtgcaga aacgcttcca aatccccgtt gtcaaaatgc tgaaggatag cttcatcatc   35580
ctgattttgg cgtttccttc gtgtctgcca ctggttccac ctcgaagcat cataacggga   35640
ggagacttct ttaagaccag aaacacgcga gcttggccgt cgaatggtca agctgacggt   35700
gcccgaggga acgtcggcg gcagacagat ttgtagtcgt tcaccaccag gaagttcagt   35760
ggcgcagagg gggttacgtg gtccgacatc ctgctttctc agcgcgcccg ctaaaatagc   35820
gatatcttca agatcatcat aagagacggg caaaggcatc ttggtaaaaa tgccggcttg   35880
gcgcacaaat gcctctccag gtcgattgat cgcaatttct tcagtcttcg ggtcatcgag   35940
ccattccaaa atcggcttca gaagaaagcg tagttgcgga tccacttcca tttacaatgt   36000
atcctatctc taagcggaaa tttgaattca ttaagagcgg cggttcctcc cccgcgtggc   36060
gccgccagtc aggcggagct ggtaaacacc aaagaaatcg aggtcccgtg ctacgaaaat   36120
ggaaacggtg tcaccctgat tcttcttcag ggttggcggt atgttgatgg ttgccttaag   36180
ggctgtctca gttgtctgct caccgttatt ttgaaagctg ttgaagctca tcccgccacc   36240
cgagctgccg gcgtaggtgc tagctgcctg gaaggcgcct tgaacaacac tcaagagcat   36300
agctccgcta aaacgctgcc agaagtggct gtcgaccgag cccggcaatc ctgagcgacc   36360
gagttcgtcc gcgcttggcg atgttaacga gatcatcgca tggtcaggtg tctcggcgcg   36420
atcccacaac acaaaaacgc gcccatctcc ctgttgcaag ccacgctgta tttcgccaac   36480
aacggtggtc ccacgatcaa gaagcacgat attgttcgtt gttccacgaa tatcctgagg   36540
caagacacac tttacatagc ctgccaaatt tgtgtcgatt gcggtttgca agatgcacgg   36600
aattattgtc ccttgcgtta ccataaaatc ggggtgcggc aagagcgtgg cgctgctggg   36660
ctgcagctcg gtgggtttca tacgtatcga caaatcgttc tcgccggaca cttcgccatt   36720
cggcaaggag ttgtcgtcac gcttgccttc ttgtcttcgg cccgtgtcgc cctgaatggc   36780
gcgtttgctg acccccttgat cgccgctgct atatgcaaaa atcggtgttt cttccggccg   36840
tggctcatgc cgctccggtt cgcccctcgg cggtagagga gcagcaggct gaacagcctc   36900
ttgaaccgct ggaggatccg gcggcacctc aatcggagct ggatgaaatg gcttggtgtt   36960
tgttgcgatc aaagttgacg gcgatgcgtt ctcattcacc ttcttttggc gcccacctag   37020
ccaaatgagg cttaatgata acgcgagaac gacacctccg acgatcaatt tctgagaccc   37080
cgaaagacgc cggcgatgtt tgtcggagac cagggatcca gatgcatcaa cctcatgtgc   37140
cgcttgctga ctatcgttat tcatcccttc gccccccttca ggacgcgttt cacatcgggc   37200
ctcaccgtgc ccgtttgcgg cctttggcca acgggatcgt aagcggtgtt ccagatacat   37260
```

```
agtactgtgt ggccatccct cagacgccaa cctcgggaaa ccgaagaaat ctcgacatcg   37320
ctcccttta  ctgaatagtt ggcaacagct tccttgccat caggattgat ggtgtagatg   37380
gagggtatgc gtacattgcc cggaaagtgg aataccgtcg taaatccatt gtcgaagact   37440
tcgagtggca acagcgaacg atcgccttgg gcgacgtagt gccaattact gtccgccgca   37500
ccaagggctg tgacaggctg atccaataaa ttctcagctt tccgttgata ttgtgcttcc   37560
gcgtgtagtc tgtccacaac agccttctgt tgtgcctccc ttcgccgagc cgccgcatcg   37620
tcggcgggt  aggcgaattg gacgctgtaa tagagatcgg gctgctcttt atcgaggtgg   37680
gacagagtct tggaacttat actgaaaaca taacggcgca tcccggagtc gcttgcggtt   37740
agcacgatta ctggctgagg cgtgaggacc tggcttgcct tgaaaaatag ataatttccc   37800
cgcggtaggg ctgctagatc tttgctattt gaaacggcaa ccgctgtcac cgtttcgttc   37860
gtggcgaatg ttacgaccaa agtagctcca accgccgtcg agaggcgcac cacttgatcg   37920
ggattgtaag ccaaataacg catgcgcgga tctagcttgc ccgccattgg agtgtcttca   37980
gcctccgcac cagtcgcagc ggcaaataaa catgctaaaa tgaaaagtgc ttttctgatc   38040
atggttcgct gtggcctacg tttgaaacgg tatcttccga tgtctgatag gaggtgacaa   38100
ccagacctgc cgggttggtt agtctcaatc tgccgggcaa gctggtcacc ttttcgtagc   38160
gaactgtcgc ggtccacgta ctcaccacag gcattttgcc gtcaacgacg agggtccttt   38220
tatagcgaat ttgctgcgtg cttggagtta catcatttga agcgatgtgc tcgacctcca   38280
ccctgccgcg tttgccaaga atgacttgag gcgaactggg attgggatag ttgaagaatt   38340
gctggtaatc ctggcgcact gttggggcac tgaagttcga taccaggtcg taggcgtact   38400
gagcggtgtc ggcatcataa ctctcgcgca ggcgaacgta ctcccacaat gaggcgttaa   38460
cgacggcctc ctcttgagtt gcaggcaatc gcgagacaga cacctcgctg tcaacggtgc   38520
cgtccggccg tatccataga tatacgggca caagcctgct caacggcacc attgtggcta   38580
tagcgaacgc ttgagcaaca tttcccaaaa tcgcgatagc tgcgacagct gcaatgagtt   38640
tggagagacg tcgcgccgat ttcgctcgcg cggtttgaaa ggcttctact tccttatagt   38700
gctcggcaag gctttcgcgc gccactagca tggcatattc aggccccgtc atagcgtcca   38760
cccgaattgc cgagctgaag atctgacgga gtaggctgcc atcgcccac  attcagcggg   38820
aagatcgggc ctttgcagct cgctaatgtg tcgtttgtct ggcagccgct caaagcgaca   38880
actaggcaca gcaggcaata cttcatagaa ttctccattg aggcgaattt ttgcgcgacc   38940
tagcctcgct caacctgagc gaagcgacgg tacaagctgc tggcagattg ggttgcgccg   39000
ctccagtaac tgcctccaat gttgccggcg atcgccggca aagcgacaat gagcgcatcc   39060
cctgtcagaa aaacatatc  gagttcgtaa agaccaatga tcttggccgc ggtcgtaccg   39120
gcgaaggtga ttacaccaag cataagggtg agcgcagtcg cttcggttag gatgacgatc   39180
gttgccacga ggtttaagag gagaagcaag agaccgtagg tgataagttg cccgatccac   39240
ttagctgcga tgtcccgcgt gcgatcaaaa atatatccga cgaggatcag aggcccgatc   39300
gcgagaagca ctttcgtgag aattccaacg gcgtcgtaaa ctccgaaggc agaccagagc   39360
gtgccgtaaa ggaccccactg tgccccttgg aaagcaagga tgtcctggtc gttcatcgga   39420
ccgatttcgg atgcgatttt ctgaaaaacg gcctgggtca cggcgaacat tgtatccaac   39480
tgtgccggaa cagtctgcag aggcaagccg gttacactaa actgctgaac aaagtttggg   39540
accgtctttt cgaagatgga aaccacatag tcttggtagt tagcctgccc aacaattaga   39600
gcaacaacga tggtgaccgt gatcacccga gtgataccgc tacgggtatc gacttcgccg   39660
```

```
cgtatgacta aaatacgctg aacaataatc caaagagtga cacaggcgat caatggcgca    39720
ctcaccgcct cctggatagt ctcaagcatc gagtccaagc ctgtcgtgaa ggctacatcg    39780
aagatcgtat gaatggccgt aaacggcgcc ggaatcgtga aattcatcga ttggacctga    39840
acttgactgg tttgtcgcat aatgttggat aaaatgagct cgcattcggc gaggatgcgg    39900
gcggatgaac aaatcgccca gccttagggg agggcaccaa agatgacagc ggtcttttga    39960
tgctccttgc gttgagcggc cgcctcttcc gcctcgtgaa ggccggcctg cgcggtagtc    40020
atcgttaata ggcttgtcgc ctgtacattt gaatcattg cgtcatggat ctgcttgaga     40080
agcaaaccat tggtcacggt tgcctgcatg atattgcgag atcgggaaag ctgagcagac    40140
gtatcagcat tcgccgtcaa gcgtttgtcc atcgtttcca gattgtcagc cgcaatgcca    40200
gcgctgtttg cggaaccggt gatctgcgat cgcaacaggt ccgcttcagc atcactaccc    40260
acgactgcac gatctgtatc gctggtgatc gcacgtgccg tggtcgacat tggcattcgc    40320
ggcgaaaaca tttcattgtc taggtccttc gtcgaaggat actgatttt ctggttgagc     40380
gaagtcagta gtccagtaac gccgtaggcc gacgtcaaca tcgtaaccat cgctatagtc    40440
tgagtgagat tctccgcagt cgcgagcgca gtcgcgagcg tctcagcctc cgttgccggg    40500
tcgctaacaa caaactgcgc ccgcgcgggc tgaatatata gaaagctgca ggtcaaaact    40560
gttgcaataa gttgcgtcgt cttcatcgtt tcctaccta tcaatcttct gcctcgtggt     40620
gacgggccat gaattcgctg agccagccag atgagttgcc ttcttgtgcc tcgcgtagtc    40680
gagttgcaaa gcgcaccgtg ttggcacgcc ccgaaagcac ggcgacatat tcacgcatat    40740
cccgcagatc aaattcgcag atgacgcttc cactttctcg tttaagaaga aacttacggc    40800
tgccgaccgt catgtcttca cggatcgcct gaaattcctt ttcggtacat ttcagtccat    40860
cgacataagc cgatcgatct gcggttggtg atggataaga aatcttcgtc atacattgcg    40920
caaccaagct ggctcctagc ggcgattcca gaacatgctc tggttgctgc gttgccagta    40980
ttagcatccc gttgttttt cgaacggtca ggaggaattt gtcgacgaca gtcgaaaatt     41040
tagggtttaa caaataggcg cgaaaactcat cgcagctcat cacaaaacgg cggccgtcga   41100
tcatggctcc aatccgatgc aggagatatg ctgcagcggg agcgcatact tcctcgtatt    41160
cgagaagatg cgtcatgtcg aagccggtaa tcgacggatc taactttact tcgtcaactt    41220
cgccgtcaaa tgcccagcca agcgcatggc cccggcacca gcgttggagc cgcgctcctg    41280
cgccttcggc gggcccatgc aacaaaaatt cacgtaaccc cgcgattgaa cgcatttgtg    41340
gatcaaacga gagctgacga tggataccac ggaccagacg gcggttctct tccggagaaa    41400
tcccaccccg accatcactc tcgatgagag ccacgatcca ttcgcgcaga aaatcgtgtg    41460
aggctgctgt gttttctagg ccacgcaacg gcgccaaccc gctgggtgtg cctctgtgaa    41520
gtgccaaata tgttcctcct gtggcgcgaa ccagcaattc gccaccccgg tccttgtcaa    41580
agaacacgac cgtacctgca cggtcgacca tgctctgttc gagcatggct agaacaaaca    41640
tcatgagcgt cgtcttaccc ctcccgatag gcccgaatat tgccgtcatg ccaacatcgt    41700
gctcatgcgg gatatagtcg aaaggcgttc cgccattggt acgaaatcgg gcaatcgcgt    41760
tgccccagtg gcctgagctg gcgccctctg gaaagttttc gaaagagaca aaccctgcga    41820
aattgcgtga agtgattgcg ccagggcgtg tgcgccactt aaaattcccc ggcaattggg    41880
accaataggc cgcttccata ccaataccctt cttggacaac cacggcacct gcatccgcca    41940
ttcgtgtccg agcccgcgcg cccctgtccc caagactatt gagatcgtct gcatagacgc    42000
```

```
aaaggctcaa atgatgtgag cccataacga attcgttgct cgcaagtgcg tcctcagcct    42060
cggataattt gccgatttga gtcacggctt tatcgccgga actcagcatc tggctcgatt    42120
tgaggctaag tttcgcgtgc gcttgcgggc gagtcaggaa cgaaaaactc tgcgtgagaa    42180
caagtggaaa atcgagggat agcagcgcgt tgagcatgcc cggccgtgtt tttgcagggt    42240
attcgcgaaa cgaatagatg gatccaacgt aactgtcttt tggcgttctg atctcgagtc    42300
ctcgcttgcc gcaaatgact ctgtcggtat aaatcgaagc gccgagtgag ccgctgacga    42360
ccggaaccgg tgtgaaccga ccagtcatga tcaaccgtag cgcttcgcca atttcggtga    42420
agagcacacc ctgcttctcg cggatgccaa gacgatgcag gccatacgct ttaagagagc    42480
cagcgacaac atgccaaaga tcttccatgt tcctgatctg gcccgtgaga tcgttttccc    42540
tttttccgct tagcttggtg aacctcctct ttaccttccc taaagccgcc tgtgggtaga    42600
caatcaacgt aaggaagtgt tcattgcgga ggagttggcc ggagagcacg cgctgttcaa    42660
aagcttcgtt caggctagcg gcgaaaacac tacggaagtg tcgcggcgcc gatgatggca    42720
cgtcggcatg acgtacgagg tgagcatata ttgacacatg atcatcagcg atattgcgca    42780
acagcgtgtt gaacgcacga caacgcgcat tgcgcatttc agtttcctca agctcgaatg    42840
caacgccatc aattctcgca atggtcatga tcgatccgtc ttcaagaagg acgatatggt    42900
cgctgaggtg gccaatataa gggagataga tctcaccgga tctttcggtc gttccactcg    42960
cgccgagcat cacaccattc ctctccctcg tgggggaacc ctaattggat ttgggctaac    43020
agtagcgccc ccccaaactg cactatcaat gcttcttccc gcggtccgca aaaatagcag    43080
gacgacgctc gccgcattgt agtctcgctc cacgatgagc cgggctgcaa accataacgg    43140
cacgagaacg acttcgtaga gcgggttctg aacgataacg atgacaaagc cggcgaacat    43200
catgaataac cctgccaatg tcagtggcac cccaagaaac aatgcgggcc gtgtggctgc    43260
gaggtaaagg gtcgattctt ccaaacgatc agccatcaac taccgccagt gagcgtttgg    43320
ccgaggaagc tcgccccaaa catgataaca atgccgccga cgacgccggc aaccagccca    43380
agcgaagccc gcccgaacat ccaggagatc ccgatagcga caatgccgag aacagcgagt    43440
gactggccga acgaccaag gataaacgtg catatattgt taaccattgt ggcggggtca    43500
gtgccgccac ccgcagattg cgctgcggcg ggtccggatg aggaaatgct ccatgcaatt    43560
gcaccgcaca agcttggggc gcagctcgat atcacgcgca tcatcgcatt cgagagcgag    43620
aggcgattta gatgtaaacg gtatctctca aagcatcgca tcaatgcgca cctccttagt    43680
ataagtcgaa taagacttga ttgtcgtctg cggatttgcc gttgtcctgg tgtggcggtg    43740
gcggagcgat taaccgcca gcgccatcct cctgcgagcg gcgctgatat gaccccccaaa    43800 catcccacgt ctcttcggat tttagcgcct cgtgatcgtc ttttggaggc tcgattaacg    43860
cgggcaccag cgattgagca gctgtttcaa cttttcgcac gtagccgttt gcaaaaccgc    43920
cgatgaaatt accggtgttg taagcggaga tcgcccgacg aagcgcaaat tgcttctcgt    43980
caatcgtttc gccgcctgca taacgacttt tcagcatgtt tgcagcggca gataatgatg    44040
tgcacgcctg gagcgcaccg tcaggtgtca gaccgagcat agaaaaattt cgagagttta    44100
tttgcatgag gccaacatcc agcgaatgcc gtgcatcgag acggtgcctg acgacttggg    44160
ttgcttggct gtgatcttgc cagtgaagcg tttcgccggt cgtgttgtca tgaatcgcta    44220
aaggatcaaa gcgactctcc accttagcta tcgccgcaag cgtagatgtc gcaactgatg    44280
gggcacactt gcgagcaaca tggtcaaact cagcagatga gagtggcgtg gcaaggctcg    44340
acgaacagaa ggagaccatc aaggcaagag aaagcgaccc cgatctctta agcataccctt    44400
```

```
atctccttag ctcgcaacta acaccgcctc tcccgttgga agaagtgcgt tgttttatgt   44460
tgaagattat cgggagggtc ggttactcga aaattttcaa ttgcttcttt atgatttcaa   44520
ttgaagcgag aaacctcgcc cggcgtcttg gaacgcaaca tggaccgaga accgcgcatc   44580
catgactaag caaccggatc gacctattca ggccgcagtt ggtcaggtca ggctcagaac   44640
gaaaatgctc ggcgaggtta cgctgtctgt aaacccattc gatgaacggg aagcttcctt   44700
ccgattgctc ttggcaggaa tattggccca tgcctgcttg cgctttgcaa atgctcttat   44760
cgcgttggta tcatatgcct tgtccgccag cagaaacgca ctctaagcga ttatttgtaa   44820
aaatgtttcg gtcatgcggc ggtcatgggc ttgacccgct gtcagcgcaa gacggatcgg   44880
tcaaccgtcg gcatcgacaa cagcgtgaat cttggtggtc aaaccgccac gggaacgtcc   44940
catacagcca tcgtcttgat cccgctgttt cccgtcgccg catgttggtg gacgcggaca   45000
caggaactgt caatcatgac gacattctat cgaaagcctt ggaaatcaca ctcagaatat   45060
gatcccagac gtctgcctca cgccatcgta caaagcgatt gtagcaggtt gtacaggaac   45120
cgtatcgatc aggaacgtct gcccagggcg ggcccgtccg gaagcgccac aagatgacat   45180
tgatcacccg cgtcaacgcg cggcacgcga cgcggcttat ttgggaacaa aggactgaac   45240
aacagtccat tcgaaatcgg tgacatcaaa gcggggacgg gttatcagtg gcctccaagt   45300
caagcctcaa tgaatcaaaa tcagaccgat ttgcaaacct gatttatgag tgtgcggcct   45360
aaatgatgaa atcgtccttc tagatcgcct ccgtggtgta gcaacacctc gcagtatcgc   45420
cgtgctgacc ttggccaggg aattgactgg caagggtgct ttcacatgac cgctcttttg   45480
gccgcgatag atgatttcgt tgctgctttg ggcacgtaga aggagagaag tcatatcgga   45540
gaaattcctc ctggcgcgag agcctgctct atcgcgacgg catcccactg tcgggaacag   45600
accggatcat tcacgaggcg aaagtcgtca acacatgcgt tataggcatc ttcccttgaa   45660
ggatgatctt gttgctgcca atctggaggt gcggcagccg caggcagatg cgatctcagc   45720
gcaacttgcg gcaaaacatc tcactcacct gaaaaccact agcgagtctc gcgatcagac   45780
gaaggccttt tacttaacga cacaatatcc gatgtctgca tcacaggcgt cgctatccca   45840
gtcaatacta aagcggtgca ggaactaaag attactgatg acttaggcgt gccacgaggc   45900
ctgagacgac gcgcgtagac agttttttga aatcattatc aaagtgatgg cctccgctga   45960
agcctatcac ctctgcgccg gtctgtcgga gagatgggca agcattatta cggtcttcgc   46020
gcccgtacat gcattggacg attgcagggt caatggatct gagatcatcc agaggattgc   46080
cgcccttacc ttccgtttcg agttggagcc agccctaaa tgagacgaca tagtcgactt    46140
gatgtgacaa tgccaagaga gagatttgct taacccgatt tttttgctca agcgtaagcc   46200
tattgaagct tgccggcatg acgtccgcgc cgaaagaata tcctacaagt aaaacattct   46260
gcacaccgaa atgcttggtg tagacatcga ttatgtgacc aagatcctta gcagtttcgc   46320
ttggggaccg ctccgaccag aaataccgaa gtgaactgac gccaatgaca ggaatccctt   46380
ccgtctgcag ataggtacca tcgatagatc tgctgcctcg cgcgtttcgg tgatgacggt   46440
gaaaacctct gacacatgca gctcccggag acggtcacag cttgtctgta agcggatgcc   46500
gggagcagac aagcccgtca gggcgcgtca gcgggtgttg gcgggtgtcg gggcgcagcc   46560
atgacccagt cacgtagcga tagcggagtg tatactggct taactatgcg gcatcagagc   46620
agattgtact gagagtgcac catatgcggt gtgaaatacc gcacagatgc gtaaggagaa   46680
aataccgcat caggcgctct tccgcttcct cgctcactga ctcgctgcgc tcggtcgttc   46740
```

```
ggctgcggcg agcggtatca gctcactcaa aggcggtaat acggttatcc acagaatcag    46800
gggataacgc aggaaagaac atgtgagcaa aaggccagca aaaggccagg aaccgtaaaa    46860
aggccgcgtt gctggcgttt ttccataggc tccgcccccc tgacgagcat cacaaaaatc    46920
gacgctcaag tcagaggtgg cgaaacccga caggactata aagataccag gcgtttcccc    46980
ctggaagctc cctcgtgcgc tctcctgttc cgaccctgcc gcttaccgga tacctgtccg    47040
cctttctccc ttcgggaagc gtggcgcttt ctcatagctc acgctgtagg tatctcagtt    47100
cggtgtaggt cgttcgctcc aagctgggct gtgtgcacga accccccgtt cagcccgacc    47160
gctgcgcctt atccggtaac tatcgtcttg agtccaaccc ggtaagacac gacttatcgc    47220
cactggcagc agccactggt aacaggatta gcagagcgag gtatgtaggc ggtgctacag    47280
agttcttgaa gtggtggcct aactacggct acactagaag gacagtattt ggtatctgcg    47340
ctctgctgaa gccagttacc ttcggaaaaa gagttggtag ctcttgatcc ggcaaacaaa    47400
ccaccgctgg tagcggtggt ttttttgttt gcaagcagca gattacgcgc agaaaaaaag    47460
gatctcaaga agatcctttg atcttttcta cggggtctga cgctcagtgg aacgaaaact    47520
cacgttaagg gattttggtc atgagattat caaaaaggat cttcacctag atccttttaa    47580
attaaaaatg aagtttttaaa tcaatctaaa gtatatatga gtaaacttgg tctgacagtt    47640
accaatgctt aatcagtgag gcacctatct cagcgatctg tctatttcgt tcatccatag    47700
ttgcctgact ccccgtcgtg tagataacta cgatacggga gggcttacca tctggcccca    47760
gtgctgcaat gataccgcga gacccacgct caccggctcc agatttatca gcaataaacc    47820
agccagccgg aagggccgag cgcagaagtg gtcctgcaac tttatccgcc tccatccagt    47880
ctattaattg ttgccgggaa gctagagtaa gtagttcgcc agttaatagt ttgcgcaacg    47940
ttgttgccat tgctgcaggg ggggggggg gggggactt ccattgttca ttccacggac     48000
aaaaacagag aaaggaaacg acagaggcca aaaagcctcg ctttcagcac ctgtcgtttc    48060
ctttcttttc agagggtatt ttaaataaaa acattaagtt atgacgaaga agaacgaaa    48120 cgccttaaac cggaaaattt tcataaatag cgaaaacccg cgaggtcgcc gccccgtagt    48180
cggatcaccg gaaaggaccc gtaaagtgat aatgattatc atctacatat cacaacgtgc    48240
gtggaggcca tcaaaccacg tcaaataatc aattatgacg caggtatcgt attaattgat    48300
ctgcatcaac ttaacgtaaa aacaacttca gacaatacaa atcagcgaca ctgaatacgg    48360
ggcaacctca tgtcccccccc cccccccccc ctgcaggcat cgtggtgtca cgctcgtcgt    48420
ttggtatggc ttcattcagc tccggttccc aacgatcaag gcgagttaca tgatccccca    48480
tgttgtgcaa aaaagcggtt agctccttcg gtcctccgat cgttgtcaga agtaagttgg    48540
ccgcagtgtt atcactcatg gttatggcag cactgcataa ttctcttact gtcatgccat    48600
ccgtaagatg cttttctgtg actggtgagt actcaaccaa gtcattctga aatagtgta    48660 tgcggcgacc gagttgctct tgcccggcgt caacacggga taataccgcg ccacatagca    48720
gaactttaaa agtgctcatc attggaaaac gttcttcggg gcgaaaactc tcaaggatct    48780
taccgctgtt gagatccagt tcgatgtaac ccactcgtgc acccaactga tcttcagcat    48840
cttttacttt caccagcgtt tctgggtgag caaaaacagg aaggcaaaat gccgcaaaaa    48900
agggaataag ggcgacacgg aaatgttgaa tactcatact cttcctttttt caatattatt    48960 gaagcattta tcagggttat tgtctcatga gcggatacat atttgaatgt atttagaaaa    49020
ataaacaaat aggggttccg cgcacatttc cccgaaaagt gccacctgac gtctaagaaa    49080
ccattattat catgacatta acctataaaa ataggcgtat cacgaggccc tttcgtcttc    49140
```

```
aagaattggt cgacgatctt gctgcgttcg gatattttcg tggagttccc gccacagacc   49200
cggattgaag gcgagatcca gcaactcgcg ccagatcatc ctgtgacgga actttggcgc   49260
gtgatgactg gccaggacgt cggccgaaag agcgacaagc agatcacgct tttcgacagc   49320
gtcggatttg cgatcgagga ttttcggcg ctgcgctacg tccgcgaccg cgttgaggga    49380
```

```
aagaattggt cgacgatctt gctgcgttcg gatattttcg tggagttccc gccacagacc   49200
cggattgaag gcgagatcca gcaactcgcg ccagatcatc ctgtgacgga actttggcgc   49260
gtgatgactg gccaggacgt cggccgaaag agcgacaagc agatcacgct tttcgacagc   49320
gtcggatttg cgatcgagga ttttcggcg ctgcgctacg tccgcgaccg cgttgaggga    49380
tcaagccaca gcagcccact cgaccttcta gccgacccag acgagccaag ggatctttt    49440
ggaatgctgc tccgtcgtca ggctttccga cgtttgggtg gttgaacaga agtcattatc   49500
gtacggaatg ccaagcactc ccgagcggaa ccctgtggtt ggcatgcaca tacaaatgga   49560
cgaacggata aaccttttca cgcccttta aatatccgtt attctaataa acgctctttt    49620
ctcttaggtt tacccgccaa tatatcctgt caaacactga tagtttaaac tgaaggcggg   49680
aaacgacaat ctgatcatga gcggagaatt aagggagtca cgttatgacc cccgccgatg   49740
acgcgggaca agccgtttta cgtttggaac tgacagaacc gcaacgttga aggagccact   49800
cagcaagctg gtacgattgt aatacgactc actatagggc gaattgagcg ctgtttaaac   49860
gctcttcaac tggaagagcg gttacccgga ccgaagcttg catgcctgca g             49911

<210> SEQ ID NO 7
<211> LENGTH: 36909
<212> TYPE: DNA
<213> ORGANISM: Artificial Sequence
<220> FEATURE:
<223> OTHER INFORMATION: PHP10523 construct

<400> SEQUENCE: 7
tctagagctc gttcctcgag gcctcgaggc ctcgaggaac ggtacctgcg gggaagctta      60
caataatgtg tgttgttaag tcttgttgcc tgtcatcgtc tgactgactt tcgtcataaa    120
tcccggcctc cgtaacccag cttttgggcaa gctcacggat ttgatccggc ggaacgggaa   180
tatcgagatg ccgggctgaa cgctgcagtt ccagctttcc ctttcgggac aggtactcca   240
gctgattgat tatctgctga agggtcttgg ttccacctcc tggcacaatg cgaatgatta   300
cttgagcgcg atcgggcatc caattttctc ccgtcaggtg cgtggtcaag tgctacaagg   360
caccttcag taacgagcga ccgtcgatcc gtcgccggga tacggacaaa atggagcgca   420
gtagtccatc gagggcggcg aaagcctcgc caaaagcaat acgttcatct cgcacagcct   480
ccagatccga tcgagggtct tcggcgtagg cagatagaag catggataca ttgcttgaga   540
gtattccgat ggactgaagt atggcttcca tcttttctcg tgtgtctgca tctatttcga   600
gaaagccccc gatgcggcgc accgcaacgc gaattgccat actatccgaa agtcccagca   660
ggcgcgcttg ataggaaaag gtttcatact cggccgatcg cagacgggca ctcacgacct   720
tgaacccttc aactttcagg gatcgatgct ggttgatggt agtctcactc gacgtggctc   780
tggtgtgttt tgacatagct tcctccaaag aaagcggaag gtctggatac tccagcacga   840
aatgtgcccg ggtagacgga tggaagtcta gccctgctca atatgaaatc aacagtacat   900
ttacagtcaa tactgaatat acttgctaca tttgcaattg tcttataacg aatgtgaaat   960
aaaaatagtg taacaacgct tttactcatc gataatcaca aaaacattta tacgaacaaa   1020
aatacaaatg cactccggtt tcacaggata ggcgggatca gaatatgcaa cttttgacgt   1080
tttgttcttt caagggggt gctggcaaaa ccaccgcact catgggcctt tgcgctgctt   1140
tggcaaatga cggtaaacga gtggccctct ttgatgccga cgaaaaccgg cctctgacgc   1200
gatggagaga aaacgcctta caaagcagta ctgggatcct cgctgtgaag tctattccgc   1260
```

-continued

```
cgacgaaatg cccottcttg aagcagccta tgaaaatgcc gagctcgaag gatttgatta    1320
tgcgttggcc gatacgcgtg gcggctcgag cgagctcaac aacacaatca tcgctagctc    1380
aaacctgctt ctgatcccca ccatgctaac gccgctcgac atcgatgagg cactatctac    1440
ctaccgctac gtcatcgagc tgctgttgag tgaaaatttg gcaattccta cagctgtttt    1500
gcgccaacgc gtcccggtcg gccgattgac aacatcgcaa cgcaggatgt cagagacgct    1560
agagagcctt ccagttgtac cgtctcccat gcatgaaaga gatgcatttg ccgcgatgaa    1620
agaacgcggc atgttgcatc ttacattact aaacacggga actgatccga cgatgcgcct    1680
catagagagg aatcttcgga ttgcgatgga ggaagtcgtg gtcatttcga aactgatcag    1740
caaaatcttg gaggcttgaa gatggcaatt cgcaagcccg cattgtcggt cggcgaagca    1800
cggcggcttg ctggtgctcg acccgagatc caccatccca acccgacact tgttccccag    1860
aagctggacc tccagcactt gcctgaaaaa gccgacgaga agaccagca acgtgagcct    1920 ctcgtcgccg atcacattta cagtcccgat cgacaactta gctaactgt ggatgccctt    1980 agtccacctc cgtccccgaa aaagctccag gttttctttt cagcgcgacc gccgcgcct    2040 caagtgtcga aaacatatga caacctcgtt cggcaataca gtccctcgaa gtcgctacaa    2100
atgattttaa ggcgcgcgtt ggacgatttc gaaagcatgc tggcagatgg atcatttcgc    2160
gtggccccga aaagttatcc gatcccttca actacagaaa aatccgttct cgttcagacc    2220
tcacgcatgt tccggttgc gttgctcgag gtcgctcgaa gtcatttga tccgttgggg    2280 ttggagaccg ctcgagcttt cggccacaag ctggctaccg ccgcgctcgc gtcattcttt    2340
gctggagaga agccatcgag caattggtga agagggacct atcggaaccc ctcaccaaat    2400
attgagtgta ggtttgaggc cgctggccgc gtcctcagtc accttttgag ccagataatt    2460
aagagccaaa tgcaattggc tcaggctgcc atcgtccccc cgtgcgaaac ctgcacgtcc    2520
gcgtcaaaga aataaccggc acctcttgct gtttttatca gttgagggct tgacggatcc    2580
gcctcaagtt tgcggcgcag ccgcaaaatg agaacatcta tactcctgtc gtaaacctcc    2640
tcgtcgcgta ctcgactggc aatgagaagt tgctcgcgcg atagaacgtc gcggggtttc    2700
tctaaaaacg cgaggagaag attgaactca cctgccgtaa gtttcacctc accgccagct    2760
tcggacatca agcgacgttg cctgagatta agtgtccagt cagtaaaaca aaaagaccgt    2820
cggtctttgg agcggacaac gttggggcgc acgcgcaagg caacccgaat gcgtgcaaga    2880
aactctctcg tactaaacgg cttagcgata aaatcacttg ctcctagctc gagtgcaaca    2940
actttatccg tctcctcaag gcggtcgcca ctgataatta tgattggaat atcagacttt    3000
gccgccagat ttcgaacgat ctcaagccca tcttcacgac ctaaatttag atcaacaacc    3060 acgcatcga ccgtcgcgga agagagtact ctagtgaact gggtgctgtc ggctaccgcg    3120
gtcactttga aggcgtggat cgtaaggtat tcgataataa gatgccgcat agcgacatcg    3180
tcatcgataa gaagaacgtg tttcaacggc tcacctttca atctaaaatc tgaacccttg    3240
ttcacagcgc ttgagaaatt ttcacgtgaa ggatgtacaa tcatctccag ctaaatgggc    3300
agttcgtcag aattgcggct gaccgcggat gacgaaaatg cgaaccaagt atttcaattt    3360
tatgacaaaa gttctcaatc gttgttacaa gtgaaacgct tcgaggttac agctactatt    3420
gattaaggag atcgcctatg gtctcgcccc ggcgtcgtgc gtccgccgcg agccagatct    3480
cgcctacttc ataaacgtcc tcataggcac ggaatggaat gatgacatcg atcgccgtag    3540
agagcatgtc aatcagtgtg cgatcttcca agctagcacc ttgggcgcta cttttgacaa    3600
gggaaaacag tttcttgaat ccttggattg gattcgcgcc gtgtattgtt gaaatcgatc    3660
```

```
ccggatgtcc cgagacgact tcactcagat aagcccatgc tgcatcgtcg cgcatctcgc    3720
caagcaatat ccggtccggc cgcatacgca gacttgcttg gagcaagtgc tcggcgctca    3780
cagcacccag cccagcaccg ttcttggagt agagtagtct aacatgatta tcgtgtggaa    3840
tgacgagttc gagcgtatct tctatggtga ttagcctttc ctgggggggg atggcgctga    3900
tcaaggtctt gctcattgtt gtcttgccgc ttccggtagg gccacatagc aacatcgtca    3960
gtcggctgac gacgcatgcg tgcagaaacg cttccaaatc cccgttgtca aaatgctgaa    4020
ggatagcttc atcatcctga ttttggcgtt tccttcgtgt ctgccactgg ttccacctcg    4080
aagcatcata acgggaggag acttctttaa gaccagaaac acgcgagctt ggccgtcgaa    4140
tggtcaagct gacggtgccc gagggaacgg tcggcggcag acagatttgt agtcgttcac    4200
caccaggaag ttcagtggcg cagaggggt acgtggtcc gacatcctgc tttctcagcg    4260
cgcccgctaa aatagcgata tcttcaagat catcataaga gacgggcaaa ggcatcttgg    4320
taaaaatgcc ggcttggcgc acaaatgcct ctccaggtcg attgatcgca atttcttcag    4380
tcttcgggtc atcgagccat tccaaaatcg gcttcagaag aaagcgtagt tgcggatcca    4440 cttccatta caatgtatcc tatctctaag cggaaatttg aattcattaa gagcggcggt    4500 tcctccccg cgtggcgccg ccagtcaggc ggagctggta acaccaaag aaatcgaggt    4560 cccgtgctac gaaaatggaa acggtgtcac cctgattctt cttcagggtt ggcggtatgt    4620
tgatggttgc cttaagggct gtctcagttg tctgctcacc gttattttga aagctgttga    4680
agctcatccc gccaccccgag ctgccggcgt aggtgctagc tgcctggaag gcgccttgaa    4740
caacactcaa gagcatagct ccgctaaaac gctgccagaa gtggctgtcg accgagcccg    4800
gcaatcctga gcgaccgagt tcgtccgcgc ttggcgatgt taacgagatc atcgcatggt    4860
caggtgtctc ggcgcgatcc cacaacacaa aaacgcgccc atctccctgt tgcaagccac    4920
gctgtatttc gccaacaacg gtggtgccac gatcaagaag cacgatattg ttcgttgttc    4980
cacgaatatc ctgaggcaag acacacttta catagcctgc caaatttgtg tcgattgcgg    5040
tttgcaagat gcacggaatt attgtccctt gcgttaccat aaaatcgggg tgcggcaaga    5100
gcgtggcgct gctgggctgc agctcggtgg gtttcatacg tatcgacaaa tcgttctcgc    5160
cggacacttc gccattcggc aaggagttgt cgtcacgctt gccttcttgt cttcggcccg    5220
tgtcgccctg aatggcgcgt ttgctgaccc cttgatcgcc gctgctatat gcaaaaatcg    5280
gtgtttcttc cggccgtggc tcatgccgct ccggttcgcc cctcggcggt agaggagcag    5340
caggctgaac agcctcttga accgctggag gatccggcgg cacctcaatc ggagctggat    5400
gaaatggctt ggtgtttgtt gcgatcaaag ttgacggcga tgcgttctca ttcaccttct    5460
tttggcgccc acctagccaa atgaggctta atgataacgc gagaacgaca cctccgacga    5520
tcaatttctg agaccccgaa agacgccggc gatgtttgtc ggagaccagg gatccagatg    5580
catcaacctc atgtgccgct tgctgactat cgttattcat cccttcgccc ccttcaggac    5640
gcgtttcaca tcgggcctca ccgtgcccgt ttgcggcctt tggccaacgg gatcgtaagc    5700
ggtgttccag atacatagta ctgtgtggcc atccctcaga cgccaacctc gggaaaccga    5760
agaaatctcg acatcgctcc ctttaactga atagttggca acagcttcct tgccatcagg    5820
attgatggtg tagatggagg gtatgcgtac attgcccgga aagtggaata ccgtcgtaaa    5880
tccattgtcg aagacttcga gtggcaacag cgaacgatcg ccttgggcga cgtagtgcca    5940
attactgtcc gccgcaccaa gggctgtgac aggctgatcc aataaattct cagctttccg    6000
```

```
ttgatattgt gcttccgcgt gtagtctgtc cacaacagcc ttctgttgtg cctcccttcg   6060
ccgagccgcc gcatcgtcgg cggggtaggc gaattggacg ctgtaataga gatcgggctg   6120
ctctttatcg aggtgggaca gagtcttgga acttatactg aaaacataac ggcgcatccc   6180
ggagtcgctt gcggttagca cgattactgg ctgaggcgtg aggacctggc ttgccttgaa   6240
aaatagataa tttccccgcg gtagggctgc tagatctttg ctatttgaaa cggcaaccgc   6300
tgtcaccgtt tcgttcgtgg cgaatgttac gaccaaagta gctccaaccg ccgtcgagag   6360
gcgcaccact tgatcgggat tgtaagccaa ataacgcatg cgcggatcta gcttgcccgc   6420
cattggagtg tcttcagcct ccgcaccagt cgcagcggca aataaacatg ctaaaatgaa   6480
aagtgctttt ctgatcatgg ttcgctgtgg cctacgtttg aaacggtatc ttccgatgtc   6540
tgataggagg tgacaaccag acctgccggg ttggttagtc tcaatctgcc gggcaagctg   6600
gtcaccttt cgtagcgaac tgtcgcggtc cacgtactca ccacaggcat tttgccgtca   6660
acgacgaggg tcctttata gcgaatttgc tgcgtgcttg gagttacatc atttgaagcg   6720
atgtgctcga cctccaccct gccgcgtttg ccaagaatga cttgaggcga actgggattg   6780
ggatagttga agaattgctg gtaatcctgg cgcactgttg gggcactgaa gttcgatacc   6840
aggtcgtagg cgtactgagc ggtgtcggca tcataactct cgcgcaggcg aacgtactcc   6900
cacaatgagg cgttaacgac ggcctcctct tgagttgcag gcaatcgcga gacagacacc   6960
tcgctgtcaa cggtgccgtc cggccgtatc catagatata cgggcacaag cctgctcaac   7020
ggcaccattg tggctatagc gaacgcttga gcaacatttc ccaaaatcgc gatagctgcg   7080
acagctgcaa tgagtttgga gagacgtcgc gccgatttcg ctcgcgcggt ttgaaaggct   7140
tctacttcct tatagtgctc ggcaaggctt tcgcgcgcca ctagcatggc atattcaggc   7200
cccgtcatag cgtccacccg aattgccgag ctgaagatct gacggagtag gctgccatcg   7260
ccccacattc agcgggaaga tcgggccttt gcagctcgct aatgtgtcgt ttgtctggca   7320
gccgctcaaa gcgacaacta ggcacagcag gcaatacttc atagaattct ccattgaggc   7380
gaattttgc gcgacctagc ctcgctcaac ctgagcgaag cgacggtaca agctgctggc   7440
agattgggtt gcgccgctcc agtaactgcc tccaatgttg ccggcgatcg ccggcaaagc   7500
gacaatgagc gcatcccctg tcagaaaaaa catatcgagt tcgtaaagac caatgatctt   7560
ggccgcggtc gtaccggcga aggtgattac accaagcata agggtgagcg cagtcgcttc   7620
ggttaggatg acgatcgttg ccacgaggtt taagaggaga agcaagagac cgtaggtgat   7680
aagttgcccg atccacttag ctgcgatgtc ccgcgtgcga tcaaaaatat atccgacgag   7740
gatcagaggc ccgatcgcga gaagcacttt cgtgagaatt ccaacggcgt cgtaaactcc   7800
gaaggcagac cagagcgtgc cgtaaaggac ccactgtgcc ccttggaaag caaggatgtc   7860
ctggtcgttc atcggaccga tttcggatgc gattttctga aaaacggcct gggtcacggc   7920
gaacattgta tccaactgtg ccggaacagt ctgcagaggc aagccggtta cactaaactg   7980
ctgaacaaag tttgggaccg tcttttcgaa gatggaaacc acatagtctt ggtagttagc   8040
ctgcccaaca attagagcaa caacgatggt gaccgtgatc acccgagtga taccgctacg   8100
ggtatcgact tcgccgcgta tgactaaaat accctgaaca ataatccaaa gagtgacaca   8160
ggcgatcaat ggcgcactca ccgcctcctg gatagtctca agcatcgagt ccaagcctgt   8220
cgtgaaggct acatcgaaga tcgtatgaat ggccgtaaac ggcgccggaa tcgtgaaatt   8280
catcgattgg acctgaactt gactggtttg tcgcataatt ttggataaaa tgagctcgca   8340
ttcggcgagg atgcgggcgg atgaacaaat cgcccagcct taggggaggg caccaaagat   8400
```

```
gacagcggtc ttttgatgct ccttgcgttg agcggccgcc tcttccgcct cgtgaaggcc   8460
ggcctgcgcg gtagtcatcg ttaataggct tgtcgcctgt acattttgaa tcattgcgtc   8520
atggatctgc ttgagaagca aaccattggt cacggttgcc tgcatgatat tgcgagatcg   8580
ggaaagctga gcagacgtat cagcattcgc cgtcaagcgt ttgtccatcg tttccagatt   8640
gtcagccgca atgccagcgc tgtttgcgga accggtgatc tgcgatcgca acaggtccgc   8700
ttcagcatca ctacccacga ctgcacgatc tgtatcgctg gtgatcgcac gtgccgtggt   8760
cgacattggc attcgcggcg aaaacatttc attgtctagg tccttcgtcg aaggatactg   8820
atttttctgg ttgagcgaag tcagtagtcc agtaacgccg taggccgacg tcaacatcgt   8880
aaccatcgct atagtctgag tgagattctc cgcagtcgcg agcgcagtcg cgagcgtctc   8940
agcctccgtt gccgggtcgc taacaacaaa ctgcgcccgc gcgggctgaa tatatagaaa   9000
gctgcaggtc aaaactgttg caataagttg cgtcgtcttc atcgtttcct accttatcaa   9060
tcttctgcct cgtggtgacg ggccatgaat tcgctgagcc agccagatga gttgccttct   9120
tgtgcctcgc gtagtcgagt tgcaaagcgc accgtgttgg cacgccccga aagcacggcg   9180
acatattcac gcatatcccg cagatcaaat tcgcagatga cgcttccact ttctcgttta   9240
agaagaaact tacggctgcc gaccgtcatg tcttcacgga tcgcctgaaa ttccttttcg   9300
gtacatttca gtccatcgac ataagccgat cgatctgcgg ttggtgatgg atagaaaatc   9360
ttcgtcatac attgcgcaac caagctggct cctagcggcg attccagaac atgctctggt   9420
tgctgcgttg ccagtattag catcccgttg ttttttcgaa cggtcaggag gaatttgtcg   9480
acgacagtcg aaaatttagg gtttaacaaa taggcgcgaa actcatcgca gctcatcaca   9540
aaacggcggc cgtcgatcat ggctccaatc cgatgcagga gatatgctgc agcgggagcg   9600
catacttcct cgtattcgag aagatgcgtc atgtcgaagc cggtaatcga cggatctaac   9660
tttacttcgt caacttcgcc gtcaaatgcc cagccaagcg catggccccg gcaccagcgt   9720
tggagccgcg ctcctgcgcc ttcggcgggc ccatgcaaca aaaattcacg taaccccgcg   9780
attgaacgca tttgtggatc aaacgagagc tgacgatgga taccacggac cagacggcgg   9840
ttctcttccg gagaaatccc accccgacca tcactctcga tgagagccac gatccattcg   9900
cgcagaaaat cgtgtgaggc tgctgtgttt tctaggccac gcaacggcgc caacccgctg   9960
ggtgtgcctc tgtgaagtgc caaatatgtt cctcctgtgg cgcgaaccag caattcgcca  10020
ccccggtcct tgtcaaagaa cacgaccgta cctgcacggt cgaccatgct ctgttcgagc  10080
atggctagaa caaacatcat gagcgtcgtc ttaccectcc cgataggccc gaatattgcc  10140
gtcatgccaa catcgtgctc atgcgggata tagtcgaaag gcgttccgcc attggtacga  10200
aatcgggcaa tcgcgttgcc ccagtggcct gagctggcgc cctctggaaa gttttcgaaa  10260
gagacaaacc ctgcgaaatt gcgtgaagtg attgcgccag ggcgtgtgcg ccacttaaaa  10320
ttccccggca attgggacca ataggccgct tccataccaa taccttcttg gacaaccacg  10380
gcacctgcat ccgccattcg tgtccgagcc cgcgcgcccc tgtccccaag actattgaga  10440
tcgtctgcat agacgcaaag gctcaaatga tgtgagccca taacgaattc gttgctcgca  10500
agtgcgtcct cagcctcgga taatttgccg atttgagtca cggctttatc gccggaactc  10560
agcatctggc tcgatttgag gctaagtttc gcgtgcgctt gcgggcgagt caggaacgaa  10620
aaactctgcg tgagaacaag tggaaaatcg agggatagca gcgcgttgag catgcccggc  10680
cgtgtttttg cagggtattc gcgaaacgaa tagatggatc caacgtaact gtcttttggc  10740
```

```
gttctgatct cgagtcctcg cttgccgcaa atgactctgt cggtataaat cgaagcgccg   10800
agtgagccgc tgacgaccgg aaccggtgtg aaccgaccag tcatgatcaa ccgtagcgct   10860
tcgccaattt cggtgaagag cacaccctgc ttctcgcgga tgccaagacg atgcaggcca   10920
tacgctttaa gagagccagc gacaacatgc caaagatctt ccatgttcct gatctggccc   10980
gtgagatcgt tttcccttttt tccgcttagc ttggtgaacc tcctctttac cttccctaaa   11040
gccgcctgtg ggtagacaat caacgtaagg aagtgttcat tgcggaggag ttggccggag   11100
agcacgcgct gttcaaaagc ttcgttcagg ctagcggcga aaacactacg aagtgtcgc   11160 ggcgccgatg atggcacgtc ggcatgacgt acgaggtgag catatattga cacatgatca   11220
tcagcgatat tgcgcaacag cgtgttgaac gcacgacaac gcgcattgcg catttcagtt   11280
tcctcaagct cgaatgcaac gccatcaatt ctcgcaatgg tcatgatcga tccgtcttca   11340
agaaggacga tatggtcgct gaggtggcca atataaggga gatagatctc accggatctt   11400
tcggtcgttc cactcgcgcc gagcatcaca ccattcctct ccctcgtggg ggaaccctaa   11460
ttggatttgg gctaacagta gcgcccccc aaactgcact atcaatgctt cttcccgcgg   11520
tccgcaaaaa tagcaggacg acgctcgccg cattgtagtc tcgctccacg atgagccggg   11580
ctgcaaacca taacggcacg agaacgactt cgtagagcgg gttctgaacg ataacgatga   11640
caaagccggc gaacatcatg aataaccctg ccaatgtcag tggcaccca agaaacaatg   11700 cgggccgtgt ggctgcgagg taaagggtcg attcttccaa acgatcagcc atcaactacc   11760
gccagtgagc gtttggccga ggaagctcgc cccaaacatg ataacaatgc gccgacgac   11820 gccggcaacc agcccaagcg aagcccgccc gaacatccag gagatcccga tagcgacaat   11880
gccgagaaca gcgagtgact ggccgaacgg accaaggata acgtgcata tattgttaac   11940 cattgtggcg gggtcagtgc cgccacccgc agattgcgct gcggcgggtc cggatgagga   12000
aatgctccat gcaattgcac cgcacaagct tggggcgcag ctcgatatca cgcgcatcat   12060
cgcattcgag agcgagaggc gatttagatg taaacggtat ctctcaaagc atcgcatcaa   12120
tgcgcacctc cttagtataa gtcgaataag acttgattgt cgtctgcgga tttgccgttg   12180
tcctggtgtg gcggtggcgg agcgattaaa ccgccagcgc catcctcctg cgagcggcgc   12240
tgatatgacc cccaaacatc ccacgtctct tcggattta gcgcctcgtg atcgtctttt   12300
ggaggctcga ttaacgcggg caccagcgat tgagcagctg tttcaacttt tcgcacgtag   12360
ccgtttgcaa aaccgccgat gaaattaccg gtgttgtaag cggagatcgc ccgacgaagc   12420
gcaaattgct tctcgtcaat cgtttcgccg cctgcataac gacttttcag catgtttgca   12480
gcggcagata atgatgtgca cgcctggagc gcaccgtcag gtgtcagacc gagcatagaa   12540
aaatttcgag agtttatttg catgaggcca acatccagcg aatgccgtgc atcgagacgg   12600
tgcctgacga cttgggttgc ttggctgtga tcttgccagt gaagcgtttc gccggtcgtg   12660
ttgtcatgaa tcgctaaagg atcaaagcga ctctccacct tagctatcgc cgcaagcgta   12720
gatgtcgcaa ctgatgggc acacttgcga gcaacatggt caaactcagc agatgagagt   12780
ggcgtggcaa ggctcgacga acagaaggag accatcaagg caagagaaag cgaccccgat   12840
ctcttaagca tacctatct ccttagctcg caactaacac cgcctctccc gttggaagaa   12900
gtgcgttgtt ttatgttgaa gattatcggg agggtcggtt actcgaaaat tttcaattgc   12960
ttctttatga tttcaattga agcgagaaac ctcgcccggc gtcttggaac gcaacatgga   13020
ccgagaaccg cgcatccatg actaagcaac cggatcgacc tattcaggcc gcagttggtc   13080
aggtcaggct cagaacgaaa atgctcggcg aggttacgct gtctgtaaac ccattcgatg   13140
```

```
aacgggaagc ttccttccga ttgctcttgg caggaatatt ggcccatgcc tgcttgcgct    13200
ttgcaaatgc tcttatcgcg ttggtatcat atgccttgtc cgccagcaga aacgcactct    13260
aagcgattat ttgtaaaaat gtttcggtca tgcgcggtc atgggcttga cccgctgtca     13320
gcgcaagacg gatcggtcaa ccgtcggcat cgacaacagc gtgaatcttg gtggtcaaac    13380
cgccacggga acgtcccata cagccatcgt cttgatcccg ctgtttccg tcgccgcatg     13440 ttggtggacg cggacacagg aactgtcaat catgacgaca ttctatcgaa agccttggaa    13500
atcacactca gaatatgatc ccagacgtct gcctcacgcc atcgtacaaa gcgattgtag    13560
caggttgtac aggaaccgta tcgatcagga acgtctgccc agggcgggcc cgtccggaag    13620
cgccacaaga tgacattgat cacccgcgtc aacgcgcggc acgcgacgcg gcttatttgg    13680
gaacaaagga ctgaacaaca gtccattcga aatcggtgac atcaaagcgg ggacgggtta    13740
tcagtggcct ccaagtcaag cctcaatgaa tcaaaatcag accgatttgc aaacctgatt    13800
tatgagtgtg cggcctaaat gatgaaatcg tccttctaga tcgcctccgt ggtgtagcaa    13860
cacctcgcag tatcgccgtg ctgaccttgg ccagggaatt gactggcaag ggtgctttca    13920
catgaccgct cttttggccg cgatagatga tttcgttgct gctttgggca cgtagaagga    13980
gagaagtcat atcggagaaa ttcctcctgg cgcgagagcc tgctctatcg cgacggcatc    14040
ccactgtcgg gaacagaccg gatcattcac gaggcgaaag tcgtcaacac atgcgttata    14100
ggcatcttcc cttgaaggat gatcttgttg ctgccaatct ggaggtgcgg cagccgcagg    14160
cagatgcgat ctcagcgcaa cttgcggcaa aacatctcac tcacctgaaa accactagcg    14220
agtctcgcga tcagacgaag gccttttact taacgacaca atatccgatg tctgcatcac    14280
aggcgtcgct atcccagtca atactaaagc ggtgcaggaa ctaaagatta ctgatgactt    14340
aggcgtgcca cgaggcctga gacgacgcgc gtagacagtt ttttgaaatc attatcaaag    14400
tgatggcctc cgctgaagcc tatcacctct cgccggtct gtcggagaga tgggcaagca    14460
ttattacggt cttcgcgccc gtacatgcat tggacgattg cagggtcaat ggatctgaga    14520
tcatccagag gattgccgcc cttaccttcc gtttcgagtt ggagccagcc cctaaatgag    14580
acgacatagt cgacttgatg tgacaatgcc aagagagaga tttgcttaac ccgatttttt    14640
tgctcaagcg taagcctatt gaagcttgcc ggcatgacgt ccgcgccgaa agaatatcct    14700
acaagtaaaa cattctgcac accgaaatgc ttggtgtaga catcgattat gtgaccaaga    14760
tccttagcag tttcgcttgg ggaccgctcc gaccagaaat accgaagtga actgacgcca    14820
atgacaggaa tcccttccgt ctgcagatag gtaccatcga tagatctgct gcctcgcgcg    14880
tttcggtgat gacggtgaaa acctctgaca catgcagctc ccggagacgg tcacagcttg    14940
tctgtaagcg gatgccggga gcagacaagc ccgtcagggc gcgtcagcgg gtgttggcgg    15000 gtgtcgggc gcagccatga cccagtcacg tagcgatagc ggagtgtata ctggcttaac     15060
tatgcggcat cagagcagat tgtactgaga gtgcaccata tgcggtgtga aataccgcac    15120
agatgcgtaa ggagaaaata ccgcatcagg cgctcttccg cttcctcgct cactgactcg    15180
ctgcgctcgg tcgttcggct gcggcgagcg gtatcagctc actcaaaggc ggtaatacgg    15240
ttatccacag aatcagggga taacgcagga agaacatgt gagcaaaagg ccagcaaaag     15300
gccaggaacc gtaaaaaggc cgcgttgctg gcgttttcc ataggctccg cccccctgac     15360
gagcatcaca aaaatcgacg ctcaagtcag aggtggcgaa acccgacagg actataaaga    15420
taccaggcgt ttccccctgg aagctccctc gtgcgctctc ctgttccgac cctgccgctt    15480
```

```
accggatacc tgtccgcctt tctcccttcg ggaagcgtgg cgctttctca tagctcacgc   15540
tgtaggtatc tcagttcggt gtaggtcgtt cgctccaagc tgggctgtgt gcacgaaccc   15600
cccgttcagc ccgaccgctg cgccttatcc ggtaactatc gtcttgagtc caacccggta   15660
agacacgact tatcgccact ggcagcagcc actggtaaca ggattagcag agcgaggtat   15720
gtaggcggtg ctacagagtt cttgaagtgg tggcctaact acggctacac tagaaggaca   15780
gtatttggta tctgcgctct gctgaagcca gttaccttcg gaaaaagagt tggtagctct   15840
tgatccggca aacaaaccac cgctggtagc ggtggttttt ttgtttgcaa gcagcagatt   15900
acgcgcagaa aaaaggatc tcaagaagat cctttgatct tttctacggg gtctgacgct   15960
cagtggaacg aaaactcacg ttaagggatt ttggtcatga gattatcaaa aaggatcttc   16020
acctagatcc ttttaaatta aaatgaagt tttaaatcaa tctaaagtat atatgagtaa   16080
acttggtctg acagttacca atgcttaatc agtgaggcac ctatctcagc gatctgtcta   16140
tttcgttcat ccatagttgc ctgactcccc gtcgtgtaga taactacgat acgggagggc   16200
ttaccatctg gccccagtgc tgcaatgata ccgcgagacc cacgctcacc ggctccagat   16260
ttatcagcaa taaaccagcc agccggaagg gccgagcgca gaagtggtcc tgcaacttta   16320
tccgcctcca tccagtctat taattgttgc cgggaagcta gagtaagtag ttcgccagtt   16380
aatagtttgc gcaacgttgt tgccattgct gcaggggggg ggggggggg gttccattgt   16440 tcattccacg gacaaaaaca gagaaaggaa acgacagagg ccaaaaagct cgctttcagc   16500
acctgtcgtt tcctttcttt tcagagggta ttttaaataa aacattaag ttatgacgaa   16560 gaagaacgga aacgccttaa accggaaaat tttcataaat agcgaaaacc cgcgaggtcg   16620
ccgccccgta acctgtcgga tcaccggaaa ggacccgtaa agtgataatg attatcatct   16680
acatatcaca acgtgcgtgg aggccatcaa accacgtcaa ataatcaatt atgacgcagg   16740
tatcgtatta attgatctgc atcaacttaa cgtaaaaaca acttcagaca atacaaatca   16800
gcgacactga atacggggca acctcatgtc cccccccccc cccccctgc aggcatcgtg   16860 gtgtcacgct cgtcgtttgg tatggcttca ttcagctccg gttcccaacg atcaaggcga   16920
gttacatgat cccccatgtt gtgcaaaaaa gcggttagct ccttcggtcc tccgatcgtt   16980
gtcagaagta agttggccgc agtgttatca ctcatggtta tggcagcact gcataattct   17040
cttactgtca tgccatccgt aagatgcttt tctgtgactg gtgagtactc aaccaagtca   17100
ttctgagaat agtgtatgcg gcgaccgagt tgctcttgcc cggcgtcaac acgggataat   17160
accgcgccac atagcagaac tttaaaagtg ctcatcattg gaaaacgttc ttcggggcga   17220
aaactctcaa ggatcttacc gctgttgaga tccagttcga tgtaacccac tcgtgcaccc   17280
aactgatctt cagcatcttt tactttcacc agcgtttctg ggtgagcaaa aacaggaagg   17340
caaaatgccg caaaaaaggg aataagggcg acacggaaat gttgaatact catactcttc   17400 cttttcaat attattgaag catttatcag ggttattgtc tcatgagcgg atacatattt   17460
gaatgtattt agaaaaataa acaaataggg gttccgcgca catttccccg aaaagtgcca   17520
cctgacgtct aagaaaccat tattatcatg acattaacct ataaaaatag gcgtatcacg   17580
aggccctttc gtcttcaaga attcggagct tttgccattc tcaccggatt cagtcgtcac   17640
tcatggtgat ttctcacttg ataaccttat ttttgacgag gggaaattaa taggttgtat   17700
tgatgttgga cgagtcggaa tcgcagaccg ataccaggat cttgccatcc tatggaactg   17760
cctcggtgag ttttctcctt cattacagaa acggcttttt caaaaatatg gtattgataa   17820
tcctgatatg aataaattgc agtttcattt gatgctcgat gagtttttct aatcagaatt   17880
```

-continued

```
ggttaattgg ttgtaacact ggcagagcat tacgctgact tgacgggacg gcggctttgt   17940
tgaataaatc gaacttttgc tgagttgaag gatcagatca cgcatcttcc cgacaacgca   18000
gaccgttccg tggcaaagca aaagttcaaa atcaccaact ggtccaccta caacaaagct   18060
ctcatcaacc gtggctccct cactttctgg ctggatgatg gggcgattca ggcctggtat   18120
gagtcagcaa caccttcttc acgaggcaga cctcagcgcc agaaggccgc cagagaggcc   18180
gagcgcggcc gtgaggcttg gacgctaggg cagggcatga aaaagcccgt agcgggctgc   18240
tacgggcgtc tgacgcggtg gaaagggggga ggggatgttg tctacatggc tctgctgtag  18300
tgagtgggtt gcgctccggc agcggtcctg atcaatcgtc acccttcctc ggtccttcaa   18360
cgttcctgac aacgagcctc cttttcgcca atccatcgac aatcaccgcg agtccctgct   18420
cgaacgctgc gtccggaccg gcttcgtcga aggcgtctat cgcggcccgc aacagcggcg   18480
agagcggagc ctgttcaacg gtgccgccgc gctcgccggc atcgctgtcg ccggcctgct   18540
cctcaagcac ggccccaaca gtgaagtagc tgattgtcat cagcgcattg acggcgtccc   18600
cggccgaaaa acccgcctcg cagaggaagc gaagctgcgc gtcggccgtt ccatctgcg    18660 gtgcgcccgg tcgcgtgccg gcatggatgc gcgcgccatc gcggtaggcg agcagcgcct   18720
gcctgaagct gcgggcattc ccgatcagaa atgagcgcca gtcgtcgtcg gctctcggca   18780
ccgaatgcgt atgattctcc gccagcatgg cttcggccag tgcgtcgagc agcgcccgct   18840
tgttcctgaa gtgccagtaa agcgccggct gctgaacccc caaccgttcc gccagtttgc   18900
gtgtcgtcag accgtctacg ccgacctcgt tcaacaggtc cagggcggca cggatcactg   18960
tattcggctg caactttgtc atgcttgaca ctttatcact gataaacata atatgtccac   19020
caacttatca gtgataaaga atccgcgcgt tcaatcggac cagcggaggc tggtccggag   19080
gccagacgtg aaacccaaca taccctgat cgtaattctg agcactgtcg cgctcgacgc   19140
tgtcggcatc ggcctgatta tgccggtgct gccgggcctc ctgcgcgatc tggttcactc   19200
gaacgacgtc accgcccact atggcattct gctggcgctg tatgcgttgg tgcaatttgc   19260
ctgcgcacct gtgctgggcg cgctgtcgga tcgtttcggg cggcggccaa tcttgctcgt   19320
ctcgctggcc ggcgccactg tcgactacgc catcatggcg acagcgcctt ccttttgggt   19380
tctctatatc gggcggatcg tggccggcat caccggggcg actggggcgg tagccggcgc   19440
ttatattgcc gatatcactg atggcgatga gcgcgcgcgg cacttcggct tcatgagcgc   19500
ctgtttcggg ttcgggatgg tcgcgggacc tgtgctcggt gggctgatgg gcggtttctc   19560
cccccacgct ccgttcttcg ccgcggcagc cttgaacgc ctcaatttcc tgacgggctg    19620
tttccttttg ccggagtcgc acaaaggcga acgccggccg ttacgccggg aggctctcaa   19680
cccgctcgct tcgttccggt gggccgggg catgaccgtc gtcgccgccc tgatggcggt    19740
cttcttcatc atgcaacttg tcggacaggt gccggccgcg ctttgggtca ttttcggcga   19800
ggatcgcttt cactgggacg cgaccacgat cggcatttcg cttgccgcat ttggcattct   19860
gcattcactc gcccaggcaa tgatcaccgg ccctgtagcc gccggctcg gcgaaaggcg    19920 ggcactcatg ctcggaatga ttgccgacgg cacaggctac atcctgcttg ccttcgcgac   19980
acggggatgg atgcgcgttcc cgatcatggt cctgcttgct tcgggtggca tcggaatgcc   20040
ggcgctgcaa gcaatgttgt ccaggcaggt ggatgaggaa cgtcaggggc agctgcaagg   20100
ctcactggcg gcgctcacca gcctgacctc gatcgtcgga cccctcctct tcacggcgat   20160
ctatgcggct tctataacaa cgtggaacgg gtgggcatgg attgcaggcg ctgccctcta   20220
```

```
cttgctctgc ctgccggcgc tgcgtcgcgg gctttggagc ggcgcagggc aacgagccga   20280
tcgctgatcg tggaaacgat aggcctatgc catgcgggtc aaggcgactt ccggcaagct   20340
atacgcgccc taggagtgcg gttggaacgt tggcccagcc agatactccc gatcacgagc   20400
aggacgccga tgatttgaag cgcactcagc gtctgatcca agaacaacca tcctagcaac   20460
acggcggtcc ccgggctgag aaagcccagt aaggaaacaa ctgtaggttc gagtcgcgag   20520
atcccccgga accaaaggaa gtaggttaaa cccgctccga tcaggccgag ccacgccagg   20580
ccgagaacat tggttcctgt aggcatcggg attggcggat caaacactaa agctactgga   20640
acgagcagaa gtcctccggc cgccagttgc caggcggtaa aggtgagcag aggcacggga   20700
ggttgccact tgcgggtcag cacggttccg aacgccatgg aaaccgcccc cgccaggccc   20760
gctgcgacgc cgacaggatc tagcgctgcg tttggtgtca acaccaacag cgccacgccc   20820
gcagttccgc aaatagcccc caggaccgcc atcaatcgta tcgggctacc tagcagagcg   20880
gcagagatga acacgaccat cagcggctgc acagcgccta ccgtcgccgc gaccccgccc   20940
ggcaggcggt agaccgaaat aaacaacaag ctccagaata gcgaaatatt aagtgcgccg   21000
aggatgaaga tgcgcatcca ccagattccc gttggaatct gtcggacgat catcacgagc   21060
aataaacccg ccggcaacgc ccgcagcagc ataccggcga cccctcggcc tcgctgttcg   21120
ggctccacga aaacgccgga cagatgcgcc ttgtgagcgt ccttgggccc gtcctcctgt   21180
ttgaagaccc acagcccaat gatctcgccg tcgatgtagg cgccgaatgc cacggcatct   21240
cgcaaccgtt cagcgaacgc ctccatgggc ttttctcct cgtgctcgta aacggacccg   21300
aacatctctg gagctttctt cagggccgac aatcggatct cgcggaaatc ctgcacgtcg   21360
gccgctccaa gccgtcgaat ctgagcctta atcacaattg tcaatttaa tcctctgttt   21420 atcggcagtt cgtagagcgc gccgtgcgtc ccgagcgata ctgagcgaag caagtgcgtc   21480
gagcagtgcc cgcttgttcc tgaaatgcca gtaaagcgct ggctgctgaa cccccagccg   21540
gaactgaccc cacaaggccc tagcgtttgc aatgcaccag gtcatcattg acccaggcgt   21600
gttccaccag gccgctgcct cgcaactctt cgcaggcttc gccgacctgc tcgcgccact   21660
tcttcacgcg ggtggaatcc gatccgcaca tgaggcggaa ggtttccagc ttgagcgggt   21720
acggctcccg gtgcgagctg aaatagtcga acatccgtcg ggccgtcggc gacagcttgc   21780
ggtacttctc ccatatgaat ttcgtgtagt ggtcgccagc aaacagcacg acgatttcct   21840
cgtcgatcag gacctggcaa cgggacgttt tcttgccacg gtccaggacg cggaagcggt   21900
gcagcagcga caccgattcc aggtgcccaa cgcggtcgga cgtgaagccc atcgccgtcg   21960
cctgtaggcg cgacaggcat tcctcggcct tcgtgtaata ccggccattg atcgaccagc   22020
ccaggtcctg gcaaagctcg tagaacgtga aggtgatcgg ctcgccgata ggggtgcgct   22080
tcgcgtactc caacacctgc tgccacacca gttcgtcatc gtcggcccgc agctcgacgc   22140
cggtgtaggt gatcttcacg tccttgttga cgtggaaaat gaccttgttt tgcagcgcct   22200
cgcgcgggat tttcttgttg cgcgtggtga acagggcaga gcgggccgtg tcgtttggca   22260
tcgctcgcat cgtgtccggc cacggcgcaa tatcgaacaa ggaaagctgc atttccttga   22320
tctgctgctt cgtgtgtttc agcaacgcgg cctgcttggc ctcgctgacc tgttttgcca   22380
ggtcctcgcc ggcggttttt cgcttcttgg tcgtcatagt tcctcgcgtg tcgatggtca   22440
tcgacttcgc caaacctgcc gcctcctgtt cgagacgacg cgaacgctcc acggcggccg   22500
atggcgcggg cagggcaggg ggagccagtt gcacgctgtc gcgctcgatc ttggcctag   22560 cttgctggac catcgagccg acggactgga aggtttcgcg gggcgcacgc atgacggtgc   22620
```

```
ggcttgcgat ggtttcggca tcctcggcgg aaaaccccgc gtcgatcagt tcttgcctgt   22680
atgccttccg gtcaaacgtc cgattcattc accctccttg cgggattgcc ccgactcacg   22740
ccggggcaat gtgcccttat tcctgatttg acccgcctgg tgccttggtg tccagataat   22800
ccaccttatc ggcaatgaag tcggtcccgt agaccgtctg gccgtccttc tcgtacttgg   22860
tattccgaat cttgccctgc acgaatacca gcgacccctt gcccaaatac ttgccgtggg   22920
cctcggcctg agagccaaaa cacttgatgc ggaagaagtc ggtgcgctcc tgcttgtcgc   22980
cggcatcgtt gcgccactct tcattaaccg ctatatcgaa aattgcttgc ggcttgttag   23040
aattgccatg acgtacctcg gtgtcacggg taagattacc gataaactgg aactgattat   23100
ggctcatatc gaaagtctcc ttgagaaagg agactctagt ttagctaaac attggttccg   23160
ctgtcaagaa cttagcggc taaaattttg cgggccgcga ccaaaggtgc gaggggcggc   23220
ttccgctgtg tacaaccaga tattttcac caacatcctt cgtctgctcg atgagcgggg   23280
catgacgaaa catgagctgt cggagagggc aggggtttca atttcgtttt tatcagactt   23340
aaccaacggt aaggccaacc cctcgttgaa ggtgatggag gccattgccg acgccctgga   23400
aactccccta cctcttctcc tggagtccac cgacctgac cgcgaggcac tcgcggagat   23460
tgcgggtcat cctttcaaga gcagcgtgcc gcccggatac gaacgcatca gtgtggtttt   23520
gccgtcacat aaggcgttta tcgtaaagaa atggggcgac dacacccgaa aaagctgcg   23580 tggaaggctc tgacgccaag ggttagggct tgcacttcct tctttagccg ctaaaacggc   23640
cccttctctg cgggccgtcg gctcgcgcat catatcgaca tcctcaacgg aagccgtgcc   23700
gcgaatggca tcggcgggt gcgctttgac agttgttttc tatcagaacc cctacgtcgt   23760
gcggttcgat tagctgtttg tcttgcaggc taaacacttt cggtatatcg tttgcctgtg   23820
cgataatgtt gctaatgatt tgttgcgtag gggttactga aaagtgagcg ggaaagaaga   23880
gtttcagacc atcaaggagc gggccaagcg caagctggaa cgcgacatgg gtgcggacct   23940
gttggccgcg ctcaacgacc cgaaaaccgt tgaagtcatg ctcaacgcgg acggcaaggt   24000
gtggcacgaa cgccttggcg agccgatgcg gtacatctgc gacatgcggc ccagccagtc   24060
gcaggcgatt atagaaacgg tggccggatt ccacggcaaa gaggtcacgc ggcattcgcc   24120
catcctggaa ggcgagttcc ccttggatgg cagccgcttt gccggccaat gccgccggt   24180 cgtggccgcg ccaacctttg cgatccgcaa gcgcgcggtc gccatcttca cgctggaaca   24240
gtacgtcgag gcgggcatca tgacccgcga gcaatacgag gtcattaaaa gcgccgtcgc   24300
ggcgcatcga aacatcctcg tcattggcgg tactggctcg ggcaagacca cgctcgtcaa   24360
cgcgatcatc aatgaaatgg tcgccttcaa cccgtctgag cgcgtcgtca tcatcgagga   24420
caccggcgaa atccagtgcg ccgcagagaa cgccgtccaa taccacacca gcatcgacgt   24480
ctcgatgacg ctgctgctca agacaacgct gcgtatgcgc cccgaccgca tcctggtcgg   24540
tgaggtacgt ggccccgaag cccttgatct gttgatggcc tggaacaccg ggcatgaagg   24600
aggtgccgcc accctgcacg caaacaaccc caaagcgggc ctgagccggc tcgccatgct   24660
tatcagcatg cacccggatt caccgaaacc cattgagccg ctgattggcg aggcggttca   24720
tgtggtcgtc catatcgcca ggaccctag cggccgtcga gtgcaagaaa ttctcgaagt   24780
tcttggttac gagaacggcc agtacatcac caaaaccctg taaggagtat tccaatgac   24840 aacggctgtt ccgttccgtc tgaccatgaa tcgcggcatt tgttctacc ttgccgtgtt   24900 cttcgttctc gctctcgcgt tatccgcgca tccggcgatg gcctcggaag gcaccggcgg   24960
```

```
cagcttgcca tatgagagct ggctgacgaa cctgcgcaac tccgtaaccg gcccggtggc   25020
cttcgcgctg tccatcatcg gcatcgtcgt cgccggcggc gtgctgatct tcggcggcga   25080
actcaacgcc ttcttccgaa ccctgatctt cctggttctg gtgatggcgc tgctggtcgg   25140
cgcgcagaac gtgatgagca ccttcttcgg tcgtggtgcc gaaatcgcgg ccctcggcaa   25200
cggggcgctg caccaggtgc aagtcgcggc ggcggatgcc gtgcgtgcgg tagcggctgg   25260
acggctcgcc taatcatggc tctgcgcacg atccccatcc gtcgcgcagg caaccgagaa   25320
aacctgttca tgggtggtga tcgtgaactg gtgatgttct cgggcctgat ggcgtttgcg   25380
ctgattttca gcgcccaaga gctgcgggcc accgtggtcg gtctgatcct gtggttcggg   25440
gcgctctatg cgttccgaat catggcgaag gccgatccga agatgcggtt cgtgtacctg   25500
cgtcaccgcc ggtacaagcc gtattacccg gcccgctcga ccccgttccg cgagaacacc   25560
aatagccaag ggaagcaata ccgatgatcc aagcaattgc gattgcaatc gcgggcctcg   25620
gcgcgcttct gttgttcatc ctctttgccc gcatccgcgc ggtcgatgcc gaactgaaac   25680
tgaaaaagca tcgttccaag gacgccggcc tggccgatct gctcaactac gccgctgtcg   25740
tcgatgacgg cgtaatcgtg ggcaagaacg gcagctttat ggctgcctgg ctgtacaagg   25800
gcgatgacaa cgcaagcagc accgaccagc agcgcgaagt agtgtccgcc cgcatcaacc   25860
aggccctcgc gggcctggga agtgggtgga tgatccatgt ggacgccgtg cggcgtcctg   25920
ctccgaacta cgcggagcgg ggcctgtcgg cgttccctga ccgtctgacg gcagcgattg   25980
aagaagagcg ctcggtcttg ccttgctcgt cggtgatgta cttcaccagc tccgcgaagt   26040
cgctcttctt gatggagcgc atgggacgt gcttggcaat cacgcgcacc ccccggccgt   26100
tttagcggct aaaaaagtca tggctctgcc ctcgggcgga ccacgcccat catgaccttg   26160
ccaagctcgt cctgcttctc ttcgatcttc gccagcaggg cgaggatcgt ggcatcaccg   26220
aaccgcgccg tgcgcgggtc gtcggtgagc cagagtttca gcaggccgcc caggcggccc   26280
aggtcgccat tgatgcgggc cagctcgcgg acgtgctcat agtccacgac gcccgtgatt   26340
ttgtagccct ggccgacggc cagcaggtag gccgacaggc tcatgccggc gccgccgcc   26400 ttttcctcaa tcgctcttcg ttcgtctgga aggcagtaca ccttgatagg tgggctgccc   26460
ttcctggttg gcttggtttc atcagccatc cgcttgccct catctgttac gccggcggta   26520
gccggccagc ctcgcagagc aggattcccg ttgagcaccg ccaggtgcga ataagggaca   26580
gtgaagaagg aacacccgct cgcgggtggg cctacttcac ctatcctgcc cggctgacgc   26640
cgttggatac accaaggaaa gtctacacga acccttggc aaaatcctgt atatcgtgcg   26700
aaaaaggatg gatataccga aaaaatcgct ataatgaccc cgaagcaggg ttatgcagcg   26760
gaaaagcgct gcttccctgc tgttttgtgg aatatctacc gactggaaac aggcaaatgc   26820
aggaaattac tgaactgagg ggacaggcga gagacgatgc caaagagcta caccgacgag   26880
ctggccgagt gggttgaatc ccgcgcgcc aagaagcgcc ggcgtgatga ggctgcggtt   26940
gcgttcctgg cggtgagggc ggatgtcgag gcggcgttag cgtccggcta tgcgctcgtc   27000
accatttggg agcacatgcg ggaaacgggg aaggtcaagt tctcctacga cgcgttccgc   27060
tcgcacgcca ggcggcacat caaggccaag cccgccgatg tgcccgcacc gcaggccaag   27120
gctgcggaac ccgcgccggc acccaagacg ccggagccac ggcggccgaa gcaggggggc   27180
aaggctgaaa agccggcccc cgctgcggcc ccgaccggct tcaccttcaa cccaacaccg   27240
gacaaaaagg atctactgta atggcgaaaa ttcacatggt tttgcagggc aagggcgggg   27300
tcggcaagtc ggccatcgcc gcgatcattg cgcagtacaa gatggacaag ggcagacac   27360
```

```
ccttgtgcat cgacaccgac ccggtgaacg cgacgttcga gggctacaag gccctgaacg   27420
tccgccggct gaacatcatg gccggcgacg aaattaactc gcgcaacttc gacaccctgg   27480
tcgagctgat tgcgccgacc aaggatgacg tggtgatcga caacggtgcc agctcgttcg   27540
tgcctctgtc gcattacctc atcagcaacc aggtgccggc tctgctgcaa gaaatggggc   27600
atgagctggt catccatacc gtcgtcaccg gcggccaggc tctcctggac acggtgagcg   27660
gcttcgccca gctcgccagc cagttcccgg ccgaagcgct tttcgtggtc tggctgaacc   27720
cgtattgggg gcctatcgag catgagggca agagctttga gcagatgaag gcgtacacgg   27780
ccaacaaggc ccgcgtgtcg tccatcatcc agattccggc cctcaaggaa gaaacctacg   27840
gccgcgattt cagcgacatg ctgcaagagc ggctgacgtt cgaccaggcg ctggccgatg   27900
aatcgctcac gatcatgacg cggcaacgcc tcaagatcgt gcggcgcggc ctgtttgaac   27960
agctcgacgc ggcggccgtg ctatgagcga ccagattgaa gagctgatcc gggagattgc   28020
ggccaagcac ggcatcgccg tcggccgcga cgacccggtg ctgatcctgc ataccatcaa   28080
cgcccggctc atggccgaca gtgcggccaa gcaagaggaa atccttgccg cgttcaagga   28140
agagctggaa gggatcgccc atcgttgggg cgaggacgcc aaggccaaag cggagcggat   28200
gctgaacgcg gccctggcgg ccagcaagga cgcaatggcg aaggtaatga aggacagcgc   28260
cgcgcaggcg gccgaagcga tccgcaggga atcgacgac ggccttggcc gccagctcgc   28320
ggccaaggtc gcggacgcgc ggcgcgtggc gatgatgaac atgatcgccg gcggcatggt   28380
gttgttcgcg gccgccctgg tggtgtgggc ctcgttatga atcgcagagg cgcagatgaa   28440
aaagcccggc gttgccgggc tttgtttttg cgttagctgg gcttgtttga caggcccaag   28500
ctctgactgc gcccgcgctc gcgctcctgg gcctgtttct tctcctgctc ctgcttgcgc   28560
atcagggcct ggtgccgtcg ggctgcttca cgcatcgaat cccagtcgcc ggccagctcg   28620
ggatgctccg cgcgcatctt gcgcgtcgcc agttcctcga tcttgggcgc gtgaatgccc   28680
atgccttcct tgatttcgcg caccatgtcc agccgcgtgt gcagggtctg caagcgggct   28740
tgctgttggg cctgctgctg ctgccaggcg gccttgtac gcggcaggga cagcaagccg   28800
ggggcattgg actgtagctg ctgcaaacgc gcctgctgac ggtctacgag ctgttctagg   28860
cggtcctcga tgcgctccac ctggtcatgc tttgcctgca cgtagagcgc aagggtctgc   28920
tggtaggtct gctcgatggg cgcggattct aagagggcct gctgttccgt ctcggcctcc   28980
tgggccgcct gtagcaaatc ctcgccgctg ttgccgctgg actgctttac tgccggggac   29040
tgctgttgcc ctgctcgcgc cgtcgtcgca gttcggcttg cccccactcg attgactgct   29100
tcatttcgag ccgcagcgat gcgatctcgg attgcgtcaa cggacggggc agcgcggagg   29160
tgtccggctt ctccttgggt gagtcggtcg atgccatagc caaaggtttc cttccaaaat   29220
gcgtccattg ctggaccgtg tttctcattg atgcccgcaa gcatcttcgg cttgaccgcc   29280
aggtcaagcg cgccttcatg gcggtcatg acggacgccg ccatgacctt gccgccgttg   29340
ttctcgatgt agccgcgtaa tgaggcaatg gtgccgccca tcgtcagcgt gtcatcgaca   29400
acgatgtact tctggccggg gatcacctcc ccctcgaaag tcggttgaa cgccaggcga   29460 tgatctgaac cggctccggt tcgggcgacc ttctcccgct gcacaatgtc cgtttcgacc   29520
tcaaggccaa ggcggtcggc cagaacgacc gccatcatgg ccggaatctt gttgttcccc   29580
gccgcctcga cggcgaggac tggaacgatg cggggcttgt cgtcgccgat cagcgtcttg   29640
agctgggcaa cagtgtcgtc cgaaatcagg cgctcgacca aattaagcgc gcttccgcg   29700
```

```
tcgccctgct tcgcagcctg gtattcaggc tcgttggtca aagaaccaag gtcgccgttg   29760
cgaaccacct tcgggaagtc tccccacggt gcgcgctcgg ctctgctgta gctgctcaag   29820
acgcctccct ttttagccgc taaaactcta acgagtcgcg ccgcgactca acttgacgct   29880
ttcggcactt acctgtgcct tgccacttgc gtcataggtg atgcttttcg cactcccgat   29940
ttcaggtact ttatcgaaat ctgaccgggc gtgcattaca aagttcttcc ccacctgttg   30000
gtaaatgctg ccgctatctg cgtggacgat gctgccgtcg tggcgctgcg acttatcggc   30060
cttttgggcc atatagatgt tgtaaatgcc aggtttcagg ccccggcttt tatctacctt   30120
ctggttcgtc catgcgcctt ggttctcggt ctggacaatt cttttgccca ttcatgaccag   30180 gaggcggtgt tcattgggt gactcctgac ggttgcctct ggtgttaaac gtgtcctggt   30240
cgcttgccgg ctaaaaaaaa gccgacctcg gcagttcgag gccggctttc cctagagccg   30300
ggcgcgtcaa ggttgttcca tctattttag tgaactgcgt tcgatttatc agttactttc   30360
ctcccgcttt gtgtttcctc ccactcgttt ccgcgtctag ccgacccctc aacatagcgg   30420
cctcttcttg ggctgccttt gcctcttgcc gcgcttcgtc acgctcggct tgcaccgtcg   30480
taaagcgctc ggcctgcctg gccgcctctt gcgccgccaa cttcctttgc tcctggtggg   30540
cctcggcgtc ggcctgcgcc ttcgctttca ccgctgccaa ctccgtgcgc aaactctccg   30600
cttcgcgcct ggtggcgtcg cgctcgccgc gaagcgcctg catttcctgg ttggccgcgt   30660
ccagggtctt gcggctctct tctttgaatg cgcgggcgtc ctggtgagcg tagtccagct   30720
cggcgcgcag ctcctgcgct cgacgctcca cctcgtcggc ccgctgcgtc gccagcgcgg   30780
cccgctgctc ggctcctgcc agggcggtgc gtgcttcggc cagggcttgc cgctggcgtg   30840
cggccagctc ggccgcctcg gcggcctgct gctctagcaa tgtaacgcgc gcctgggctt   30900 cttcagctc gcgggcctgc gcctcgaagg cgtcggccag ctccccgcgc acggcttcca   30960
actcgttgcg ctcacgatcc cagccggctt gcgctgcctg caacgattca ttggcaaggg   31020
cctgggcggg ttgccagagg gcggccacgg cctggttgcc ggcctgctgc accgcgtccg   31080
gcacctggac tgccagcggg gcggcctgcg ccgtgcgctg gcgtcgccat tcgcgcatgc   31140
cggcgctggc gtcgttcatg ttgacgcggg cggccttacg cactgcatcc acggtcggga   31200
agttctcccg gtcgccttgc tcgaacagct cgtccgcagc cgcaaaaatg cggtcgcgcg   31260
tctctttgtt cagttccatg ttggctccgg taattggtaa gaataataat actcttacct   31320
accttatcag cgcaagagtt tagctgaaca gttctcgact taacgcagg ttttttagcg   31380 gctgaagggc aggcaaaaaa agcccgcac ggtcggcggg ggcaaagggt cagcgggaag   31440
gggattagcg ggcgtcgggc ttcttcatgc gtcggggccg cgcttcttgg gatggagcac   31500
gacgaagcgc gcacgcgcat cgtcctcggc cctatcggcc cgcgtcgcgg tcaggaactt   31560
gtcgcgcgct aggtcctccc tggtgggcac caggggcatg aactcggcct gctcgatgta   31620
ggtccactcc atgaccgcat cgcagtcgag gccgcgttcc ttcaccgtct cttgcaggtc   31680
gcggtacgcc cgctcgttga gcggctggta acgggccaat tggtcgtaaa tggctgtcgg   31740
ccatgagcgg cctttcctgt tgagccagca gccgacgacg aagccggcaa tgcaggcccc   31800
tggcacaacc aggccgacgc cggggcagg ggatggcagc agctcgccaa ccaggaaccc   31860
cgccgcgatg atgccgatgc cggtcaacca gcccttgaaa ctatccggcc ccgaaacacc   31920
cctgcgcatt gcctggatgc tgcgccggat agcttgcaac atcaggagcc gtttcttttg   31980
ttcgtcagtc atggtccgcc ctcaccagtt gttcgtatcg gtgtcggacg aactgaaatc   32040
gcaagagctg ccggtatcgg tccagccgct gtccgtgtcg ctgctgccga agcacggcga   32100
```

```
ggggtccgcg aacgccgcag acggcgtatc cggccgcagc gcatcgccca gcatggcccc   32160
ggtcagcgag ccgccggcca ggtagcccag catggtgctg ttggtcgccc cggccaccag   32220
ggccgacgtg acgaaatcgc cgtcattccc tctggattgt tcgctgctcg gcggggcagt   32280
gcgccgcgcc ggcggcgtcg tggatggctc gggttggctg gcctgcgacg gccggcgaaa   32340
ggtgcgcagc agctcgttat cgaccggctg cggcgtcggg gccgccgcct tgcgctgcgg   32400
tcggtgttcc ttcttcggct cgcgcagctt gaacagcatg atcgcggaaa ccagcagcaa   32460
cgccgcgcct acgcctcccg cgatgtagaa cagcatcgga ttcattcttc ggtcctcctt   32520
gtagcggaac cgttgtctgt gcggcgcggg tggcccgcgc cgctgtcttt ggggatcagc   32580
cctcgatgag cgcgaccagt ttcacgtcgg caaggttcgc ctcgaactcc tggccgtcgt   32640
cctcgtactt caaccaggca tagccttccg ccggcggccg acggttgagg ataaggcggg   32700
cagggcgctc gtcgtgctcg acctggacga tggcctttt cagcttgtcc gggtccggct   32760
ccttcgcgcc cttttccttg gcgtccttac cgtcctggtc gccgtcctcg ccgtcctggc   32820
cgtcgccggc ctccgcgtca cgctcggcat cagtctggcc gttgaaggca tcgacggtgt   32880
tgggatcgcg gcccttctcg tccaggaact cgcgcagcag cttgaccgtg ccgcgcgtga   32940
tttcctgggt gtcgtcgtca agccacgcct cgacttcctc cgggcgcttc ttgaaggccg   33000
tcaccagctc gttcaccacg gtcacgtcgc gcacgcggcc ggtgttgaac gcatcggcga   33060
tcttctccgg caggtccagc agcgtgacgt gctgggtgat gaacgccggc gacttgccga   33120
tttccttggc gatatcgcct ttcttcttgc ccttcgccag ctcgcggcca atgaagtcgg   33180
caatttcgcg cggggtcagc tcgttgcgtt gcaggttctc gataacctgg tcggcttcgt   33240
tgtagtcgtt gtcgatgaac gccgggatgg acttcttgcc ggcccacttc gagccacggt   33300
agcggcgggc gccgtgattg atgatatagc ggcccggctg ctcctggttc tcgcgcaccg   33360
aaatgggtga cttcaccccg cgctctttga tcgtggcacc gatttccgcg atgctctccg   33420
gggaaaagcc ggggttgtcg gccgtccgcg gctgatgcgg atcttcgtcg atcaggtcca   33480
ggtccagctc gatagggccg gaaccgcccc gagacgccgc aggagcgtcc aggaggctcg   33540
acaggtcgcc gatgctatcc aaccccaggc cggacggctg cgccgcgcct gcggcttcct   33600
gagcggccgc agcggtgttt ttcttggtgg tcttggcttg agccgcagtc attgggaaat   33660
ctccatcttc gtgaacacgt aatcagccag ggcgcgaacc tctttcgatg ccttgcgcgc   33720
ggccgttttc ttgatcttcc agaccggcac accggatgcg agggcatcgg cgatgctgct   33780
gcgcaggcca acgtggccg gaatcatcat cttggggtac gcggccagca gctcggcttg   33840
gtggcgcgcg tggcgcggat tccgcgcatc gaccttgctg ggcaccatgc caaggaattg   33900
cagcttggcg ttcttctggc gcacgttcgc aatggtcgtg accatcttct tgatgccctg   33960
gatgctgtac gcctcaagct cgatgggga cagcacatag tcggccgcga agagggcggc   34020
cgccaggcca acgccaaggg tcgggccgt gtcgatcagg cacacgtcga agccttggtt   34080
cgccagggcc ttgatgttcg ccccgaacag ctcgcgggcg tcgtccagcg acagccgttc   34140
ggcgttcgcc agtaccgggt tggactcgat gagggcgagg cgcgcggcct ggccgtcgcc   34200
ggctgcgggt gcggtttcgg tccagccgcc ggcaggaca cgccgaaca gcttgcttgc   34260
atgcaggccg gtagcaaagt ccttgagcgt gtaggacgca ttgccctggg ggtccaggtc   34320
gatcacggca acccgcaagc cgcgctcgaa aaagtcgaag gcaagatgca caagggtcga   34380
agtcttgccg acgccgcctt tctggttggc cgtgaccaaa gttttcatcg tttggtttcc   34440
```

```
tgttttttct tggcgtccgc ttcccacttc cggacgatgt acgcctgatg ttccggcaga    34500
accgccgtta cccgcgcgta cccctcgggc aagttcttgt cctcgaacgc ggcccacacg    34560
cgatgcaccg cttgcgacac tgcgccctg gtcagtccca gcgacgttgc gaacgtcgcc    34620
tgtggcttcc catcgactaa gacgcccgc gctatctcga tggtctgctg ccccacttcc    34680 agccctgga tcgcctcctg gaactggctt tcggtaagcc gtttcttcat ggataacacc    34740
cataatttgc tccgcgcctt ggttgaacat agcggtgaca gccgccagca catgagagaa    34800
gtttagctaa acatttctcg cacgtcaaca cctttagccg ctaaaactcg tccttggcgt    34860
aacaaaacaa aagcccggaa accgggcttt cgtctcttgc cgcttatggc tctgcacccg    34920
gctccatcac caacaggtcg cgcacgcgct tcactcggtt gcggatcgac actgccagcc    34980
caacaaagcc ggttgccgcc gccgccagga tcgcgccgat gatgccggcc acaccggcca    35040
tcgcccacca ggtcgccgcc ttccggttcc attcctgctg gtactgcttc gcaatgctgg    35100
acctcggctc accataggct gaccgctcga tggcgtatgc cgcttctccc cttggcgtaa    35160
aacccagcgc cgcaggcggc attgccatgc tgcccgccgc tttcccgacc acgacgcgcg    35220
caccaggctt gcggtccaga ccttcggcca cggcgagctg cgcaaggaca taatcagccg    35280
ccgacttggc tccacgcgcc tcgatcagct cttgcactcg cgcgaaatcc ttggcctcca    35340
cggccgccat gaatcgcgca cgcggcgaag gctccgcagg gccggcgtcg tgatcgccgc    35400
cgagaatgcc cttcaccaag ttcgacgaca cgaaaatcat gctgacggct atcaccatca    35460
tgcagacgga tcgcacgaac ccgctgaatt gaacacgagc acggcacccg cgaccactat    35520
gccaagaatg cccaaggtaa aaattgccgg ccccgccatg aagtccgtga atgccccgac    35580
ggccgaagtg aagggcaggc cgccacccag gccgccgccc tcactgcccg gcacctggtc    35640
gctgaatgtc gatgccagca cctgcggcac gtcaatgctt ccgggcgtcg cgctcgggct    35700
gatcgcccat cccgttactg ccccgatccc ggcaatggca aggactgcca gcgctgccat    35760
tttgggtgtg aggccgttcg cggccgaggg gcgcagcccc tgggggatg ggaggcccgc    35820 gttagcgggc cgggagggtt cgagaagggg gggcacccc cttcggcgtg cgcggtcacg    35880
cgcacagggc gcagccctgg ttaaaaacaa ggtttataaa tattggttta aaagcaggtt    35940
aaaagacagg ttagcggtgg ccgaaaaacg ggcggaaacc cttgcaaatg ctggatttc    36000 tgcctgtgga cagcccctca aatgtcaata gtgtcgcccc tcatctgtca gcactctgcc    36060
cctcaagtgt caaggatcgc gcccctcatc tgtcagtagt cgcgccccctc aagtgtcaat    36120 accgcagggc acttatcccc aggcttgtcc acatcatctg tgggaaactc gcgtaaaatc    36180
aggcgttttc gccgatttgc gaggctggcc agctccacgt cgccggccga aatcgagcct    36240
gcccctcatc tgtcaacgcc gcgccgggtg agtcggcccc tcaagtgtca acgtccgccc    36300
ctcatctgtc agtgagggcc aagttttccg cgaggtatcc acaacgccgg cggccgcggt    36360
gtctcgcaca cggcttcgac ggcgtttctg gcgcgtttgc agggccatag acggccgcca    36420
gcccagcggc gagggcaacc agcccggtga gcgtcggaaa ggcgctggaa gccccgtagc    36480
gacgcggaga ggggcgagac aagccaaggg cgcaggctcg atgcgcagca cgacatagcc    36540
ggttctcgca aggacgagaa tttccctgcg gtgcccctca gtgtcaatg aaagtttcca    36600 acgcgagcca ttcgcgagag ccttgagtcc acgctagatg agagctttgt tgtaggtgga    36660
ccagttggtg attttgaact tttgctttgc cacggaacgg tctgcgttgt cgggaagatg    36720
cgtgatctga tccttcaact cagcaaaagt tcgatttatt caacaaagcc acgttgtgtc    36780
tcaaaatctc tgatgttaca ttgcacaaga taaaaatata tcatcatgaa caataaaact    36840
```

```
gtctgcttac ataaacagta atacaagggg tgttatgagc catattcaac gggaaacgtc    36900
ttgctcgac                                                             36909

<210> SEQ ID NO 8
<211> LENGTH: 13019
<212> TYPE: DNA
<213> ORGANISM: Artificial Sequence
<220> FEATURE:
<223> OTHER INFORMATION: PHP23235 construct

<400> SEQUENCE: 8
gttacccgga ccgaagctta gcccgggcat gcctgcagtg cagcgtgacc cggtcgtgcc      60
cctctctaga gataatgagc attgcatgtc taagttataa aaattacca catattttt     120 ttgtcacact tgtttgaagt gcagtttatc tatctttata catatattta aactttactc    180
tacgaataat ataatctata gtactacaat aatatcagtg ttttagagaa tcatataaat    240
gaacagttag acatggtcta aaggacaatt gagtattttg acaacaggac tctacagttt    300
tatcttttta gtgtgcatgt gttctccttt ttttttgcaa atagcttcac ctatataata    360
cttcatccat tttattagta catccattta gggtttaggg ttaatggttt ttatagacta    420
atttttttag tacatctatt ttattctatt ttagcctcta aattaagaaa actaaaactc    480
tattttagtt tttttattta ataatttaga tataaaatag aataaaataa agtgactaaa    540
aattaaacaa ataccctta agaaattaaa aaaactaagg aaacattttt cttgtttcga    600
gtagataatg ccagcctgtt aaacgccgtc gacgagtcta acggacacca accagcgaac    660
cagcagcgtc gcgtcgggcc aagcgaagca gacggcacgg catctctgtc gctgcctctg    720 gaccctctc gagagttccg ctccaccgtt ggacttgctc cgctgtcggc atccagaaat    780
tgcgtggcgg agcggcagac gtgagccggc acggcaggcg gcctcctcct cctctcacgg    840
cacggcagct acggggatt cctttcccac cgctccttcg ctttccttc ctcgcccgcc    900 gtaataaata gacaccccct ccacaccctc tttccccaac ctcgtgttgt tcggagcgca    960
cacacacaca accagatctc ccccaaatcc acccgtcggc acctccgctt caaggtacgc   1020
cgctcgtcct cccccccccc ccctctctac cttctctaga tcggcgttcc ggtccatggt   1080
tagggcccgg tagttctact tctgttcatg tttgtgttag atccgtgttt gtgttagatc   1140
cgtgctgcta gcgttcgtac acggatgcga cctgtacgtc agacacgttc tgattgctaa   1200
cttgccagtg tttctctttg gggaatcctg ggatggctct agccgttccg cagacgggat   1260
cgatttcatg atttttttg tttcgttgca tagggtttgg tttgccctt tccttatt    1320 caatatatgc cgtgcacttg tttgtcgggt catctttca tgctttttt tgtcttggtt   1380 gtgatgatgt ggtctggttg ggcggtcgtt ctagatcgga gtagaattct gtttcaaact   1440
acctggtgga tttattaatt ttggatctgt atgtgtgtgc catacatatt catagttacg   1500
aattgaagat gatggatgga aatatcgatc taggataggt atacatgttg atgcgggttt   1560
tactgatgca tatacagaga tgctttttgt tcgcttggtt gtgatgatgt ggtgtggttg   1620
ggcggtcgtt cattcgttct agatcggagt agaatactgt ttcaaactac ctggtgtatt   1680
tattaatttt ggaactgtat gtgtgtgtca tacatcttca tagttacgag tttaagatgg   1740
atggaaatat cgatctagga taggtataca tgttgatgtg ggttttactg atgcatatac   1800
atgatggcat atgcagcatc tattcatatg ctctaacctt gagtacctat ctattataat   1860
aaacaagtat gttttataat tattttgatc ttgatatact tggatgatgg catatgcagc   1920
```

-continued

```
agctatatgt ggattttttt agccctgcct tcatacgcta tttatttgct tggtactgtt    1980
tcttttgtcg atgctcaccc tgttgtttgg tgttacttct gcaggtcgac tctagaggat    2040
ccacaagttt gtacaaaaaa gctgaacgag aaacgtaaaa tgatataaat atcaatatat    2100
taaattagat tttgcataaa aaacagacta cataatactg taaaacacaa catatccagt    2160
cactatggcg gccgcattag gcaccccagg ctttacactt tatgcttccg gctcgtataa    2220
tgtgtggatt ttgagttagg atttaaatac gcgttgatcc ggcttactaa agccagata    2280 acagtatgcg tatttgcgcg ctgatttttg cggtataaga atatatactg atatgtatac    2340
ccgaagtatg tcaaaaagag gtatgctatg aagcagcgta ttacagtgac agttgacagc    2400
gacagctatc agttgctcaa ggcatatatg atgtcaatat ctccggtctg gtaagcacaa    2460
ccatgcagaa tgaagcccgt cgtctgcgtg ccgaacgctg gaaagcgaaa atcaggaag    2520 ggatggctga ggtcgcccgg tttattgaaa tgaacggctc ttttgctgac gagaacaggg    2580
gctggtgaaa tgcagtttaa ggtttacacc tataaaagag agagccgtta tcgtctgttt    2640
gtggatgtac agagtgatat cattgacacg cccggtcgac ggatggtgat cccctggcc    2700 agtgcacgtc tgctgtcaga taaagtctcc cgtgaacttt acccggtggt gcatatcggg    2760
gatgaaagct ggcgcatgat gaccaccgat atggccagtg tgccggtctc cgttatcggg    2820
gaagaagtgg ctgatctcag ccaccgcgaa aatgacatca aaaacgccat taacctgatg    2880 ttctgggaa tataaatgtc aggctccctt atacacagcc agtctgcagg tcgaccatag    2940
tgactggata tgttgtgttt tacagtatta tgtagtctgt tttttatgca aaatctaatt    3000
taatatattg atatttatat cattttacgt ttctcgttca gctttcttgt acaaagtggt    3060
gttaacctag acttgtccat cttctggatt ggccaactta attaatgtat gaaatataaag    3120 gatgcacaca tagtgacatg ctaatcacta taatgtgggc atcaaagttg tgtgttatgt    3180
gtaattacta gttatctgaa taaaagagaa agagatcatc catatttctt atcctaaatg    3240
aatgtcacgt gtctttataa ttctttgatg aaccagatgc atttcattaa ccaaatccat    3300
atacatataa atattaatca tatataatta atatcaattg ggttagcaaa acaaatctag    3360
tctaggtgtg ttttgcgaat tgcggccgcc accgcggtgg agctcgaatt ccggtccggg    3420
tcacctttgt ccaccaagat ggaactgcgg ccgctcatta attaagtcag gcgcgcctct    3480
agttgaagac acgttcatgt cttcatcgta agaagacact cagtagtctt cggccagaat    3540
ggccatctgg attcagcagg cctagaaggc catttaaatc ctgaggatct ggtcttccta    3600
aggacccggg atatcggacc gattaaactt taattcggtc cgaagcttgc atgcctgcag    3660
tgcagcgtga cccggtcgtg cccctctcta gagataatga gcattgcatg tctaagttat    3720
aaaaaattac cacatatttt ttttgtcaca cttgtttgaa gtgcagttta tctatcttta    3780
tacatatatt taaactttac tctacgaata atataatcta tagtactaca ataatatcag    3840
tgttttagag aatcatataa atgaacagtt agacatggtc taaaggacaa ttgagtattt    3900
tgacaacagg actctacagt tttatctttt tagtgtgcat gtgttctcct tttttttgc    3960 aaatagcttc acctatataa tacttcatcc attttattag tacatccatt tagggtttag    4020
ggttaatggt tttatagac taattttttt agtacatcta ttttattcta ttttagcctc    4080
taaattaaga aaactaaaac tctattttag ttttttattt taataattta gatataaat    4140 agaataaaat aaagtgacta aaattaaac aaatacccct taagaaatta aaaaactaa    4200 ggaaacattt ttcttgtttc gagtagataa tgccagcctg ttaaacgccg tcgacgagtc    4260
taacggacac caaccagcga accagcagcg tcgcgtcggg ccaagcgaag cagacggcac    4320
```

```
ggcatctctg tcgctgcctc tggacccctc tcgagagttc cgctccaccg ttggacttgc   4380
tccgctgtcg gcatccagaa attgcgtggc ggagcggcag acgtgagccg gcacggcagg   4440
cggcctcctc ctcctctcac ggcaccggca gctacggggg attcctttcc caccgctcct   4500
tcgctttccc ttcctcgccc gccgtaataa atagacaccc cctccacacc ctctttcccc   4560
aacctcgtgt tgttcggagc gcacacacac acaaccagat ctcccccaaa tccacccgtc   4620
ggcacctccg cttcaaggta cgccgctcgt cctcccccccc cccctctct accttctcta   4680
gatcggcgtt ccgtccatg catggttagg gcccggtagt tctacttctg ttcatgtttg   4740
tgttagatcc gtgtttgtgt tagatccgtg ctgctagcgt tcgtacacgg atgcgacctg   4800
tacgtcagac acgttctgat tgctaacttg ccagtgtttc tctttgggga atcctgggat   4860
ggctctagcc gttccgcaga cgggatcgat ttcatgattt tttttgtttc gttgcatagg   4920
gtttggtttg ccctttttcct ttatttcaat atatgccgtg cacttgtttg tcgggtcatc   4980
ttttcatgct ttttttttgtc ttggttgtga tgatgtggtc tggttgggcg gtcgttctag   5040
atcggagtag aattctgttt caaactacct ggtggattta ttaattttgg atctgtatgt   5100
gtgtgccata catattcata gttacgaatt gaagatgatg gatggaaata tcgatctagg   5160
ataggtatac atgttgatgc gggttttact gatgcatata cagagatgct ttttgttcgc   5220
ttggttgtga tgatgtggtg tggttgggcg gtcgttcatt cgttctagat cggagtagaa   5280
tactgtttca aactacctgg tgtatttatt aattttggaa ctgtatgtgt gtgtcataca   5340
tcttcatagt tacgagttta agatggatgg aaatatcgat ctaggatagg tatacatgtt   5400
gatgtgggtt ttactgatgc atatacatga tggcatatgc agcatctatt catatgctct   5460
aaccttgagt acctatctat tataataaac aagtatgttt tataattatt ttgatcttga   5520
tatacttgga tgatggcata tgcagcagct atatgtggat ttttttagcc ctgccttcat   5580
acgctattta tttgcttggt actgtttctt ttgtcgatgc tcaccctgtt gtttggtgtt   5640
acttctgcag gtcgacttta acttagccta ggatccacac gacaccatgt cccccgagcg   5700
ccgccccgtc gagatccgcc cggccaccgc cgccgacatg gccgccgtgt gcgacatcgt   5760
gaaccactac atcgagacct ccaccgtgaa cttccgcacc gagccgcaga ccccgcagga   5820
gtggatcgac gacctggagc gcctccagga ccgctacccg tggctcgtgg ccgaggtgga   5880
gggcgtggtg gccggcatcg cctacgccgg cccgtggaag gccgcaacg cctacgactg   5940
gaccgtggag tccaccgtgt acgtgtccca ccgccaccag cgcctcggcc tcggctccac   6000
cctctacacc cacctcctca agagcatgga ggcccagggc ttcaagtccg tggtggccgt   6060
gatcggcctc ccgaacgacc cgtccgtgcg cctccacgag gccctcggct acaccgcccg   6120
cggcacccgc cgcgccgccg gctacaagca cggcggctgg cacgacgtcg gcttctggca   6180
gcgcgacttc gagctgccgg ccccgccgcg cccggtgcgc ccggtgacgc agatctgagt   6240
cgaaacctag acttgtccat cttctggatt ggccaactta attaatgtat gaaataaaag   6300
gatgcacaca tagtgacatg ctaatcacta taatgtgggc atcaaagttg tgtgttatgt   6360
gtaattacta gttatctgaa taaaagagaa agagatcatc catatttctt atcctaaatg   6420
aatgtcacgt gtctttataa ttctttgatg aaccagatgc atttcattaa ccaaatccat   6480
atacatataa atattaatca tatataatta atatcaattg ggttagcaaa acaaatctag   6540
tctaggtgtg ttttgcgaat tgcggccgcc accgcgtgg agctcgaatt cattccgatt   6600
aatcgtggcc tcttgctctt caggatgaag agctatgttt aaacgtgcaa gcgctactag   6660
```

```
acaattcagt acattaaaaa cgtccgcaat gtgttattaa gttgtctaag cgtcaatttg    6720
tttacaccac aatatatcct gccaccagcc agccaacagc tccccgaccg gcagctcggc    6780
acaaaatcac cactcgatac aggcagccca tcagtccggg acggcgtcag cgggagagcc    6840
gttgtaaggc ggcagacttt gctcatgtta ccgatgctat tcggaagaac ggcaactaag    6900
ctgccgggtt tgaaacacgg atgatctcgc ggagggtagc atgttgattg taacgatgac    6960
agagcgttgc tgcctgtgat caaatatcat ctccctcgca gagatccgaa ttatcagcct    7020
tcttattcat ttctcgctta accgtgacag gctgtcgatc ttgagaacta tgccgacata    7080
ataggaaatc gctggataaa gccgctgagg aagctgagtg cgctatttc tttagaagtg     7140
aacgttgacg atcgtcgacc gtaccccgat gaattaattc ggacgtacgt tctgaacaca    7200
gctggatact tacttgggcg attgtcatac atgacatcaa caatgtaccc gtttgtgtaa    7260
ccgtctcttg gaggttcgta tgacactagt ggttcccctc agcttgcgac tagatgttga    7320
ggcctaacat tttattagag agcaggctag ttgcttagat acatgatctt caggccgtta    7380
tctgtcaggg caagcgaaaa ttggccattt atgacgacca atgccccgca gaagctccca    7440
tctttgccgc catagacgcc gcgccccct tttggggtgt agaacatcct tttgccagat     7500
gtggaaaaga agttcgttgt cccattgttg gcaatgacgt agtagccggc gaaagtgcga    7560
gacccatttg cgctatatat aagcctacga tttccgttgc gactattgtc gtaattggat    7620
gaactattat cgtagttgct ctcagagttg tcgtaatttg atggactatt gtcgtaattg    7680
cttatggagt tgtcgtagtt gcttggagaa atgtcgtagt tggatgggga gtagtcatag    7740
ggaagacgag cttcatccac taaaacaatt ggcaggtcag caagtgcctg ccccgatgcc    7800
atcgcaagta cgaggcttag aaccaccttc aacagatcgc gcatagtctt ccccagctct    7860
ctaacgcttg agttaagccg cgccgcgaag cggcgtcggc ttgaacgaat tgttagacat    7920
tatttgccga ctaccttggt gatctcgcct ttcacgtagt gaacaaattc ttccaactga    7980
tctgcgcgcg aggccaagcg atcttcttgt ccaagataag cctgcctagc ttcaagtatg    8040
acgggctgat actgggccgg caggcgctcc attgcccagt cggcagcgac atccttcggc    8100
gcgattttgc cggttactgc gctgtaccaa atgcgggaca acgtaagcac tacatttcgc    8160
tcatcgccag cccagtcggg cggcgagttc catagcgtta aggtttcatt tagcgcctca    8220
aatagatcct gttcaggaac cggatcaaag agttcctccg ccgctggacc taccaaggca    8280
acgctatgtt ctcttgctttt tgtcagcaag atagccagat caatgtcgat cgtggctggc   8340
tcgaagatac ctgcaagaat gtcattgcgc tgccattctc caaattgcag ttcgcgctta    8400
gctggataac gccacggaat gatgtcgtcg tgcacaacaa tggtgacttc tacagcgcgg    8460
agaatctcgc tctctccagg ggaagccgaa gtttccaaaa ggtcgttgat caaagctcgc    8520
cgcgttgttt catcaagcct tacagtcacc gtaaccagca aatcaatatc actgtgtggc    8580
ttcaggccgc catccactgc ggagccgtac aaatgtacgg ccagcaacgt cggttcgaga    8640
tggcgctcga tgacgccaac tacctctgat agttgagtcg atacttcggc gatcaccgct    8700
tccctcatga tgtttaactc ctgaattaag ccgcgccgcg aagcggtgtc ggcttgaatg    8760
aattgttagg cgtcatcctg tgctcccgag aaccagtacc agtacatcgc tgtttcgttc    8820
gagacttgag gtctagtttt atacgtgaac aggtcaatgc cgccgagagt aaagccacat    8880
tttgcgtaca aattgcaggc aggtacattg ttcgtttgtg tctctaatcg tatgccaagg    8940
agctgtctgc ttagtgccca cttttttcgca aattcgatga gactgtgcgc gactcctttg    9000
cctcggtgcg tgtgcgacac aacaatgtgt tcgatagagg ctagatcgtt ccatgttgag    9060
```

```
ttgagttcaa tcttcccgac aagctcttgg tcgatgaatg cgccatagca agcagagtct   9120
tcatcagagt catcatccga gatgtaatcc ttccggtagg ggctcacact tctggtagat   9180
agttcaaagc cttggtcgga taggtgcaca tcgaacactt cacgaacaat gaaatggttc   9240
tcagcatcca atgtttccgc cacctgctca gggatcaccg aaatcttcat atgacgccta   9300
acgcctggca cagcggatcg caaacctggc gcggcttttg cacaaaaagg cgtgacaggt   9360
ttgcgaatcc gttgctgcca cttgttaacc cttttgccag atttggtaac tataattttat   9420
gttagaggcg aagtcttggg taaaaactgg cctaaaattg ctggggattt caggaaagta   9480
aacatcacct tccggctcga tgtctattgt agatatatgt agtgtatcta cttgatcggg   9540
ggatctgctg cctcgcgcgt ttcggtgatg acggtgaaaa cctctgacac atgcagctcc   9600
cggagacggt cacagcttgt ctgtaagcgg atgccgggag cagacaagcc cgtcagggcg   9660
cgtcagcggg tgttggcggg tgtcggggcg cagccatgac ccagtcacgt agcgatagcg   9720
gagtgtatac tggcttaact atgcggcatc agagcagatt gtactgagag tgcaccatat   9780
gcggtgtgaa ataccgcaca gatgcgtaag gagaaaatac cgcatcaggc gctcttccgc   9840
ttcctcgctc actgactcgc tgcgctcggt cgttcggctg cggcgagcgg tatcagctca   9900
ctcaaaggcg gtaatacggt tatccacaga atcagggggat aacgcaggaa agaacatgtg   9960
agcaaaaggc cagcaaaagg ccaggaaccg taaaaaggcc gcgttgctgg cgttttccca  10020
taggctccgc cccctgacg agcatcacaa aaatcgacgc tcaagtcaga ggtggcgaaa  10080
cccgacagga ctataaagat accaggcgtt tcccctgga agctccctcg tgcgctctcc  10140
tgttccgacc ctgccgctta ccggatacct gtccgccttt ctcccttcgg gaagcgtggc  10200
gctttctcat agctcacgct gtaggtatct cagttcggtg taggtcgttc gctccaagct  10260
gggctgtgtg cacgaacccc ccgttcagcc cgaccgctgc gccttatccg gtaactatcg  10320
tcttgagtcc aacccggtaa gacacgactt atcgccactg gcagcagcca ctggtaacag  10380
gattagcaga gcgaggtatg taggcggtgc tacagagttc ttgaagtggt ggcctaacta  10440
cggctacact agaaggacag tatttggtat ctgcgctctg ctgaagccag ttaccttcgg  10500
aaaaagagtt ggtagctctt gatccggcaa acaaaccacc gctggtagcg gtggtttttt  10560
tgtttgcaag cagcagatta cgcgcagaaa aaaaggatct caagaagatc ctttgatctt  10620
ttctacgggg tctgacgctc agtggaacga aaactcacgt taagggattt tggtcatgag  10680
attatcaaaa aggatcttca cctagatcct tttaaattaa aaatgaagtt ttaaatcaat  10740
ctaaagtata tatgagtaaa cttggtctga cagttaccaa tgcttaatca gtgaggcacc  10800
tatctcagcg atctgtctat ttcgttcatc catagttgcc tgactcccccg tcgtgtagat  10860
aactacgata cgggagggct taccatctgg ccccagtgct gcaatgatac cgcgagaccc  10920
acgctcaccg gctccagatt tatcagcaat aaaccagcca gccggaaggg ccgagcgcag  10980
aagtggtcct gcaactttat ccgcctccat ccagtctatt aattgttgcc gggaagctag  11040
agtaagtagt tcgccagtta atagtttgcg caacgttgtt gccattgctg caggggggggg  11100
ggggggggggg gacttccatt gttcattcca cggacaaaaa cagagaaagg aaacgacaga  11160
ggccaaaaag cctcgctttc agcacctgtc gtttcctttc ttttcagagg gtattttaaa  11220
taaaaacatt aagttatgac gaagaagaac ggaaacgcct taaaccggaa aattttcata  11280
aatagcgaaa acccgcgagg tcgccgcccc gtaacctgtc ggatcaccgg aaaggacccg  11340
taaagtgata atgattatca tctacatatc acaacgtgcg tggaggccat caaaccacgt  11400
```

-continued

| | |
|---|---|
| caaataatca attatgacgc aggtatcgta ttaattgatc tgcatcaact taacgtaaaa | 11460 |
| acaacttcag acaatacaaa tcagcgacac tgaatacggg gcaacctcat gtcccccccc | 11520 |
| cccccccccc tgcaggcatc gtggtgtcac gctcgtcgtt tggtatggct tcattcagct | 11580 |
| ccggttccca acgatcaagg cgagttacat gatcccccat gttgtgcaaa aaagcggtta | 11640 |
| gctccttcgg tcctccgatc gttgtcagaa gtaagttggc cgcagtgtta tcactcatgg | 11700 |
| ttatggcagc actgcataat tctcttactg tcatgccatc cgtaagatgc ttttctgtga | 11760 |
| ctggtgagta ctcaaccaag tcattctgag aatagtgtat gcggcgaccg agttgctctt | 11820 |
| gcccggcgtc aacacgggat aataccgcgc cacatagcag aactttaaaa gtgctcatca | 11880 |
| ttggaaaacg ttcttcgggg cgaaaactct caaggatctt accgctgttg agatccagtt | 11940 |
| cgatgtaacc cactcgtgca cccaactgat cttcagcatc ttttactttc accagcgttt | 12000 |
| ctgggtgagc aaaaacagga aggcaaaatg ccgcaaaaaa gggaataagg gcgacacgga | 12060 |
| aatgttgaat actcatactc ttcctttttc aatattattg aagcatttat cagggttatt | 12120 |
| gtctcatgag cggatacata tttgaatgta tttagaaaaa taaacaaata ggggttccgc | 12180 |
| gcacatttcc ccgaaaagtg ccacctgacg tctaagaaac cattattatc atgacattaa | 12240 |
| cctataaaaa taggcgtatc acgaggccct ttcgtcttca agaattggtc gacgatcttg | 12300 |
| ctgcgttcgg atattttcgt ggagttcccg ccacagaccc ggattgaagg cgagatccag | 12360 |
| caactcgcgc cagatcatcc tgtgacgaaa ctttggcgcg tgatgactgg ccaggacgtc | 12420 |
| ggccgaaaga gcgacaagca gatcacgctt ttcgacagcg tcggatttgc gatcgaggat | 12480 |
| ttttcggcgc tgcgctacgt ccgcgaccgc gttgagggat caagccacag cagcccactc | 12540 |
| gaccttctag ccgacccaga cgagccaagg gatctttttg gaatgctgct ccgtcgtcag | 12600 |
| gctttccgac gtttgggtgg ttgaacagaa gtcattatcg tacggaatgc caagcactcc | 12660 |
| cgaggggaac cctgtggttg gcatgcacat acaaatggac gaacggataa accttttcac | 12720 |
| gcccttttaa atatccgtta ttctaataaa cgctctttc tcttaggttt acccgccaat | 12780 |
| atatcctgtc aaacactgat agtttaaact gaaggcggga acgacaatc tgatcatgag | 12840 |
| cggagaatta agggagtcac gttatgaccc ccgccgatga cgcgggacaa gccgttttac | 12900 |
| gtttggaact gacagaaccg caacgttgaa ggagccactc agcaagctgg tacgattgta | 12960 |
| atacgactca ctatagggcg aattgagcgc tgtttaaacg ctcttcaact ggaagagcg | 13019 |

<210> SEQ ID NO 9
<211> LENGTH: 2991
<212> TYPE: DNA
<213> ORGANISM: Artificial Sequence
<220> FEATURE:
<223> OTHER INFORMATION: PHP20234 construct

<400> SEQUENCE: 9

| | |
|---|---|
| ctttcctgcg ttatccctg attctgtgga taaccgtatt accgcctttg agtgagctga | 60 |
| taccgctcgc cgcagccgaa cgaccgagcg cagcgagtca gtgagcgagg aagcggaaga | 120 |
| gcgcccaata cgcaaaccgc ctctccccgc gcgttggccg attcattaat gcagctggca | 180 |
| cgacaggttt cccgactgga aagcgggcag tgagcgcaac gcaattaata cgcgtaccgc | 240 |
| tagccaggaa gagtttgtag aaacgcaaaa aggccatccg tcaggatggc cttctgctta | 300 |
| gtttgatgcc tggcagttta tggcgggcgt cctgcccgcc accctccggg ccgttgcttc | 360 |
| acaacgttca aatccgctcc cggcggattt gtcctactca ggagagcgtt caccgacaaa | 420 |
| caacagataa aacgaaaggc ccagtcttcc gactgagcct ttcgttttat ttgatgcctg | 480 |

```
gcagttccct actctcgcgt taacgctagc atggatgttt tcccagtcac gacgttgtaa    540
aacgacggcc agtcttaagc tcgggccctg cagctctaga gctcgaattc tacaggtcac    600
taataccatc taagtagttg gttcatagtg actgcatatg ttgtgtttta cagtattatg    660
tagtctgttt tttatgcaaa atctaattta atatattgat atttatatca ttttacgttt    720
ctcgttcaac tttcttgtac aaagtggccg ttaacggatc cagacttgtc catcttctgg    780
attggccaac ttaattaatg tatgaaataa aaggatgcac acatagtgac atgctaatca    840
ctataatgtg ggcatcaaag ttgtgtgtta tgtgtaatta ctagttatct gaataaaaga    900
gaaagagatc atccatattt cttatcctaa atgaatgtca cgtgtcttta taattctttg    960
atgaaccaga tgcatttcat taaccaaatc catatacata taaatattaa tcatatataa   1020
ttaatatcaa ttgggttagc aaaacaaatc tagtctaggt gtgttttgcg aattgcggca   1080
agcttgcggc cgccccgggc aactttatta tacaaagttg gcattataaa aaagcattgc   1140
ttatcaattt gttgcaacga acaggtcact atcagtcaaa ataaaatcat tatttggagc   1200
tccatggtag cgttaacgcg gccgcgatat cccctatagt gagtcgtatt acatggtcat   1260 agctgttcc tggcagctct ggcccgtgtc tcaaaatctc tgatgttaca ttgcacaaga   1320
taaaaatata tcatcatgaa caataaaact gtctgcttac ataaacagta atacaagggg   1380
tgttatgagc catattcaac gggaaacgtc gaggccgcga ttaaattcca acatggatgc   1440
tgatttatat gggtataaat gggctcgcga taatgtcggg caatcaggtg cgacaatcta   1500
tcgcttgtat gggaagcccg atgcgccaga gttgtttctg aaacatggca aaggtagcgt   1560
tgccaatgat gttacagatg agatggtcag actaaactgg ctgacggaat ttatgcctct   1620
tccgaccatc aagcatttta tccgtactcc tgatgatgca tggttactca ccactgcgat   1680
ccccggaaaa acagcattcc aggtattaga agaatatcct gattcaggtg aaaatattgt   1740
tgatgcgctg gcagtgttcc tgcgccggtt gcattcgatt cctgtttgta attgtccttt   1800
taacagcgat cgcgtatttc gtctcgctca ggcgcaatca cgaatgaata acggtttggt   1860
tgatgcgagt gattttgatg acgagcgtaa tggctggcct gttgaacaag tctggaaaga   1920
aatgcataaa cttttgccat tctcaccgga ttcagtcgtc actcatggtg atttctcact   1980
tgataacctt attttgacg aggggaaatt aataggttgt attgatgttg acgagtcgg   2040 aatcgcagac cgataccagg atcttgccat cctatgaac tgcctcggtg agttttctcc   2100
ttcattacag aaacggcttt ttcaaaaata tggtattgat aatcctgata tgaataaatt   2160
gcagtttcat ttgatgctcg atgagttttt ctaatcagaa ttggttaatt ggttgtaaca   2220
ctggcagagc attacgctga cttgacggga cggcgcaagc tcatgaccaa atcccttaa   2280 cgtgagttac gcgtcgttcc actgagcgtc agacccgta gaaagatca aaggatcttc   2340 ttgagatcct ttttttctgc gcgtaatctg ctgcttgcaa acaaaaaaac caccgctacc   2400
agcggtggtt tgtttgccgg atcaagagct accaactctt tttccgaagg taactggctt   2460
cagcagagcg cagataccaa atactgtcct tctagtgtag ccgtagttag gccaccactt   2520
caagaactct gtagcaccgc ctacatacct cgctctgcta atcctgttac cagtggctgc   2580
tgccagtggc gataagtcgt gtcttaccgg gttggactca agacgatagt taccggataa   2640
ggcgcagcgg tcgggctgaa cggggggttc gtgcacacag cccagcttgg agcgaacgac   2700
ctacaccgaa ctgagatacc tacagcgtga gcattgagaa agcgccacgc ttcccgaagg   2760
gagaaaggcg gacaggtatc cggtaagcgg cagggtcgga acaggagagc gcacgaggga   2820
```

```
gcttccaggg ggaaacgcct ggtatcttta tagtcctgtc gggtttcgcc acctctgact   2880
tgagcgtcga tttttgtgat gctcgtcagg ggggcggagc ctatggaaaa acgccagcaa   2940
cgcggccttt ttacggttcc tggccttttg ctggcttttt gctcacatgt t            2991
```

<210> SEQ ID NO 10
<211> LENGTH: 13278
<212> TYPE: DNA
<213> ORGANISM: Artificial Sequence
<220> FEATURE:
<223> OTHER INFORMATION: PHP22655 construct (destination vector)

<400> SEQUENCE: 10

```
aagctggtac gattgtaata cgactcacta tagggcgaat tgagcgctgt ttaaacgctc     60
ttcaactgga agagcggtta ccagagctgg tcacctttgt ccaccaagat ggaactgcgg    120
ccgctcatta attaagtcag gcgcgcctct agttgaagac acgttcatgt cttcatcgta    180
agaagacact cagtagtctt cggccagaat ggccccggacc gaagctggcc gctctagaac   240
tagtggatct cgatgtgtag tctacgagaa gggttaaccg tctcttcgtg agaataaccg    300
tggcctaaaa ataagccgat gaggataaat aaaatgtggt ggtacagtac ttcaagaggt    360
ttactcatca agaggatgct tttccgatga gctctagtag tacatcggac ctcacatacc    420
tccattgtgg tgaaatattt tgtgctcatt tagtgatggg taaattttgt ttatgtcact    480
ctaggttttg acatttcagt tttgccactc ttaggttttg acaaataatt tccattccgc    540
ggcaaaagca aaacaatttt atttactttt taccactctt agctttcaca atgtatcaca    600
aatgccactc tagaaattct gtttatgcca cagaatgtga aaaaaaacac tcacttattt    660
gaagccaagg tgttcatggc atggaaatgt gacataaagt aacgttcgtg tataagaaaa    720
aattgtactc ctcgtaacaa gagacggaaa catcatgaga caatcgcgtt tggaaggctt    780
tgcatcacct ttggatgatg cgcatgaatg gagtcgtctg cttgctagcc ttcgcctacc    840
gcccactgag tccgggcggc aactaccatc ggcgaacgac ccagctgacc tctaccgacc    900
ggacttgaat gcgctacctt cgtcagcgac gatggccgcg tacgctggcg acgtgccccc    960
gcatgcatgg cggcacatgg cgagctcaga ccgtgcgtgg ctggctacaa atacgtaccc   1020
cgtgagtgcc ctagctagaa acttacacct gcaactgcga gagcgagcgt gtgagtgtag   1080
ccgagtagat ccccccggtcg ccaccatggc ctcctccgag aacgtcatca ccgagttcat   1140
gcgcttcaag gtgcgcatgg agggcaccgt gaacggccac gagttcgaga tcgagggcga   1200
gggcgagggc cgcccctacg agggccacaa caccgtgaag ctgaaggtga ccaagggcgg   1260
ccccctgccc ttcgcctggg acatcctgtc cccccagttc cagtacggct ccaaggtgta   1320
cgtgaagcac cccgccgaca tccccgacta caagaagctg tccttccccg agggcttcaa   1380
gtgggagcgc gtgatgaact cgaggacgg cggcgtggcg accgtgaccc aggactcctc   1440
cctgcaggac ggctgcttca tctacaaggt gaagttcatc ggcgtgaact tcccctccga   1500 cggcccgtg atgcagaaga gaccatggg ctggaggcc tccaccgagc gcctgtaccc   1560
ccgcgacggc gtgctgaagg gcgagaccca aggccctg aagctgaagg acggcggcca   1620
ctacctggtg gagttcaagt ccatctacat ggccaagaag cccgtgcagc tgcccggcta   1680
ctactacgtg gacgccaagc tggacatcac ctcccacaac gaggactaca ccatcgtgga   1740
gcagtacgag cgcaccgagg ccgccaccac cctgttcctg tagcggccca tggatattcg   1800
aacgcgtagg taccacatgg ttaacctaga cttgtccatc ttctggattg gccaacttaa   1860
ttaatgtatg aaataaaagg atgcacacat agtgacatgc taatcactat aatgtgggca   1920
```

```
tcaaagttgt gtgttatgtg taattactag ttatctgaat aaaagagaaa gagatcatcc    1980
atatttctta tcctaaatga atgtcacgtg tctttataat tctttgatga accagatgca    2040
tttcattaac caaatccata tacatataaa tattaatcat atataattaa tatcaattgg    2100
gttagcaaaa caaatctagt ctaggtgtgt tttgcgaatg cggccgccac cgcggtggag    2160
ctcgaattcc ggtccgggcc tagaaggcca tttaaatcct gaggatctgg tcttcctaag    2220
gacccgggat atcgctatca actttgtata gaaaagttga acgagaaacg taaaatgata    2280
taaatatcaa tatattaaat tagattttgc ataaaaaaca gactacataa tactgtaaaa    2340
cacaacatat ccagtcacta tggtcgacct gcagactggc tgtgtataag ggagcctgac    2400
atttatattc cccagaacat caggttaatg gcgtttttga tgtcattttc gcggtggctg    2460
agatcagcca cttcttcccc gataacggag accggcacac tggccatatc ggtggtcatc    2520
atgcgccagc tttcatcccc gatatgcacc accgggtaaa gttcacgggg gactttatct    2580
gacagcagac gtgcactggc caggggatc accatccgtc gcccgggcgt gtcaataata    2640
tcactctgta catccacaaa cagacgataa cggctctctc ttttataggt gtaaacctta    2700
aactgcattt caccagcccc tgttctcgtc ggcaaaagag ccgttcattt caataaaccg    2760
ggcgacctca gccatcccttt cctgattttc cgctttccag cgttcggcac gcagacgacg    2820
ggcttcattc tgcatggttg tgcttaccga accggagata ttgacatcat atatgccttg    2880
agcaactgat agctgtcgct gtcaactgtc actgtaatac gctgcttcat agcatacctc    2940
tttttgacat acttcgggta tacatatcag tatatattct tataccgcaa aaatcagcgc    3000
gcaaatacgc atactgttat ctggcttta gtaagccgga tcctctagat tacgccccgc    3060
ctgccactca tcgcagtact gttgtaattc attaagcatt ctgccgacat ggaagccatc    3120
acaaacggca tgatgaacct gaatcgccag cggcatcagc accttgtcgc cttgcgtata    3180
atatttgccc atggtgaaaa cggggggcgaa gaagttgtcc atattggcca cgtttaaatc    3240
aaaactggtg aaactcaccc agggattggc tgagacgaaa aacatattct caataaaccc    3300
tttagggaaa taggccaggt tttcaccgta acacgccaca tcttgcgaat atatgtgtag    3360
aaactgccgg aaatcgtcgt ggtattcact ccagagcgat gaaaacgttt cagtttgctc    3420
atggaaaacg gtgtaacaag ggtgaacact atcccatatc accagctcac cgtctttcat    3480
tgccatacgg aattccggat gagcattcat caggcgggca agaatgtgaa taaaggccgg    3540
ataaaacttg tgcttatttt tctttacggt ctttaaaaag gccgtaatat ccagctgaac    3600
ggtctggtta taggtacatt gagcaactga ctgaaatgcc tcaaaatgtt ctttacgatg    3660
ccattgggat atatcaacgg tggtatatcc agtgattttt ttctccattt tagcttcctt    3720
agctcctgaa aatctcgacg gatcctaact caaaatccac acattatacg agccggaagc    3780
ataaagtgta aagcctgggg tgcctaatg cggccgccat agtgactgga tatgttgtgt    3840
tttacagtat tatgtagtct gttttttatg caaaatctaa tttaatatat tgatatttat    3900
atcattttac gtttctcgtt caactttatt atacaaagtt gatagatatc ggaccgatta    3960
aactttaatt cggtccgaag cttgcatgcc tgcagtgcag cgtgacccgg tcgtgcccct    4020
ctctagagat aatgagcatt gcatgtctaa gttataaaaa attaccacat atttttttg    4080 tcacacttgt ttgaagtgca gtttatctat ctttatacat atatttaaac tttactctac    4140
gaataatata atctatagta ctacaataat atcagtgttt tagagaatca tataaatgaa    4200
cagttagaca tggtctaaag gacaattgag tattttgaca acaggactct acagttttat    4260
```

```
cttttagtg tgcatgtgtt ctcctttttt tttgcaaata gcttcaccta tataatactt    4320
catccatttt attagtacat ccatttaggg tttagggtta atggttttta tagactaatt    4380
tttttagtac atctatttta ttctatttta gcctctaaat taagaaaact aaaactctat    4440
tttagttttt ttatttaata atttagatat aaaatagaat aaaataaagt gactaaaaat    4500
taaacaaata ccctttaaga aattaaaaaa actaaggaaa cattttttct tgtttcgagta   4560 gataatgcca gcctgttaaa cgccgtcgac gagtctaacg acaccaacc agcgaaccag     4620 cagcgtcgcg tcgggccaag cgaagcagac ggcacggcat ctctgtcgct gcctctggac    4680
ccctctcgag agttccgctc caccgttgga cttgctccgc tgtcggcatc cagaaattgc    4740
gtggcggagc ggcagacgtg agccggcacg gcaggcggcc tcctcctcct ctcacggcac    4800
cggcagctac gggggattcc tttcccaccg ctccttcgct ttcccttcct cgcccgccgt    4860
aataaataga caccccctcc acaccctctt tccccaacct cgtgttgttc ggagcgcaca    4920
cacacacaac cagatctccc ccaaatccac ccgtcggcac ctccgcttca aggtacgccg    4980
ctcgtcctcc cccccccccc tctctacctt ctctagatcg gcgttccggt ccatgcatgg    5040
ttagggcccg gtagttctac ttctgttcat gtttgtgtta gatccgtgtt tgtgttagat    5100
ccgtgctgct agcgttcgta cacgatgcg acctgtacgt cagacacgtt ctgattgcta     5160
acttgccagt gtttctcttt ggggaatcct gggatggctc tagccgttcc gcagacggga    5220
tcgatttcat gatttttttt gtttcgttgc atagggtttg gtttgccctt ttcctttatt    5280
tcaatatatg ccgtgcactt gtttgtcggg tcatcttttc atgctttttt ttgtcttggt    5340
tgtgatgatg tggtctggtt gggcggtcgt tctagatcgg agtagaattc tgtttcaaac    5400
tacctggtgg atttattaat tttggatctg tatgtgtgtg ccatacatat tcatagttac    5460
gaattgaaga tgatggatgg aaatatcgat ctaggatagg tatacatgtt gatgcgggtt    5520
ttactgatgc atatacagag atgcttttg ttcgcttggt tgtgatgatg tggtgtggtt     5580
gggcggtcgt tcattcgttc tagatcggag tagaatactg tttcaaacta cctggtgtat    5640
ttattaattt tggaactgta tgtgtgtgtc atacatcttc atagttacga gtttaagatg    5700
gatgaaaata tcgatctagg ataggtatac atgttgatgt gggttttact gatgcatata    5760
catgatggca tatgcagcat ctattcatat gctctaacct tgagtaccta tctattataa    5820
taaacaagta tgttttataa ttattttgat cttgatatac ttggatgatg gcatatgcag    5880
cagctatatg tggattttt tagccctgcc ttcatacgct atttatttgc ttggtactgt     5940
ttcttttgtc gatgctcacc ctgttgtttg gtgttacttc tgcaggtcga ctttaactta    6000
gcctaggatc cacacgacac catgtccccc gagcgccgcc ccgtcgagat ccgcccggcc    6060
accgccgccg acatggccgc cgtgtgcgac atcgtgaacc actacatcga gacctccacc    6120
gtgaacttcc gcaccgagcc gcagacccgc aggagtgga tcgacgacct ggagcgcctc     6180
caggaccgct acccgtggct cgtggccgag gtggaggcg tggtggccgg catcgcctac    6240
gccggcccgt ggaaggcccg caacgcctac gactggaccg tggagtccac cgtgtacgtg    6300
tcccaccgcc accagcgcct cggcctcggc tccaccctct acacccacct cctcaagagc    6360
atggaggccc agggcttcaa gtccgtggtg gccgtgatcg gcctcccgaa cgaccgtcc     6420 gtgcgcctcc acgaggccct cggctacacc gcccgcggca ccctccgcgc cgccggctac    6480
aagcacggcg gctggcacga cgtcggcttc tggcagcgcg acttcgagct gccggccccg    6540
ccgcgcccgg tgcgccggt gacgcagatc tgagtcgaaa cctagacttg tccatcttct    6600
ggattggcca acttaattaa tgtatgaaat aaaaggatgc acacatagtg acatgctaat    6660
```

```
cactataatg tgggcatcaa agttgtgtgt tatgtgtaat tactagttat ctgaataaaa   6720
gagaaagaga tcatccatat ttcttatcct aaatgaatgt cacgtgtctt tataattctt   6780
tgatgaacca gatgcatttc attaaccaaa tccatataca tataaatatt aatcatatat   6840
aattaatatc aattgggtta gcaaaacaaa tctagtctag gtgtgttttg cgaattgcgg   6900
ccgccaccgc ggtggagctc gaattcattc cgattaatcg tggcctcttg ctcttcagga   6960
tgaagagcta tgtttaaacg tgcaagcgct actagacaat tcagtacatt aaaaacgtcc   7020
gcaatgtgtt attaagttgt ctaagcgtca atttgtttac accacaatat atcctgccac   7080
cagccagcca acagctcccc gaccggcagc tcggcacaaa atcaccactc gatacaggca   7140
gcccatcagt ccgggacggc gtcagcggga gagccgttgt aaggcggcag actttgctca   7200
tgttaccgat gctattcgga agaacggcaa ctaagctgcc gggtttgaaa cacgatgat   7260 ctcgcggagg gtagcatgtt gattgtaacg atgacagagc gttgctgcct gtgatcaaat   7320
atcatctccc tcgcagagat ccgaattatc agccttctta ttcatttctc gcttaaccgt   7380
gacaggctgt cgatcttgag aactatgccg acataatagg aaatcgctgg ataaagccgc   7440
tgaggaagct gagtggcgct atttctttag aagtgaacgt tgacgatcgt cgaccgtacc   7500
ccgatgaatt aattcggacg tacgttctga acacagctgg atacttactt gggcgattgt   7560
catacatgac atcaacaatg tacccgtttg tgtaaccgtc tcttggaggt tcgtatgaca   7620
ctagtggttc ccctcagctt gcgactagat gttgaggcct aacatttat tagagagcag   7680 gctagttgct tagatacatg atcttcaggc cgttatctgt cagggcaagc gaaaattggc   7740
catttatgac gaccaatgcc ccgcagaagc tcccatcttt gccgccatag acgccgcgcc   7800
ccccttttgg ggtgtagaac atccttttgc cagatgtgga aaagaagttc gttgtcccat   7860
tgttggcaat gacgtagtag ccggcgaaag tgcgagaccc atttgcgcta tatataagcc   7920
tacgatttcc gttgcgacta ttgtcgtaat tggatgaact attatcgtag ttgctctcag   7980
agttgtcgta atttgatgga ctattgtcgt aattgcttat ggagttgtcg tagttgcttg   8040
gagaaatgtc gtagttggat ggggagtagt cataggaaag acgagcttca tccactaaaa   8100
caattggcag gtcagcaagt gcctgccccg atgccatcgc aagtacgagg cttagaacca   8160
ccttcaacag atcgcgcata gtcttcccca gctctctaac gcttgagtta agccgcgccg   8220
cgaagcggcg tcggcttgaa cgaattgtta gacattattt gccgactacc ttggtgatct   8280
cgcctttcac gtagtgaaca aattcttcca actgatctgc gcgcgaggcc aagcgatctt   8340
cttgtccaag ataagcctgc ctagcttcaa gtatgacggg ctgatactgg gccggcaggc   8400
gctccattgc ccagtcggca gcgacatcct tcggcgcgat tttgccggtt actgcgctgt   8460
accaaatgcg ggacaacgta agcactacat ttcgctcatc gccagcccag tcgggcggcg   8520
agttccatag cgttaaggtt tcatttagcg cctcaaatag atcctgttca ggaaccggat   8580
caaagagttc ctccgccgct ggacctacca aggcaacgct atgttctctt gcttttgtca   8640
gcaagatagc cagatcaatg tcgatcgtgg ctggctcgaa gatacctgca agaatgtcat   8700
tgcgctgcca ttctccaaat tgcagttcgc gcttagctgg ataacgccac ggaatgatgt   8760
cgtcgtgcac aacaatggtg acttctacag cgcggagaat ctcgctctct ccaggggaag   8820
ccgaagtttc caaaaggtcg ttgatcaaag ctcgccgcgt tgtttcatca agccttacag   8880
tcaccgtaac cagcaaatca atatcactgt gtggcttcag gccgccatcc actgcggagc   8940
cgtacaaatg tacggccagc aacgtcggtt cgagatggcg ctcgatgacg ccaactacct   9000
```

```
ctgatagttg agtcgatact tcggcgatca ccgcttccct catgatgttt aactcctgaa    9060
ttaagccgcg ccgcgaagcg gtgtcggctt gaatgaattg ttaggcgtca tcctgtgctc    9120
ccgagaacca gtaccagtac atcgctgttt cgttcgagac ttgaggtcta gttttatacg    9180
tgaacaggtc aatgccgccg agagtaaagc cacattttgc gtacaaattg caggcaggta    9240
cattgttcgt ttgtgtctct aatcgtatgc caaggagctg tctgcttagt gcccacttttt   9300
tcgcaaattc gatgagactg tgcgcgactc ctttgcctcg gtgcgtgtgc gacacaacaa    9360
tgtgttcgat agaggctaga tcgttccatg ttgagttgag ttcaatcttc ccgacaagct    9420
cttggtcgat gaatgcgcca tagcaagcag agtcttcatc agagtcatca tccgagatgt    9480
aatccttccg gtaggggctc acacttctgg tagatagttc aaagccttgg tcggataggt    9540
gcacatcgaa cacttcacga caatgaaat ggttctcagc atccaatgtt tccgccacct     9600
gctcagggat caccgaaatc ttcatatgac gcctaacgcc tggcacagcg gatcgcaaac    9660
ctggcgcggc ttttggcaca aaaggcgtga caggtttgcg aatccgttgc tgccacttgt    9720
taacccttttt gccagatttg gtaactataa tttatgttag aggcgaagtc ttgggtaaaa   9780
actggcctaa aattgctggg gatttcagga agtaaacat caccttccgg ctcgatgtct     9840
attgtagata tatgtagtgt atctacttga tcggggatc tgctgcctcg cgcgtttcgg     9900
tgatgacggt gaaaacctct gacacatgca gctcccggag acggtcacag cttgtctgta    9960
agcggatgcc gggagcagac aagcccgtca gggcgcgtca gcgggtgttg gcgggtgtcg   10020
gggcgcagcc atgacccagt cacgtagcga tagcggagtg tatactggct taactatgcg   10080
gcatcagagc agattgtact gagagtgcac catatgcggt gtgaaatacc gcacagatgc   10140
gtaaggagaa aataccgcat caggcgctct tccgcttcct cgctcactga ctcgctgcgc   10200
tcggtcgttc ggctgcggcg agcggtatca gctcactcaa aggcggtaat acggttatcc   10260
acagaatcag gggataacgc aggaaagaac atgtgagcaa aaggccagca aaaggccagg   10320
aaccgtaaaa aggccgcgtt gctggcgttt ttccataggc tccgcccccc tgacgagcat   10380
cacaaaaatc gacgctcaag tcagaggtgg cgaaacccga caggactata agataccag    10440
gcgtttcccc ctggaagctc cctcgtgcgc tctcctgttc cgaccctgcc gcttaccgga   10500
tacctgtccg cctttctccc ttcgggaagc gtggcgcttt ctcatagctc acgctgtagg   10560
tatctcagtt cggtgtaggt cgttcgctcc aagctgggct gtgtgcacga accccccgtt   10620
cagcccgacc gctgcgcctt atccggtaac tatcgtcttg agtccaaccc ggtaagacac   10680
gacttatcgc cactggcagc agccactggt aacaggatta gcagagcgag gtatgtaggc   10740
ggtgctacag agttcttgaa gtggtggcct aactacggct acactagaag gacagtattt   10800
ggtatctgcg ctctgctgaa gccagttacc ttcggaaaaa gagttggtag ctcttgatcc   10860
ggcaaacaaa ccaccgctgg tagcggtggt ttttttgttt gcaagcagca gattacgcgc   10920
agaaaaaaag gatctcaaga agatcctttg atcttttcta cggggtctga cgctcagtgg   10980
aacgaaaact cacgttaagg gattttggtc atgagattat caaaaaggat cttcacctag   11040
atccttttaa attaaaaatg aagttttaaa tcaatctaaa gtatatatga gtaaacttgg   11100
tctgacagtt accaatgctt aatcagtgag gcacctatct cagcgatctg tctatttcgt   11160
tcatccatag ttgcctgact ccccgtcgtg tagataacta cgatacggga gggcttacca   11220
tctggcccca gtgctgcaat gataccgcga gacccacgct caccggctcc agatttatca   11280
gcaataaacc agccagccgg aagggccgag cgcagaagtg gtcctgcaac tttatccgcc   11340
tccatccagt ctattaattg ttgccgggaa gctagagtaa gtagttcgcc agttaatagt   11400
```

```
ttgcgcaacg ttgttgccat tgctgcaggg ggggggggg ggggggactt ccattgttca    11460
ttccacggac aaaaacagag aaaggaaacg acagaggcca aaaagcctcg ctttcagcac    11520
ctgtcgtttc ctttctttc agagggtatt ttaaataaaa acattaagtt atgacgaaga    11580
agaacggaaa cgccttaaac cggaaaattt tcataaatag cgaaacccg cgaggtcgcc    11640
gccccgtaac ctgtcggatc accggaaagg acccgtaaag tgataatgat tatcatctac    11700
atatcacaac gtgcgtggag gccatcaaac cacgtcaaat aatcaattat gacgcaggta    11760
tcgtattaat tgatctgcat caacttaacg taaaaacaac ttcagacaat acaaatcagc    11820
gacactgaat acggggcaac ctcatgtccc ccccccccc cccctgcag gcatcgtggt    11880
gtcacgctcg tcgtttggta tggcttcatt cagctccggt tcccaacgat caaggcgagt    11940
tacatgatcc cccatgttgt gcaaaaaagc ggttagctcc ttcggtcctc cgatcgttgt    12000
cagaagtaag ttggccgcag tgttatcact catggttatg gcagcactgc ataattctct    12060
tactgtcatg ccatccgtaa gatgcttttc tgtgactggt gagtactcaa ccaagtcatt    12120
ctgagaatag tgtatgcggc gaccgagttg ctcttgcccg gcgtcaacac gggataatac    12180
cgcgccacat agcagaactt taaaagtgct catcattgga aaacgttctt cggggcgaaa    12240
actctcaagg atcttaccgc tgttgagatc cagttcgatg taacccactc gtgcacccaa    12300
ctgatcttca gcatcttta ctttcaccag cgtttctggg tgagcaaaaa caggaaggca    12360
aaatgccgca aaaaagggaa taagggcgac acggaaatgt tgaatactca tactcttcct    12420
ttttcaatat tattgaagca tttatcaggg ttattgtctc atgagcggat acatatttga    12480
atgtatttag aaaaataaac aaatagggt tccgcgcaca tttccccgaa aagtgccacc    12540
tgacgtctaa gaaaccatta ttatcatgac attaacctat aaaaataggc gtatcacgag    12600
gcccttcgt cttcaagaat tggtcgacga tcttgctgcg ttcggatatt ttcgtggagt    12660
tcccgccaca gacccggatt gaaggcgaga tccagcaact cgcgccagat catcctgtga    12720
cggaactttg gcgcgtgatg actggccagg acgtcggccg aaagagcgac aagcagatca    12780
cgcttttcga cagcgtcgga tttgcgatcg aggattttc ggcgctgcgc tacgtccgcg    12840
accgcgttga gggatcaagc cacagcagcc cactcgacct tctagccgac ccagacgagc    12900
caagggatct ttttggaatg ctgctccgtc gtcaggcttt ccgacgtttg ggtggttgaa    12960
cagaagtcat tatcgtacgg aatgccaagc actcccgagg ggaaccctgt ggttggcatg    13020
cacatacaaa tggacgaacg gataaacctt ttcacgccct tttaaatatc cgttattcta    13080
ataaacgctc ttttctctta ggtttacccg ccaatatatc ctgtcaaaca ctgatagttt    13140
aaactgaagg cgggaaacga caatctgatc atgagcggag aattaaggga gtcacgttat    13200
gacccccgcc gatgacgcgg gacaagccgt tttacgtttg gaactgacag aaccgcaacg    13260
ttgaaggagc cactcagc                                                  13278
```

<210> SEQ ID NO 11
<211> LENGTH: 50
<212> TYPE: DNA
<213> ORGANISM: Artificial Sequence
<220> FEATURE:
<223> OTHER INFORMATION: poly-linker

<400> SEQUENCE: 11
gatcactagt ggcgcgccta ggagatctcg agtagggata acagggtaat                50

<210> SEQ ID NO 12

```
<211> LENGTH: 25
<212> TYPE: DNA
<213> ORGANISM: Artificial Sequence
<220> FEATURE:
<223> OTHER INFORMATION: attB1 seqeunce

<400> SEQUENCE: 12
acaagtttgt acaaaaaagc aggct                                            25

<210> SEQ ID NO 13
<211> LENGTH: 25
<212> TYPE: DNA
<213> ORGANISM: Artificial Sequence
<220> FEATURE:
<223> OTHER INFORMATION: attB2 sequence

<400> SEQUENCE: 13
accactttgt acaagaaagc tgggt                                            25

<210> SEQ ID NO 14
<211> LENGTH: 4778
<212> TYPE: DNA
<213> ORGANISM: Artificial Sequence
<220> FEATURE:
<223> OTHER INFORMATION: PHP23112 construct

<400> SEQUENCE: 14
gaaaggccca gtcttccgac tgagcctttc gttttatttg atgcctggca gttccctact      60
ctcgcgttaa cgctagcatg gatgttttcc cagtcacgac gttgtaaaac gacggccagt     120
cttaagctcg ggcccgcgtt aacgctacca tggagctcca ataatgatt ttattttgac      180 tgatagtgac ctgttcgttg caacaaattg ataagcaatg cttttttata atgccaactt    240
tgtatagaaa agttgggccg aattcgagct cggtacggcc agaatggccc ggaccgggtt    300
accgaattcg agctcggtac cctgggatca gcttgcatgc ctgcagtgca gcgtgacccg    360
gtcgtgcccc tctctagaga taatgagcat tgcatgtcta agttataaaa aattaccaca    420
tatttttttt gtcacacttg tttgaagtgc agtttatcta tctttataca tatatttaaa    480
ctttactcta cgaataatat aatctatagt actacaataa tatcagtgtt ttagagaatc    540
atataaatga acagttagac atggtctaaa ggacaattga gtattttgac aacaggactc    600
tacagtttta tcttttttagt gtgcatgtgt tctcctttt ttttgcaaat agcttcacct    660 ataataatact tcatccattt tattagtaca tccatttagg gtttagggtt aatggtttt    720 atagactaat ttttttagta catctattt attctattt agcctctaaa ttaagaaaac    780
taaaactcta ttttagtttt tttatttaat aatttagata taaaatagaa taaaataaag    840
tgactaaaaa ttaaacaaat acccttaag aaattaaaaa aactaaggaa acatttttct    900
tgtttcgagt agataatgcc agcctgttaa acgccgtcga cgagtctaac ggacaccaac    960
cagcgaacca gcagcgtcgc gtcgggccaa gcgaagcaga cggcacggca tctctgtcgc   1020
tgcctctgga cccctctcga gagttccgct ccaccgttgg acttgctccg ctgtcggcat   1080
ccagaaattg cgtggcggag cggcagacgt gagccggcac ggcaggcggc ctcctcctcc   1140
tctcacggca ccggcagcta cgggggattc ctttcccacc gctccttcgc tttcccttcc   1200
tcgcccgccg taataaatag acacccctc cacaccctct ttccccaacc tcgtgttgtt    1260
cggagcgcac acacacacaa ccagatctcc cccaaatcca ccgtcggca cctccgcttc   1320 aaggtacgcc gctcgtcctc ccccccccc ctctctacct tctctagatc ggcgttccgg   1380
tccatgcatg gttagggccc ggtagttcta cttctgttca tgtttgtgtt agatccgtgt   1440
```

```
ttgtgttaga tccgtgctgc tagcgttcgt acacggatgc gacctgtacg tcagacacgt    1500
tctgattgct aacttgccag tgtttctctt tggggaatcc tgggatggct ctagccgttc    1560
cgcagacggg atcgatttca tgatttttt tgtttcgttg catagggttt ggtttgccct     1620
tttcctttat ttcaatatat gccgtgcact tgtttgtcgg gtcatctttt catgcttttt    1680
tttgtcttgg ttgtgatgat gtggtctggt tgggcggtcg ttctagatcg gagtagaatt    1740
ctgtttcaaa ctacctggtg gatttattaa ttttggatct gtatgtgtgt gccatacata    1800
ttcatagtta cgaattgaag atgatggatg gaaatatcga tctaggatag gtatacatgt    1860
tgatgcgggt tttactgatg catatacaga gatgcttttt gttcgcttgg ttgtgatgat    1920
gtggtgtggt tgggcggtcg ttcattcgtt ctagatcgga gtagaatact gtttcaaact    1980
acctggtgta tttattaatt ttggaactgt atgtgtgtgt catacatctt catagttacg    2040
agtttaagat ggatggaaat atcgatctag gataggtata catgttgatg tgggttttac    2100
tgatgcatat acatgatggc atatgcagca tctattcata tgctctaacc ttgagtacct    2160
atctattata ataaacaagt atgttttata attatttga tcttgatata cttggatgat     2220
ggcatatgca gcagctatat gtggattttt ttagccctgc cttcatacgc tatttatttg    2280
cttggtactg tttcttttgt cgatgctcac cctgttgttt ggtgttactt ctgcaggtcg    2340
actctagagg atcagcttgg tcacccggtc cgggcctaga aggccagctt caagtttgta    2400
caaaaaagtt gaacgagaaa cgtaaaatga tataaatatc aatatattaa attagatttt    2460
gcataaaaaa cagactacat aatactgtaa aacacaacat atgcagtcac tatgaatcaa    2520
ctacttagat ggtattagtg acctgtagaa ttcgagctct agagctgcag ggcggccgcg    2580
atatccccta tagtgagtcg tattacatgg tcatagctgt ttcctggcag ctctggcccg    2640
tgtctcaaaa tctctgatgt tacattgcac aagataaaaa tatatcatca tgaacaataa    2700
aactgtctgc ttacataaac agtaatacaa ggggtgttat gagccatatt caacgggaaa    2760
cgtcgaggcc gcgattaaat tccaacatgg atgctgattt atatgggtat aaatgggctc    2820
gcgataatgt cgggcaatca ggtgcgacaa tctatcgctt gtatgggaag cccgatgcgc    2880
cagagttgtt tctgaaacat ggcaaaggta gcgttgccaa tgatgttaca gatgagatgg    2940
tcagactaaa ctggctgacg gaatttatgc ctcttccgac catcaagcat tttatccgta    3000
ctcctgatga tgcatggtta ctcaccactg cgatccccgg aaaaacagca ttccaggtat    3060
tagaagaata tcctgattca ggtgaaaata ttgttgatgc gctggcagtg ttcctgcgcc    3120
ggttgcattc gattcctgtt tgtaattgtc cttttaacag cgatcgcgta tttcgtctcg    3180
ctcaggcgca atcacgaatg aataacggtt tggttgatgc gagtgatttt gatgacgagc    3240
gtaatggctg gcctgttgaa caagtctgga agaaatgcat aaacttttg ccattctcac     3300 cggattcagt cgtcactcat ggtgatttct cacttgataa ccttatttt gacgagggga     3360 aattaatagg ttgtattgat gttggacgag tcggaatcgc agaccgatac caggatcttg    3420
ccatcctatg gaactgcctc ggtgagtttt ctccttcatt acagaaacgg cttttcaaa     3480 aatatggtat tgataatcct gatatgaata aattgcagtt tcatttgatg ctcgatgagt    3540
ttttctaatc agaattggtt aattggttgt aacactggca gagcattacg ctgacttgac    3600
gggacggcgc aagctcatga ccaaaatccc ttaacgtgag ttacgcgtcg ttccactgag    3660
cgtcagaccc cgtagaaaag atcaaaggat cttcttgaga tccttttttt ctgcgcgtaa    3720
tctgctgctt gcaaacaaaa aaaccaccgc taccagcggt ggtttgtttg ccggatcaag    3780
```

```
agctaccaac tcttttccg aaggtaactg gcttcagcag agcgcagata ccaaatactg    3840
tccttctagt gtagccgtag ttaggccacc acttcaagaa ctctgtagca ccgcctacat    3900
acctcgctct gctaatcctg ttaccagtgg ctgctgccag tggcgataag tcgtgtctta    3960
ccgggttgga ctcaagacga tagttaccgg ataaggcgca gcggtcgggc tgaacgggg     4020 gttcgtgcac acagcccagc ttggagcgaa cgacctacac cgaactgaga tacctacagc    4080
gtgagcattg agaaagcgcc acgcttcccg aagggagaaa ggcggacagg tatccggtaa    4140
gcggcagggt cggaacagga gagcgcacga gggagcttcc aggggaaac gcctggtatc     4200 tttatagtcc tgtcgggttt cgccacctct gacttgagcg tcgattttg tgatgctcgt     4260 caggggggcg gagcctatgg aaaaacgcca gcaacgcggc cttttacgg ttcctggcct     4320 tttgctggcc ttttgctcac atgttctttc ctgcgttatc ccctgattct gtggataacc    4380
gtattaccgc ctttgagtga gctgataccg ctcgccgcag ccgaacgacc gagcgcagcg    4440
agtcagtgag cgaggaagcg gaagagcgcc caatacgcaa accgcctctc ccgcgcgtt     4500 ggccgattca ttaatgcagc tggcacgaca ggtttcccga ctggaaagcg ggcagtgagc    4560
gcaacgcaat taatacgcgt accgctagcc aggaagagtt tgtagaaacg caaaaaggcc    4620
atccgtcagg atggccttct gcttagtttg atgcctggca gtttatggcg ggcgtcctgc    4680
ccgccaccct ccgggccgtt gcttcacaac gttcaaatcc gctcccggcg atttgtcct    4740 actcaggaga gcgttcaccg acaaacaaca gataaaac                          4778

<210> SEQ ID NO 15
<211> LENGTH: 54
<212> TYPE: DNA
<213> ORGANISM: Artificial Sequence
<220> FEATURE:
<223> OTHER INFORMATION: forward primer VC062

<400> SEQUENCE: 15
ttaaacaagt ttgtacaaaa aagcaggctg caattaaccc tcactaaagg gaac           54

<210> SEQ ID NO 16
<211> LENGTH: 53
<212> TYPE: DNA
<213> ORGANISM: Artificial Sequence
<220> FEATURE:
<223> OTHER INFORMATION: reverse primer VC063

<400> SEQUENCE: 16
ttaaaccact ttgtacaaga aagctgggtg cgtaatacga ctcactatag ggc            53

<210> SEQ ID NO 17
<211> LENGTH: 1216
<212> TYPE: DNA
<213> ORGANISM: Zea mays

<400> SEQUENCE: 17
cgcagcccgc ccctctctct ctctctctcg gttcctgcgc acgcacacac gcacgtttcc    60
agttcgaccg agccagagcc ccgccccggg cagtttccat tcgctgtcgc gctcctcctc    120
ctcctcctgc acatcccctc cccccgaatt cgagccggag gaccgaagag tagatctgcg    180
ccgggcgacc agaggatggc cgtcaactgg gagctgcagg gctgctgcca ccgcgaccag    240
aggatcttca tcgccgccgt tggagtctcc accgtcgtca tcctcctcct ctggaggacg    300
ttcctgctca cgccgttcaa gctcatcacc gtcttcctcc acgagaccag ccacgcgctc    360
gcctgcaagc tcacctgcgg cgatgtagaa ggcatgcagg tccatgcgaa tgagggtggc    420
```

-continued

```
gttactcaaa ctcggggtgg catatattgg ataatcttgc ccgctggata tctgggttca      480
tcattttggg gaatggtgtt catacttgca tccacaaatc tcctcactac aagaattgca      540
gcgggttgtt tcatacttgc actgtttatt gtccttttttg ttgcagacaa ttggtttctt     600
cgctggctct gccttggatt cattgtattc attgctgttg tttgggtcat acaagaattt      660
acatctttcc atattctgaa atatgtgatc ttattcatag gtgtgatgaa cagcttattt      720
tcagtttatg atatttatga cgacttgata tcccgaagag ttaatacaag tgatgctgag      780
aagtttgctg aaatatgccc ttgcccttgc aatggttttg catgggtgt tatatgggga      840 ttcatctcgt ttatcttcct ctgcgcttca atataccttg gactggtcat attgtcttga      900
gggttccaac ctcgcgcacg ccgttttgat ctgacaacca actctggttg gcttttttcca    960 gagttctcct tgctctagat tttgggttca aacttacatt gttctggcgg ctgtacagta     1020
tacatgtagg gtaaacatgt acatccatcg tggagttaat tcggcgggga ttgttcatgt     1080
gattcttcga ttttagcggt tctatagata ccattgctca tttatggtct gtagcctcat    1140
tgctcatttg accaatttga aatcgtattc agaaacgcca aaaaaaaaaa aaaaaaaaa     1200 aaaaaaaaaa aaaaag                                                    1216
```

<210> SEQ ID NO 18
<211> LENGTH: 234
<212> TYPE: PRT
<213> ORGANISM: Zea mays

<400> SEQUENCE: 18

```
Met Ala Val Asn Trp Glu Leu Gln Gly Cys Cys His Arg Asp Gln Arg
1               5                   10                  15

Ile Phe Ile Ala Ala Val Gly Val Ser Thr Val Val Ile Leu Leu Leu
            20                  25                  30

Trp Arg Thr Phe Leu Leu Thr Pro Phe Lys Leu Ile Thr Val Phe Leu
        35                  40                  45

His Glu Thr Ser His Ala Leu Ala Cys Lys Leu Thr Cys Gly Asp Val
    50                  55                  60

Glu Gly Met Gln Val His Ala Asn Glu Gly Gly Val Thr Gln Thr Arg
65                  70                  75                  80

Gly Gly Ile Tyr Trp Ile Ile Leu Pro Ala Gly Tyr Leu Gly Ser Ser
                85                  90                  95

Phe Trp Gly Met Val Phe Ile Leu Ala Ser Thr Asn Leu Leu Thr Thr
            100                 105                 110

Arg Ile Ala Ala Gly Cys Phe Ile Leu Ala Leu Phe Ile Val Leu Phe
        115                 120                 125

Val Ala Asp Asn Trp Phe Leu Arg Trp Leu Cys Leu Gly Phe Ile Val
    130                 135                 140

Phe Ile Ala Val Val Trp Val Ile Gln Glu Phe Thr Ser Phe His Ile
145                 150                 155                 160

Leu Lys Tyr Val Ile Leu Phe Ile Gly Val Met Asn Ser Leu Phe Ser
                165                 170                 175

Val Tyr Asp Ile Tyr Asp Asp Leu Ile Ser Arg Arg Val Asn Thr Ser
            180                 185                 190

Asp Ala Glu Lys Phe Ala Glu Ile Cys Pro Cys Pro Cys Asn Gly Phe
        195                 200                 205

Ala Trp Gly Val Ile Trp Gly Phe Ile Ser Phe Ile Phe Leu Cys Ala
    210                 215                 220
```

```
Ser Ile Tyr Leu Gly Leu Val Ile Leu Ser
225                 230
```

<210> SEQ ID NO 19
<211> LENGTH: 877
<212> TYPE: DNA
<213> ORGANISM: Zea mays

<400> SEQUENCE: 19

```
agagccccgc cgggcagttt ccgttcgctg ttgcgatcca cctcctgcct gcacatcccc      60
tcccccgagt tcgagccgga gggccgaaga gtagatctgc ggcggcggcc agaggatggc     120
cgtcaactgg gagctgcggg gctgctgcga ccacgaccag aggatcttca tcgccgccgt     180
cggcgtctcc accgtcgtca tcctcctcct ctggaggacg ttcctgctca cgccgttcaa     240
gctcatcacc gtcttcctcc acgagaccag ccacgcgctt gcctgcaagc tcacttgcgg     300
cgatgtagaa ggcatgcagg tccatgcgaa tgagggtggc gttactcaaa cccggggtgg     360
catatattgg ataatcttgc ccgctggata tctgggttca tcattttggg gaatggtctt     420
catacttgca tccacaaatc tcctcactac aagaattgca gcgggttgtt tcatacttgc     480
attgtttatt gttcttttg ttgcagaaaa ttggtttctt cgctggctct gccttggatt     540
cattgtgttc attgctgttg tttgggtcat acaagaattt acatctttcc atgttctgaa     600
atatgtgatc ttattcatag gtgtgatgaa cagcttattt tcagtttacg atatttatga     660
tgacttgata tcccgaagag ttaacacaag tgatgctgaa aagtttgctg aaatctgccc     720
ttgcccctgc aatggttttg catggggtgt tatatgggga ttcatctcgt ttatctttct     780
ctgcgcttca atataccttg gactggtcat attgtcttga gggttcgcca ttttgatctg     840
acaatcgact ctggttggct ttttcgaagc ttcgttg                              877
```

<210> SEQ ID NO 20
<211> LENGTH: 234
<212> TYPE: PRT
<213> ORGANISM: Zea mays

<400> SEQUENCE: 20

```
Met Ala Val Asn Trp Glu Leu Arg Gly Cys Cys Asp His Asp Gln Arg
1               5                   10                  15

Ile Phe Ile Ala Ala Val Gly Val Ser Thr Val Ile Leu Leu Leu
            20                  25                  30

Trp Arg Thr Phe Leu Leu Thr Pro Phe Lys Leu Ile Thr Val Phe Leu
        35                  40                  45

His Glu Thr Ser His Ala Leu Ala Cys Lys Leu Thr Cys Gly Asp Val
    50                  55                  60

Glu Gly Met Gln Val His Ala Asn Glu Gly Gly Val Thr Gln Thr Arg
65                  70                  75                  80

Gly Gly Ile Tyr Trp Ile Ile Leu Pro Ala Gly Tyr Leu Gly Ser Ser
                85                  90                  95

Phe Trp Gly Met Val Phe Ile Leu Ala Ser Thr Asn Leu Leu Thr Thr
            100                 105                 110

Arg Ile Ala Ala Gly Cys Phe Ile Leu Ala Leu Phe Ile Val Leu Phe
        115                 120                 125

Val Ala Glu Asn Trp Phe Leu Arg Trp Leu Cys Leu Gly Phe Ile Val
    130                 135                 140

Phe Ile Ala Val Val Trp Val Ile Gln Glu Phe Thr Ser Phe His Val
145                 150                 155                 160
```

Leu Lys Tyr Val Ile Leu Phe Ile Gly Val Met Asn Ser Leu Phe Ser
             165                 170                 175

Val Tyr Asp Ile Tyr Asp Asp Leu Ile Ser Arg Arg Val Asn Thr Ser
         180                 185                 190

Asp Ala Glu Lys Phe Ala Glu Ile Cys Pro Cys Pro Cys Asn Gly Phe
     195                 200                 205

Ala Trp Gly Val Ile Trp Gly Phe Ile Ser Phe Ile Phe Leu Cys Ala
 210                 215                 220

Ser Ile Tyr Leu Gly Leu Val Ile Leu Ser
225                 230

<210> SEQ ID NO 21
<211> LENGTH: 1114
<212> TYPE: DNA
<213> ORGANISM: Glycine max

<400> SEQUENCE: 21

```
gtttctttga ttctctctcc tacacccacc aaaccaaaaa cgcttccttt aatcagaaga      60
ttcagaacaa aacccatcac caccattcaa caaagtttaa tccttttcac ttcaattcat     120
cattgccttt tcgtttaagc acaaaagcta tgccgaactg ggagctcagg aactgttgtg     180
accacgacca gaaggtcttc attgcttgtg ttgctgcctt caccgttgta atcctcgtgc     240
tatggaggac ctttctactt acacctttta agctcatcac cgtgtttctg catgaagcaa     300
gtcatgccat tgcttgctgg ctcacttgtg gcaaggtgga gggaattcag gttcatgcaa     360
atgagggtgg ggtaacccag actcgtggtg gcatatactg ggtgatcctg cctgctggat     420
atctcggttc atcattttgg ggaatggctt tgatacttgc gtccacaaat cttctcactg     480
caaaaattgc tgctggttgc tttattgctg ctttaattgt tgtgctcttt ctcgcaaaaa     540
attggaccct ccgaggactc tgtattggat ttattgtttt tattgctgta atttggcttc     600
tgcaagagaa acaacagtc acgttcttc gctatgtgat tctctttatt ggtgtgatga     660
acagtttgtt ttcagtttat gatatttacg atgatttaat atctcggaga gtccactcta     720
gtgatgctga aaagtttgca gaagtttgcc catgcccttg taatggtttt ggatggggag     780
ttatttgggg aatgatatca tttgcatttc tttgcgcatc tttgtacctt ggcttggtca     840
tattatcagg ttgagaatgt tgtatccaag cggtttggta ctgcaaagag cttgaccttt     900
ctcttttgat gatttgtatt tttcttctaa ttttttttcta tctgctggga gtttgctctc     960
tcaatgttac tcccatgcct tcattctttg cagcctatta tgggttgctt gatacatgat    1020
tgcttttgta tagaaactta gttccatgta ttgagttatt tgggcagatt tacatttagt    1080
gaaaaaaaaa aaaaaaaaa aaaaaaaaaa aaaa                                 1114
```

<210> SEQ ID NO 22
<211> LENGTH: 234
<212> TYPE: PRT
<213> ORGANISM: Glycine max

<400> SEQUENCE: 22

Met Pro Asn Trp Glu Leu Arg Asn Cys Cys Asp His Asp Gln Lys Val
1               5                   10                  15

Phe Ile Ala Cys Val Ala Ala Phe Thr Val Val Ile Leu Val Leu Trp
             20                  25                  30

Arg Thr Phe Leu Leu Thr Pro Phe Lys Leu Ile Thr Val Phe Leu His
         35                  40                  45

Glu Ala Ser His Ala Ile Ala Cys Trp Leu Thr Cys Gly Lys Val Glu

```
            50                  55                  60
Gly Ile Gln Val His Ala Asn Glu Gly Val Thr Gln Thr Arg Gly
 65                  70                  75                  80

Gly Ile Tyr Trp Val Ile Leu Pro Ala Gly Tyr Leu Gly Ser Ser Phe
                 85                  90                  95

Trp Gly Met Ala Leu Ile Leu Ala Ser Thr Asn Leu Leu Thr Ala Lys
                100                 105                 110

Ile Ala Ala Gly Cys Phe Ile Ala Leu Ile Val Val Leu Phe Leu
                115                 120                 125

Ala Lys Asn Trp Thr Leu Arg Gly Leu Cys Ile Gly Phe Ile Val Phe
    130                 135                 140

Ile Ala Val Ile Trp Leu Leu Gln Glu Lys Thr Thr Val His Val Leu
145                 150                 155                 160

Arg Tyr Val Ile Leu Phe Ile Gly Val Met Asn Ser Leu Phe Ser Val
                165                 170                 175

Tyr Asp Ile Tyr Asp Asp Leu Ile Ser Arg Arg Val His Ser Ser Asp
                180                 185                 190

Ala Glu Lys Phe Ala Glu Val Cys Pro Cys Pro Cys Asn Gly Phe Gly
    195                 200                 205

Trp Gly Val Ile Trp Gly Met Ile Ser Phe Ala Phe Leu Cys Ala Ser
    210                 215                 220

Leu Tyr Leu Gly Leu Val Ile Leu Ser Gly
225                 230

<210> SEQ ID NO 23
<211> LENGTH: 1261
<212> TYPE: DNA
<213> ORGANISM: Glycine max

<400> SEQUENCE: 23
ctcctacacc caccaaacca aaacgcttcc ttaatcataa gattcagaac aaaacccatc      60
accaccattc attaaagttc aatcctttc actttaattc atcattgccg tttcgtttaa     120
gcacaaaagc tatgccgaac tgggagctca ggaactgttg tgaccatgac cagaagatct     180
tcattgcttg tgttgctgcc ttcaccgttg taatcctcgt gctatggagg accttctac     240
ttacaccttt taagctcatc actgtgtttc tgcatgaagc gagtcatgcc attgcttgct     300
ggctcacttg tggcaaggtg gagggaattc aggttcatgc aaatgagggt ggggtaaccc     360
agactcgtgg tggcatatac tgggtgatct tgcctgctgg atatcttggt tcatcatttt     420
ggggaatggt tttgatactt gcgtccacaa atcttctcac tgcaaaaatt gctgctggtt     480
gcttcattgc tgctctaatt gttgtgctat tcttgcaaa aaattggacc ctccgaggac     540
tctgtattgg atttattgtt tttattgctg taatttggct tctgcaagag aaaacaactg     600
tccatgttct tcgctatgtc attctcttta ttggtgtgat gaacagtttg ttttcagttt     660
atgatattta tgatgattta atatctcgga gagtccactc tagtgatgct gaaaagtttg     720
cagaagtttg cccatgccct tgtaatggtt ttggatgggg agttatttgg ggaatgatat     780
catttgcatt tctttgcgca tctttgtacc ttggcttggt catattatca ggttgagaaa     840
gttgtatttg gtactgcaaa gaaattgacc ctttctcttt tgagggtttg cattttttgtt     900
ctaatttttt ctttctgctg ggagtttgct ctctcaatgt tactcccatg ccttcattct     960
ttgcagccta ttctgggttg cttgatacat gattgctttt gtatagaaaa cttagttcca    1020
tgtattgaat tattgggggc cgatttacag ttagtgaaat acatgtgagt atttcaatag    1080
```

```
ataggttgcc tttggcactt gcagctatta ttctcccttt ttttccctcc aaattttttca   1140 tgtctatgta aaagcataca actgggctgg tttaggggta ttcgagacct taagtgcaaa   1200
acgttgtggc atcttaataa tataaaatac attgtacaaa aaaaaaaaaa aaaaaaaaa    1260 a                                                                   1261
```

<210> SEQ ID NO 24
<211> LENGTH: 234
<212> TYPE: PRT
<213> ORGANISM: Glycine max

<400> SEQUENCE: 24

```
Met Pro Asn Trp Glu Leu Arg Asn Cys Cys Asp His Asp Gln Lys Ile
1               5                   10                  15

Phe Ile Ala Cys Val Ala Ala Phe Thr Val Val Ile Leu Val Leu Trp
            20                  25                  30

Arg Thr Phe Leu Leu Thr Pro Phe Lys Leu Ile Thr Val Phe Leu His
        35                  40                  45

Glu Ala Ser His Ala Ile Ala Cys Trp Leu Thr Cys Gly Lys Val Glu
    50                  55                  60

Gly Ile Gln Val His Ala Asn Glu Gly Val Thr Gln Thr Arg Gly
65                  70                  75                  80

Gly Ile Tyr Trp Val Ile Leu Pro Ala Gly Tyr Leu Gly Ser Ser Phe
                85                  90                  95

Trp Gly Met Val Leu Ile Leu Ala Ser Thr Asn Leu Leu Thr Ala Lys
            100                 105                 110

Ile Ala Ala Gly Cys Phe Ile Ala Ala Leu Ile Val Val Leu Phe Leu
        115                 120                 125

Ala Lys Asn Trp Thr Leu Arg Gly Leu Cys Ile Gly Phe Ile Val Phe
    130                 135                 140

Ile Ala Val Ile Trp Leu Leu Gln Glu Lys Thr Thr Val His Val Leu
145                 150                 155                 160

Arg Tyr Val Ile Leu Phe Ile Gly Val Met Asn Ser Leu Phe Ser Val
                165                 170                 175

Tyr Asp Ile Tyr Asp Asp Leu Ile Ser Arg Arg Val His Ser Ser Asp
            180                 185                 190

Ala Glu Lys Phe Ala Glu Val Cys Pro Cys Pro Cys Asn Gly Phe Gly
        195                 200                 205

Trp Gly Val Ile Trp Gly Met Ile Ser Phe Ala Phe Leu Cys Ala Ser
    210                 215                 220

Leu Tyr Leu Gly Leu Val Ile Leu Ser Gly
225                 230
```

<210> SEQ ID NO 25
<211> LENGTH: 1018
<212> TYPE: DNA
<213> ORGANISM: Helianthus sp.

<400> SEQUENCE: 25

```
aaaagccacc tcattctctc tctctctctc taacaatcat attttcaaac ttcttcgagg    60
agttgaagag agaaacgca acagtcactg atgacgtcac ctaattggga gctcaagaat    120
tgctgcgatc gcgaccagaa attctttctc gctaccgtcg gcatctattc tctcgtcatt    180
ctcgcgttat ggaggacatt tctgcttaca ccattcaagc ttatcacagt ctttcttcat    240
gaagctagcc atgcaatcgc ttgtaagctc acatgtggag aggtcatggg catggaggtt    300
```

```
catgccaatg agggtggggt gacgcagaca cgcggtggag tatattggtt aatattgcca      360
gccggatatc tcggttcatc gttttgggga atgcttttga tcctggcatc tactgacctt      420
ttaactgcga gaattgctgc cggatgttta gcagccgcct tgcttatcgt gctcttcatt      480
gccaaaaatt ggactcttcg aggactctgc attggattca tcgtattcct tgctattgtt      540
tggctactgc aagaaaaaac cacagtccgt atccttcgtt acgtcattct attcatcggt      600
gtcatgaaca gcttgttttc ggtttatgat atttatgatg atttaatttc ccggcgagtt      660
aattctagtg acgctgaaaa gtttgccgaa atttgtcctt gcccgtgtaa tggtgttgct      720
tggggagtca tatggggaat gatatccttc acttttctca gtgcttcagt ttacctggga      780
cttgtaatct tgtcatgaga ttcatggact ttgaacttca ttcatggggc tgtcttgatg      840
tgatctgatt atttactgca ctaacttta gtttcattct tttgacccct tggttgggtta      900 catacatatt gttgctttgt gtgcatacag tttcagtgta gcaaaaaatt attttgtact      960
ttttttgtgg atatgcaaat tcaaatctag agtttcaaaa aaaaaaaaaa aaaaaaa      1018
```

<210> SEQ ID NO 26
<211> LENGTH: 235
<212> TYPE: PRT
<213> ORGANISM: Helianthus sp.

<400> SEQUENCE: 26

```
Met Thr Ser Pro Asn Trp Glu Leu Lys Asn Cys Cys Asp Arg Asp Gln
1               5                   10                  15

Lys Phe Phe Leu Ala Thr Val Gly Ile Tyr Ser Leu Val Ile Leu Ala
            20                  25                  30

Leu Trp Arg Thr Phe Leu Leu Thr Pro Phe Lys Leu Ile Thr Val Phe
        35                  40                  45

Leu His Glu Ala Ser His Ala Ile Ala Cys Lys Leu Thr Cys Gly Glu
    50                  55                  60

Val Met Gly Met Glu Val His Ala Asn Glu Gly Val Thr Gln Thr
65                  70                  75                  80

Arg Gly Gly Val Tyr Trp Leu Ile Leu Pro Ala Gly Tyr Leu Gly Ser
                85                  90                  95

Ser Phe Trp Gly Met Leu Leu Ile Leu Ala Ser Thr Asp Leu Leu Thr
            100                 105                 110

Ala Arg Ile Ala Ala Gly Cys Leu Ala Ala Ala Leu Leu Ile Val Leu
        115                 120                 125

Phe Ile Ala Lys Asn Trp Thr Leu Arg Gly Leu Cys Ile Gly Phe Ile
    130                 135                 140

Val Phe Leu Ala Ile Val Trp Leu Leu Gln Glu Lys Thr Thr Val Arg
145                 150                 155                 160

Ile Leu Arg Tyr Val Ile Leu Phe Ile Gly Val Met Asn Ser Leu Phe
                165                 170                 175

Ser Val Tyr Asp Ile Tyr Asp Asp Leu Ile Ser Arg Arg Val Asn Ser
            180                 185                 190

Ser Asp Ala Glu Lys Phe Ala Glu Ile Cys Pro Cys Pro Cys Asn Gly
        195                 200                 205

Val Ala Trp Gly Val Ile Trp Gly Met Ile Ser Phe Thr Phe Leu Ser
    210                 215                 220

Ala Ser Val Tyr Leu Gly Leu Val Ile Leu Ser
225                 230                 235
```

<210> SEQ ID NO 27

<211> LENGTH: 1144
<212> TYPE: DNA
<213> ORGANISM: Helianthus sp.

<400> SEQUENCE: 27

```
gccgaatttt ctcagaatat ttgtaaaata ttcattgacc cctggcttcc ataaataaat    60
catgcccatt tcttctctag atcccaaccc acctcataat ttccttaaat cccactcatt   120
tcccatcaat ctttattctt tctagagata aacatggcta attgggagct cagagactgt   180
tgtaatcatg atcagttgct gtttcttatc actctggctt tctgtgtcat tgtcattctt   240
gcgctatgga ggacaatagt gcttttacca ttcaagcttg tcactatttt tcttcatgaa   300
gccagtcatg ctgttgcttg caaacttaca tgtggccatg tggaaggaat gcaaattttt   360
gccgatgaag gtggaatgac ccaaacacgc ggcggtgtat attggtttat attaccagct   420
ggatatttag gatcctcatt tggggggatg gttttgatac tggcgtcgac aaatcttata   480
gctgcaagag ttgctgctgg atgtttagca gctgccttga ttattgtgct ttttgtggct   540
aaaaattgga cgcttcgcgg gctttgcata ggatttattg tggtccttgc tgtggtttgg   600
attttgcaag aaacaacaaa agttcgaatt cttcggtaca tcataatgtt cattggtgtg   660
atgaacagtg tgttttctat ctatgatata tacggtgatc taatatccag acaggttcac   720
actagtgatg ctgagaagtt cgcagaagta tgtccttgtc cgtgtaatgg tgtcgggtgg   780
ggtgtcatat ggggtcttat atctctcatt tttctcggta tagctacata ctttggtctt   840
gtgatcttgt ctcaagtata actggtcata atttaatgca cagatagttg atgattgaag   900
ctgagagcaa catatgcaat atacattttt ggtataatct tgaatatcta taagggtcg   960
gctgattgta tttttatata aaatggtat agttaattct tttgtcaaat aaaagacttt  1020
ttgtttgact gcatgaaaga gttgataata gtagagttct tggttttatg gttaaaaaaa  1080
aaaaaaaaaa aaaaaaaaaa aaaaaaaaaa aaaaaaaaaa aaaaaaaaaa aaaaaaaaaa  1140
aaaa                                                              1144
```

<210> SEQ ID NO 28
<211> LENGTH: 235
<212> TYPE: PRT
<213> ORGANISM: Helianthus sp.

<400> SEQUENCE: 28

```
Met Ala Asn Trp Glu Leu Arg Asp Cys Cys Asn His Asp Gln Leu Leu
1               5                   10                  15

Phe Leu Ile Thr Leu Ala Phe Cys Val Ile Val Ile Leu Ala Leu Trp
            20                  25                  30

Arg Thr Ile Val Leu Leu Pro Phe Lys Leu Val Thr Ile Phe Leu His
        35                  40                  45

Glu Ala Ser His Ala Val Ala Cys Lys Leu Thr Cys Gly His Val Glu
    50                  55                  60

Gly Met Gln Ile Phe Ala Asp Glu Gly Gly Met Thr Gln Thr Arg Gly
65                  70                  75                  80

Gly Val Tyr Trp Phe Ile Leu Pro Ala Gly Tyr Leu Gly Ser Ser Phe
                85                  90                  95

Trp Gly Met Val Leu Ile Leu Ala Ser Thr Asn Leu Ile Ala Ala Arg
                100                 105                 110

Val Ala Ala Gly Cys Leu Ala Ala Ala Leu Ile Ile Val Leu Phe Val
            115                 120                 125

Ala Lys Asn Trp Thr Leu Arg Gly Leu Cys Ile Gly Phe Ile Val Val
```

```
                      130                 135                 140
Leu Ala Val Val Trp Ile Leu Gln Glu Thr Thr Lys Val Arg Ile Leu
145                 150                 155                 160

Arg Tyr Ile Ile Met Phe Ile Gly Val Met Asn Ser Val Phe Ser Ile
                165                 170                 175

Tyr Asp Ile Tyr Gly Asp Leu Ile Ser Arg Gln Val His Thr Ser Asp
            180                 185                 190

Ala Glu Lys Phe Ala Glu Val Cys Pro Cys Pro Cys Asn Gly Val Gly
        195                 200                 205

Trp Gly Val Ile Trp Gly Leu Ile Ser Leu Ile Phe Leu Gly Ile Ala
    210                 215                 220

Thr Tyr Phe Gly Leu Val Ile Leu Ser Gln Val
225                 230                 235

<210> SEQ ID NO 29
<211> LENGTH: 1305
<212> TYPE: DNA
<213> ORGANISM: Oryza sativa

<400> SEQUENCE: 29
gcagagctta caccagttcg aacgtttca  atttcctcgt gttttcctgc ctcctcctcc    60
tcctcctcgt cctcttctcc ccccatttcc cttgagggcg cagcagatct gcggcgagga   120
acgacgagga tggtgaaggt gaactgggag ctgcaggat  gctgcgaccg cgaccagaag   180
atcttcatag ccgccgtcgg cgtctccacc gtcgtcatcc tcctcgtgag cacaccctcc   240
ctagctccgt ccttctccct gctttgcttg gtttggttgt gttgtgttgc ttctgaatcg   300
ggttcgttgt gtgtgggggg tttgggtttt tgctctgcct ttggattgca gctgtggagg   360
acgttcctgc tcacgccctt caaactcatc accgtcttcc tccacgagac cagccacgcc   420
ctcgcctgca agctcacctg cggagatgta agttgagggc atgcaggtcc atcctaatga   480
gggcggtgtt actcaaactc ggggcggcat atattggata tcttgcctg  ctggatatct   540 gggttcatca ttttggggaa tggtcttcat actggcttcc acaaatctcc tcactactag   600
aattgcagcg ggttgcttca ttcttgcatt aatcgttgtt cttttttgttg ctaaaaattg   660 gtttcttcgc tggctctgca ttggtttcat cgtattcctt gctgttgttt gggtcattca   720
agaattcaca aaattccata gtctcaagta tgtaattta  ttcataggtg tgatgaatag   780
cttgttttca gtctacgata tctatgatga cttgatatca cgaagagttc attcaagtga   840
tgctgagaaa tttgctgaaa tctgcccatg tccttgcaat ggttgtgcat ggggtgtcat   900 atgggcttc  atctcgttta tctttctttg cgcatcaata taccttggac tggttatatt   960
gtcttgagga ttccaatctt ccatatacca ttttgatatg agaaccaagt caagctgtgc  1020
tctcctgtat ttgcattgct ctggatgttg gctccagctt gtattgatct catgtgtcat  1080
gagttgtaga aagttcatac aaacggcaat cgatttatgc caattggagt tgatgggata  1140
gggattagtc attcgattct tccatttagt gcttctgtag atagcattct gcttatagtt  1200
catcttcata gctgattagc tgtcattta  gtactatctc atctcttgaa ttgttactat  1260
tcatcaacat atagaaattt actcgacaaa aaaaaaaaaa aaaaa                  1305

<210> SEQ ID NO 30
<211> LENGTH: 168
<212> TYPE: PRT
<213> ORGANISM: Oryza sativa

<400> SEQUENCE: 30
```

```
Met Gln Val His Pro Asn Glu Gly Gly Val Thr Gln Thr Arg Gly Gly
1               5                   10                  15

Ile Tyr Trp Ile Ile Leu Pro Ala Gly Tyr Leu Gly Ser Ser Phe Trp
            20                  25                  30

Gly Met Val Phe Ile Leu Ala Ser Thr Asn Leu Leu Thr Thr Arg Ile
        35                  40                  45

Ala Ala Gly Cys Phe Ile Leu Ala Leu Ile Val Val Leu Phe Val Ala
    50                  55                  60

Lys Asn Trp Phe Leu Arg Trp Leu Cys Ile Gly Phe Ile Val Phe Leu
65                  70                  75                  80

Ala Val Val Trp Val Ile Gln Glu Phe Thr Lys Phe His Ser Leu Lys
                85                  90                  95

Tyr Val Ile Leu Phe Ile Gly Val Met Asn Ser Leu Phe Ser Val Tyr
                100                 105                 110

Asp Ile Tyr Asp Asp Leu Ile Ser Arg Arg Val His Ser Ser Asp Ala
            115                 120                 125

Glu Lys Phe Ala Glu Ile Cys Pro Cys Pro Cys Asn Gly Cys Ala Trp
        130                 135                 140

Gly Val Ile Trp Gly Phe Ile Ser Phe Ile Phe Leu Cys Ala Ser Ile
145                 150                 155                 160

Tyr Leu Gly Leu Val Ile Leu Ser
                165
```

<210> SEQ ID NO 31
<211> LENGTH: 1084
<212> TYPE: DNA
<213> ORGANISM: Arabidopsis thaliana

<400> SEQUENCE: 31

```
ttcgtccatt tttccctctt ttcttttct ctttctttct cccaatcact cttcagattc      60
cggggaagag aaaagagaga aagaaagaaa gattcaatct ttattagccg agatggatt     120
cgccaaactg ggaactccgt ggttgttgta accggaatca aaatactttc ctcatcacca    180
tcggagtctt caccgtagtt atccttctgc tatggaggac atttctattg actccattta    240
aactcattac ggtgtttttg cacgaagcta gtcatgccgt tgcttgcaag cttacatgtg    300
gagatgtaga ggggatggag gtgaatgcaa atgaaggggg ttcgaccaca acacgtggtg    360
gcatttattg gttgatctta cctgctggct atcttggctc atcattttgg ggaatggcat    420
tgattcttgc atctaccaat ctgcttacag caagaatagc tgctgctggt cttggtcttg    480
ctttattcat cgttctcttc attgccaaaa actggacgct tcgagggctt tgtataggtt    540
tcatagtttt cctcgctgtc atatgggttc tacaagagtt aactacagtc aaaattctcc    600
gttatgtcat tctgttttatt ggtgtgatga atagcttatt ctcagtttac gatatctatg    660
atgatttgat atctcggagg gtccattcga gcgatgctga aagttcgca gagatctgtc    720
cttgctgtac cggttgtggc tggggtgtca tctgggaat gatatcattt gcgtttcttt    780
gtgcatcgct ctatctcggg ctagtgatcc tatcataaga gggtattctt gttactcag    840
gttcagattc ttcccagtga aatgcatgca aagacaaata gtttgacaaa agattgatt    900
ctttagatcc ccttgatgtg tttgggatta acattgtcca ttgaaagttt aggttttatt    960
tgaaagtttg tattcttttt atattggagc gtgttgatta gaattcattg gatatttgat   1020
ttggtctatg tttaatgtat tgaaagttcg ttgactttt caatagaaga tgtccgttga   1080
cttt                                                               1084
```

<210> SEQ ID NO 32
<211> LENGTH: 234
<212> TYPE: PRT
<213> ORGANISM: Arabidopsis thaliana

<400> SEQUENCE: 32

Met Asp Ser Pro Asn Trp Glu Leu Arg Gly Cys Cys Asn Arg Asn Gln
1               5                   10                  15

Asn Thr Phe Leu Ile Thr Ile Gly Val Phe Thr Val Val Ile Leu Leu
            20                  25                  30

Leu Trp Arg Thr Phe Leu Leu Thr Pro Phe Lys Leu Ile Thr Val Phe
        35                  40                  45

Leu His Glu Ala Ser His Ala Val Ala Cys Lys Leu Thr Cys Gly Asp
    50                  55                  60

Val Glu Gly Met Glu Val Asn Ala Asn Glu Gly Gly Ser Thr Thr Thr
65                  70                  75                  80

Arg Gly Gly Ile Tyr Trp Leu Ile Leu Pro Ala Gly Tyr Leu Gly Ser
                85                  90                  95

Ser Phe Trp Gly Met Ala Leu Ile Leu Ala Ser Thr Asn Leu Leu Thr
            100                 105                 110

Ala Arg Ile Ala Ala Ala Gly Leu Gly Leu Ala Leu Phe Ile Val Leu
        115                 120                 125

Phe Ile Ala Lys Asn Trp Thr Leu Arg Gly Leu Cys Ile Gly Phe Ile
    130                 135                 140

Val Phe Leu Ala Val Ile Trp Val Leu Gln Glu Leu Thr Thr Val Lys
145                 150                 155                 160

Ile Leu Arg Tyr Val Ile Leu Phe Ile Gly Val Met Asn Ser Leu Phe
                165                 170                 175

Ser Val Tyr Asp Ile Tyr Asp Asp Leu Ile Ser Arg Arg Val His Ser
            180                 185                 190

Ser Asp Ala Glu Lys Phe Ala Glu Ile Cys Pro Cys Cys Thr Gly Cys
        195                 200                 205

Gly Trp Gly Val Ile Trp Gly Met Ile Ser Phe Ala Phe Leu Cys Ala
    210                 215                 220

Ser Leu Tyr Leu Gly Leu Val Ile Leu Ser
225                 230

<210> SEQ ID NO 33
<211> LENGTH: 233
<212> TYPE: PRT
<213> ORGANISM: Vitis vinifera

<400> SEQUENCE: 33

Met Ala Asn Trp Glu Leu Lys Asn Cys Cys Lys His Asp Gln Val Val
1               5                   10                  15

Phe Leu Ala Thr Ile Gly Val Phe Thr Val Val Ile Leu Leu Leu Trp
            20                  25                  30

Arg Thr Phe Leu Leu Thr Pro Phe Lys Leu Ile Thr Val Phe Leu His
        35                  40                  45

Glu Ala Ser His Ala Ile Ala Cys Lys Leu Thr Cys Gly Gln Val Glu
    50                  55                  60

Gly Ile Gln Val Asn Ala Asp Glu Gly Gly Val Thr Gln Thr Arg Gly
65                  70                  75                  80

Gly Val Tyr Trp Leu Ile Leu Pro Ala Gly Tyr Leu Gly Ser Ser Phe
                85                  90                  95

```
Trp Gly Met Val Phe Ile Leu Ala Ser Thr Asn Leu Leu Thr Ser Arg
            100                 105                 110

Ile Ala Ala Gly Cys Phe Ala Val Ala Leu Ile Val Val Leu Phe Ile
            115                 120                 125

Ala Lys Asn Trp Thr Leu Arg Gly Leu Cys Ile Gly Phe Ile Ile Phe
130                 135                 140

Leu Ala Ile Ile Trp Val Leu Gln Glu Thr Thr Lys Val Arg Ile Leu
145                 150                 155                 160

Arg Phe Phe Ile Leu Phe Met Gly Val Met Asn Ser Leu Phe Ser Val
                165                 170                 175

Tyr Asp Ile Tyr Asp Asp Leu Ile Ser Arg Arg Val His Ser Ser Asp
            180                 185                 190

Ala Glu Lys Phe Ala Glu Ile Cys Pro Cys Pro Cys Asn Gly Val Gly
            195                 200                 205

Trp Gly Val Ile Trp Gly Met Ile Ser Phe Ile Phe Leu Ala Ala Ala
            210                 215                 220

Met Tyr Leu Gly Leu Val Ile Leu Ser
225                 230

<210> SEQ ID NO 34
<211> LENGTH: 233
<212> TYPE: PRT
<213> ORGANISM: Vitis vinifera

<400> SEQUENCE: 34

Met Ala Asn Trp Glu Leu Lys Lys Cys Cys Asn His Glu Gln Val Val
1               5                   10                  15

Phe Leu Thr Thr Ile Ser Ile Cys Thr Val Val Ile Leu Ala Leu Trp
            20                  25                  30

Arg Thr Ile Leu Leu Thr Pro Phe Lys Leu Val Thr Val Phe Leu His
            35                  40                  45

Glu Ala Ser His Ala Ile Ala Cys Lys Leu Thr Cys Gly His Val Glu
        50                  55                  60

Gly Ile Gln Val His Ala Asp Glu Gly Thr Thr Gln Thr Arg Gly
65                  70                  75                  80

Gly Ile Tyr Trp Leu Ile Leu Pro Ala Gly Tyr Leu Gly Ser Phe
                85                  90                  95

Trp Gly Met Val Leu Ile Ile Ala Ser Thr Asn Val Leu Thr Ala Lys
            100                 105                 110

Ile Ala Ala Gly Cys Phe Ala Phe Ala Leu Leu Val Val Leu Phe Val
            115                 120                 125

Ala Lys Asn Trp Thr Leu Arg Gly Leu Cys Ile Gly Phe Ile Ile Leu
130                 135                 140

Ile Ala Val Val Trp Leu Leu Gln Glu Thr Thr Glu Ile Arg Ile Leu
145                 150                 155                 160

Arg Tyr Ile Ile Leu Phe Ile Gly Val Met Asn Ser Leu Phe Ser Val
                165                 170                 175

Tyr Asp Ile Tyr Asp Asp Leu Ile Ser Arg Arg Val Asn Ser Ser Asp
            180                 185                 190

Ala Glu Lys Phe Ala Glu Val Cys Pro Cys Pro Cys Asn Gly Val Gly
            195                 200                 205

Trp Gly Val Ile Trp Gly Leu Ile Ser Phe Leu Phe Leu Cys Gly Ala
            210                 215                 220

Met Tyr Leu Gly Leu Val Ile Leu Ser
```

```
225               230

<210> SEQ ID NO 35
<211> LENGTH: 55
<212> TYPE: DNA
<213> ORGANISM: Artificial
<220> FEATURE:
<223> OTHER INFORMATION: At1g67060-5' attB F primer

<400> SEQUENCE: 35
ttaaacaagt ttgtacaaaa aagcaggctc aacaatggat tcgccaaact gggaa          55

<210> SEQ ID NO 36
<211> LENGTH: 50
<212> TYPE: DNA
<213> ORGANISM: artificial
<220> FEATURE:
<223> OTHER INFORMATION: At1g67060-3' attB R primer

<400> SEQUENCE: 36
ttaaaccact ttgtacaaga aagctgggtt tatgatagga tcactagccc                50

<210> SEQ ID NO 37
<211> LENGTH: 234
<212> TYPE: PRT
<213> ORGANISM: Zea mays

<400> SEQUENCE: 37

Met Ala Val Asn Trp Glu Leu Gln Gly Cys Cys His Arg Asp Gln Arg
1               5                   10                  15

Ile Phe Ile Ala Ala Val Gly Val Ser Thr Val Val Ile Leu Leu Leu
            20                  25                  30

Trp Arg Thr Phe Leu Leu Thr Pro Phe Lys Leu Ile Thr Val Phe Leu
        35                  40                  45

His Glu Thr Ser His Ala Leu Ala Cys Lys Leu Thr Cys Gly Asp Val
    50                  55                  60

Glu Gly Met Gln Val His Ala Asn Glu Gly Gly Val Thr Gln Thr Arg
65                  70                  75                  80

Gly Gly Ile Tyr Trp Ile Ile Leu Pro Ala Gly Tyr Leu Gly Ser Ser
                85                  90                  95

Phe Trp Gly Met Val Phe Ile Leu Ala Ser Thr Asn Leu Leu Thr Thr
            100                 105                 110

Arg Ile Ala Ala Gly Cys Phe Ile Leu Ala Leu Phe Ile Val Leu Phe
        115                 120                 125

Val Ala Asp Asn Trp Phe Leu Arg Trp Leu Cys Leu Gly Phe Ile Val
    130                 135                 140

Phe Ile Ala Val Val Trp Val Ile Gln Glu Phe Thr Ser Phe His Ile
145                 150                 155                 160

Leu Lys Tyr Val Ile Leu Phe Ile Gly Val Met Asn Ser Leu Phe Ser
                165                 170                 175

Val Tyr Asp Ile Tyr Asp Asp Leu Ile Ser Arg Arg Val Asn Thr Ser
            180                 185                 190

Asp Ala Glu Lys Phe Ala Glu Ile Cys Pro Cys Pro Cys Asn Gly Phe
        195                 200                 205

Ala Trp Gly Val Ile Trp Gly Phe Ile Ser Phe Ile Phe Leu Cys Ala
    210                 215                 220

Ser Ile Tyr Leu Gly Leu Val Ile Leu Ser
225                 230
```

US 9,040,773 B2

PLANTS HAVING ALTERED AGRONOMIC CHARACTERISTICS UNDER NITROGEN LIMITING CONDITIONS AND RELATED CONSTRUCTS AND METHODS INVOLVING GENES ENCODING LNT1 POLYPEPTIDES AND HOMOLOGS THEREOF

CROSS REFERENCE TO RELATED APPLICATIONS

This application is a Divisional of U.S. application Ser. No. 12/999,074, filed Jul. 8, 2009, now allowed, which is a 371 filing of International Application No. PCT/US09/49878, filed Jul. 8, 2009, now expired, which claims the benefit of U.S. Provisional Application No. 61/078,949, filed Jul. 8, 2008, the entire content of which is herein incorporated by reference.

FIELD OF THE INVENTION

The field of invention relates to plant breeding and genetics and, in particular, relates to recombinant DNA constructs useful in plants for conferring nitrogen use efficiency and/or tolerance to nitrogen limiting conditions.

BACKGROUND OF THE INVENTION

Abiotic stressors significantly limit crop production worldwide. Cumulatively, these factors are estimated to be responsible for an average 70% reduction in agricultural production. Plants are sessile and have to adjust to the prevailing environmental conditions of their surroundings. This has led to their development of a great plasticity in gene regulation, morphogenesis, and metabolism. Adaptation and defense strategies involve the activation of genes encoding proteins important in the acclimation or defense towards the different stressors.

The adsorption of nitrogen by plants plays an important role in their growth (Gallais et al., *J. Exp. Bot.* 55(396):295-306 (2004)). Plants synthesize amino acids from inorganic nitrogen in the environment. Consequently, nitrogen fertilization has been a powerful tool for increasing the yield of cultivated plants, such as maize and soybean. Today farmers desire to reduce the use of nitrogen fertilizer, in order to avoid pollution by nitrates and to maintain a sufficient profit margin. If the nitrogen assimilation capacity of a plant can be increased, then increases in plant growth and yield increase are also expected. In summary, plant varieties that have a better nitrogen use efficiency (NUE) are desirable.

Activation tagging can be utilized to identify genes with the ability to affect a trait. This approach has been used in the model plant species *Arabidopsis thaliana* (Weigel et al., *Plant Physiol.* 122:1003-1013 (2000)). Insertions of transcriptional enhancer elements can dominantly activate and/or elevate the expression of nearby endogenous genes. This method can be used to identify genes of interest for a particular trait (e.g. nitrogen use efficiency in a plant), genes that when placed in an organism as a transgene can alter that trait.

SUMMARY OF THE INVENTION

The present invention includes:

In one embodiment, a plant comprising in its genome a recombinant DNA construct comprising a polynucleotide operably linked to at least one regulatory element, wherein said polynucleotide encodes a polypeptide having an amino acid sequence of at least 50% sequence identity, based on the Clustal V method of alignment, when compared to SEQ ID NO:18, 20, 22, 24, 26, 28, 30, 32, 33, 34, or 37, and wherein said plant exhibits increased nitrogen stress tolerance when compared to a control plant not comprising said recombinant DNA construct.

In another embodiment, a method of increasing nitrogen stress tolerance in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:18, 20, 22, 24, 26, 28, 30, 32, 33, 34, or 37; (b) regenerating a transgenic plant from the regenerable plant cell after step (a), wherein the transgenic plant comprises in its genome the recombinant DNA construct and exhibits increased nitrogen stress tolerance when compared to a control plant not comprising the recombinant DNA construct; and optionally, (c) obtaining a progeny plant derived from the transgenic plant, wherein said progeny plant comprises in its genome the recombinant DNA construct and exhibits increased nitrogen stress tolerance when compared to a control plant not comprising the recombinant DNA construct.

In another embodiment, a method of evaluating nitrogen stress tolerance in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:18, 20, 22, 24, 26, 28, 30, 32, 33, 34, or 37; (b) regenerating a transgenic plant from the regenerable plant cell after step (a), wherein the transgenic plant comprises in its genome the recombinant DNA construct; and (c) evaluating the transgenic plant for nitrogen stress tolerance compared to a control plant not comprising the recombinant DNA construct; and optionally, (d) obtaining a progeny plant derived from the transgenic plant, wherein the progeny plant comprises in its genome the recombinant DNA construct; and optionally, (e) evaluating the progeny plant for nitrogen stress tolerance compared to a control plant not comprising the recombinant DNA construct.

In another embodiment, a method of evaluating nitrogen stress tolerance in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:18, 20, 22, 24, 26, 28, 30, 32, 33, 34, or 37; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) evaluating the progeny plant for nitrogen stress tolerance compared to a control plant not comprising the recombinant DNA construct.

In another embodiment, the present invention includes any of the methods of the present invention wherein the plant is a maize plant or a soybean plant.

In another embodiment, the present invention includes an isolated polynucleotide comprising: (a) a nucleotide sequence encoding an LNT1 or LNT1-like polypeptide, wherein the polypeptide has an amino acid sequence of at least 90% or 95% sequence identity, based on the Clustal V method of alignment, when compared to one of SEQ ID NO:26, 28 or 30, or (b) a full complement of the nucleotide sequence, wherein the full complement and the nucleotide sequence consist of the same number of nucleotides and are 100% complementary. The polypeptide may comprise the amino acid sequence of SEQ ID NO: 26, 28 or 30. The nucleotide sequence may comprise the nucleotide sequence of SEQ ID NO: 25, 27 or 29.

In another embodiment, the present invention concerns a recombinant DNA construct comprising any of the isolated polynucleotides of the present invention operably linked to at least one regulatory sequence, and a cell, a plant, and a seed comprising the recombinant DNA construct.

In another embodiment, the present invention includes a vector comprising any of the isolated polynucleotides of the present invention.

In another embodiment, the present invention concerns a cell, plant or seed comprising any of the recombinant DNA constructs of the present invention. The cell may be eukaryotic, e.g., a yeast, insect or plant cell, or prokaryotic, e.g., a bacterium.

BRIEF DESCRIPTION OF THE DRAWINGS AND SEQUENCE LISTINGS

The invention can be more fully understood from the following detailed description and the accompanying drawings and Sequence Listing which form a part of this application.

FIG. 11 shows a typical grid pattern for five lines (labeled 1 through 5—eleven individuals for each line), plus wild-type control C1 (nine individuals), used in screens.

FIG. 13 shows the growth medium used for semi-hydroponics maize growth in Example 18.

FIG. 14 shows a chart setting forth data relating to the effect of different nitrate concentrations on the growth and development of Gaspe Flint derived maize lines in Example 18.

FIGS. 15A-15C show the multiple alignment of the full length amino acid sequences of the *Arabidopsis thaliana* LNT1 polypeptide (SEQ ID NO:32) and the LNT1 homologs of SEQ ID NOs: 18, 20, 22, 24, 26, 28, 30, 33, 34, and 37.

FIG. 16 shows a chart of the percent sequence identity and the divergence values for each pair of amino acids sequences displayed in FIGS. 15A-15C.

FIGS. 17A-E shows an evaluation of individual Gaspe Flint derived maize lines transformed with PHP30116.

FIG. 18 shows a summary evaluation of Gaspe Flint derived maize lines transformed with PHP30116.

The sequence descriptions and Sequence Listing attached hereto comply with the rules governing nucleotide and/or amino acid sequence disclosures in patent applications as set forth in 37 C.F.R. §1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. §1.822.

Table 1 lists certain polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing.

TABLE 1

| Low Nitrogen tolerant proteins (LNT) | | | |
|---|---|---|---|
| | | SEQ ID NO: | |
| | Clone Designation | Nucleotide | Amino Acid |
| LNT1-like | cfp7n.pk064.p15:fis | 17 | 18 |
| LNT1-like | cr1.pk0018.c9:fis | 19 | 20 |
| LNT1-like | srr1c.pk002.g4:fis | 21 | 22 |
| LNT1-like | sfl1.pk0086.d10:fis | 23 | 24 |
| LNT1-like | hso1c.pk016.m11:fis | 25 | 26 |
| LNT1-like | hhs1c.pk009.j19:fis | 27 | 28 |
| LNT1-like | rl0n.pk135.l9:fis | 29 | 30 |

Figure 1:
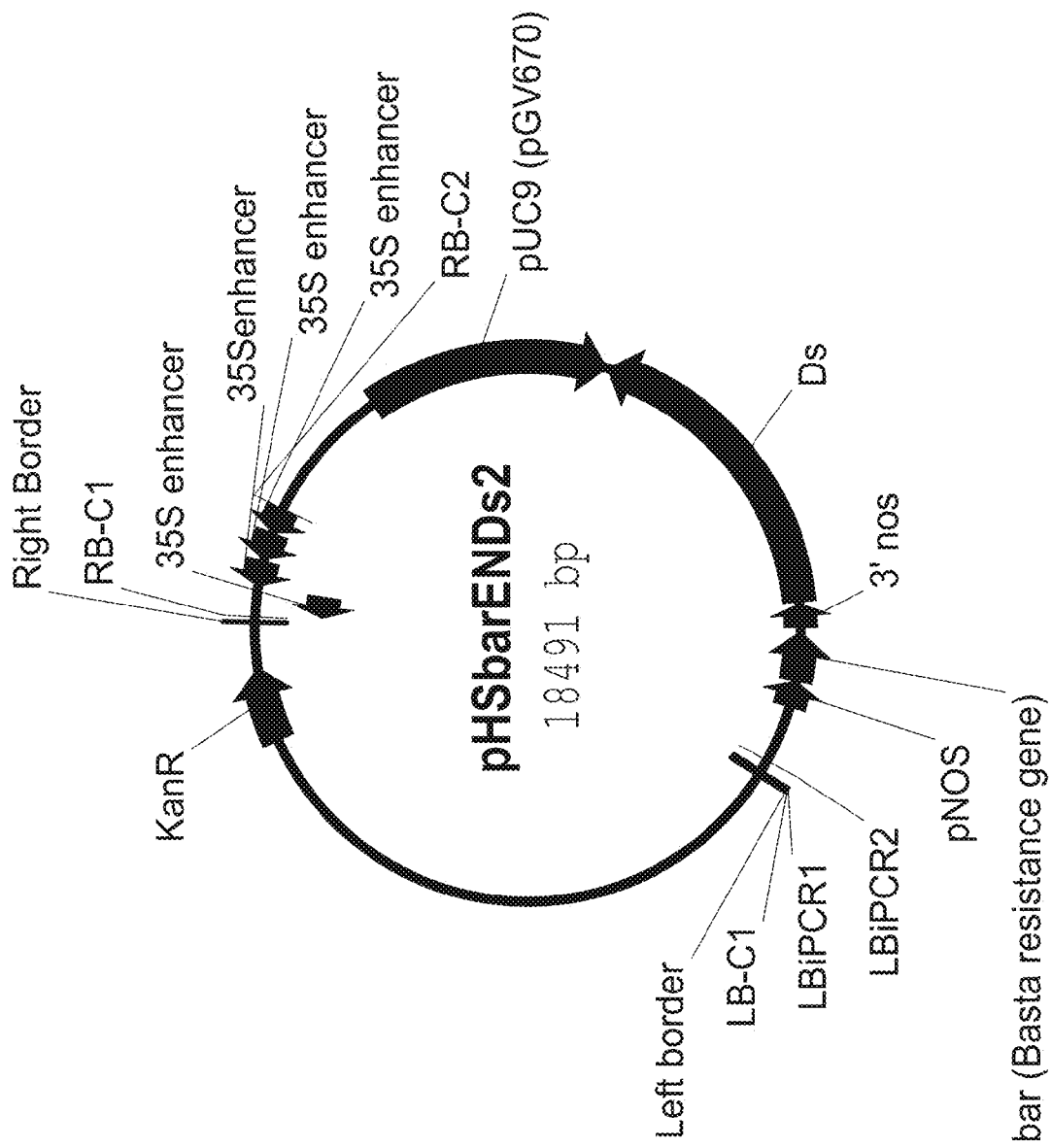
FIG. 1 shows a schematic of the pHSbarENDs2 activation tagging construct used to make the *Arabidopsis* populations (SEQ ID NO:1).

SEQ ID NO:1 is the nucleotide sequence of the pHSbarENDs2 activation tagging vector (FIG. 1).

Figure 2:
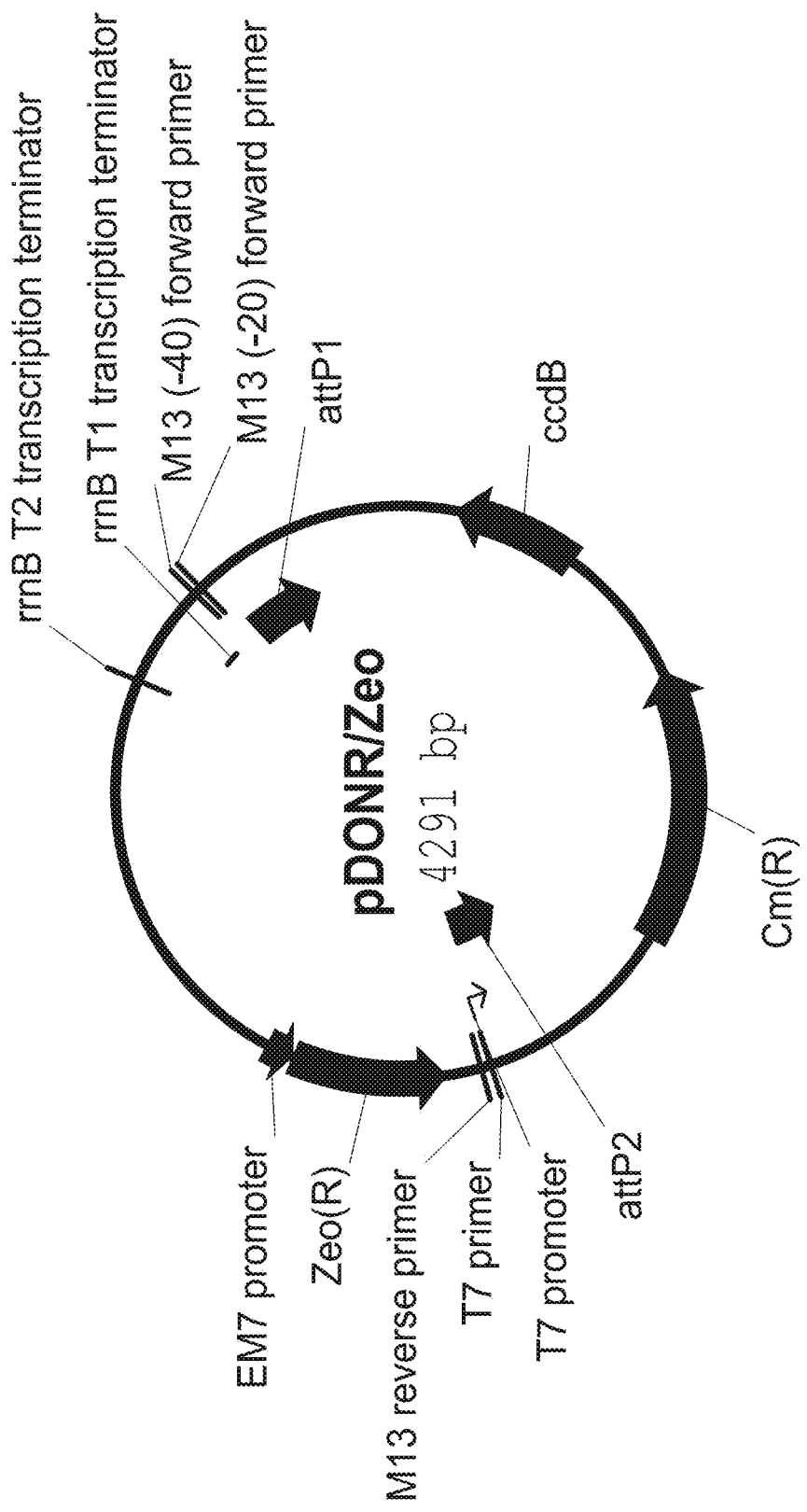
FIG. 2 shows a schematic of the vector pDONR™Zeo (SEQ ID NO:2), GATEWAY® donor vector. The attP1 site is at nucleotides 570-801; the attP2 site is at nucleotides 2754-2985 (complementary strand).

SEQ ID NO:2 is the nucleotide sequence of the pDONR™Zeo construct (FIG. 2).

Figure 3:
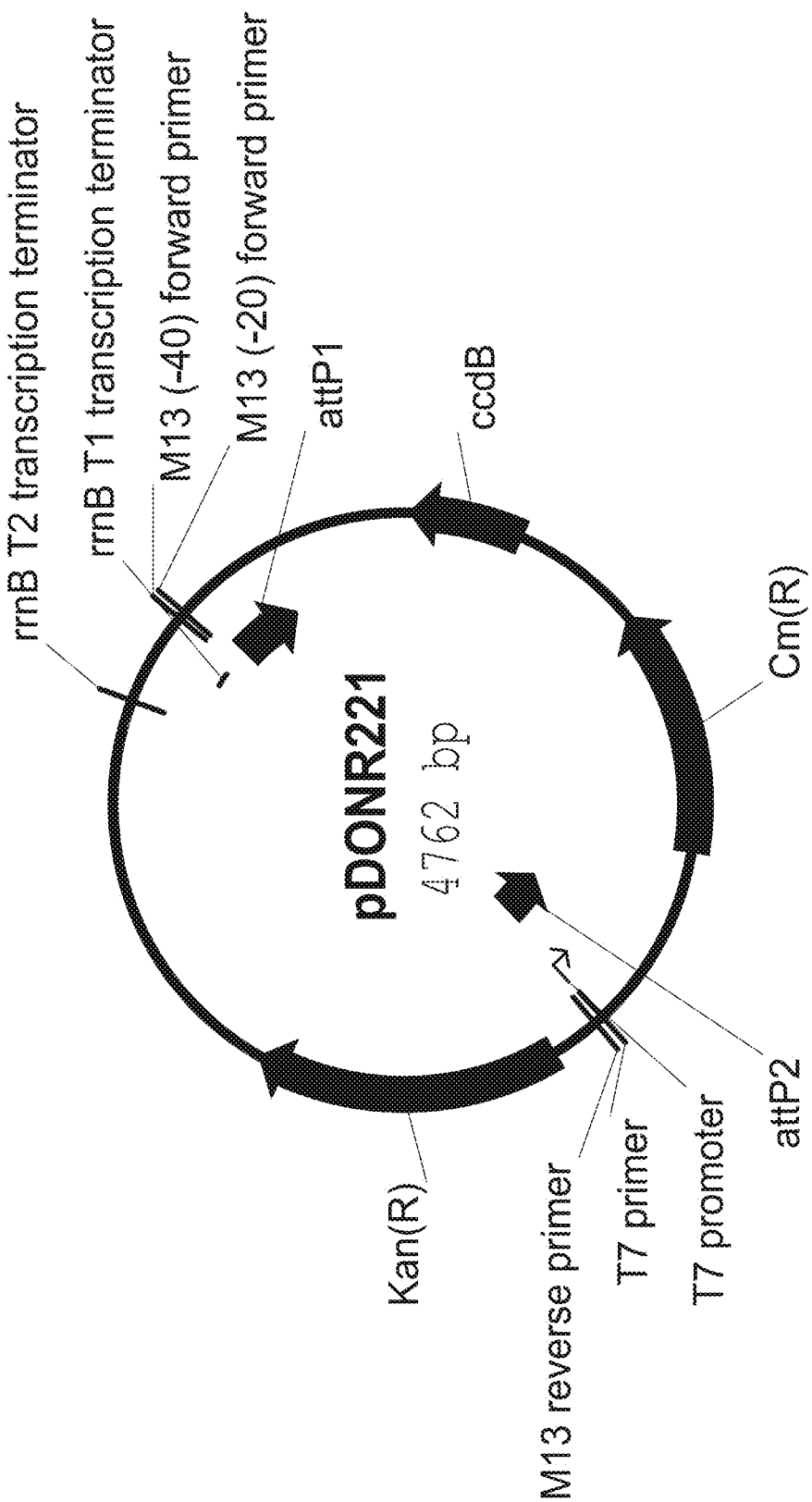
FIG. 3 shows a schematic of the vector pDONR™221 (SEQ ID NO:3), GATEWAY® donor vector. The attP1 site is at nucleotides 570-801; the attP2 site is at nucleotides 2754-2985 (complementary strand).

SEQ ID NO:3 is the nucleotide sequence of the pDONR™221 construct (FIG. 3).

Figure 4:
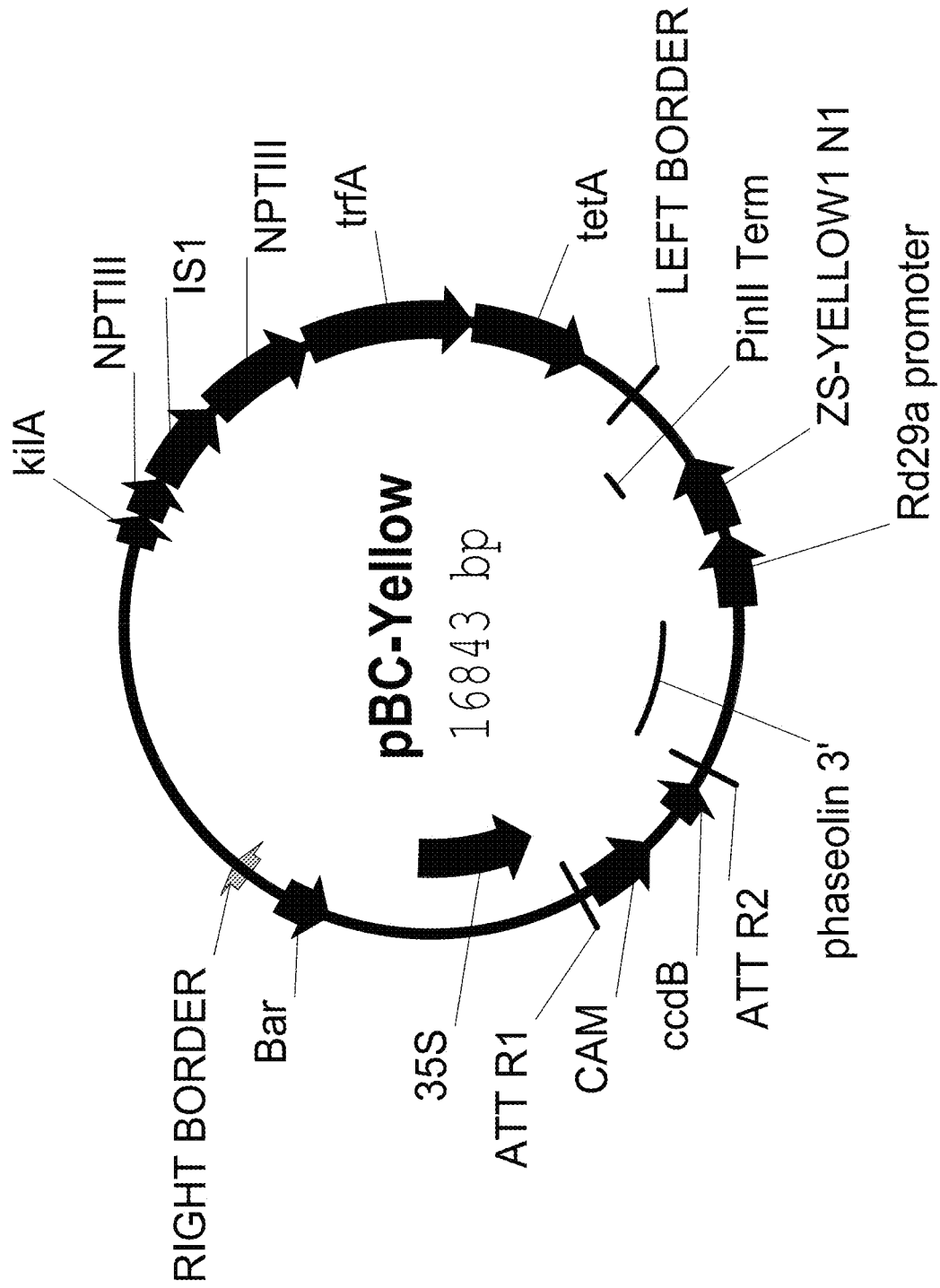
FIG. 4 shows a schematic of the vector pBC-yellow (SEQ ID NO:4), a destination vector for use in construction of expression vectors for *Arabidopsis*. The attR1 site is at nucleotides 11276-11399 (complementary strand); the attR2 site is at nucleotides 9695-9819 (complementary strand).

SEQ ID NO:4 is the nucleotide sequence of the pBC-yellow vector (FIG. 4).

Figure 5:
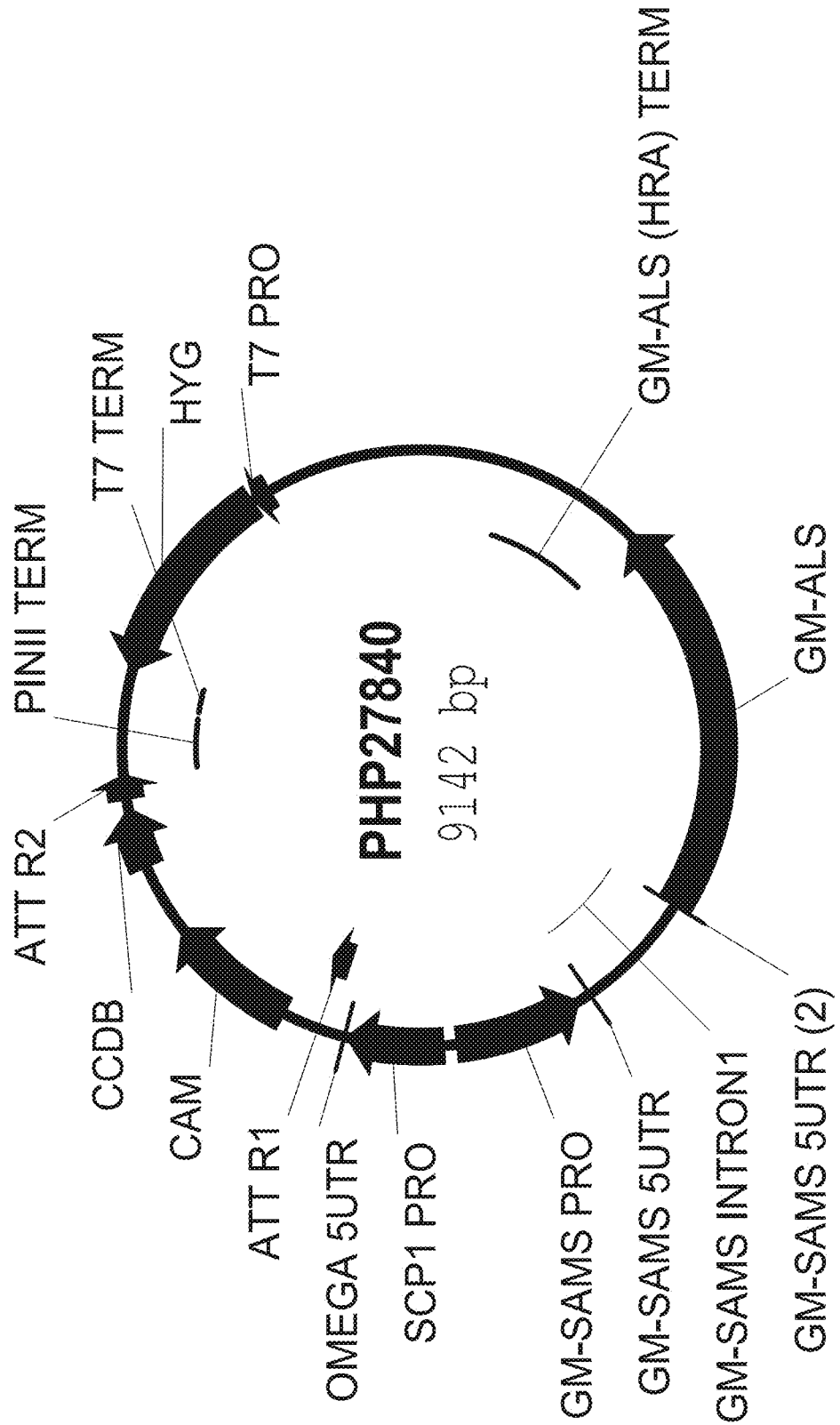
FIG. 5 shows a schematic of the vector PHP27840 (SEQ ID NO:5), a destination vector for use in construction of expression vectors for soybean. The attR1 site is at nucleotides 7310-7434; the attR2 site is at nucleotides 8890-9014.

SEQ ID NO:5 is the nucleotide sequence of the PHP27840 vector (FIG. 5).

Figure 6:
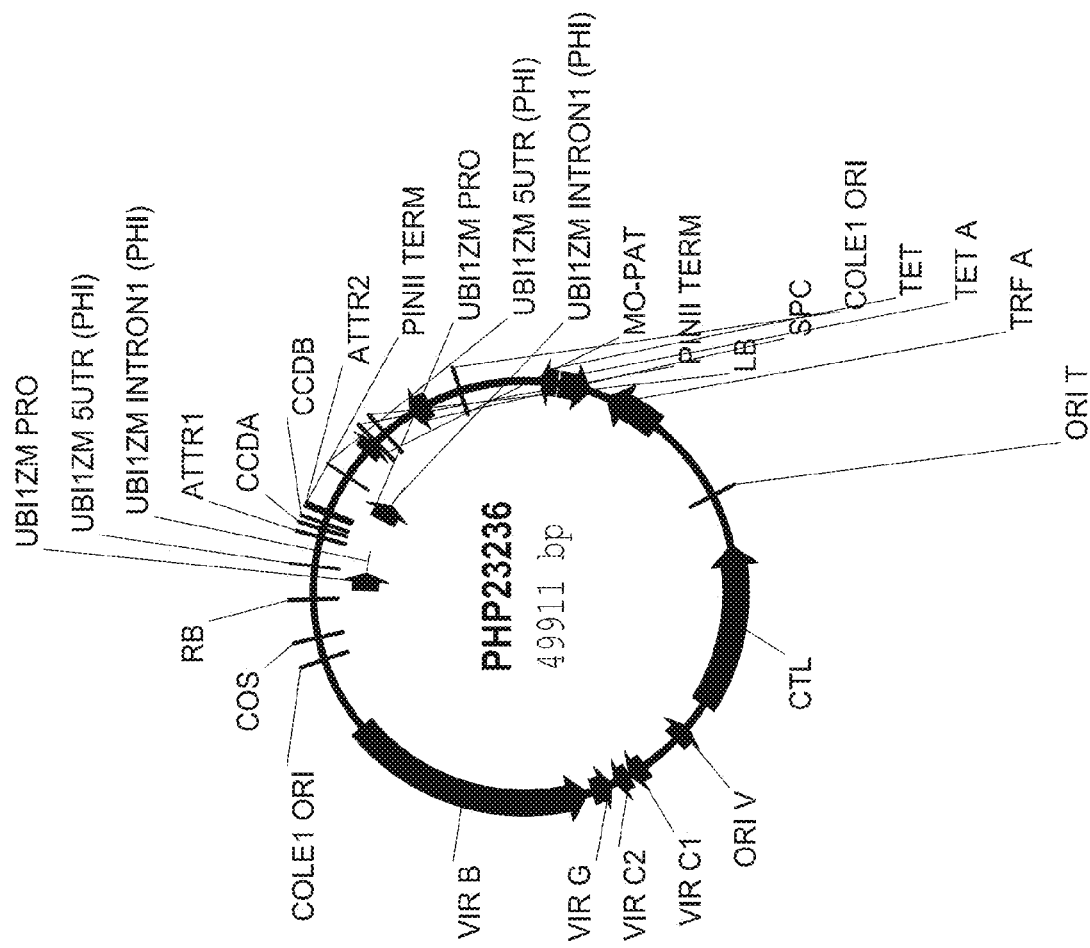
FIG. 6 shows a schematic of the vector PHP23236 (SEQ ID NO:6), a destination vector for use in construction of expression vectors for Gaspe Flint derived maize lines. The attR1 site is at nucleotides 2006-2130; the attR2 site is at nucleotides 2899-3023.

SEQ ID NO:6 is the nucleotide sequence of the destination vector PHP23236 (FIG. 6).

Figure 7:
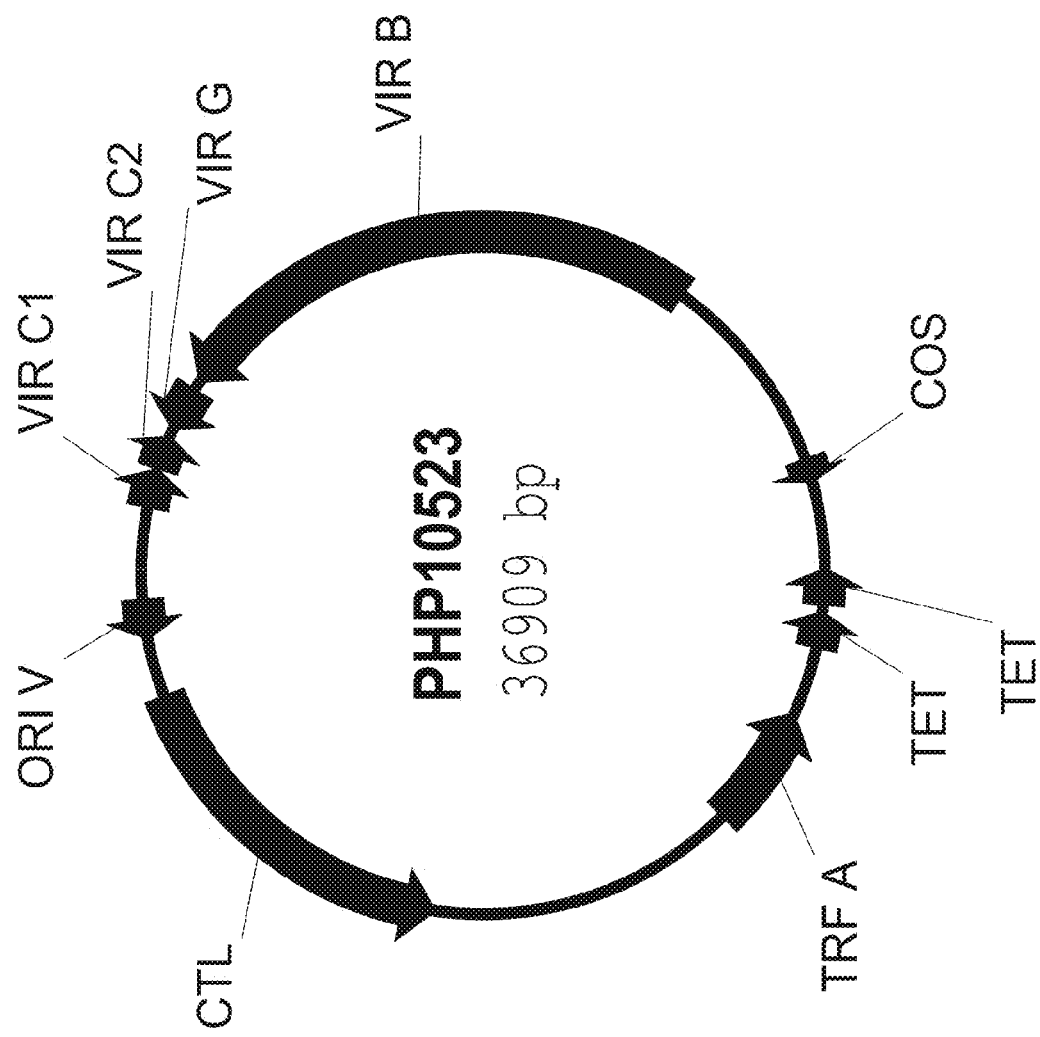
FIG. 7 shows a schematic of the vector PHP10523 (SEQ ID NO:7), a plasmid DNA present in *Agrobacterium* strain LBA4404 (Komari et al., *Plant J.* 10:165-174 (1996); NCBI General Identifier No. 59797027).

SEQ ID NO:7 is the nucleotide sequence of the PHP10523 vector (FIG. 7).

Figure 8:
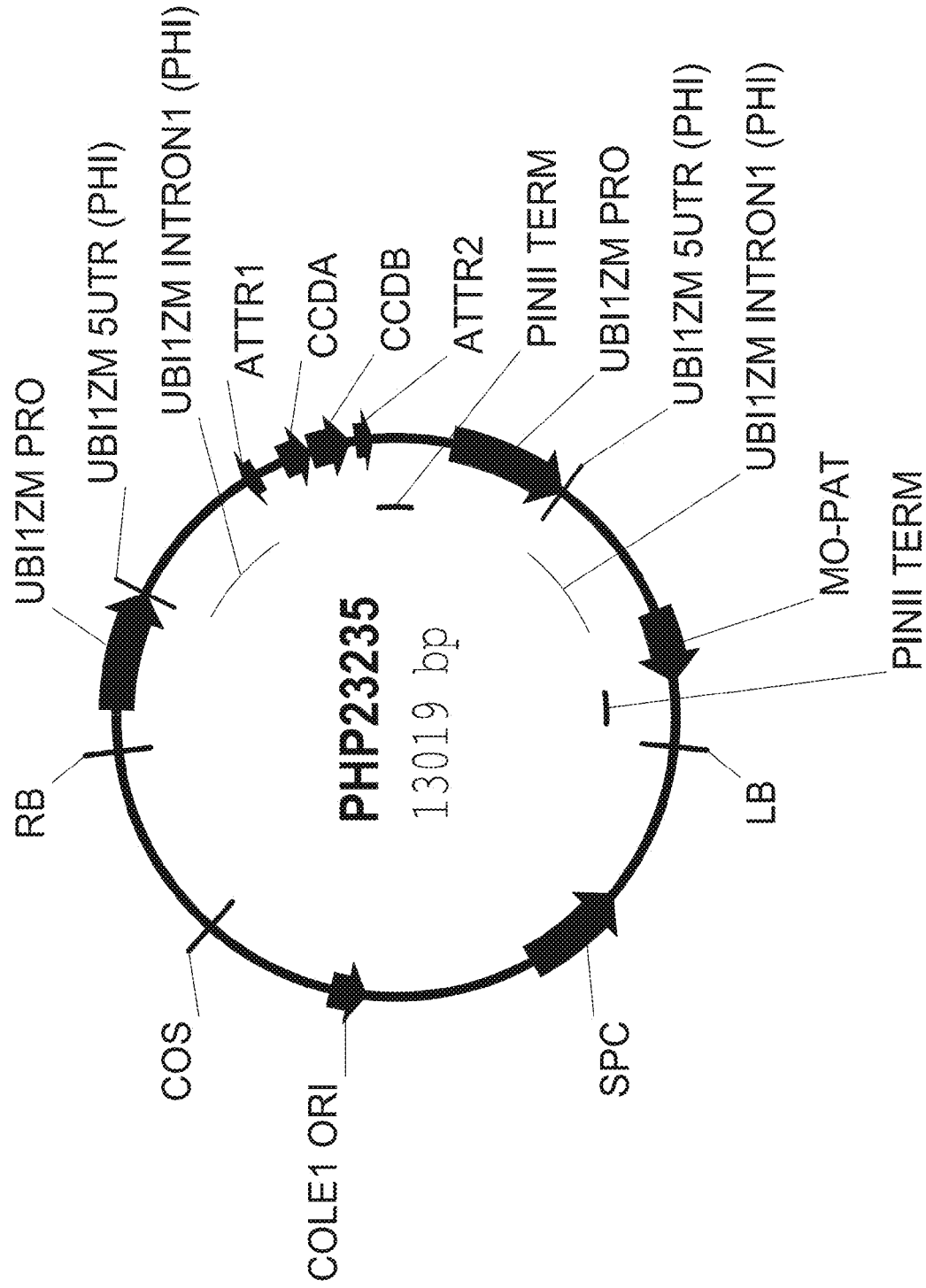
FIG. 8 shows a schematic of the vector PHP23235 (SEQ ID NO:8), a vector used to construct the destination vector PHP23236.

SEQ ID NO:8 is the nucleotide sequence of the PHP23235 vector (FIG. 8).

Figure 9:
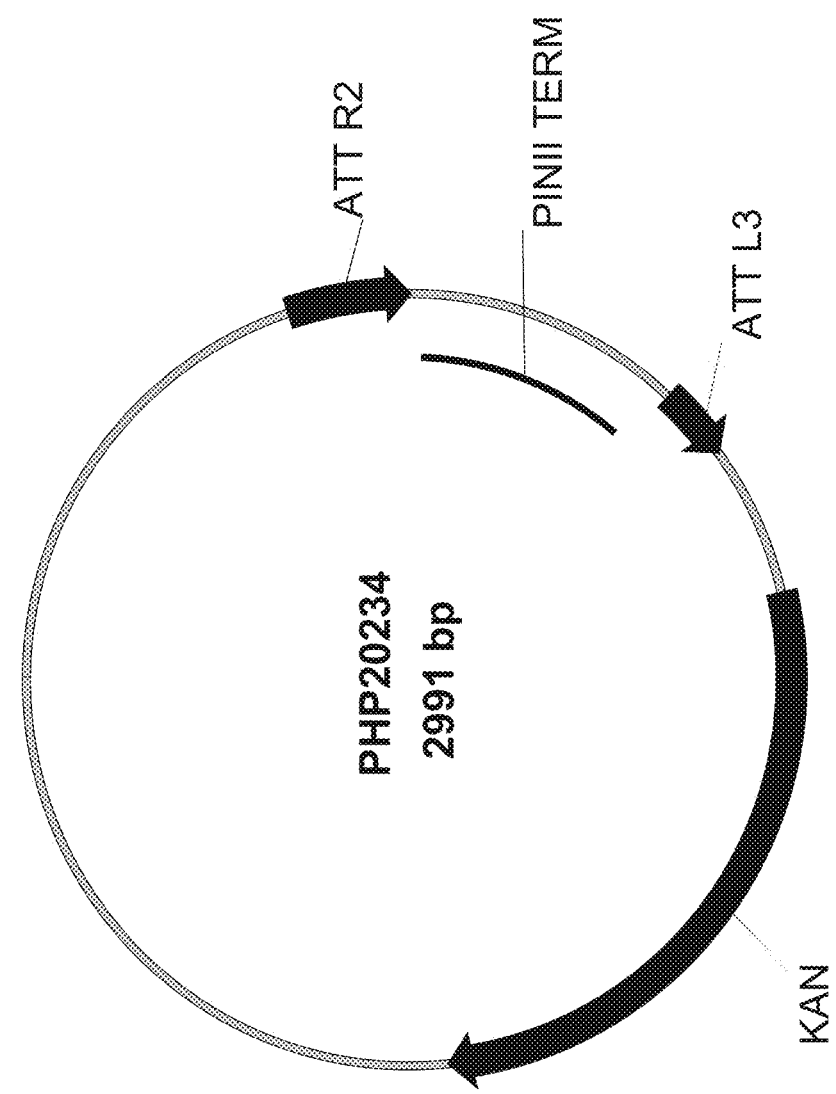
FIG. 9 shows a schematic of the vector PHP20234 (SEQ ID NO:9).

SEQ ID NO:9 is the nucleotide sequence of the PHP20234 vector (FIG. 9).

Figure 10:
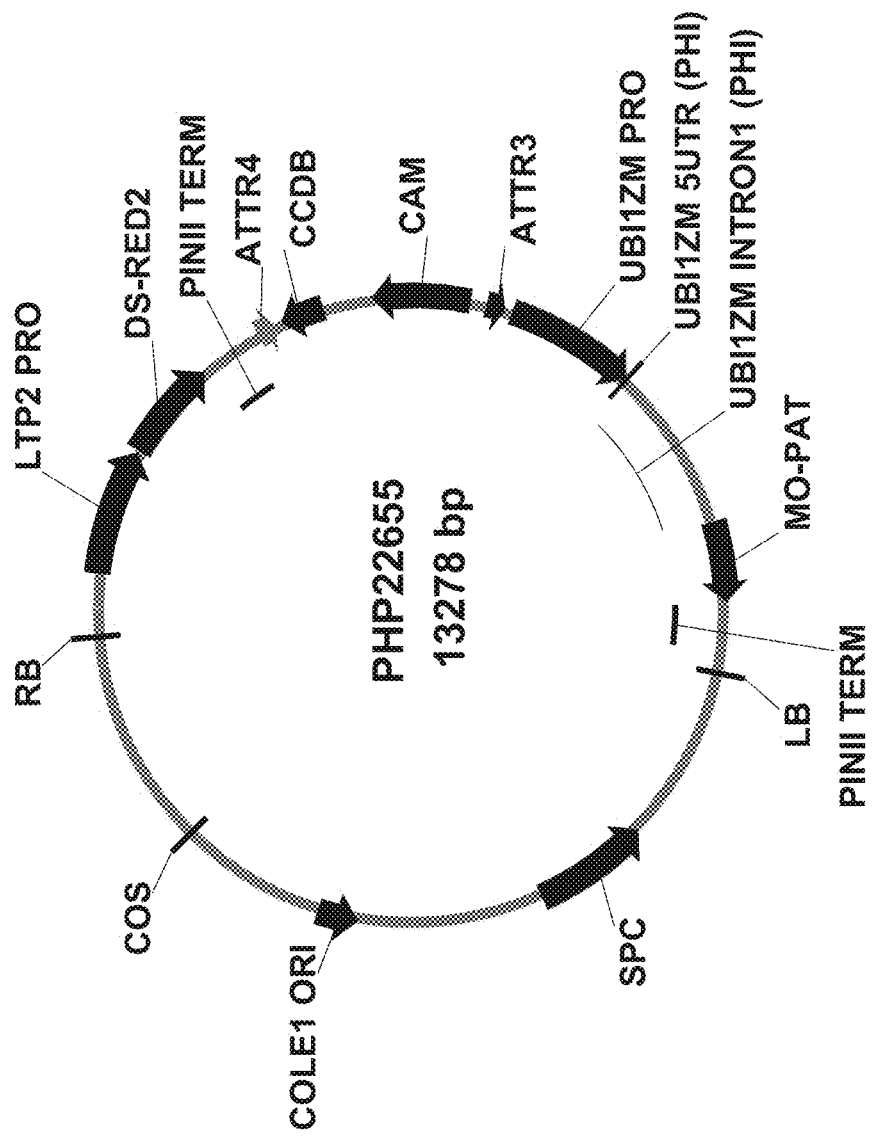
FIG. 10 shows a schematic of the destination vector PHP22655 (SEQ ID NO:10).

SEQ ID NO:10 is the nucleotide sequence of the destination vector PHP22655 (FIG. 10).

SEQ ID NO:11 is the nucleotide sequence of the polylinker used to substitute the PacI restriction site at position 5775 of pHSbarENDs2.

SEQ ID NO:12 is the nucleotide sequence of the attB1 sequence.

SEQ ID NO:13 is the nucleotide sequence of the attB2 sequence.

SEQ ID NO:14 is the nucleotide sequence of the entry clone PHP23112.

SEQ ID NO:15 is the forward primer VC062 in Example 9.

SEQ ID NO:16 is the reverse primer VC063 in Example 9.

SEQ ID NOs:17-30 (see Table 1).

SEQ ID NO:31 is the nucleotide sequence of the gene that encodes the *Arabidopsis thaliana* "unknown protein" (LNT1) (At1g67060; NCBI General Identifier No. 145337238).

SEQ ID NO:32 is the amino acid sequence of the *Arabidopsis thaliana* "unknown protein" (LNT1) (At1g67060; NCBI General Identifier No. 42563004).

SEQ ID NO:33 corresponds to NCBI GI No. 157341431, which is the amino acid sequence of a *Vitis vinifera* LNT1-like polypeptide.

SEQ ID NO:34 corresponds to NCBI GI No. 157343572, which is the amino acid sequence of a *Vitis vinifera* LNT1-like polypeptide.

SEQ ID NO:35 is the nucleotide sequence of the At1g67060-5' attB forward primer.

SEQ ID NO:36 is the nucleotide sequence of the At1g67060-3' attB reverse primer.

SEQ ID NO:37 corresponds to NCBI GI No. 212275704, which is the amino acid sequence of a *Zea mays* "hypothetical protein".

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

"Nitrogen limiting conditions" refers to conditions where the amount of total available nitrogen (e.g., from nitrates, ammonia, or other known sources of nitrogen) is not sufficient to sustain optimal plant growth and development. One skilled in the art would recognize conditions where total available nitrogen is sufficient to sustain optimal plant growth and development. One skilled in the art would recognize what constitutes sufficient amounts of total available nitrogen, and what constitutes soils, media and fertilizer inputs for providing nitrogen to plants. Nitrogen limiting conditions will vary depending upon a number of factors, including but not limited to, the particular plant and environmental conditions.

"Agronomic characteristic" is a measurable parameter including but not limited to, greenness, yield, growth rate, biomass, fresh weight at maturation, dry weight at maturation, fruit yield, seed yield, total plant nitrogen content, fruit nitrogen content, seed nitrogen content, nitrogen content in vegetative tissue, whole plant amino acid content, vegetative tissue free amino acid content, fruit free amino acid content, total plant protein content, seed free amino acid content, fruit protein content, seed protein content, protein content in a vegetative tissue, drought tolerance, nitrogen uptake, resistance to root lodging, harvest index, stalk lodging, plant height, ear height, and ear length.

"Harvest index" refers to the grain weight divided by the total plant weight.

"Int1" refers to the *Arabidopsis thaliana* locus, At1g67060 (SEQ ID NO: 31). "LNT1" refers to the protein (SEQ ID NO:32) encoded by At1g67060.

"Int1-like" refers to nucleotide homologs from different species, such as corn and soybean, of the *Arabidopsis thaliana* "Int1" locus, At1g67060 (SEQ ID NO: 31) and includes without limitation any of the nucleotide sequences of SEQ ID NOs: 17, 19, 21, 23, 25, 27, and 29.

"LNT1-like" refers to protein homologs from different species, such as corn and soybean, of the *Arabidopsis thaliana* "LNT1" (SEQ ID NO: 32) and includes without limitation any of the amino acid sequences of SEQ ID NOs: 18, 20, 22, 24, 26, 28, 30, 33, 34, and 37.

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"Nitrogen stress tolerance" is a trait of a plant and refers to the ability of the plant to survive under nitrogen limiting conditions.

"Increased nitrogen stress tolerance" of a plant is measured relative to a reference or control plant, and means that the nitrogen stress tolerance of the plant is increased by any amount or measure when compared to the nitrogen stress tolerance of the reference or control plant.

A "nitrogen stress tolerant plant" is a plant that exhibits nitrogen stress tolerance. A nitrogen stress tolerant plant may be a plant that exhibits an increase in at least one agronomic characteristic relative to a control plant under nitrogen limiting conditions.

"Environmental conditions" refer to conditions under which the plant is grown, such as the availability of water, availability of nutrients (for example nitrogen), or the presence of insects or disease.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, *CABIOS.* 5:151-153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Turning now to the embodiments:

Embodiments include isolated polynucleotides and polypeptides, recombinant DNA constructs, compositions (such as plants or seeds) comprising these recombinant DNA constructs, and methods utilizing these recombinant DNA constructs.

Isolated Polynucleotides and Polypeptides

The present invention includes the following isolated polynucleotides and polypeptides:

An isolated polynucleotide comprising: (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs (including suppression DNA constructs) of the present invention. The polypeptide is preferably an LNT1 or LNT1-like protein.

An isolated polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37. The polypeptide is preferably an LNT1 or LNT1-like protein.

An isolated polynucleotide comprising (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:17, 19, 21, 23, 25, 27, 29, or 31; or (ii) a full complement of the nucleic acid sequence of (i). Any of the foregoing isolated polynucleotides may be utilized in any recombinant DNA constructs (including suppression DNA constructs) of the present invention. The isolated polynucleotide preferably encodes an LNT1 or LNT1-like protein.

Recombinant DNA Constructs and Suppression DNA Constructs

In one aspect, the present invention includes recombinant DNA constructs (including suppression DNA constructs).

In one embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 17, 19, 21, 23, 25, 27, 29, or 31; or (ii) a full complement of the nucleic acid sequence of (i).

FIGS. 15A-15C show the multiple alignment of the amino acid sequences of SEQ ID NOs:18, 20, 22, 24, 26, 28, 30, 32, 33, 34, and 37. The multiple alignment of the sequences was performed using the MEGALIGN® program of the LASER-GENE® bioinformatics computing suite (DNASTAR® Inc., Madison, Wis.); in particular, using the Clustal V method of alignment (Higgins and Sharp, *CABIOS.* 5:151-153 (1989)) with the multiple alignment default parameters of GAP PENALTY=10 and GAP LENGTH PENALTY=10, and the pairwise alignment default parameters of KTUPLE=1, GAP PENALTY=3, WINDOW=5 and DIAGONALS SAVED=5.

FIG. 16 is a chart of the percent sequence identity and the divergence values for each pair of amino acids sequences displayed in FIGS. 15A-15C.

In another embodiment, a recombinant DNA construct comprises a polynucleotide operably linked to at least one regulatory sequence (e.g., a promoter functional in a plant), wherein said polynucleotide encodes an LNT1 or LNT1-like protein. The LNT1 or LNT1-like polypeptide may be from *Arabidopsis thaliana, Zea mays, Glycine max, Glycine tabacina, Glycine soja,* and *Glycine tomentella.*

In another aspect, the present invention includes suppression DNA constructs.

A suppression DNA construct may comprise at least one regulatory sequence (e.g., a promoter functional in a plant) operably linked to (a) all or part of: (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; or (ii) a full complement of the nucleic acid sequence of (a)(i); or (b) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT1 or LNT1-like protein; or (c) all or part of: (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:17, 19, 21, 23, 25, 27, 29, or 31; or (ii) a full complement of the nucleic acid sequence of (c)(i). The suppression DNA construct may comprise a cosuppression construct, antisense construct, viral-suppression construct, hairpin suppression construct, stem-loop suppression construct, double-stranded RNA-producing construct, RNAi construct, or small RNA construct (e.g., an sRNA construct or an miRNA construct).

It is understood, as those skilled in the art will appreciate, that the invention encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, includes lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as sRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al., *Plant J.* 16:651-659 (1998); and Gura, *Nature* 404:804-808 (2000)).

Another variation describes the use of plant viral sequences to direct the suppression of proximal mRNA encoding sequences (PCT Publication No. WO 98/36083 published on Aug. 20, 1998).

RNA interference refers to the process of sequence-specific post-transcriptional gene silencing in animals mediated by short interfering RNAs (siRNAs) (Fire et al., *Nature* 391:806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 (1999)).

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides (nt) in length that have been identified in both animals and plants (Lagos-Quintana et al., *Science* 294:853-858 (2001), Lagos-Quintana et al., *Curr. Biol.* 12:735-739 (2002); Lau et al., *Science* 294:858-862 (2001); Lee and Ambros, *Science* 294:862-864 (2001); Llave et al., *Plant Cell* 14:1605-1619 (2002); Mourelatos et al., *Genes. Dev.* 16:720-728 (2002); Park et al., *Curr. Biol.* 12:1484-1495 (2002); Reinhart et al., *Genes. Dev.* 16:1616-1626 (2002)). They are processed from longer precursor transcripts that range in size from approximately 70 to 200 nt, and these precursor transcripts have the ability to form stable hairpin structures.

MicroRNAs (miRNAs) appear to regulate target genes by binding to complementary sequences located in the transcripts produced by these genes. It seems likely that miRNAs can enter at least two pathways of target gene regulation: (1) translational inhibition and (2) RNA cleavage. MicroRNAs entering the RNA cleavage pathway are analogous to the 21-25 nt short interfering RNAs (siRNAs) generated during RNA interference (RNAi) in animals and posttranscriptional gene silencing (PTGS) in plants, and likely are incorporated into an RNA-induced silencing complex (RISC) that is similar or identical to that seen for RNAi.

Regulatory Sequences:

A recombinant DNA construct (including a suppression DNA construct) of the present invention may comprise at least one regulatory sequence.

A regulatory sequence may be a promoter.

A number of promoters can be used in recombinant DNA constructs (and suppression DNA constructs) of the present invention. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High level, constitutive expression of the candidate gene under control of the 35S or UBI promoter may (or may not) have pleiotropic effects, although candidate gene efficacy may be estimated when driven by a constitutive promoter. Use of tissue-specific and/or stress-specific promoters may eliminate undesirable effects, but retain the ability to enhance nitrogen tolerance. This type of effect has been observed in *Arabidopsis* for drought and cold tolerance (Kasuga et al., *Nature Biotechnol.* 17:287-91 (1999)).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., *Nature* 313:810-812 (1985)); rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the invention, it may be desirable to use a tissue-specific or developmentally regulated promoter.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present invention which causes the desired temporal and spatial expression.

Promoters which are seed or embryo-specific and may be useful in the invention include soybean Kunitz trypsin inhibitor (Kti3, Jofuku and Goldberg, *Plant Cell* 1:1079-1093 (1989)), patatin (potato tubers) (Rocha-Sosa, M., et al., *EMBO J.* 8:23-29 (1989)), convicilin, vicilin, and legumin (pea cotyledons) (Rerie, W. G., et al., *Mol. Gen. Genet.* 259:149-157 (1991); Newbigin, E. J., et al., *Planta* 180:461-470 (1990); Higgins, T. J. V., et al., *Plant. Mol. Biol.* 11:683-695 (1988)), zein (maize endosperm) (Schemthaner, J. P., et al., *EMBO J.* 7:1249-1255 (1988)), phaseolin (bean cotyledon) (Segupta-Gopalan, C., et al., *Proc. Natl. Acad. Sci. U.S.A.* 82:3320-3324 (1995)), phytohemagglutinin (bean cotyledon) (Voelker, T. et al., *EMBO J.* 6:3571-3577 (1987)), B-conglycinin and glycinin (soybean cotyledon) (Chen, Z-L, et al., *EMBO J.* 7:297-302 (1988)), glutelin (rice endosperm), hordein (barley endosperm) (Marris, C., et al., *Plant Mol. Biol.* 10:359-366 (1988)), glutenin and gliadin (wheat endosperm) (Colot, V., et al., *EMBO J.* 6:3559-3564 (1987)), and sporamin (sweet potato tuberous root) (Hattori, T., et al., *Plant Mol. Biol.* 14:595-604 (1990)). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., *Bio/Technology* 7:L929-932 (1989)), bean lectin and bean beta-phaseolin promoters to express luciferase (Riggs et al., *Plant Sci.* 63:47-57 (1989)), and wheat glutenin promoters to express chloramphenicol acetyl transferase (Colot et al., *EMBO J.* 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters for use in the current invention include the following: 1) the stress-inducible RD29A promoter (Kasuga et al., *Nature Biotechnol.* 17:287-91 (1999)); 2) the barley promoter, B22E; expression of B22E is specific to the pedicel in developing maize kernels ("Primary Structure of a Novel Barley Gene Differentially Expressed in Immature Aleurone Layers", Klemsdal et al., *Mol. Gen. Genet.* 228(1/2):9-16 (1991)); and 3) maize promoter, Zag2 ("Identification and molecular characterization of ZAG1, the maize homolog of the *Arabidopsis* floral homeotic gene AGAMOUS", Schmidt et al., *Plant Cell* 5(7):729-737 (1993); "Structural characterization, chromosomal localization and phylogenetic evaluation of two pairs of AGAMOUS-like MADS-box genes from maize", Theissen et al., *Gene* 156(2):155-166 (1995); NCBI GenBank Accession No. X80206)). Zag2 transcripts can be detected five days prior to pollination to seven to eight days after pollination ("DAP"), and directs expression in the carpel of developing female inflorescences and CimI which is specific to the nucleus of developing maize kernels. CimI transcript is detected four to five days before pollination to six to eight DAP. Other useful promoters include any promoter which can be derived from a gene whose expression is maternally associated with developing female florets.

Additional promoters for regulating the expression of the nucleotide sequences of the present invention in plants are stalk-specific promoters. Such stalk-specific promoters include the alfalfa S2A promoter (GenBank Accession No. EF030816; Abrahams et al., *Plant Mol. Biol.* 27:513-528 (1995)) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments.

Promoters for use in the current invention may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (GenBank Accession No. EF030817), and the constitutive promoter GOS2 from *Zea mays*. Other promoters include root preferred promoters, such as the maize NAS2 promoter, the maize Cyclo promoter (US Publication No. 2006/0156439, published Jul. 13, 2006), the maize ROOTMET2 promoter (WO 2005/063998, published Jul. 14, 2005), the CR1BIO promoter (WO 2006/055487, published May 26, 2006), the CRWAQ81 (WO 2005/035770, published Apr. 21, 2005) and the maize ZRP2.47 promoter (NCBI Accession No. U38790; NCBI GI No. 1063664).

Recombinant DNA constructs (and suppression DNA constructs) of the present invention may also include other regulatory sequences including, but not limited to, translation leader sequences, introns, and polyadenylation recognition sequences. In another embodiment of the present invention, a recombinant DNA construct of the present invention further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, *Mol. Cell Biol.* 8:4395-4405 (1988); Callis et al., *Genes Dev.* 1:1183-1200 (1987)).

Any plant can be selected for the identification of regulatory sequences and genes to be used in recombinant DNA constructs of the present invention. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, maize, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini.

Compositions:

A composition of the present invention is a plant comprising in its genome any of the recombinant DNA constructs (including any of the suppression DNA constructs) of the present invention (such as any of the constructs discussed above). Compositions also include any progeny of the plant, and any seed obtained from the plant or its progeny, wherein the progeny or seed comprises within its genome the recombinant DNA construct (or suppression DNA construct). Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct (or suppression DNA construct). These seeds can be grown to produce plants that would exhibit an altered agronomic characteristic (e.g., an increased agronomic characteristic optionally under nitrogen limiting conditions), or used in a breeding program to produce hybrid seed, which can be grown to produce plants that would exhibit such an altered agronomic characteristic. The seeds may be maize seeds.

The plant may be a monocotyledonous or dicotyledonous plant, for example, a maize or soybean plant, such as a maize hybrid plant or a maize inbred plant. The plant may also be sunflower, sorghum, canola, wheat, alfalfa, cotton, rice, barley or millet.

The recombinant DNA construct may be stably integrated into the genome of the plant.

Embodiments include but are not limited to the following:

1. A plant (for example, a maize or soybean plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37, and wherein said plant exhibits increased nitrogen stress tolerance when compared to a control plant not comprising said recombinant DNA construct. The plant may further exhibit an alteration of at least one agronomic characteristic when compared to the control plant.

2. A plant (for example, a maize or soybean plant) comprising in its genome a recombinant DNA construct comprising:
   (a) a polynucleotide operably linked to at least one regulatory element, wherein said polynucleotide encodes a polypeptide having an amino acid sequence of at least 50% sequence identity, based on the Clustal V method of alignment, when compared to SEQ ID NO:18, 20, 22, 24, 26, 28, 30, 32, 33, 34, or 37; or
   (b) a suppression DNA construct comprising at least one regulatory element operably linked to:
      (i) all or part of: (A) a nucleic acid sequence encoding a polypeptide having an amino acid sequence of at least 50% sequence identity, based on the Clustal V method of alignment, when compared to SEQ ID NO:18, 20, 22, 24, 26, 28, 30, 32, 33, 34, or 37, or (B) a full complement of the nucleic acid sequence of (b)(i)(A); or
      (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes an LNT1 or LNT1-like polypeptide,
   and wherein said plant exhibits an alteration of at least one agronomic characteristic when compared to a control plant not comprising said recombinant DNA construct.

3. A plant (for example, a maize or soybean plant) comprising in its genome a recombinant DNA construct comprising a polynucleotide operably linked to at least one regulatory sequence, wherein said polynucleotide encodes an LNT1 or LNT1-like polypeptide, and wherein said plant exhibits increased nitrogen stress tolerance when compared to a control plant not comprising said recombinant DNA construct. The plant may further exhibit an alteration of at least one agronomic characteristic when compared to the control plant.

The LNT1 polypeptide may be from *Arabidopsis thaliana*, *Zea mays*, *Glycine max*, *Glycine tabacina*, *Glycine soja* or *Glycine tomentella*.

4. A plant (for example, a maize or soybean plant) comprising in its genome a recombinant DNA construct comprising a polynucleotide operably linked to at least one regulatory sequence, wherein said polynucleotide encodes an LNT1 or LNT1-like polypeptide, and wherein said plant exhibits an alteration of at least one agronomic characteristic under nitrogen limiting conditions when compared to a control plant not comprising said recombinant DNA construct. The LNT1 polypeptide may be from *Arabidopsis thaliana*, *Zea mays*, *Glycine max*, *Glycine tabacina*, *Glycine soja* or *Glycine tomentella*.

5. A plant (for example, a maize or soybean plant) comprising in its genome a recombinant DNA construct comprising a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37, and wherein said plant exhibits an alteration of at least one agronomic characteristic under nitrogen limiting conditions when compared to a control plant not comprising said recombinant DNA construct.

6. A plant (for example, a maize or soybean plant) comprising in its genome a suppression DNA construct comprising at least one regulatory element operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT1 or LNT1-like polypeptide, and wherein said plant exhibits an alteration of at least one agronomic characteristic under nitrogen limiting conditions when compared to a control plant not comprising said suppression DNA construct.

7. A plant (for example, a maize or soybean plant) comprising in its genome a suppression DNA construct comprising at least one regulatory element operably linked to all or part of: (a) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; or (b) a full complement of the nucleic acid sequence of (a), and wherein said plant exhibits an alteration of at least one agronomic characteristic under nitrogen limiting conditions when compared to a control plant not comprising said suppression DNA construct.

8. Any progeny of the above plants in embodiments 1-7, any seeds of the above plants in embodiments 1-7, any seeds of progeny of the above plants in embodiments 1-7, and cells from any of the above plants in embodiments 1-7 and progeny thereof.

In any of the foregoing embodiments 1-8 or any other embodiments of the present invention, the recombinant DNA construct (or suppression DNA construct) may comprise at least a promoter functional in a plant as a regulatory sequence.

In any of the foregoing embodiments 1-8 or any other embodiments of the present invention, the alteration of at least one agronomic characteristic is either an increase or decrease.

In any of the foregoing embodiments 1-8 or any other embodiments of the present invention, the at least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, whole plant amino acid content, vegetative tissue free amino acid content, fruit free amino acid content, seed free amino acid content, total plant protein content, fruit protein content, seed protein content, protein content in a vegetative tissue, drought tolerance, nitrogen uptake, resistance to root lodging, harvest index, stalk lodging, plant height, ear height, ear length, early seedling vigor, and seedling emergence under low temperature stress. For example, the alteration of at least one agronomic characteristic may be an increase in yield, greenness, or biomass.

In any of the foregoing embodiments 1-8 or any other embodiments of the present invention, the plant may exhibit the alteration of at least one agronomic characteristic when compared, under nitrogen stress conditions, to a control plant not comprising said recombinant DNA construct (or suppression DNA construct).

One of ordinary skill in the art is familiar with protocols for simulating nitrogen conditions, whether limiting or non-limiting, and for evaluating plants that have been subjected to simulated or naturally-occurring nitrogen conditions, whether limiting or non-limiting. For example, one can simulate nitrogen conditions by giving plants less nitrogen than normally required or no nitrogen over a period of time, and one can evaluate such plants by looking for differences in agronomic characteristics, e.g., changes in physiological and/or physical condition, including (but not limited to) vigor, growth, size, or root length, or in particular, leaf color or leaf area size. Other techniques for evaluating such plants include measuring chlorophyll fluorescence, photosynthetic rates, root growth or gas exchange rates.

The Examples below describe some representative protocols and techniques for simulating nitrogen limiting conditions and/or evaluating plants under such conditions.

One can also evaluate nitrogen stress tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring low or high nitrogen conditions (e.g., by measuring for substantially equivalent yield under low or high nitrogen conditions compared to normal nitrogen conditions, or by measuring for less yield loss under low or high nitrogen conditions compared to a control or reference plant).

One of ordinary skill in the art would readily recognize a suitable control or reference plant to be utilized when assessing or measuring an agronomic characteristic or phenotype of a transgenic plant in any embodiment of the present invention in which a control plant is utilized (e.g., compositions or methods as described herein). For example, by way of non-limiting illustrations:

1. Progeny of a transformed plant which is hemizygous with respect to a recombinant DNA construct (or suppression DNA construct), such that the progeny are segregating into plants either comprising or not comprising the recombinant DNA construct (or suppression DNA construct): the progeny comprising the recombinant DNA construct (or suppression DNA construct) would be typically measured relative to the progeny not comprising the recombinant DNA construct (or suppression DNA construct) (i.e., the progeny not comprising the recombinant DNA construct (or the suppression DNA construct) is the control or reference plant).

2. Introgression of a recombinant DNA construct (or suppression DNA construct) into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines, and the second hybrid line is produced from the same two parent inbred lines except that one of the parent inbred lines contains a recombinant DNA construct (or suppression DNA construct): the second hybrid line would typically be measured relative to the first hybrid line (i.e., the first hybrid line is the control or reference plant).

4. A plant comprising a recombinant DNA construct (or suppression DNA construct): the plant may be assessed or measured relative to a control plant not comprising the recombinant DNA construct (or suppression DNA construct) but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct (or suppression DNA construct)). There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

Furthermore, one of ordinary skill in the art would readily recognize that a suitable control or reference plant to be utilized when assessing or measuring an agronomic characteristic or phenotype of a transgenic plant would not include a plant that had been previously selected, via mutagenesis or transformation, for the desired agronomic characteristic or phenotype.

Methods

Methods include but are not limited to methods for increasing nitrogen stress tolerance in a plant, methods for evaluating nitrogen stress tolerance in a plant, methods for altering an agronomic characteristic in a plant, methods for determining an alteration of an agronomic characteristic in a plant, and methods for producing seed. The plant may be a monocotyledonous or dicotyledonous plant, for example, a maize or soybean plant. The plant may also be sunflower, sorghum, canola, wheat, alfalfa, cotton, rice, barley, or millet. The seed may be a maize or soybean seed, for example a maize hybrid seed or maize inbred seed.

Methods include but are not limited to the following:

A method for transforming a cell comprising transforming a cell with any of the isolated polynucleotides of the present invention. The cell transformed by this method is also included. In particular embodiments, the cell is eukaryotic cell, e.g., a yeast, insect or plant cell, or prokaryotic, e.g., a bacterium.

A method for producing a transgenic plant comprising transforming a plant cell with any of the isolated polynucleotides or recombinant DNA constructs of the present invention and regenerating a transgenic plant from the transformed plant cell. The invention is also directed to the transgenic plant produced by this method, and transgenic seed obtained from this transgenic plant.

A method for isolating a polypeptide of the invention from a cell or culture medium of the cell, wherein the cell comprises a recombinant DNA construct comprising a polynucleotide of the invention operably linked to at least one regulatory sequence, and wherein the transformed host cell is grown under conditions that are suitable for expression of the recombinant DNA construct.

A method of altering the level of expression of a polypeptide of the invention in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the polypeptide of the invention in the transformed host cell.

A method of increasing nitrogen stress tolerance in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; and (b) regenerating a transgenic plant from the regenerable plant cell after step (a), wherein the transgenic plant comprises in its genome the recombinant DNA construct and exhibits increased nitrogen stress tolerance when compared to a control plant not comprising the recombinant DNA construct. The method may further comprise (c) obtaining a progeny plant derived from the transgenic plant, wherein said progeny plant comprises in its genome the suppression DNA construct and exhibits increased nitrogen stress tolerance when compared to a control plant not comprising the recombinant DNA construct.

A method of increasing nitrogen stress tolerance in a plant, comprising: (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37, or (ii) a full complement of the nucleic acid sequence of (a)(i); and (b) regenerating a transgenic plant from the regenerable plant cell after step (a), wherein the transgenic plant comprises in its genome the suppression DNA construct and exhibits increased nitrogen stress tolerance when compared to a control plant not comprising the suppression DNA construct. The method may further comprise (c) obtaining a progeny plant derived from the transgenic plant, wherein said progeny plant comprises in its genome the suppression DNA construct and exhibits increased nitrogen stress tolerance when compared to a control plant not comprising the suppression DNA construct.

A method of increasing nitrogen stress tolerance in a plant, comprising: (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT1 or LNT1-like polypeptide; and (b) regenerating a transgenic plant from the regenerable plant cell after step (a), wherein the transgenic plant comprises in its genome the suppression DNA construct and exhibits increased nitrogen stress tolerance when compared to a control plant not comprising the suppression DNA construct. The method may further comprise (c) obtaining a progeny plant derived from the transgenic plant, wherein said progeny plant comprises in its genome the suppression DNA construct and exhibits increased nitrogen stress tolerance when compared to a control plant not comprising the suppression DNA construct.

A method of evaluating nitrogen stress tolerance in a plant, comprising (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; (b) regenerating a transgenic plant from the regenerable plant cell after step (a), wherein the transgenic plant comprises in its genome the recombinant DNA construct; and (c) evaluating the transgenic plant for nitrogen stress tolerance compared to a control plant not comprising the recombinant DNA construct. The method may further comprise (d) obtaining a progeny plant derived from the transgenic plant, wherein the progeny plant comprises in its genome the recombinant DNA construct; and (e) evaluating the progeny plant for nitrogen stress tolerance compared to a control plant not comprising the recombinant DNA construct.

A method of evaluating nitrogen stress tolerance in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; or (ii) a full complement of the nucleic acid sequence of (a)(i); (b) regenerating a transgenic plant from the regenerable plant cell after step (a), wherein the transgenic plant comprises in its genome the suppression DNA construct; and (c) evaluating the transgenic plant for nitrogen stress tolerance compared to a control plant not comprising the suppression DNA construct. The method may further comprise (d) obtaining a progeny plant derived from the transgenic plant, wherein the progeny plant comprises in its genome the suppression DNA construct; and (e) evaluating the progeny plant for nitrogen stress tolerance compared to a control plant not comprising the suppression DNA construct.

A method of evaluating nitrogen stress tolerance in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT1 or LNT1-like polypeptide; (b) regenerating a transgenic plant from the regenerable plant cell after step (a), wherein the transgenic plant comprises in its genome the suppression DNA construct; and (c) evaluating the transgenic plant for nitrogen stress tolerance compared to a control plant not comprising the suppression DNA construct. The method may further comprise (d) obtaining a progeny plant derived from the transgenic plant, wherein the progeny plant comprises in its genome the suppression DNA construct; and (e) evaluating the progeny plant for nitrogen stress tolerance compared to a control plant not comprising the suppression DNA construct.

A method of evaluating nitrogen stress tolerance in a plant, comprising (a) introducing into a regenerable plant cell a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; (b) regenerating a transgenic plant from the regenerable plant cell after step (a), wherein the transgenic plant comprises in its genome the recombinant DNA construct; (c) obtaining a progeny plant derived from said transgenic plant, wherein the progeny plant comprises in its genome the recombinant DNA construct; and (d) evaluating the progeny plant for nitrogen stress tolerance compared to a control plant not comprising the recombinant DNA construct.

A method of evaluating nitrogen stress tolerance in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; or (ii) a full complement of the nucleic acid sequence of (a)(i); (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) evaluating the progeny plant for nitrogen stress tolerance compared to a control plant not comprising the recombinant DNA construct.

A method of evaluating nitrogen stress tolerance in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT1 or LNT1-like polypeptide; (b) regenerating a transgenic plant from the regenerable plant cell after step (a), wherein the transgenic plant comprises in its genome the suppression DNA construct; (c) obtaining a progeny plant derived from the transgenic plant, wherein the progeny plant comprises in its genome the suppression DNA construct; and (d) evaluating the progeny plant for nitrogen stress tolerance compared to a control plant not comprising the recombinant DNA construct.

A method of determining an alteration of an agronomic characteristic in a plant, comprising (a) introducing into a regenerable plant cell a recombinant DNA construct comprising a polynucleotide operably linked to at least on regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; (b)

regenerating a transgenic plant from the regenerable plant cell after step (a), wherein the transgenic plant comprises in its genome said recombinant DNA construct; and (c) determining whether the transgenic plant exhibits an alteration of at least one agronomic characteristic when compared, optionally under nitrogen limiting conditions, to a control plant not comprising the recombinant DNA construct. The method may further comprise (d) obtaining a progeny plant derived from the transgenic plant, wherein the progeny plant comprises in its genome the recombinant DNA construct; and (e) determining whether the progeny plant exhibits an alteration of at least one agronomic characteristic when compared, optionally under nitrogen limiting conditions, to a control plant not comprising the recombinant DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; or (ii) a full complement of the nucleic acid sequence of (i); (b) regenerating a transgenic plant from the regenerable plant cell after step (a), wherein the transgenic plant comprises in its genome the suppression DNA construct; and (c) determining whether the transgenic plant exhibits an alteration of at least one agronomic characteristic when compared, optionally under nitrogen limiting conditions, to a control plant not comprising the suppression DNA construct. The method may further comprise (d) obtaining a progeny plant derived from the transgenic plant, wherein the progeny plant comprises in its genome the suppression DNA construct; and (e) determining whether the progeny plant exhibits an alteration of at least one agronomic characteristic when compared, optionally under nitrogen limiting conditions, to a control plant not comprising the suppression DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT1 or LNT1-like polypeptide; (b) regenerating a transgenic plant from the regenerable plant cell after step (a), wherein the transgenic plant comprises in its genome the suppression DNA construct; and (c) determining whether the transgenic plant exhibits an alteration of at least one agronomic characteristic when compared, optionally under nitrogen limiting conditions, to a control plant not comprising the suppression DNA construct. The method may further comprise (d) obtaining a progeny plant derived from the transgenic plant, wherein the progeny plant comprises in its genome the suppression DNA construct; and (e) determining whether the progeny plant exhibits an alteration of at least one agronomic characteristic when compared, optionally under nitrogen limiting conditions, to a control plant not comprising the suppression DNA construct.

A method of determining an alteration of an agronomic characteristic in a plant, comprising (a) introducing into a regenerable plant cell a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; (b) regenerating a transgenic plant from the regenerable plant cell after step (a), wherein the transgenic plant comprises in its genome said recombinant DNA construct; (c) obtaining a progeny plant derived from said transgenic plant, wherein the progeny plant comprises in its genome the recombinant DNA construct; and (d) determining whether the progeny plant exhibits an alteration of at least one agronomic characteristic when compared, optionally under nitrogen limiting conditions, to a control plant not comprising the recombinant DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; or (ii) a full complement of the nucleic acid sequence of (i); (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) determining whether the progeny plant exhibits an alteration of at least one agronomic characteristic when compared, optionally under nitrogen limiting conditions, to a control plant not comprising the recombinant DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT1 or LNT1-like polypeptide; (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) determining whether the progeny plant exhibits an alteration of at least one agronomic characteristic when compared, optionally under nitrogen limiting conditions, to a control plant not comprising the suppression DNA construct.

A method of producing seed (for example, seed that can be sold as a nitrogen stress tolerant product offering) comprising any of the preceding methods, and further comprising obtaining seeds from said progeny plant, wherein said seeds comprise in their genome said recombinant DNA construct (or suppression DNA construct).

In any of the foregoing methods or any other embodiments of methods of the present invention, the step of determining an alteration of an agronomic characteristic in a transgenic plant, if applicable, may comprise determining whether the transgenic plant exhibits an alteration of at least one agronomic characteristic when compared, under varying environmental conditions, to a control plant not comprising the recombinant DNA construct.

In any of the foregoing methods or any other embodiments of methods of the present invention, the step of determining an alteration of an agronomic characteristic in a progeny plant, if applicable, may comprise determining whether the progeny plant exhibits an alteration of at least one agronomic characteristic when compared, under varying environmental conditions, to a control plant not comprising the recombinant DNA construct.

In any of the preceding methods or any other embodiments of methods of the present invention, in said introducing step said regenerable plant cell may comprise a callus cell, an embryogenic callus cell, a gametic cell, a meristematic cell, or a cell of an immature embryo. The regenerable plant cells may derive from an inbred maize plant.

In any of the preceding methods or any other embodiments of methods of the present invention, said regenerating step may comprise: (i) culturing said transformed plant cells in a media comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding methods or any other embodiments of methods of the present invention, the at least one agronomic characteristic is preferably selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, whole plant amino acid content, vegetative tissue free amino acid content, fruit free amino acid content, seed free amino acid content, total plant protein content, fruit protein content, seed protein content, protein content in a vegetative tissue, drought tolerance, nitrogen uptake, resistance to root lodging, harvest index, stalk lodging, plant height, ear height, ear length, early seedling vigor, and seedling emergence under low temperature stress. The alteration of at least one agronomic characteristic may be an increase in yield, greenness, or biomass.

In any of the preceding methods or any other embodiments of methods of the present invention, the plant may exhibit the alteration of at least one agronomic characteristic when compared, under nitrogen stress conditions, to a control plant not comprising said recombinant DNA construct (or suppression DNA construct).

In any of the preceding methods or any other embodiments of methods of the present invention, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, optionally as part of a transposable element), and then screen for an event in which the regulatory sequence is operably linked to an endogenous gene encoding a polypeptide of the instant invention.

The introduction of recombinant DNA constructs of the present invention into plants may be carried out by any suitable technique, including but not limited to direct DNA uptake, chemical treatment, electroporation, microinjection, cell fusion, infection, vector mediated DNA transfer, bombardment, or *Agrobacterium* mediated transformation. Techniques for plant transformation and regeneration have been described in International Patent Publication WO 2009/006276, the contents of which are herein incorporated by reference.

The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

EXAMPLES

The present invention is further illustrated in the following Examples, in which parts and percentages are by weight and degrees are Celsius, unless otherwise stated. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Furthermore, various modifications of the invention in addition to those shown and described herein will be apparent to those skilled in the art from the foregoing description. Such modifications are also intended to fall within the scope of the appended claims.

Example 1

Creation of an *Arabidopsis* Population with Activation-Tagged Genes

An 18.49-kb T-DNA based binary construct was created, pHSbarENDs2 (SEQ ID NO:1; FIG. 1), that contains four multimerized enhancer elements derived from the Cauliflower Mosaic Virus 35S promoter (corresponding to sequences −341 to −64, as defined by Odell et al., *Nature* 313:810-812 (1985)). The construct also contains vector sequences (pUC9) and a poly-linker (SEQ ID NO:11) to allow plasmid rescue, transposon sequences (Ds) to remobilize the T-DNA, and the bar gene to allow for glufosinate selection of transgenic plants. In principle, only the 10.8-kb segment from the right border (RB) to left border (LB) inclusive will be transferred into the host plant genome. Since the enhancer elements are located near the RB, they can induce cis-activation of genomic loci following T-DNA integration.

*Arabidopsis* activation-tagged populations were created by whole plant *Agrobacterium* transformation. The pHS-barENDs2 construct was transformed into *Agrobacterium tumefaciens* strain C58, grown in lysogeny broth medium at 25° C. to OD600 ~1.0. Cells were then pelleted by centrifugation and resuspended in an equal volume of 5% sucrose/ 0.05% Silwet L-77 (OSI Specialties, Inc). At early bolting, soil grown *Arabidopsis thaliana* ecotype Col-0 were top watered with the *Agrobacterium* suspension. A week later, the same plants were top watered again with the same *Agrobacterium* strain in sucrose/Silwet. The plants were then allowed to set seed as normal. The resulting T1 seed were sown on soil, and transgenic seedlings were selected by spraying with glufosinate (FINALE®; AgrEvo; Bayer Environmental Science). A total of 100,000 glufosinate resistant T1 seedlings were selected. T2 seed from each line was kept separate.

Example 2

Screens to Identify Lines with Tolerance to Low Nitrogen

From each of 100,000 separate T1 activation-tagged lines, eleven T2 plants are sown on square plates (15 mm×15 mm) containing 0.5×N-Free Hoagland's, 0.4 mM potassium nitrate, 0.1% sucrose, 1 mM MES and 0.25% Phytagel™ (Low N medium). Five lines are plated per plate, and the inclusion of 9 wild-type individuals on each plate makes for a total of 64 individuals in an 8×8 grid pattern (see FIG. 11). Plates are kept for three days in the dark at 4° C. to stratify seeds and then placed horizontally for nine days at 22° C. light and 20° C. dark. Photoperiod is sixteen hours light and eight hours dark, with an average light intensity of ~200 mmol/m²/s. Plates are rotated and shuffled daily within each shelf. At day twelve (nine days of growth), seedling status is evaluated by imaging the entire plate.

Figure 12:
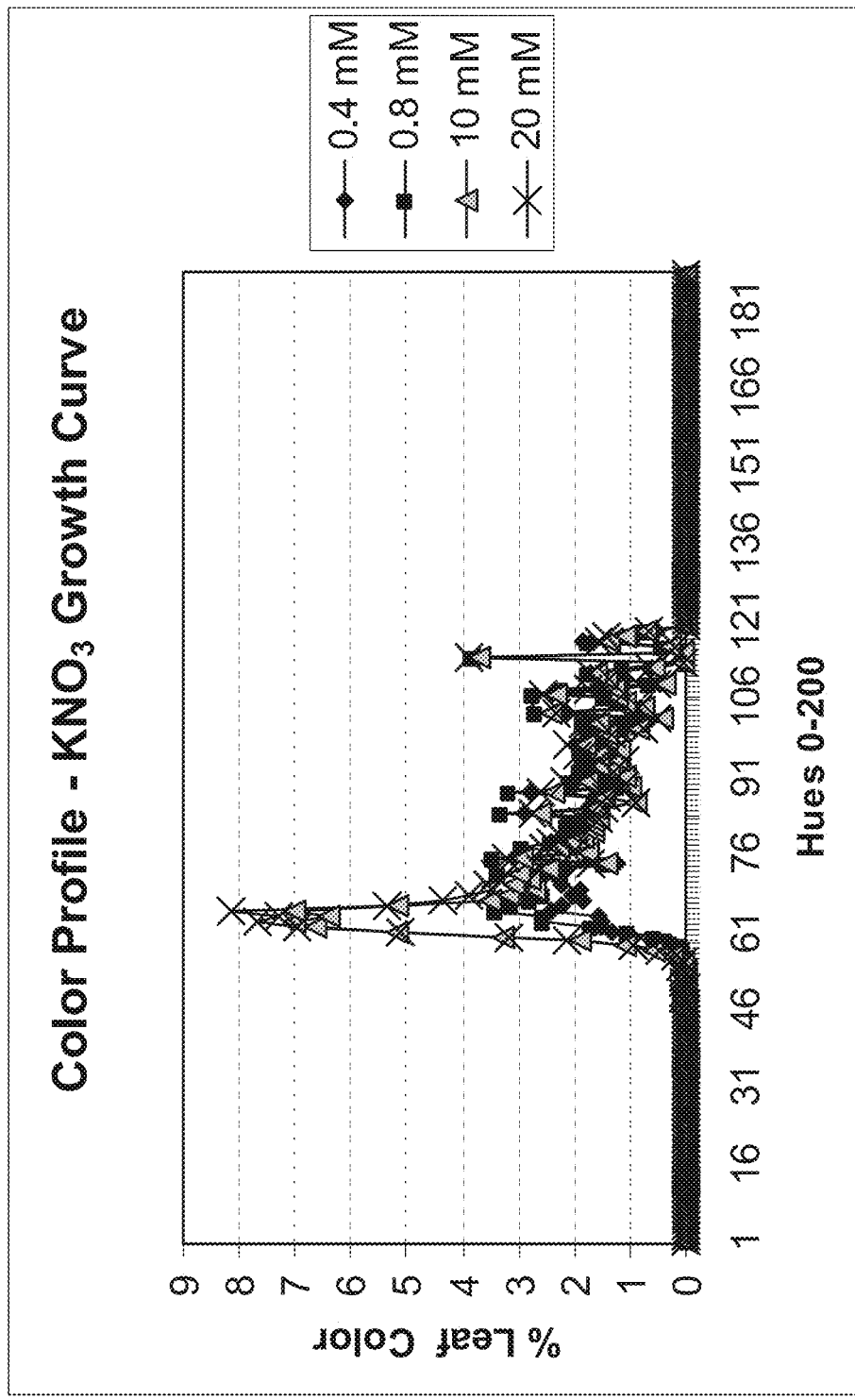
FIG. 12 shows a graph showing the effect of several different potassium nitrate concentrations on plant color as determined by image analysis. The response of the green color bin (hues 50 to 66) to nitrate dosage demonstrates that this bin can be used as an indicator of nitrogen assimilation.

After masking the plate image to remove background color, two different measurements are collected for each individual: total rosette area, and the percentage of color that falls into a green color bin. Using hue, saturation and intensity data (HSI), the green color bin consists of hues 50 to 66. Total rosette area is used as a measure of plant biomass, whereas the green color bin has been shown by dose-response studies to be an indicator of nitrogen assimilation (see FIG. 12).

Lines with a significant increase in total rosette area and/or green color bin, when compared to the wild-type controls, are designated as Phase 1 hits. Phase 1 hits are re-screened in duplicate under the same assay conditions (Phase 2 screen). A Phase 3 screen is also employed to further validate mutants that pass through Phases 1 and 2. In Phase 3, each line is plated separately on Low N medium, such that 32 T2 individuals are grown next to 32 wild-type individuals on one plate, providing greater statistical rigor to the analysis. If a line shows a significant difference from the controls in Phase 3, the line is then considered a validated nitrogen-deficiency tolerant line.

Example 3

Identification of Activation-Tagged Genes

Genes flanking the T-DNA insert in nitrogen tolerant lines are identified using one, or both, of the following two standard procedures: (1) thermal asymmetric interlaced (TAIL) PCR (Liu et al., *Plant J.* 8:457-63 (1995)); and (2) SAIFF PCR (Siebert et al., *Nucleic Acids Res.* 23:1087-1088 (1995)). In lines with complex multimerized T-DNA inserts, TAIL PCR and SAIFF PCR may both prove insufficient to identify candidate genes. In these cases, other procedures, including inverse PCR, plasmid rescue and/or genomic library construction, can be employed.

A successful result is one where a single TAIL or SAIFF PCR fragment contains a T-DNA border sequence and *Arabidopsis* genomic sequence. Once a tag of genomic sequence flanking a T-DNA insert is obtained, candidate genes are identified by alignment to publicly available *Arabidopsis* genome sequence. Specifically, the annotated gene nearest the 35S enhancer elements/T-DNA RB are candidates for genes that are activated.

To verify that an identified gene is truly near a T-DNA and to rule out the possibility that the TAIL/SAIFF fragment is a chimeric cloning artifact, a diagnostic PCR on genomic DNA is done with one oligo in the T-DNA and one oligo specific for the candidate gene. Genomic DNA samples that give a PCR product are interpreted as representing a T-DNA insertion. This analysis also verifies a situation in which more than one insertion event occurs in the same line, e.g., if multiple differing genomic fragments are identified in TAIL and/or SAIFF PCR analyses.

Example 4

Identification of Activation-Tagged Int1 Gene

An activation tagged-line (line 110629) showing nitrogen-deficiency tolerance was further analyzed. DNA from the line was extracted, and genes flanking the T-DNA insert in the mutant line were identified using ligation-mediated PCR (Siebert et al., *Nucleic Acids Res.* 23:1087-1088 (1995)). A single amplified fragment was identified that contained a T-DNA border sequence and *Arabidopsis* genomic sequence. Once a tag of genomic sequence flanking a T-DNA insert was obtained, a candidate gene was identified by alignment to the completed *Arabidopsis* genome. Specifically, the annotated gene nearest the 35S enhancer elements/T-DNA RB was the candidate for the gene activated in the line. In the case of line 110629 the gene nearest the 35S enhancers was At1g67060 (SEQ ID NO:31; NCBI GI No: 145337238), encoding the *Arabidopsis thaliana* "unknown protein" referred to herein as LNT1 (SEQ ID NO:32; NCBI GI 42563004).

Example 5

Validation of Candidate *Arabidopsis* Gene (At1g67060) Via Transformation into *Arabidopsis*

Candidate genes can be transformed into *Arabidopsis* and overexpressed under the 35S promoter. If the same or similar phenotype is observed in the transgenic line as in the parent activation-tagged line, then the candidate gene is considered to be a validated "lead gene" in *Arabidopsis*.

The *Arabidopsis* At1g67060 gene (SEQ ID NO:31) was tested for its ability to confer nitrogen-deficiency tolerance in the following manner.

The At1g67060 cDNA was amplified by RT-PCR with the following primers:

1. At1g67060-5' attB forward primer (SEQ ID NO:35)
The forward primer contains the attB1 sequence (ACAAGTTTGTACAAAAAAGCAGGCT; SEQ ID NO:12) and a consensus Kozak sequence (CAACA) upstream of the first 21 nucleotides of the protein-coding region, beginning with the ATG start codon, of said cDNA.

2. At1g67060-3' attB reverse primer (SEQ ID NO:36)
The reverse primer contains the attB2 sequence (ACCACTTTGTACAAGAAAGCTGGGT; SEQ ID NO:13) adjacent to the reverse complement of the last 21 nucleotides of the protein-coding region, beginning with the reverse complement of the stop codon, of said cDNA.

Using the INVITROGEN™ GATEWAY® CLONASE™ technology, a BP Recombination Reaction was performed for the RT-PCR product with pDONR™Zeo (SEQ ID NO:2; FIG. 2). This process removes the bacteria lethal ccdB gene, as well as the chloramphenicol resistance gene (CAM) from pDONR™Zeo and directionally clones the PCR product with flanking attB1 and attB2 sites, creating an entry clone. This entry clone was used for a subsequent LR Recombination Reaction with a destination vector, as follows.

A 16.8-kb T-DNA based binary vector (destination vector), called pBC-yellow (SEQ ID NO:4; FIG. 4), was constructed with a 1.3-kb 35S promoter immediately upstream of the INVITROGEN™ GATEWAY C1 conversion insert, which contains the bacterial lethal ccdB gene as well as the chloramphenicol resistance gene (CAM) flanked by attR1 and attR2 sequences. The vector also contains the RD29a promoter driving expression of the gene for ZS-Yellow (INVITROGEN™), which confers yellow fluorescence to transformed seed. Using the INVITROGEN™ GATEWAY® technology, an LR Recombination Reaction was performed on the entry clone containing the directionally cloned PCR product and pBC-yellow. This amplification allowed for rapid and directional cloning of the At1g67060 gene (SEQ ID NO:31) behind the 35S promoter in pBC-yellow.

Applicants then introduced the 35S promoter::At1g67060 expression construct into wild-type *Arabidopsis* ecotype Col-0, using the same *Agrobacterium*-mediated transformation procedure described in Example 1. Transgenic T1 seeds were selected by yellow fluorescence, and 32 of these T1 seeds were plated next to 32 wild-type *Arabidopsis* ecotype Col-0 seeds on low nitrogen medium. All subsequent growth conditions and imaging analyses were performed as described in Example 1. It was found that the original phenotype from activation tagging, tolerance to nitrogen limiting conditions, could be recapitulated in wild-type *Arabidopsis* plants that were transformed with a construct where At1g67060 was directly expressed by the 35S promoter.

Example 6

Composition of cDNA Libraries, Isolation and Sequencing of cDNA Clones cDNA libraries may be prepared by any one of many methods available. For example, the cDNAs may be introduced into plasmid vectors by first preparing the cDNA libraries in UNI-ZAP™ XR vectors according to the manufacturer's protocol (Stratagene Cloning Systems, La Jolla, Calif.). The UNI-ZAP™ XR libraries are converted into plasmid libraries according to the protocol provided by Stratagene. Upon conversion, cDNA inserts will be contained in the plasmid vector pBLUESCRIPT®. In addition, the cDNAs may be introduced directly into precut BLUESCRIPT® II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBLUESCRIPT® plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., *Science* 252:1651-1656 (1991)). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke, *Nucleic Acids Res.* 22:3765-3772 (1994)). The in vitro transposition system places unique binding sites randomly throughout a population of large DNA molecules. The transposed DNA is then used to transform DH10B electro-competent cells (GIBCO BRL/Life Technologies, Rockville, Md.) via electroporation. The transposable element contains an additional selectable marker (named DHFR; Fling and Richards, *Nucleic Acids Res.* 11:5147-5158 (1983)), allowing for dual selection on agar plates of only those subclones containing the integrated transposon. Multiple subclones are randomly selected from each transposition reaction, plasmid DNAs are prepared via alkaline lysis, and templates are sequenced (ABI PRISM dye-terminator ReadyReaction mix) outward from the transposition event site, utilizing unique primers specific to the binding sites within the transposon.

Sequence data is collected (ABI PRISM® Collections) and assembled using Phred and Phrap (Ewing et al., *Genome Res.* 8:175-185 (1998); Ewing et al., *Genome Res.* 8:186-194 (1998)). Phred is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (Gordon et al., *Genome Res.* 8:195-202 (1998)).

In some of the clones the cDNA fragment corresponds to a portion of the 3'-terminus of the gene and does not cover the entire open reading frame. In order to obtain the upstream information one of two different protocols is used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries sometimes are chosen based on previous knowledge that the specific gene should be found in a certain tissue and sometimes are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBLUE-SCRIPT® vector using a commercial kit and following the manufacturer's protocol. This kit is selected from many available from several vendors including INVITROGEN™ (Carlsbad, Calif.), Promega Biotech (Madison, Wis.), and GIBCO-BRL (Gaithersburg, Md.). The plasmid DNA is isolated by alkaline lysis method and submitted for sequencing and assembly using Phred/Phrap, as above.

Example 7

Identification of cDNA Clones cDNA clones encoding LNT1-like polypeptides were identified by conducting BLAST (Basic Local Alignment Search Tool; Altschul et al., *J. Mol. Biol.* 215:403-410 (1993); see also the explanation of the BLAST algorithm on the world wide web site for the National Center for Biotechnology Information at the National Library of Medicine of the National Institutes of Health) searches for similarity to amino acid sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The DNA sequences from clones can be translated in all reading frames and compared for similarity to all publicly available protein sequences contained in the "nr" database using the BLASTX algorithm (Gish and States, *Nat. Genet.* 3:266-272 (1993)) provided by the NCBI. Alternatively, the polypeptides encoded by the cDNA sequences can be analyzed for similarity to all publicly available amino acid sequences contained in the "nr" database using the BLASTP algorithm provided by the National Center for Biotechnology Information (NCBI). For convenience, the P-value (probability) or the E-value (expection) of observing a match of a cDNA-encoded sequence to a sequence contained in the searched databases merely by chance as calculated by BLAST are reported herein as "pLog" values, which represent the negative of the logarithm of the reported P-value or E-value. Accordingly, the greater the pLog value, the greater the likelihood that the cDNA-encoded sequence and the BLAST "hit" represent homologous proteins.

EST sequences can be compared to the GenBank database as described above. ESTs that contain sequences more 5- or 3-prime can be found by using the BLASTN algorithm (Altschul et al., *Nucleic Acids Res.* 25:3389-3402 (1997)) against the DUPONT proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described above.

Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 8

Characterization of cDNA Clones Encoding LNT1-Like Polypeptides cDNA libraries representing mRNAs from various tissues of *Zea mays* (maize), *Oryza sativa* (rice), *Glycine max* (soybean), and *Helianthus annuus* (sunflower) were prepared. The characteristics of the libraries are described below.

TABLE 2 cDNA Libraries from Maize, Soybean, and Sunflower

| Library | Description (tissue) | Clone |
|---------|---------------------|-------|
| cfp7n | Maize Root, Pooled stages, Full-length enriched, normalized | cfp7n.pk064.p15:fis |
| cr1 | Corn (*Zea mays* L.) root from 7 day seedlings grown in light | cr1.pk0018.c9:fis |
| srr1c | Soybean (*Glycine max* L., 9281) roots control for src1c. | srr1c.pk002.g4:fis |
| sfl1 | Soybean (*Glycine max* L.) immature flower | sfl1.pk0086.d10:fis |
| hso1c | Oxalate oxidase-transgenic sunflower plants | hso1c.pk016.m11:fis |
| hhs1c | Sunflower (*Helianthus* sp.) head tissue infected with *sclerotinia* | hhs1c.pk009.j19:fis |
| rl0n | Rice 15 Day Old Leaf* | rl0n.pk135.l9 |

*These libraries were normalized essentially as described in U.S. Pat. No. 5,482,845

As shown in Table 3, FIGS. 15A-15C, and FIG. 16, cDNAs identified in Table 2 encode polypeptides similar to the LNT1 polypeptide from *Arabidopsis thaliana* (At1g67060; NCBI General Identifier No. 42563004; SEQ ID NO:32) and to two unknown polypeptides from *Vitis vinifera* (NCBI General Identifier No. 157343572 (SEQ ID NO:34) and NCBI General Identifier No. 157341431 (SEQ ID NO:33)) and one polypeptide from *Zea mays* (NCBI General Identifier No. 212275704).

Shown in Table 3 (non-patent literature) and Table 4 (patent literature) are the BLAST results for individual ESTs ("EST"), the sequences of the entire cDNA inserts comprising the indicated cDNA clones ("FIS"), the sequences of contigs assembled from two or more EST, FIS or PCR sequences ("Contig"), or sequences encoding an entire or functional protein derived from an FIS or a contig ("CGS"). Also shown in Tables 3 and 4 are the percent sequence identity values for each pair of amino acid sequences using the Clustal V method of alignment with default parameters (described below).

TABLE 3

BLASTP Results for Polypeptides Homologous to LNT1

| Sequence (SEQ ID NO: #) | Status | NCBI GI No. | % identity | BLASTP pLog Score |
|---|---|---|---|---|
| cfp7n.pk064.p15:fis (SEQ ID NO: 18) | CGS | 157341431 (SEQ ID NO: 33) | 78.1 | 108 |
| cr1.pk0018.c9:fis (SEQ ID NO: 20) | CGS | 157341431 (SEQ ID NO: 33) | 78.1 | 109 |
| srr1c.pk002.g4:fis (SEQ ID NO: 22) | CGS | 157341431 (SEQ ID NO: 33) | 82.8 | 114 |
| sfl1.pk0086.d10:fis (SEQ ID NO: 24) | CGS | 157341431 (SEQ ID NO: 33) | 82.8 | 115 |
| hso1c.pk016.m11:fis (SEQ ID NO: 26) | CGS | 157341431 (SEQ ID NO: 33) | 82.8 | 113 |
| hhs1c.pk009.j19:fis (SEQ ID NO: 28) | CGS | 157343572 (SEQ ID NO: 34) | 78.5 | 106 |
| rl0n.pk135.l9:fis (SEQ ID NO: 30) | CGS | 212275704 (SEQ ID NO: 37) | 92.9 | 87 |

TABLE 4

BLASTP Results for Polypeptides Homologous to LNT1

| Sequence (SEQ ID NO: #) | Status | Reference | % Identity | BLAST pLog Score |
|---|---|---|---|---|
| cfp7n.pk064.p15:fis (SEQ ID NO: 18) | CGS | SEQ ID NO: 302196 in US2004214272 | 100.0 | 135 |
| cr1.pk0018.c9:fis (SEQ ID NO: 20) | CGS | SEQ ID NO: 7336 in US2004216190 | 97.9 | 133 |
| srr1c.pk002.g4:fis (SEQ ID NO: 22) | CGS | SEQ ID NO: 279794 in US2004031072 | 99.1 | 134 |
| sfl1.pk0086.d10:fis (SEQ ID NO: 24) | CGS | SEQ ID NO: 279794 in US2004031072 | 100.0 | 134 |
| hso1c.pk016.m11:fis (SEQ ID NO: 26) | CGS | SEQ ID NO: 27974 in US2004031072 | 82.9 | 114 |
| hhs1c.pk009.j19:fis (SEQ ID NO: 28) | CGS | SEQ ID NO: 279794 in US2004031072 | 73.5 | 103 |
| rl0n.pk135.l9:fis (SEQ ID NO: 30) | CGS | SEQ ID NO: 302199 in US20040214272 and in US20090087878 | 92.9 | 88 |

FIGS. 15A-15C present an alignment of the amino acid sequences set forth in SEQ ID NOs:18, 20, 22, 24, 26, 28, 30, 33, 34, and 37, and the amino acid sequence of the LNT1 polypeptide from *Arabidopsis thaliana* (GI No. 42563004) (SEQ ID NO: 32). FIG. 16 is a chart of the percent sequence identity and the divergence values for each pair of amino acids sequences presented in FIGS. 15A-15C.

Sequence alignments and percent identity calculations were performed using the MEGALIGN® program of the LASERGENE® bioinformatics computing suite (DNASTAR® Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Example 9

Preparation of a Plant Expression Vector Containing a Homolog to the *Arabidopsis* Lead Gene Sequences homologous to the lead LNT1 gene can be identified using sequence comparison algorithms such as BLAST (Basic Local Alignment Search Tool; Altschul et al., *J. Mol. Biol.* 215:403-410 (1993); see also the explanation of the BLAST algorithm on the world wide web site for the National Center for Biotechnology Information at the National Library of Medicine of the National Institutes of Health). Homologous LNT1-like sequences, such as the ones described in Example 8, can be PCR-amplified by either of the following methods.

Method 1 (RNA-based): If the 5' and 3' sequence information for the protein-coding region of an LNT1 homolog is available, gene-specific primers can be designed as outlined in Example 5. RT-PCR can be used with plant RNA to obtain a nucleic acid fragment containing the protein-coding region flanked by attB1 (SEQ ID NO:12) and attB2 (SEQ ID NO:13) sequences. The primer may contain a consensus Kozak sequence (CAACA) upstream of the start codon.

Method 2 (DNA-based): Alternatively, if a cDNA clone is available for the LNT1 homolog, the entire cDNA insert (containing 5' and 3' non-coding regions) can be PCR amplified. Forward and reverse primers can be designed that contain either the attB1 sequence and vector-specific sequence that precedes the cDNA insert or the attB2 sequence and vector-specific sequence that follows the cDNA insert, respectively. For a cDNA insert cloned into the vector pBLUESCRIPT SK+, the forward primer VC062 (SEQ ID NO:15) and the reverse primer VC063 (SEQ ID NO:16) can be used.

Methods 1 and 2 can be modified according to procedures known by one skilled in the art. For example, the primers of Method 1 may contain restriction sites instead of attB1 and attB2 sites, for subsequent cloning of the PCR product into a vector containing attB1 and attB2 sites. Additionally, Method 2 can involve amplification from a cDNA clone, a lambda clone, a BAC clone or genomic DNA.

A PCR product obtained by either method above can be combined with a GATEWAY® donor vector, such as pDONR™Zeo (SEQ ID NO:2; FIG. 2) or pDONR™221 (SEQ ID NO:3; FIG. 3), using a BP Recombination Reaction. This process removes the bacteria lethal ccdB gene, as well as the chloramphenicol resistance gene (CAM), from pDONR™Zeo or pDONR™221 and directionally clones the PCR product with flanking attB1 and attB2 sites to create an entry clone. Using the INVITROGEN™ GATEWAY® CLONASE™ technology, the sequence encoding the homologous LNT1 polypeptide from the entry clone can then be transferred to a suitable destination vector, such as pBC-Yellow (SEQ ID NO:4; FIG. 4), PHP27840 (SEQ ID NO:5; FIG. 5), or PHP23236 (SEQ ID NO:6; FIG. 6), to obtain a plant expression vector for use with *Arabidopsis*, soybean, and corn, respectively.

The attP1 and attP2 sites of donor vectors pDONR™/Zeo or pDONR™221 are shown in FIGS. 2 and 3, respectively. The attR1 and attR2 sites of destination vectors pBC-Yellow, PHP27840 and PHP23236 are shown in FIGS. 4, 5, and 6, respectively.

Alternatively a MultiSite GATEWAY® LR recombination reaction between multiple entry clones and a suitable destination vector can be performed to create an expression vector.

Example 10

Preparation of Soybean Expression Vectors and Transformation of Soybean with Validated *Arabidopsis* Lead Genes Soybean plants can be transformed to overexpress each validated *Arabidopsis* gene or the corresponding homologs from various species in order to examine the resulting phenotype.

The same GATEWAY® entry clone described in Example 5 can be used to directionally clone each gene into the PHP27840 vector (SEQ ID NO:5; FIG. 5) such that expression of the gene is under control of the SCP1 promoter.

Soybean embryos may then be transformed with the expression vector comprising sequences encoding the instant polypeptides.

To induce somatic embryos, cotyledons, 3-5 mm in length dissected from surface sterilized, immature seeds of the soybean cultivar A2872, can be cultured in the light or dark at 26° C. on an appropriate agar medium for six to ten weeks. Somatic embryos, which produce secondary embryos, are then excised and placed into a suitable liquid medium. After repeated selection for clusters of somatic embryos which multiply as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium. Soybean embryogenic suspension cultures may then be transformed by the method of particle gun bombardment (Klein et al., *Nature* (London) 327:70-73 (1987), U.S. Pat. No. 4,945,050). A DUPONT BIOLISTIC™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al., *Nature* 313:810-812 (1985)), the hygromycin phosphotransferase gene from plasmid pJR225 (from *E. coli*; Gritz et al., *Gene* 25:179-188 (1983)) and the 3' region of the nopaline synthase gene from the T-DNA of the Ti plasmid of *Agrobacterium tumefaciens*. Another selectable marker gene which can be used to facilitate soybean transformation is an herbicide-resistant acetolactate synthase (ALS) gene from soybean or *Arabidopsis*. ALS is the first common enzyme in the biosynthesis of the branched-chain amino acids valine, leucine and isoleucine. Mutations in ALS have been identified that convey resistance to some or all of three classes of inhibitors of ALS (U.S. Pat. No. 5,013,659; the entire contents of which are herein incorporated by reference). Expression of the herbicide-resistant ALS gene can be under the control of a SAM synthetase promoter (U.S. Patent Application No. US-2003-0226166-A1; the entire contents of which are herein incorporated by reference).

To 50 µL of a 60 mg/mL 1 µm gold particle suspension is added (in order): 5 µL DNA (1 µg/µL), 20 µL spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment, with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Soybean plants transformed with validated genes can be assayed to study agronomic characteristics relative to control or reference plants. For example, yield enhancement and/or stability under low and high nitrogen conditions (e.g., nitrogen limiting conditions and nitrogen-sufficient conditions) can be assayed.

Example 11

Transformation of Maize with Validated *Arabidopsis* Lead Genes Using Particle Bombardment Maize plants can be transformed to overexpress a validated *Arabidopsis* lead gene or the corresponding homologs from various species in order to examine the resulting phenotype.

The same GATEWAY® entry clone described in Example 5 can be used to directionally clone each gene into a maize transformation vector. Expression of the gene in the maize transformation vector can be under control of a constitutive promoter such as the maize ubiquitin promoter (Christensen et al., *Plant Mol. Biol.* 12:619-632 (1989) and Christensen et al., *Plant Mol. Biol.* 18:675-689 (1992))

The recombinant DNA construct described above can then be introduced into maize cells by the following procedure. Immature maize embryos can be dissected from developing caryopses derived from crosses of the inbred maize lines H99 and LH132. The embryos are isolated ten to eleven days after pollination when they are 1.0 to 1.5 mm long. The embryos are then placed with the axis-side facing down and in contact with agarose-solidified N6 medium (Chu et al., *Sci. Sin. Peking* 18:659-668 (1975)). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every two to three weeks.

The plasmid, p35S/Ac (obtained from Dr. Peter Eckes, Hoechst Ag, Frankfurt, Germany) may be used in transformation experiments in order to provide for a selectable marker. This plasmid contains the pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al., *Nature* 313:810-812 (1985)) and the 3' region of the nopaline synthase gene from the T-DNA of the Ti plasmid of *Agrobacterium tumefaciens*.

The particle bombardment method (Klein et al., *Nature* 327:70-73 (1987)) may be used to transfer genes to the callus culture cells. According to this method, gold particles (1 µm in diameter) are coated with DNA using the following technique. Ten μg of plasmid DNAs are added to 50 μL of a suspension of gold particles (60 mg per mL). Calcium chloride (50 μL) of a 2.5 M solution) and spermidine free base (20 μL of a 1.0 M solution) are added to the particles. The suspension is vortexed during the addition of these solutions. After ten minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a KAPTON™ flying disc (Bio-Rad Labs). The particles are then accelerated into the maize tissue with a BIOLISTIC™ PDS-1000/He (Bio-Rad Instruments, Hercules Calif.), using a helium pressure of 1000 psi, a gap distance of 0.5 cm, and a flying distance of 1.0 cm.

For bombardment, the embryogenic tissue is placed on filter paper over agarose-solidified N6 medium. The tissue is arranged as a thin lawn and covers a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialaphos (5 mg per liter) and lacks casein or proline. The tissue continues to grow slowly on this medium. After an additional two weeks the tissue can be transferred to fresh N6 medium containing bialaphos. After six weeks, areas of about 1 cm in diameter of actively growing callus can be identified on some of the plates containing the bialaphos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., *Bio/Technology* 8:833-839 (1990)). Transgenic T0 plants can be regenerated and their phenotype determined following HTP procedures. T1 seed can be collected.

T1 plants can be grown under nitrogen limiting conditions, for example 1 mM nitrate, and analyzed for phenotypic changes. The following parameters can be quantified using image analysis: plant area, volume, growth rate and color analysis can be collected and quantified. Overexpression constructs that result in an alteration, compared to suitable control plants, in greenness (green color bin), yield, growth rate, biomass, fresh or dry weight at maturation, fruit or seed yield, total plant nitrogen content, fruit or seed nitrogen content, nitrogen content in vegetative tissue, free amino acid content in the whole plant, free amino acid content in vegetative tissue, free amino acid content in the fruit or seed, protein content in the fruit or seed, or protein content in a vegetative tissue can be considered evidence that the *Arabidopsis* lead gene functions in maize to enhance tolerance to nitrogen deprivation (increased nitrogen stress tolerance).

Furthermore, a recombinant DNA construct containing a validated *Arabidopsis* gene can be introduced into a maize inbred line either by direct transformation or introgression from a separately transformed line.

Example 12

Electroporation of *Agrobacterium tumefaciens* LBA4404 (General Description)

Electroporation competent cells (40 μL), such as *Agrobacterium tumefaciens* LBA4404 (containing PHP10523), are thawed on ice (20-30 min). PHP10523 contains VIR genes for T-DNA transfer, an *Agrobacterium* low copy number plasmid origin of replication, a tetracycline resistance gene, and a Cos site for in vivo DNA bimolecular recombination. Meanwhile the electroporation cuvette is chilled on ice. The electroporator settings are adjusted to 2.1 kV. A DNA aliquot (0.5 μL parental DNA at a concentration of 0.2 μg-1.0 μg in low salt buffer or twice distilled $H_2O$) is mixed with the thawed *Agrobacterium tumefaciens* LBA4404 cells while still on ice. The mixture is transferred to the bottom of electroporation cuvette and kept at rest on ice for 1-2 min. The cells are electroporated (Eppendorf electroporator 2510) by pushing the "pulse" button twice (ideally achieving a 4.0 millisecond pulse). Subsequently, 0.5 mL of room temperature 2×YT medium (or SOC medium) are added to the cuvette and transferred to a 15 mL snap-cap tube (e.g., FALCON™ tube). The cells are incubated at 28-30° C., 200-250 rpm for 3 h.

Aliquots of 250 μL are spread onto plates containing YM medium and 50 μg/mL spectinomycin and incubated three days at 28-30° C. To increase the number of transformants one of two optional steps can be performed:

Option 1: Overlay plates with 30 μL of 15 mg/mL rifampicin. LBA4404 has a chromosomal resistance gene for rifampicin. This additional selection eliminates some contaminating colonies observed when using poorer preparations of LBA4404 competent cells.

Option 2: Perform two replicates of the electroporation to compensate for poorer electrocompetent cells.

Identification of Transformants:

Four independent colonies are picked and streaked on plates containing AB minimal medium and 50 μg/mL spectinomycin for isolation of single colonies. The plates are incubated at 28° C. for two to three days. A single colony for each putative cointegrate is picked and inoculated with 4 mL of 10 g/L bactopeptone, 10 g/L yeast extract, 5 g/L sodium chloride, and 50 mg/L spectinomycin. The mixture is incubated for 24 h at 28° C. with shaking. Plasmid DNA from 4 mL of culture is isolated using QIAGEN Miniprep and an optional Buffer PB wash. The DNA is eluted in 30 μL. Aliquots of 2 μL are used to electroporate 20 μL of DH10b+20 μL of twice distilled $H_2O$ as per above. Optionally a 15 μL aliquot can be used to transform 75-100 μL of INVITROGEN™ Library Efficiency DH5α. The cells are spread on plates containing LB medium and 50 μg/mL spectinomycin and incubated at 37° C. overnight.

Three to four independent colonies are picked for each putative cointegrate and inoculated 4 mL of 2×YT medium (10 g/L bactopeptone, 10 g/L yeast extract, 5 g/L sodium chloride) with 50 μg/mL spectinomycin. The cells are incubated at 37° C. overnight with shaking. Next, plasmid DNA is isolated from 4 mL of culture using QIAprep® Miniprep with optional Buffer PB wash (elute in 50 μL). 8 μL are used for digestion with SalI (using parental DNA and PHP10523 as controls). Three more digestions using restriction enzymes BamHI, EcoRI, and HindIII are performed for 4 plasmids that represent 2 putative cointegrates with correct SalI digestion pattern (using parental DNA and PHP10523 as controls). Electronic gels are recommended for comparison.

Alternatively, for high throughput applications, such as that described for Gaspe Flint Derived Maize Lines (Example 16), instead of evaluating the resulting cointegrate vectors by restriction analysis, three colonies can be simultaneously used for the infection step as described in Example 13 (transformation via *Agrobacterium*).

Example 13

Transformation of Maize Using *Agrobacterium*

Maize plants can be transformed to overexpress a validated *Arabidopsis* lead gene or the corresponding homologs from various species in order to examine the resulting phenotype.

*Agrobacterium*-mediated transformation of maize is performed essentially as described by Zhao et al., in *Meth. Mol. Biol.* 318:315-323 (2006) (see also Zhao et al., *Mol. Breed.* 8:323-333 (2001) and U.S. Pat. No. 5,981,840 issued Nov. 9, 1999, incorporated herein by reference). The transformation process involves bacterium inoculation, co-cultivation, resting, selection, and plant regeneration.

1. Immature Embryo Preparation:

Immature maize embryos are dissected from caryopses and placed in a 2 mL microtube containing 2 mL PHI-A medium.

2. *Agrobacterium* Infection and Co-Cultivation of Immature Embryos:

2.1 Infection Step:

PHI-A medium of (1) is removed with 1 mL micropipettor, and 1 mL of *Agrobacterium* suspension is added. The tube is gently inverted to mix. The mixture is incubated for 5 min at room temperature.

2.2 Co-Culture Step:

The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for three days. L-Cysteine can be used in the co-cultivation phase. With the standard binary vector, the co-cultivation medium supplied with 100-400 mg/L L-cysteine is critical for recovering stable transgenic events.

3. Selection of Putative Transgenic Events:

To each plate of PHI-D medium in a 100×15 mm Petri dish, 10 embryos are transferred, maintaining orientation, and the dishes are sealed with parafilm. The plates are incubated in darkness at 28° C. Actively growing putative events, evinced as pale yellow embryonic tissue, are expected to be visible in six to eight weeks. Embryos that produce no events may be brown and necrotic, and little friable tissue growth is evident. Putative transgenic embryonic tissue is subcultured to fresh PHI-D plates at two-three week intervals, depending on growth rate. The events are recorded.

4. Regeneration of T0 Plants:

Embryonic tissue propagated on PHI-D medium is subcultured to PHI-E medium (somatic embryo maturation medium), in 100×25 mm Petri dishes and incubated at 28° C., in darkness, until somatic embryos mature, for about ten to eighteen days. Individual, matured somatic embryos with well-defined scutellum and coleoptile are transferred to PHI-F embryo germination medium and incubated at 28° C. in the light (about 80 µE from cool white or equivalent fluorescent lamps). In seven to ten days, regenerated plants, about 10 cm tall, are potted in horticultural mix and hardened-off using standard horticultural methods.

Media for Plant Transformation:

1. PHI-A: 4 g/L CHU basal salts, 1.0 mL/L 1000× Eriksson's vitamin mix, 0.5 mg/L thiamin HCl, 1.5 mg/L 2,4-D, 0.69 g/L L-proline, 68.5 g/L sucrose, 36 g/L glucose, pH 5.2. Add 100 µM acetosyringone (filter-sterilized).

2. PHI-B: PHI-A without glucose, increase 2,4-D to 2 mg/L, reduce sucrose to 30 g/L and supplemented with 0.85 mg/L silver nitrate (filter-sterilized), 3.0 g/L GELRITE®, 100 µM acetosyringone (filter-sterilized), pH 5.8.

3. PHI-C: PHI-B without GELRITE® and acetosyringonee, reduce 2,4-D to 1.5 mg/L and supplemented with 8.0 g/L agar, 0.5 g/L 2-[N-morpholino]ethane-sulfonic acid (MES) buffer, 100 mg/L carbenicillin (filter-sterilized).

4. PHI-D: PHI-C supplemented with 3 mg/L bialaphos (filter-sterilized).

5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myoinositol, 0.5 mg/L zeatin (Sigma, Cat. No. Z-0164), 1 mg/L indole acetic acid (IAA), 26.4 µg/L abscisic acid (ABA), 60 g/L sucrose, 3 mg/L bialaphos (filter-sterilized), 100 mg/L carbenicillin (filter-sterilized), 8 g/L agar, pH 5.6.

6. PHI-F: PHI-E without zeatin, IAA, ABA; reduce sucrose to 40 g/L; replacing agar with 1.5 g/L GELRITE®; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm et al., *Bio/Technology* 8:833-839 (1990)).

Transgenic T0 plants can be regenerated and their phenotype determined. T1 seed can be collected. T1 plants can be grown under nitrogen limiting conditions, for example 1 mM nitrate, and analyzed for phenotypic changes. The following parameters can be quantified using image analysis: plant area, volume, growth rate and color analysis can be collected and quantified. Overexpression constructs that result in an alteration, compared to suitable control plants, in greenness (green color bin), yield, growth rate, biomass, fresh or dry weight at maturation, fruit or seed yield, total plant nitrogen content, fruit or seed nitrogen content, nitrogen content in vegetative tissue, free amino acid content in the whole plant, free amino acid content in vegetative tissue, free amino acid content in the fruit or seed, protein content in the fruit or seed, or protein content in a vegetative tissue can be considered evidence that the *Arabidopsis* lead gene functions in maize to enhance tolerance to nitrogen deprivation (increased nitrogen stress tolerance).

Furthermore, a recombinant DNA construct containing a validated *Arabidopsis* gene can be introduced into a maize inbred line either by direct transformation or introgression from a separately transformed line.

Example 14A

Preparation of Expression Vector for Transformation of Maize Lines with Validated Candidate *Arabidopsis* Gene (At1g67060) Using *Agrobacterium*

Using the INVITROGEN™ GATEWAY® technology, an LR Recombination Reaction can be performed with the same GATEWAY® entry clone described in Example 5 (containing the *Arabidopsis* LNT1 gene), entry clone PHP23112 (SEQ ID NO:14), entry clone PHP20234 (SEQ ID NO:9; FIG. 9), and destination vector PHP22655 (SEQ ID NO:10) to create a precursor plasmid with the following expression cassettes:

1. Ubiquitin promoter::moPAT::PinII terminator cassette expressing the PAT herbicide resistance gene used for selection during the transformation process.
2. LTP2 promoter::DS-RED2::PinII terminator cassette expressing the DS-RED color marker gene used for seed sorting.
3. Ubiquitin promoter::AT-LNT1::PinII terminator cassette over expressing the gene of interest, *Arabidopsis* LNT1 (At1g67060).

Example 14B

Transformation of Maize Lines with Validated Candidate *Arabidopsis* Gene (At1 g67060) Using *Agrobacterium*

The LNT1 expression cassette described in Example 14A can be introduced into a maize inbred line, or a transformable maize line derived from an elite maize inbred line, using *Agrobacterium*-mediated transformation as described in Examples 12 and 13.

The expression vector can be electroporated into the LBA4404 *Agrobacterium* strain containing vector PHP10523 (SEQ ID NO:7, FIG. 7) to create a co-integrate vector, formed by recombination via COS sites contained on each vector. The cointegrate vector would contain the same three expression cassettes as above (Example 14A) in addition to other genes (TET, TET, TRFA, ORI terminator, CTL, ORI V, VIR C1, VIR C2, VIR G, VIR B) needed for the *Agrobacterium* strain and the *Agrobacterium*-mediated transformation. The electroporation protocol in, but not limited to, Example 12 may be used.

Example 15

Preparation of the Destination Vector PHP23236 for Transformation into Gaspe Flint Derived Maize Lines Destination vector PHP23236 (FIG. 6; SEQ ID NO:6) was obtained by transformation of *Agrobacterium* strain LBA4404 containing PHP10523 (FIG. 7; SEQ ID NO:7) with vector PHP23235 (FIG. 8; SEQ ID NO:8) and isolation of the resulting co-integration product.

Destination vector PHP23236 can be used in a recombination reaction with an entry clone, as described in Example 16, to create a maize expression vector for transformation of Gaspe Flint derived maize lines.

Example 16

Preparation of Expression Constructs for Transformation into Gaspe Flint Derived Maize Lines Using the INVITROGEN™ GATEWAY® LR Recombination technology, the same entry clone described in Example 5 (containing the *Arabidopsis* LNT1 gene) can be directionally cloned into the GATEWAY® destination vector PHP23236 (SEQ ID NO:6; FIG. 6) to create an expression vector. This expression vector contains the cDNA of interest under control of the UBI promoter and is a T-DNA binary for *Agrobacterium*-mediated transformation into maize as described, but not limited to, the examples described herein.

Example 17A

Transformation of Gaspe Flint Derived Maize Lines with Validated Candidate *Arabidopsis* Gene (At1g67060)

Maize plants can be transformed to overexpress the *Arabidopsis* At1g67060 gene (and the corresponding homologs from other species) in order to examine the resulting phenotype. Expression constructs such as the one described in Example 16 may be used.

Recipient Plants

Recipient plant cells can be from a uniform maize line having a short life cycle ("fast cycling"), a reduced size, and high transformation potential. Typical of these plant cells for maize are plant cells from any of the publicly available Gaspe Flint (GF) line varieties. One possible candidate plant line variety is the F1 hybrid of GF×QTM (Quick Turnaround Maize, a publicly available form of Gaspe Flint selected for growth under greenhouse conditions) disclosed in Tomes et al. (U.S. application Ser. No. 10/367,416 filed Feb. 13, 2003; U.S. Patent Publication No. 2003/0221212 A1 published Nov. 27, 2003). Transgenic plants obtained from this line are of such a reduced size that they can be grown in four inch pots (¼ the space needed for a normal sized maize plant) and mature in less than 2.5 months. (Traditionally 3.5 months is required to obtain transgenic T0 seed once the transgenic plants are acclimated to the greenhouse.) Another suitable line includes but is not limited to a double haploid line of GS3 (a highly transformable line)×Gaspe Flint. Yet another suitable line is a transformable elite maize inbred line carrying a transgene which causes early flowering, reduced stature, or both.

Transformation Protocol

Any suitable method may be used to introduce the transgenes into the maize cells, including but not limited to, inoculation type procedures using *Agrobacterium* based vectors (see, for example, Examples 12 and 13). Transformation may be performed on immature embryos of the recipient (target) plant.

Precision Growth and Plant Tracking

The event population of transgenic (T0) plants resulting from the transformed maize embryos is grown in a controlled greenhouse environment using a modified randomized block design to reduce or eliminate environmental error. A randomized block design is a plant layout in which the experimental plants are divided into groups (e.g., thirty plants per group), referred to as blocks, and each plant is randomly assigned a location within the block.

For a group of thirty plants, twenty-four transformed, experimental plants and six control plants (plants with a set phenotype) (collectively, a "replicate group") are placed in pots which are arranged in an array (a.k.a. a replicate group or block) on a table located inside a greenhouse. Each plant, control or experimental, is randomly assigned to a location within the block which is mapped to a unique, physical greenhouse location as well as to the replicate group. Multiple replicate groups of thirty plants each may be grown in the same greenhouse in a single experiment. The layout (arrangement) of the replicate groups should be determined to minimize space requirements as well as environmental effects within the greenhouse. Such a layout may be referred to as a compressed greenhouse layout.

An alternative to the addition of a specific control group is to identify those transgenic plants that do not express the gene of interest. A variety of techniques such as RT-PCR can be applied to quantitatively assess the expression level of the introduced gene. T0 plants that do not express the transgene can be compared to those which do.

Each plant in the event population is identified and tracked throughout the evaluation process, and the data gathered from that plant is automatically associated with that plant so that the gathered data can be associated with the transgene carried by the plant. For example, each plant container can have a machine readable label (such as a Universal Product Code (UPC) bar code) which includes information about the plant identity, which in turn is correlated to a greenhouse location so that data obtained from the plant can be automatically associated with that plant.

Alternatively any efficient, machine readable, plant identification system can be used, such as two-dimensional matrix codes or even radio frequency identification tags (RFID) in which the data is received and interpreted by a radio frequency receiver/processor. See U.S. application Ser. No. 10/324,288 filed Dec. 19, 2002 (U.S. Patent Publication No. 2004/0122592 A1 published Jun. 24, 2004), incorporated herein by reference.

Phenotypic Analysis Using Three-Dimensional Imaging

Each greenhouse plant in the T0 event population, including any control plants, is analyzed for agronomic characteristics of interest, and the agronomic data for each plant is recorded or stored in a manner so that it is associated with the identifying data (see above) for that plant. Confirmation of a phenotype (gene effect) can be accomplished in the T1 generation with a similar experimental design to that described above.

The T0 plants are analyzed at the phenotypic level using quantitative, non-destructive imaging technology throughout the plant's entire greenhouse life cycle to assess the traits of interest. A digital imaging analyzer may be used for automatic multi-dimensional analyzing of total plants. The imaging may be done inside the greenhouse. Two camera systems, located at the top and side, and an apparatus to rotate the plant, are used to view and image plants from all sides. Images are acquired from the top, front and side of each plant. All three images together provide sufficient information to evaluate, for example, the biomass, size, and morphology of each plant.

Due to the change in size of the plants from the time the first leaf appears from the soil to the time the plants are at the end of their development, the early stages of plant development are best documented with a higher magnification from the top. This imaging may be accomplished by using a motorized zoom lens system that is fully controlled by the imaging software.

In a single imaging analysis operation, the following events occur: (1) the plant is conveyed inside the analyzer area, rotated 360 degrees so its machine readable label can be read, and left at rest until its leaves stop moving; (2) the side image is taken and entered into a database; (3) the plant is rotated 90 degrees and again left at rest until its leaves stop moving, and (4) the plant is transported out of the analyzer.

Plants are allowed at least six hours of darkness per twenty four hour period in order to have a normal day/night cycle.

Imaging Instrumentation

Any suitable imaging instrumentation may be used, including but not limited to light spectrum digital imaging instrumentation commercially available from LemnaTec GmbH of Wurselen, Germany. The images are taken and analyzed with a LemnaTec Scanalyzer HTS LT-0001-2 having a ½" IT Progressive Scan IEE CCD imaging device. The imaging cameras may be equipped with a motor zoom, motor aperture, and motor focus. All camera settings may be made using LemnaTec software. For example, the instrumental variance of the imaging analyzer is less than about 5% for major components and less than about 10% for minor components.

Software

The imaging analysis system comprises a LemnaTec HTS Bonit software program for color and architecture analysis and a server database for storing data from about 500,000 analyses, including the analysis dates. The original images and the analyzed images are stored together to allow the user to do as much reanalyzing as desired. The database can be connected to the imaging hardware for automatic data collection and storage. A variety of commercially available software systems (e.g., Matlab, others) can be used for quantitative interpretation of the imaging data, and any of these software systems can be applied to the image data set.

Conveyor System

A conveyor system with a plant rotating device may be used to transport the plants to the imaging area and rotate them during imaging. For example, up to four plants, each with a maximum height of 1.5 m, are loaded onto cars that travel over the circulating conveyor system and through the imaging measurement area. In this case the total footprint of the unit (imaging analyzer and conveyor loop) is about 5 m×5 m.

The conveyor system can be enlarged to accommodate more plants at a time. The plants are transported along the conveyor loop to the imaging area and are analyzed for up to 50 seconds per plant. Three views of the plant are taken. The conveyor system, as well as the imaging equipment, should be capable of being used in greenhouse environmental conditions.

Illumination

Any suitable mode of illumination may be used for the image acquisition. For example, a top light above a black background can be used. Alternatively, a combination of top- and backlight using a white background can be used. The illuminated area should be housed to ensure constant illumination conditions. The housing should be longer than the measurement area so that constant light conditions prevail without requiring the opening and closing or doors. Alternatively, the illumination can be varied to cause excitation of either transgene (e.g., green fluorescent protein (GFP), red fluorescent protein (RFP)) or endogenous (e.g. Chlorophyll) fluorophores).

Biomass Estimation Based on Three-Dimensional Imaging

For best estimation of biomass the plant images should be taken from at least three axes, for example, the top and two side (sides 1 and 2) views. These images are then analyzed to separate the plant from the background, pot and pollen control bag (if applicable). The volume of the plant can be estimated by the calculation:

$$\text{Volume(voxels)} = \sqrt{\text{TopArea(pixels)}} \times \sqrt{\text{Side1Area(pixels)}} \times \sqrt{\text{Side2Area(pixels)}}$$

In the equation above the units of volume and area are "arbitrary units". Arbitrary units are entirely sufficient to detect gene effects on plant size and growth in this system because what is desired is to detect differences (both positive-larger and negative-smaller) from the experimental mean, or control mean. The arbitrary units of size (e.g. area) may be trivially converted to physical measurements by the addition of a physical reference to the imaging process. For instance, a physical reference of known area can be included in both top and side imaging processes. Based on the area of these physical references a conversion factor can be determined to allow conversion from pixels to a unit of area such as square centimeters ($cm^2$). The physical reference may or may not be an independent sample. For instance, the pot, with a known diameter and height, could serve as an adequate physical reference.

Color Classification

The imaging technology may also be used to determine plant color and to assign plant colors to various color classes. The assignment of image colors to color classes is an inherent feature of the LemnaTec software. With other image analysis software systems color classification may be determined by a variety of computational approaches.

For the determination of plant size and growth parameters, a useful classification scheme is to define a simple color scheme including two or three shades of green (for example, hues 50-66, see FIG. 12) and, in addition, a color class for chlorosis, necrosis and bleaching, should these conditions occur. A background color class which includes non plant colors in the image (for example pot and soil colors) is also used and these pixels are specifically excluded from the determination of size. The plants are analyzed under controlled constant illumination so that any change within one plant over time, or between plants or different batches of plants (e.g. seasonal differences) can be quantified.

In addition to its usefulness in determining plant size growth, color classification can be used to assess other yield component traits. For these other yield component traits additional color classification schemes may be used. For instance, the trait known as "staygreen", which has been associated with improvements in yield, may be assessed by a color classification that separates shades of green from shades of yellow and brown (which are indicative of senescing tissues). By applying this color classification to images taken toward the end of the T0 or T1 plants' life cycle, plants that have increased amounts of green colors relative to yellow and brown colors (expressed, for instance, as Green/Yellow Ratio) may be identified. Plants with a significant difference in this Green/Yellow ratio can be identified as carrying transgenes which impact this important agronomic trait.

The skilled plant biologist will recognize that other plant colors arise which can indicate plant health or stress response (for instance anthocyanins), and that other color classification schemes can provide further measures of gene action in traits related to these responses.

Plant Architecture Analysis

Transgenes which modify plant architecture parameters may also be identified using the present invention, including such parameters as maximum height and width, internodal distances, angle between leaves and stem, number of leaves starting at nodes, and leaf length. The LemnaTec system software may be used to determine plant architecture as follows. The plant is reduced to its main geometric architecture in a first imaging step and then, based on this image, parameterized identification of the different architecture parameters can be performed. Transgenes that modify any of these architecture parameters either singly or in combination can be identified by applying the statistical approaches previously described.

Pollen Shed Date

Pollen shed date is an important parameter to be analyzed in a transformed plant, and may be determined by the first appearance on the plant of an active male flower. To find the male flower object, the upper end of the stem is classified by color to detect yellow or violet anthers. This color classification analysis is then used to define an active flower, which in turn can be used to calculate pollen shed date.

Alternatively, pollen shed date and other easily visually detected plant attributes (e.g., pollination date, first silk date) can be recorded by the personnel responsible for performing plant care. To maximize data integrity and process efficiency, this data is tracked by utilizing the same barcodes utilized by the LemnaTec light spectrum digital analyzing device. A computer with a barcode reader, a palm device, or a notebook PC may be used for ease of data capture recording time of observation, plant identifier, and the operator who captured the data.

Orientation of the Plants

Mature maize plants grown at densities approximating commercial planting often have a planar architecture. That is, the plant has a clearly discernable broad side, and a narrow side. The image of the plant from the broadside is determined. To each plant a well defined basic orientation is assigned to obtain the maximum difference between the broadside and edgewise images. The top image is used to determine the main axis of the plant, and an additional rotating device is used to turn the plant to the appropriate orientation prior to starting the main image acquisition.

Example 17B

Transformation of Gaspe Flint Derived Maize Lines with Maize Homologs

Using the INVITROGEN™ GATEWAY® LR Recombination technology, an entry clone may be created for a maize homolog (SEQ ID NO:17 OR SEQ ID NO:19) (see Example 5 for entry clone preparation) and then directionally cloned into the GATEWAY® destination vector PHP23236 (SEQ ID NO:6; FIG. 6) to create a corresponding expression vector. Hence, the expression vectors PHP30106 and PHP30116 were constructed from SEQ ID NO:17 and SEQ ID NO:19, respectively. Each expression vector contains the cDNA of interest under control of the UBI promoter and is a T-DNA binary for *Agrobacterium*-mediated transformation into maize as described, but not limited to, the examples described herein.

Example 18A

Screening of Gaspe Flint Derived Maize Lines Under Nitrogen Limiting Conditions

Transgenic plants can contain two or three doses of Gaspe Flint-3 with one dose of GS3 (GS3/(Gaspe-3)2× or GS3/(Gaspe-3)3×) and segregate 1:1 for a dominant transgene. Transgenic plants can be planted in 100% TURFACE, a commercial potting medium, and can be watered four times each day with 1 mM $KNO_3$ growth medium and with 2 mM $KNO_3$, or higher, growth medium (see FIG. 13). Control plants grown in 1 mM $KNO_3$ medium would be less green, produce less biomass, and have a smaller ear at anthesis (see FIG. 14 for an illustration of sample data).

Statistics would be used to decide if differences seen between treatments are really different. FIG. 14 illustrates one method which places letters after the values. Those values in the same column that have the same letter (not group of letters) following them are not significantly different. Using this method, if there are no letters following the values in a column, then there are no significant differences between any of the values in that column or, in other words, all the values in that column are equal.

Expression of a transgene would result in plants with improved plant growth in 1 mM KNO3 when compared to a transgenic null. Thus biomass and greenness (as described in Example 11) would be monitored during growth and compared to a transgenic null. Improvements in growth, greenness, and ear size at anthesis would be indications of increased nitrogen stress tolerance.

Example 18B

Procedure for Evaluation of Gaspe Flint Derived Maize Lines Under Nitrogen Limiting Conditions Gaspe Flint derived maize lines may be transformed via *Agrobacterium*. Typically, four transformation events for each plasmid construct may be evaluated under nitrogen limiting conditions in the following manner. Plants are planted in 100% Turface and watered until emergence. Following emergence, plants are divided equally between treatment groups and watered as appropriate to achieve saturation using drip irrigation. Daily irrigation schedule consists of a 9:00 AM, 12:00 PM, and 3:00 PM nutrient watering for 3 minutes (156 ml) between 13 and 24 days after planting (DAP). A fourth watering is added at 5:00 AM on 25 DAP, and a fifth watering is added at 5:00 PM on 31 DAP. Two treatments are applied, optimal (6.5 mMol KNO3) and reduced nitrogen (1.0 mMol KNO3). pH is monitored at least three times weekly for each table. The target pH for the experiment is 5.75-6.0. Imaging to assess surface area accumulation and specific growth rates (sgr) is performed for each plant three times per week, Monday, Wednesday and Friday. Plants are sampled for ELISA MoPAT on 9 DAP, and for expression and metabolic profiling analysis on 36 DAP. At 50% shed, 36 DAP, destructive ear and shoot phenotypes are collected manually. At 38 DAP, harvested tissue is oven dried (70 C for 120 hrs.) to obtain dry weight data. The probability of a greater Student's one tailed t Test is calculated for each transgenic mean compared to the appropriate null mean (either segregant null or construct null). A minimum (P<t) of 0.1 is used as a cut off for a statistically significant result.

Example 18C

Transformation and Evaluation of Gaspe Flint Derived Maize Lines Under Nitrogen Limiting Conditions A Gaspe Flint derived maize line was transformed via *Agrobacterium* with plasmid PHP30116, encoding the *Zea mays* LNT1-like polypeptide (SEQ ID NO:20). Six transformation events were evaluated following a procedure similar to that described in Example 18B.

Tables 5 and 6 show the number of variables for each transgenic event that were significantly altered, as compared to the segregant nulls. A "positive effect" was defined as a statistically significant improvement in that variable for the transgenic event relative to the null control. A "negative effect" was defined as a statistically significant improvement in that variable for the null control relative to the transgenic event. Table 5 presents the number of variables with a significant change for individual events transformed with the PHP30116 construct. Table 6 presents the number of events that showed a significant change for each individual variable. The variables designated with "_end exponential" indicate that the variables were measured at the end of exponential growth. The variables designated with "_harvest" indicate that the variables were measured at the time of harvest.

TABLE 5

Number of Variables with a Significant Change* for Individual Events Transformed with PHP30116 Encoding the *Zea mays* LNT1-like Polypeptide (SEQ ID NO: 20)

| | 1.0 mMol KNO3 | | 6.5 mMol KNO3 | |
| --- | --- | --- | --- | --- |
| Event | Positive Effect | Negative Effect | Positive Effect | Negative Effect |
| EA2393.375.1.1 | 1 | 0 | 5 | 0 |
| EA2393.375.1.11 | 0 | 0 | 0 | 5 |
| EA2393.375.1.3 | 2 | 1 | 0 | 8 |
| EA2393.375.1.6 | 0 | 2 | 3 | 3 |
| EA2393.375.1.7 | 6 | 0 | 0 | 1 |
| EA2393.375.1.9 | 1 | 4 | 1 | 2 |

*P-value less than or equal to 0.1

TABLE 6

Number of Events Transformed with PHP30116 Encoding the *Zea mays* LNT1-like polypeptide (SEQ ID NO: 20) with a Significant Change* for Individual Variables

| | 1.0 mMol KNO3 | | 6.5 mMol KNO3 | |
| --- | --- | --- | --- | --- |
| Variable | Positive Effect | Negative Effect | Positive Effect | Negative Effect |
| area_end exponential | 1 | 0 | 1 | 3 |
| area_harvest | 1 | 1 | 0 | 2 |
| ear diameter | 0 | 1 | 2 | 2 |
| ear dry weight | 0 | 0 | 2 | 0 |
| ear fresh weight | 0 | 0 | 2 | 0 |
| maximum area | 1 | 1 | 0 | 2 |
| sgr – r2 > 0.9 | 1 | 1 | 0 | 2 |
| shoot dry weight | 1 | 0 | 1 | 3 |
| shoot fresh weight | 2 | 1 | 0 | 3 |
| shoot + ear dry weight | 1 | 0 | 0 | 1 |
| shoot + ear fresh weight | 1 | 0 | 0 | 1 |
| stalk + ear diameter | 1 | 2 | 1 | 0 |

*P-value less than or equal to 0.1

For construct PHP30116, the statistical value associated with each improved variable is presented in FIGS. 17-18. A significant positive effect had a P-value of less than or equal to 0.1. A significant negative effect is shown in parentheses. A blank entry indicates that a significant difference was not observed between the transgenic event and the null segregant. The results for each of six transformed maize lines are presented in FIGS. 17A-E. Events EA2393.375.1.3 and EA2393.375.1.7 had at least two variables with improved effects under reduced nitrogen conditions, while events EA2393.375.1.1 and EA2393.375.1.6 had at least two variables with improved effects under optimal nitrogen conditions. The summary evaluation for all six events with construct PHP30116 is presented in FIG. 18. When all events are combined, events with construct PHP30116 showed significant increases in area (taken at harvest) and in shoot fresh weight, under reduced nitrogen conditions.

Example 19

Nitrogen Utilization Efficiency (NUE) Maize Seedling Assay

Seeds of transgenic events can also be evaluated using a maize seedling assay. The maize seedling assay is implemented by separating into Transgenic (Treatment 1) and Null (Treatment 2) seed using a seed color marker and randomly assigning each treatment to blocks of 54 pots (experimental units) arranged in 6 rows by 9 columns. Each treatment (Transgenic or Bulked Nulls) can be replicated 9 times.

All seeds are planted in 4 inch, square pots containing Turface on 8 inch, staggered centers and watered four times each day with a solution containing the following nutrients:

| 1 mM CaCl$_2$ | 2 mM MgSO$_4$ | 0.5 mM KH$_2$PO$_4$ | 83 ppm Sprint330 |
|---|---|---|---|
| 3 mM KCl | 1 mM KNO$_3$ | 1 µM ZnSO$_4$ | 1 µM MnCl$_2$ |
| 3 µM H$_3$BO$_4$ | 1 µM MnCl$_2$ | 0.1 µM CuSO$_4$ | 0.1 µM NaMoO$_4$ |

After emergence the plants are thinned to one seed per pot. At harvest, plants are removed from the pots, and the Turface is washed from the roots. The roots are separated from the shoot, placed in a paper bag, and dried at 70° C. for 70 hr. The dried plant parts (roots and shoots) are weighed and placed in a 50 ml conical tube with approximately 20 5/32 inch steel balls and then ground by shaking in a paint shaker. Approximately, 30 mg of the ground tissue (weight recorded for later adjustment) is hydrolyzed in 2 ml of 20% H$_2$O$_2$ and 6M H$_2$SO$_4$ for 30 min at 170° C. After cooling, water is added to 20 ml, mixed thoroughly, and a 50 µl aliquot is removed and added to 950 µl 1M Na$_2$CO$_3$. The ammonia in this solution is used to estimate total reduced plant nitrogen by placing 100 µl of this solution into individual wells of a 96 well plate followed by adding 50 µl of OPA solution. Fluorescence, excitation=360 nM/emission=530 nM, is determined and compared to NH$_4$Cl standards dissolved in a similar solution and treated with OPA solution.
OPA solution—5 µl Mercaptoethanol+1 ml OPA stock solution
OPA stock—50 mg o-phthadialdehyde (OPA—Sigma #P0657) dissolved in 1.5 ml methanol+4.4 ml 1M Borate buffer pH9.5 (3.09 g H$_3$BO$_4$+1 g NaOH in 50 ml water)+0.55 ml 20% SDS
The following parameters are measured, and means of Transgenic parameters are compared to means of Null parameters using a Student's t test:

| Total Plant Biomass | (Total plant Dwt) |
|---|---|
| Root Biomass | (Root Dwt) |
| Shoot Biomass | (Shoot Dwt) |
| Root/Shoot Ratio | |
| Plant N concentration | ([N] = mg N/plant Dwt) |
| Total Plant N | (Total Plant N) |

Variance is calculated within each block using a nearest neighbor calculation as well as by Analysis of Variance (ANOVA) using a completely random design (CRD) model. An overall treatment effect for each block is calculated using an F statistic by dividing overall block treatment mean square by the overall block error mean square. The probability of a greater Student's t test is calculated for each transgenic mean compared to the appropriate null. A minimum (P<t) of 0.1 is used to define variables that show a significant difference (*).

Example 20

Yield Analysis of Maize Lines with the *Arabidopsis* Int1 or an Int1-Like Maize Homolog Transgenic plants, either inbred or hybrid, can undergo more vigorous field-based experiments to study yield enhancement and/or stability under nitrogen limiting and non-limiting conditions.

Subsequent yield analysis can be done to determine whether plants that contain the validated *Arabidopsis* Int1 gene or a maize homolog of Int1 have an improvement in yield performance (under nitrogen limiting or non-limiting conditions), when compared to the control (or reference) plants that do not contain the validated *Arabidopsis* Int1 gene or a maize homolog of Int1. Specifically, nitrogen limiting conditions can be imposed during the flowering and/or grain fill period for plants that contain either the validated *Arabidopsis* lead gene or a maize homolog of Int1 and the control plants. Reduction in yield can be measured for both. Plants containing the validated *Arabidopsis* lead gene or a maize homolog of Int1 would have less yield loss relative to the control plants, for example, at least 25% less yield loss, under nitrogen limiting conditions, or would have increased yield relative to the control plants under nitrogen non-limiting conditions.

Example 21

Transformation and Evaluation of Soybean with Soybean Homologs of Validated Lead Genes Based on homology searches, one or several candidate soybean homologs of validated *Arabidopsis* leads can be identified and also be assessed for their ability to enhance tolerance to nitrogen limiting conditions in soybean. Vector construction, plant transformation and phenotypic analysis will be similar to that in previously described Examples.

Example 22

Transformation of *Arabidopsis* with Maize and Soybean Homologs of Validated Lead Genes Soybean and maize homologs to validated *Arabidopsis* lead genes can be transformed into *Arabidopsis* under control of the 35S promoter and assayed for leaf area and green color bin accumulation when grown on low nitrogen medium. Vector construction and plant transformation can be as described in the examples herein. Assay conditions, data capture and data analysis can be similar to that in previously described Examples.

What is claimed is:

1. A method of evaluating nitrogen stress tolerance in a plant, comprising:
   (a) introducing into a regenerable plant cell a recombinant DNA construct comprising a polynucleotide operably linked to at least one regulatory sequence, wherein the polynucleotide encodes a polypeptide having an amino acid sequence of at least 90% sequence identity, based on the Clustal V method of alignment, when compared to SEQ ID NO:32;
   (b) regenerating a transgenic plant from the regenerable plant cell after step (a), wherein the transgenic plant comprises in its genome the recombinant DNA construct; and
   (c) evaluating the transgenic plant for nitrogen stress tolerance compared to a control plant not comprising the recombinant DNA construct.

2. The method of claim 1, further comprising:
   (d) obtaining a progeny plant derived from the transgenic plant, wherein the progeny plant comprises in its genome the recombinant DNA construct; and
   (e) evaluating the progeny plant for nitrogen stress tolerance compared to a control plant not comprising the recombinant DNA construct.

3. A method of evaluating nitrogen stress tolerance in a plant, comprising:
   (a) introducing into a regenerable plant cell a recombinant DNA construct comprising a polynucleotide operably linked to at least one regulatory sequence, wherein the polynucleotide encodes a polypeptide having an amino acid sequence of at least 90% sequence identity, based on the Clustal V method of alignment, when compared to SEQ ID NO:32;
   (b) regenerating a transgenic plant from the regenerable plant cell after step (a), wherein the transgenic plant comprises in its genome the recombinant DNA construct;
   (c) obtaining a progeny plant derived from the transgenic plant, wherein the progeny plant comprises in its genome the recombinant DNA construct; and
   (d) evaluating the progeny plant for nitrogen stress tolerance compared to a control plant not comprising the recombinant DNA construct.

4. The method of claim 1, wherein the plant is a maize plant or a soybean plant.

5. The method of claim 2, wherein the plant is a maize plant or a soybean plant.

6. The method of claim 3, wherein the plant is a maize plant or a soybean plant.

* * * * *